(12) United States Patent
Bunnage et al.

(10) Patent No.: US 8,916,593 B2
(45) Date of Patent: Dec. 23, 2014

(54) ALKOXY-SUBSTITUTED 2-AMINOPYRIDINES AS ALK INHIBITORS

(75) Inventors: Mark Edward Bunnage, Concord, MA (US); Andrew Simon Cook, Sandwich (GB); Jingrong Jean Cui, San Diego, CA (US); Kevin Nell Dack, Sandwich (GB); Judith Gail Deal, San Diego, CA (US); Danlin Gu, San Diego, CA (US); Mingying He, San Diego, CA (US); Patrick Stephen Johnson, Sandwich (GB); Ted William Johnson, San Diego, CA (US); Phuong Thi Quy Le, San Diego, CA (US); Cynthia Louise Palmer, San Diego, CA (US); Hong Shen, San Diego, CA (US)

(73) Assignee: Pfizer Inc., New York, NY (US)

( * ) Notice: Subject to any disclaimer, the term of this patent is extended or adjusted under 35 U.S.C. 154(b) by 46 days.

(21) Appl. No.: 13/695,770

(22) PCT Filed: May 4, 2011

(86) PCT No.: PCT/IB2011/051981
§ 371 (c)(1),
(2), (4) Date: Mar. 8, 2013

(87) PCT Pub. No.: WO2011/138751
PCT Pub. Date: Nov. 10, 2011

(65) Prior Publication Data
US 2013/0196952 A1     Aug. 1, 2013

Related U.S. Application Data

(60) Provisional application No. 61/331,009, filed on May 4, 2010, provisional application No. 61/482,176, filed on May 3, 2011.

(51) Int. Cl.
| | | |
|---|---|---|
| A61K 31/4427 | (2006.01) |
| C07D 213/73 | (2006.01) |
| C07D 498/04 | (2006.01) |
| C07D 413/14 | (2006.01) |
| C07D 403/14 | (2006.01) |
| C07D 409/14 | (2006.01) |
| C07F 9/53 | (2006.01) |

(Continued)

(52) U.S. Cl.
CPC ............ *C07D 213/73* (2013.01); *C07D 498/04* (2013.01); *C07D 413/14* (2013.01); *C07D 403/14* (2013.01); *C07D 409/14* (2013.01); *C07F 9/5325* (2013.01); *C07D 471/04* (2013.01); *C07D 403/04* (2013.01); *C07D 417/04* (2013.01); *C07D 403/12* (2013.01); *C07F 9/65583* (2013.01); *C07F 5/025* (2013.01); *C07D 413/04* (2013.01); *C07D 417/14* (2013.01); *C07D 241/20* (2013.01); *C07D 401/14* (2013.01); *C07D 401/12* (2013.01); *C07D 451/02* (2013.01); *C07D 401/04* (2013.01); *C07F 7/1856* (2013.01)
USPC ............ 514/352; 546/311; 548/202; 548/255

(58) Field of Classification Search
CPC .......................... A61K 31/4427; C07D 213/73
USPC .................... 514/352; 546/311; 548/202, 255
See application file for complete search history.

(56) References Cited

U.S. PATENT DOCUMENTS

| | | |
|---|---|---|
| 7,230,098 B2 | 6/2007 | Cui |
| 7,825,137 B2 | 11/2010 | Christensen |

(Continued)

FOREIGN PATENT DOCUMENTS

| | | |
|---|---|---|
| WO | WO 2004/076412 A2 | 9/2004 |
| WO | WO 2006/021881 A2 | 3/2006 |

(Continued)

OTHER PUBLICATIONS

International Report on Patentability Publication No. WO 2011/138751, Appln. No. PCT/IB2011/051981 issued Nov. 6, 2012.
International Search Report for Publication No. WO 2011/138751, Appln. No. PCT/IB2011/051981 completed Nov. 22, 2011.
Written Opinion of the International Searching Authority Publication No. WO 2011/138751, Appl. No. PCT/IB2011/051981.

*Primary Examiner* — Douglas M Willis
(74) *Attorney, Agent, or Firm* — Leslie A. Robinson

(57) ABSTRACT

The invention relates to compounds of Formula (1) and to processes for the preparation of, intermediates used in the preparation of, compositions containing and the uses of, such derivatives. The compounds according to the present invention are useful in numerous diseases in which ALK protein is involved or in which inhibition of ALK activity may induce benefit, especially for the treatment of cancer mediated by a mutated EML4-ALK fusion protein.

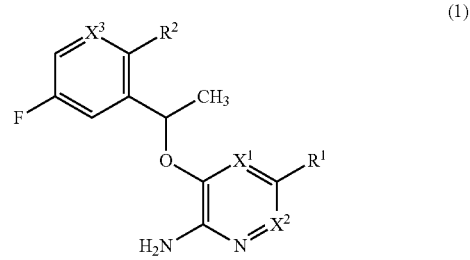

(1)

5 Claims, No Drawings

(51) Int. Cl.
*C07D 471/04* (2006.01)
*C07D 403/04* (2006.01)
*C07D 417/04* (2006.01)
*C07D 403/12* (2006.01)
*C07F 9/6558* (2006.01)
*C07F 5/02* (2006.01)
*C07D 413/04* (2006.01)
*C07D 417/14* (2006.01)
*C07D 241/20* (2006.01)
*C07D 401/14* (2006.01)
*C07D 401/12* (2006.01)
*C07D 451/02* (2006.01)
*C07D 401/04* (2006.01)
*C07F 7/18* (2006.01)

(56) References Cited

U.S. PATENT DOCUMENTS

| | | | |
|---|---|---|---|
| 7,858,643 | B2 | 12/2010 | Cui |
| 8,106,197 | B2 | 1/2012 | Cui |
| 8,217,057 | B2 | 7/2012 | Cui |
| 2006/0128724 | A1 | 6/2006 | Cui |
| 2010/0324061 | A1 | 12/2010 | Cui |
| 2012/0263706 | A1 | 10/2012 | Cui |

FOREIGN PATENT DOCUMENTS

| | | |
|---|---|---|
| WO | WO 2008/053157 A1 | 5/2008 |
| WO | WO 2008/088881 A1 | 7/2008 |
| WO | WO 2011/138751 A2 | 11/2011 |

ALKOXY-SUBSTITUTED 2-AMINOPYRIDINES AS ALK INHIBITORS

CROSS-REFERENCE TO RELATED APPLICATIONS

This application is the national stage filing under 35 U.S.C. 371 of Patent Cooperation Treaty Patent Application No. PCT/IB2011/051981, filed May 4, 2011, which claims the benefit of U.S. Provisional Application No. 61/331,009, filed May 4, 2010, and U.S. Provisional Application No. 61/482,176, filed May 3, 2011, the contents of which are hereby incorporated by reference in their entireties.

BACKGROUND OF THE INVENTION

1. Field of the Invention

This invention relates to ALK inhibitors of general formula:

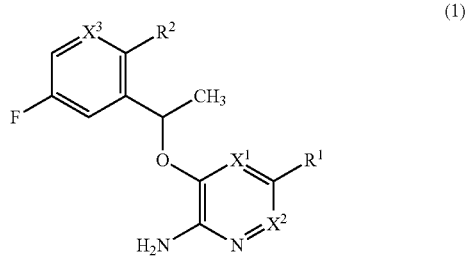

(1)

in which $R^1$, $R^2$, $X^1$, $X^2$ and $X^3$ have the meanings indicated below, and to processes for the preparation of, compositions containing and the uses of such derivatives.

2. Description of Related Art

Anaplastic lymphoma kinase (ALK) is a member of the receptor tyrosine kinase superfamily, and at an amino acid sequence level is most closely related to members such as Ros-1, leucocyte tyrosine kinase, the insulin receptor and cMet (hepatic growth factor receptor) (Kostich M et al, Genome Biology, 2002, 3, 1-12). As with all members of this gene family, it possesses an extracellular ligand binding domain, a transmembrane spanning sequence, and an intracellular kinase catalytic region/signalling domain. The identity of the signalling ligand for ALK is not yet elucidated and different mechanisms have been proposed in the literature (Stoica G E et al J. Biol. Chem. 2001, 276, 16772-16779; Stoica G E et al J Biol Chem 2002, 277, 35990-35999; Mewng K et al, PNAS 2000, 97, 2603-2608; Perez-Pinera P et al, J Biol Chem 2007, 282, 28683-28690). The stimulation of ALK leads to an intracellular signalling cascade via phopholipase-C γ, PI3Kinase and STAT3 (amongst other signalling proteins) (Turner S D et al, Cell Signal 2007, 19, 740-747).

ALK is largely expressed in the developing nervous system (Iwahara T et al, Oncogene 1997, 14, 439-449). Its relative abundance does tend to decrease in the adult animal, though its expression is maintained in certain regions of the brain, spinal cord and the eye (Vernersson E et al, Gene Expression Patterns, 2006, 6, 448-461).

Investigation of the biological role of ALK in cell culture systems, such as neuronal type cells, has suggested a role in neuronal differentiation (Souttou B, et al, J Biol Chem, 2001, 276, 9526-9531). Its role in-vivo has emerged from study of the ALK knockout mouse (Bilsland J G et al, Neuropsychopharmacology 2008, 33, 685-700). This mouse is viable and has no overt phenotype. This mouse does however have an increased level of neural progenitor cells in the hippocampus (a region of the brain known to be a site of "neurogenesis") and also showed changes in certain behavioral tests considered to be a measure of antidepressant activity (the tail suspension test and the Porsolt swim test), and in the novel object-recognition test (considered to be a measure of cognitive performance). Neurochemical analysis of the ALK knockout mouse brains also revealed an increase in dopaminergic signalling within the frontal cortex. These results lead the authors to suggest that one role of ALK in the adult brain may be to regulate the function of the frontal cortex and hippocampus, with potential implications for psychiatric and neurological disease.

ALK also has an important role in oncology (Webb T R et al, Expert Reviews in Anticancer Therapy 2009 9 331-355). Point mutations in the full length ALK enzyme that lead to activation of the enzyme, and also increase in expression of the full length enzyme, have both been shown to lead to neuroblastoma. In addition, the fusion of ALK with other proteins due to genetic translocation events, has also been shown to lead to activated kinase domain associated with cancer. A number of such ALK translocations leading to gene fusions are seen in lymphomas, the most prevalent being the nucleophosmin (NPM)-ALK fusion seen in anaplastic large cell lymphomas. ALK fusion with EML4 leads to a chimeric protein (EML4-ALK) thought to be responsible for a small percentage of non small cell lung carcinomas (NSCLC) (Soda M et al, Nature 2007 448 561-567).

Crizotinib is a potent dual tyrosine kinase inhibitor (TKI) targeting c-Met and ALK that has recently found application in the treatment of NSCLC patients harbouring the EML4-ALK fusion event (Kwak et al, New Eng. J. of Med. 2010 363 18 1693-1703). Crizotinib is disclosed in PCT Publication No. WO 2006/021884 and U.S. Pat. No. 7,858,643. While response to treatment with crizotinib in the appropriate subpopulation of NSCLC patients has been promising, a recent case has revealed acquired resistance to crizotinib treatment. Acquired TKI resistance has been seen with other targeted therapies such as in epidermal growth factor receptor (EGFR) mutant lung cancers (Bean J, et al Proc. Nat. Acad. Sci. 2007 104 20932-20937). As a result, there is a need for finding therapeutics active against cells resistant to TKIs, e.g. crizotinib.

In the case of reported acquired resistance of crizotinib, a patient (positive for the EML4-ALK gene fusion) enrolled in a clinical trial of crizotinib on Nov. 28, 2008. The patient responded to the drug for the first 5-months showing partial response over that time but not a complete eradication of their pleural effusion. After 5-months of treatment, the patient's tumor abruptly began growing, and the patient was withdrawn from trial on May 25, 2009. A sample of the patient's pleural effusion was taken and molecular analysis revealed a L1196M and a C1156Y mutation in the EML4-ALK protein (Choi Y L et al, N. Engl. J. Med. 2010 363 18 1734-1739). As crizotinib therapy becomes more widely available to patients harbouring the EML4-ALK gene fusion event, it is likely that the L1196M and C1156Y mutations and possibly other mutations will play a more prevalent role in acquired resistance to crizotinib therapy.

All of these examples clearly mark out ALK as an important target in ALK dependent tumours.

Accordingly, there is a need for ALK inhibitors and EML4-ALK inhibitors that would have an appropriate pharmacological profile, for example in terms of potency, selectivity, pharmacokinetics, ability to cross the blood brain barrier and duration of action. More specifically, there is a need for ALK inhibitors that inhibit the EML4-ALK L1196M mutated protein. In this context, the present invention relates to novel ALK inhibitors.

BRIEF SUMMARY OF THE INVENTION

It will be understood that each embodiment describing the inventive compounds herein may be combined alone or in combination with any other embodiment describing the inventive compounds provided that such embodiments are not inconsistent with each other.

In one embodiment, the invention provides for a compound of the formula (1),

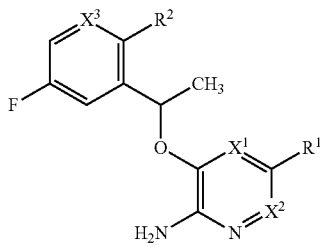

(1)

or a pharmaceutically acceptable salt thereof, wherein
$R^1$ is a 5- or 6-membered heteroaryl containing 1, 2 or 3 heteroatoms independently selected from O, N and S, a 4-6-membered heterocyclic containing 1, 2 or 3 heteroatoms independently selected from O, N, and $S(O)_p$, or a $C_6$-$C_{10}$ aryl, wherein said 5- or 6-membered heteroaryl, 4-6-membered heterocyclic and $C_6$-$C_{10}$ aryl are optionally substituted with one, two or three $R^3$ groups, or $R^3$ substituents on adjacent ring atoms of said 5- or 6-membered heteroaryl or $C_6$-$C_{10}$ aryl may combine to form a fused 5- or 6-membered carbocyclic ring optionally substituted with one, two or three groups selected from oxo, $C_1$-$C_6$ alkyl, hydroxyl, amino and halogen or a fused 5- or 6-membered heterocyclic ring containing one, two or three ring heteroatoms selected from N, O and $S(O)_p$ optionally substituted with one, two or three groups selected from oxo, $C_1$-$C_6$ alkyl, hydroxyl, amino and halogen;
$X^1$ is N or CH and $X^2$ is N or CH, provided that when $X^2$ is N then $X^1$ is CH;
$X^3$ is N or CH;
$R^2$ is —$OCH_3$, F, Cl, Br, CN, a 5- or 6-membered heteroaryl containing 1, 2 or 3 heteroatoms independently selected from O, N and S, or a 4-6-membered heterocyclic containing 1, 2 or 3 heteroatoms independently selected from O, N and $S(O)_p$, wherein said 5- or 6-membered heteroaryl and 4-6-membered heterocyclic are optionally substituted with one, two or three groups independently selected from the group consisting of $C_1$-$C_6$ alkyl, $C_2$-$C_4$ alkenyl, —O—$C_1$-$C_6$ alkyl, halogen, amino, —$SO_2CH_3$, oxo and hydroxyl, and wherein said $C_1$-$C_6$ alkyl and O—$C_1$-$C_6$ alkyl are optionally substituted with one or two hydroxyl groups; or,
$X^3$ together with $R^2$ and the carbon atom to which $R^2$ is bound forms a 5- or 6-membered heteroaryl containing 1, 2 or 3 heteroatoms independently selected from O, N or S;
each $R^3$ is independently selected from halogen, $C_1$-$C_6$ alkyl, $C_2$-$C_4$ alkenyl, —$(CH_2)_n$CN, —$(CH_2)_n$S(O)$_2$CH$_3$, —S(O)$_2$NR$^4$R$^5$, —PO(CH$_3$)$_2$, —(CR$^4$R$^5$)$_n$NR$^4$R$^5$, —(CR$^4$R$^5$)$_n$OR$^4$, —OCH$_2$(CR$^4$R$^5$)$_n$OR$^4$, —(CR$^4$R$^5$)$_n$CO (CR$^4$R$^5$)$_m$NR$^4$R$^5$, —(CR$^4$R$^5$)$_n$CR$^4$(OR$^5$)(CR$^4$R$^5$)OR$^5$, oxo, —O(4-6-membered heterocyclic containing 1, 2 or 3 heteroatoms independently selected from O, N and $S(O)_p$), and 4-6-membered heterocyclic containing 1, 2 or 3 heteroatoms independently selected from O, N and $S(O)_p$; wherein said $C_1$-$C_6$ alkyl is optionally substituted with one or two hydroxy groups, and wherein each said 4-6-membered heterocycle is optionally substituted with one or more halogen, hydroxyl, oxo, —(CR$^4$R$^5$)$_n$CO(CR$^4$R$^5$)$_m$NR$^4$R$^5$ or $C_1$-$C_6$ alkyl, or substituents on two ring atoms of said 4-6-membered heterocycle may optionally combine to form a 5- or 6-membered bridged ring that is either carbocyclic or heterocyclic containing one, two or three ring heteroatoms selected from N, O and $S(O)_p$;
each $R^4$ or $R^5$ is independently H or $C_1$-$C_6$ alkyl;
each m is independently 0, 1, 2 or 3;
each n is independently 0, 1, 2 or 3; and
each p is independently 0, 1 or 2.

In a further embodiment, the invention provides a compound of the formula (1),

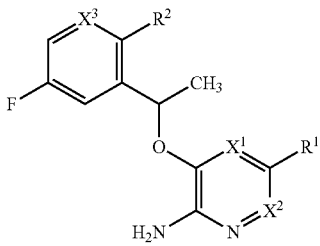

(1)

or a pharmaceutically acceptable salt thereof, wherein
$R^1$ is a 5- or 6-membered heteroaryl containing 1, 2 or 3 heteroatoms independently selected from O, N and S, a 4-6-membered heterocyclic containing 1, 2 or 3 heteroatoms independently selected from O, N, and $S(O)_p$, or a $C_6$-$C_{10}$ aryl, wherein said 5 or 6-membered heteroaryl, 4-6-membered heterocyclic and $C_6$-$C_{10}$ aryl are optionally substituted with one, two or three $R^3$ groups, or $R^3$ substituents on adjacent ring atoms of said 5- or 6-membered heteroaryl or $C_6$-$C_{10}$ aryl may combine to form a fused 5- or 6-membered carbocyclic ring optionally substituted with one, two or three groups selected from oxo, $C_1$-$C_6$ alkyl, hydroxyl, amino and halogen or a fused 5- or 6-membered heterocyclic ring containing one, two or three ring heteroatoms selected from N, O and $S(O)_p$ optionally substituted with one, two or three groups selected from oxo, $C_1$-$C_6$ alkyl, hydroxyl, amino and halogen;
$X^1$ is N or CH and $X^2$ is N or CH, provided that when $X^2$ is N then $X^1$ is CH;
$X^3$ is N or CH;
$R^2$ is —$OCH_3$, a 5- or 6-membered heteroaryl containing 1, 2 or 3 heteroatoms independently selected from O, N and S, or a 4-6-membered heterocyclic containing 1, 2 or 3 heteroatoms independently selected from O, N and $S(O)_p$, wherein said 5- or 6-membered heteroaryl and said 4-6-membered heterocyclic are optionally substituted with one, two or three groups independently selected from the group consisting of $C_1$-$C_6$ alkyl, $C_2$-$C_4$ alkenyl, —O—$C_1$-$C_6$ alkyl, halogen, amino, —$SO_2CH_3$, oxo and hydroxyl, and wherein said $C_1$-$C_6$ alkyl and —O—$C_1$-$C_6$ alkyl are optionally substituted with one or two hydroxyl groups;
$R^3$ is selected from halogen, $C_1$-$C_6$ alkyl, $C_2$-$C_4$ alkenyl, —$(CH_2)_n$CN, —$(CH_2)_n$SO$_2$CH$_3$, —SO$_2$NR$^4$R$^5$, —PO (CH$_3$)$_2$, —(CR$^4$R$^5$)$_m$NR$^4$R$^5$, —(CR$^4$R$^5$)$_n$OR$^4$, —OCH$_2$ (CR$^4$R$^5$)$_n$OR$^4$, —(CR$^4$R$^5$)$_n$CO(CR$^4$R$^5$)$_m$NR$^4$R$^5$, —(CR$^4$ R$^5$)$_n$CR$^4$(OR$^5$)(CR$^4$R$^5$)OR$^5$, oxo, —O(4-6-membered heterocyclic containing 1, 2 or 3 heteroatoms independently selected from O, N and S(O)$_p$), and 4-6-membered heterocyclic containing 1, 2 or 3 heteroatoms independently selected from O, N and S(O)$_p$; wherein said $C_1$-$C_6$ alkyl is optionally substituted with one or two hydroxy groups, and wherein each said 4-6-membered heterocyclic is independently optionally substituted with one or more halogen, hydroxyl, oxo, —(CR$^4$R$^5$)$_n$CO(CR$^4$R$^5$)$_m$NR$^4$R$^5$ or $C_1$-$C_4$ alkyl, or substituents on two ring atoms of said 4-6-membered heterocycle may optionally combine to form a 5- or 6-membered bridged ring that is either carbocyclic or heterocyclic containing one, two or three ring heteroatoms selected from N, O and S(O)$_p$;

each $R^4$ or $R^5$ is independently H or $C_1$-$C_6$ alkyl;

each m is independently 0, 1, 2 or 3;

each n is independently 0, 1, 2 or 3; and each p is independently 0, 1 or 2.

In some embodiments, $X^1$ is N and $X^2$ is CH. In some embodiments, $X^1$ is CH and $X^2$ is N. In some embodiments, $X^1$ is CH and $X^2$ is CH.

In some embodiments, $R^1$ is 5- or 6-membered heteroaryl containing 1, 2 or 3 heteroatoms independently selected from O, N and S, and optionally substituted with one, two or three $R^3$ groups. In some embodiments, $R^1$ is thiazolyl, oxazolyl, pyrazolyl, imidazolyl, triazolyl, 1,2,4-thiadiazolyl, pyridinyl or pyrimidinyl, optionally substituted with one, two or three $R^3$ groups. In some embodiments, $R^1$ is $C_6$-$C_{10}$ aryl optionally substituted with one, two or three $R^3$ groups. In some embodiments, $R^1$ is phenyl optionally substituted with one, two or three $R^3$ groups. In some embodiments, $R^1$ is 4-6-membered heterocycle containing 1, 2 or 3 heteroatoms independently selected from O, N and S(O)$_p$ optionally substituted with one, two or three $R^3$ groups.

In some embodiments, $R^2$ is selected from —OCH$_3$, F, Cl, Br and CN. In some embodiments, $R^2$ is OCH$_3$. In some embodiments, $R^2$ is a 5-membered heteroaryl containing 1, 2 or 3 heteroatoms independently selected from O, N and S. In some embodiments, $R^2$ is a 5-membered heteroaryl containing 1, 2 or 3 nitrogen atoms. In some embodiments, $R^2$ is selected from pyrazolyl, imidazolyl and triazolyl. In some embodiments, $R^2$ is triazolyl.

In some embodiments, $R^1$ is selected from the group consisting of

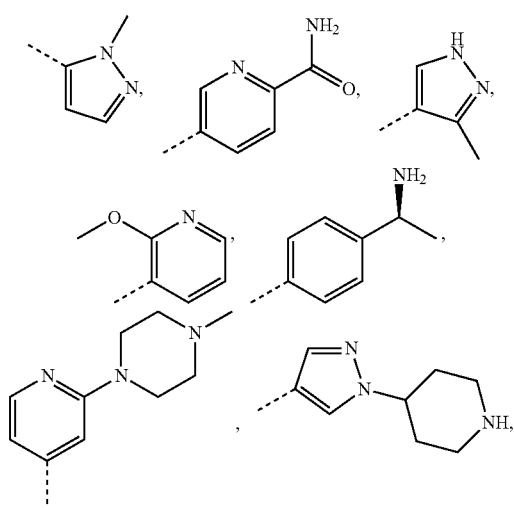

-continued

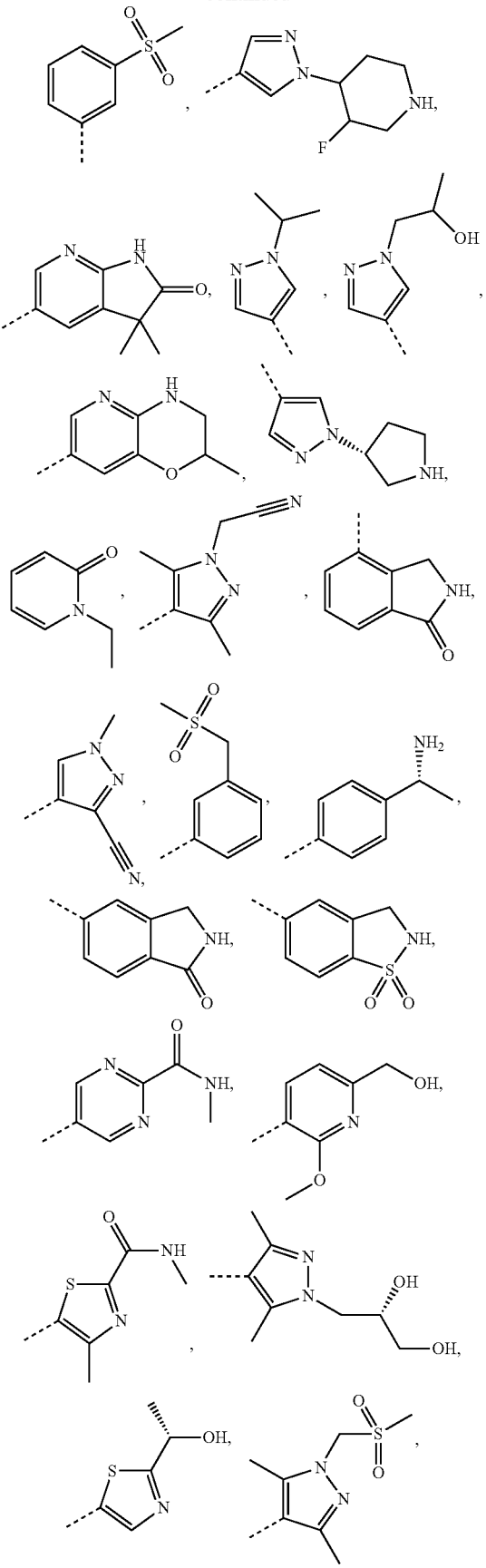

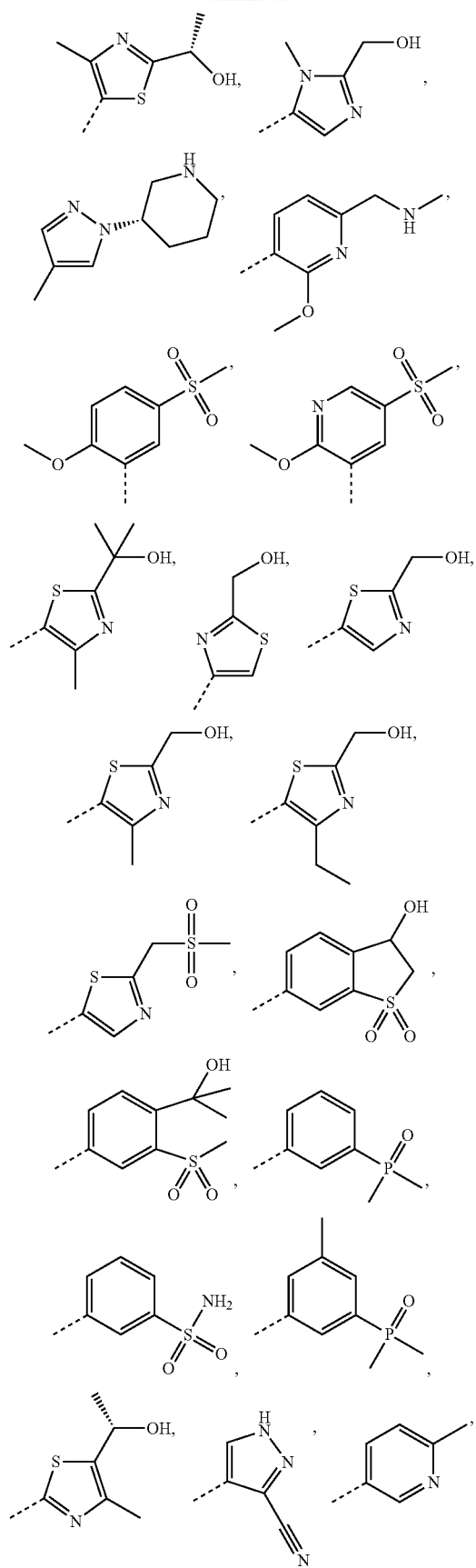
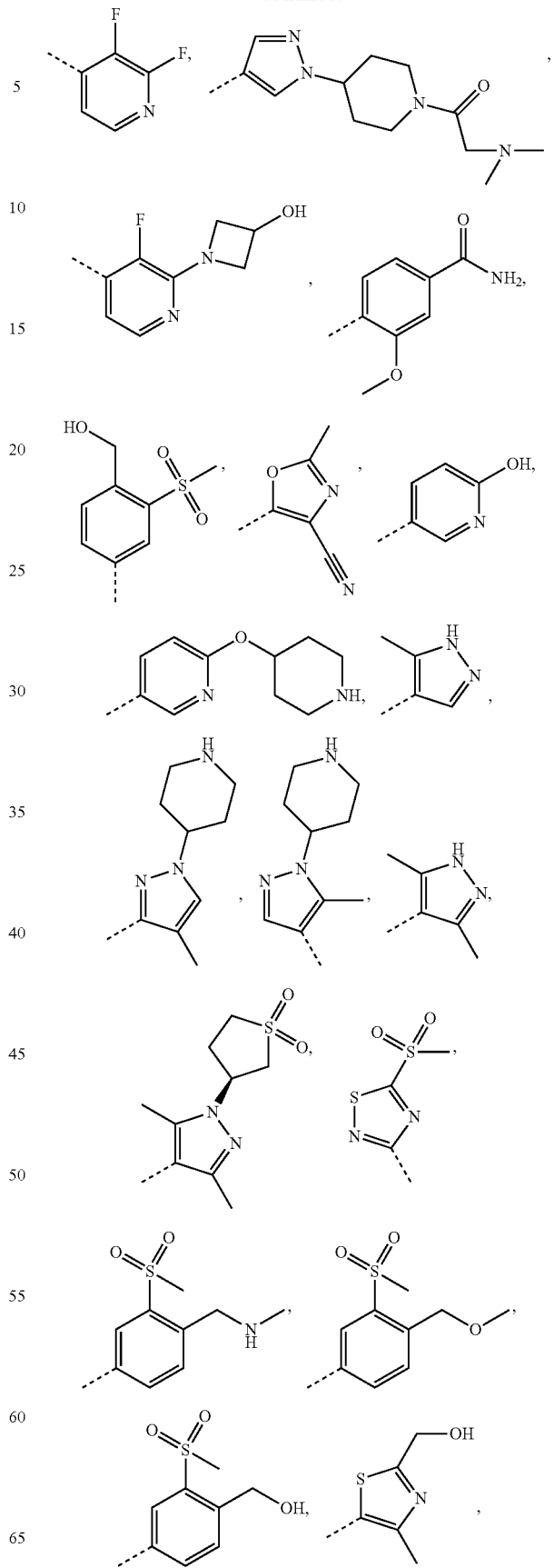

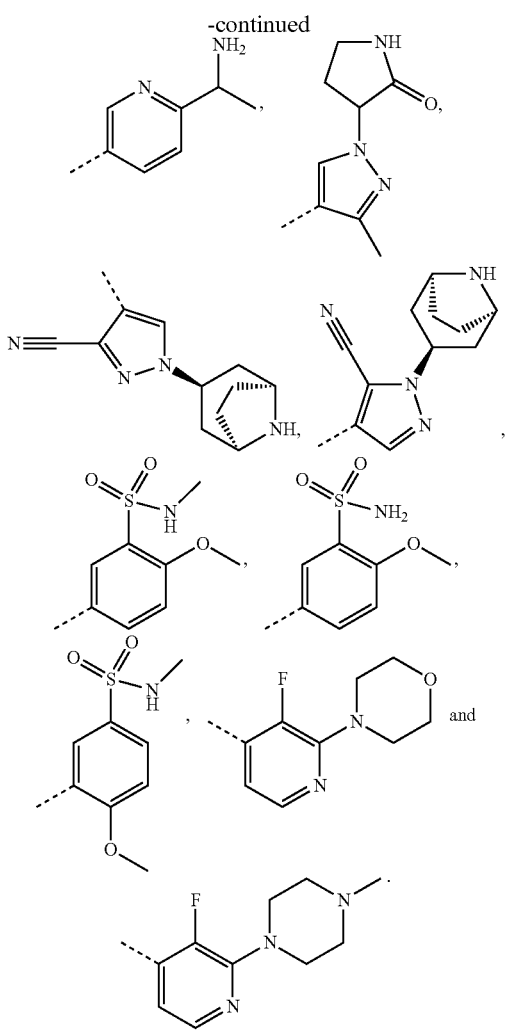

In a further embodiment, the invention provides a compound of formula (2),

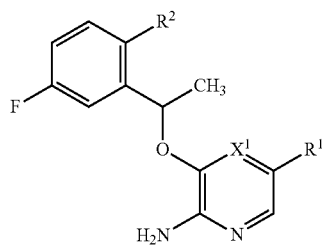

(2)

or a pharmaceutically acceptable salt thereof, wherein $R^1$ is a 5- or 6-membered heteroaryl containing 1, 2 or 3 heteroatoms independently selected from O, N and S or a $C_6$-$C_{10}$ aryl, wherein said 5 or 6-membered heteroaryl and $C_6$-$C_{10}$ aryl are optionally substituted with one, two or three $R^3$ groups;

$X^1$ is N or CH;

$R^2$ is —$OCH_3$ or 5- or 6-membered heteroaryl containing 1, 2 or 3 heteroatoms independently selected from O, N and S optionally substituted with one, two or three groups independently selected from the group consisting of $C_1$-$C_6$ alkyl, $C_2$-$C_4$ alkenyl, —O—$C_1$-$C_6$ alkyl, halogen, amino, —$SO_2CH_3$, oxo and hydroxyl, and wherein said $C_1$-$C_6$ alkyl and —O—$C_1$-$C_6$ alkyl are optionally substituted with one or two hydroxyl groups;

$R^3$ is selected from halogen, $C_1$-$C_6$ alkyl, $C_2$-$C_4$ alkenyl, —$(CH_2)_nCN$, —$(CH_2)_nSO_2CH_3$, —$SO_2NR^4R^5$, —PO$(CH_3)_2$, —$(CR^4R^5)_nNR^4R^5$, —$(CR^4R^5)_nOR^4$, —$OCH_2(CR^4R^5)_nOR^4$, —$(CR^4R^5)_nCO(CR^4R^5)_mNR^4R^5$, —$(CR^4R^5)_nCR^4(OR^5)(CR^4R^5)OR^5$, oxo, —O(4-6-membered heterocyclic containing 1, 2 or 3 heteroatoms independently selected from O, N and $S(O)_p$), and 4-6-membered heterocyclic containing 1, 2 or 3 heteroatoms independently selected from O, N and $S(O)_p$; wherein said $C_1$-$C_6$ alkyl is optionally substituted with one or two hydroxy groups, and wherein each said 4-6-membered heterocyclic is independently optionally substituted with one or more halogen, hydroxyl, oxo, —$(CR^4R^5)_nCO(CR^4R^5)_mNR^4R^5$ or $C_1$-$C_4$ alkyl, or substituents on two ring atoms of said 4-6-membered heterocycle may optionally combine to form a 5- or 6-membered bridged ring that is either carbocyclic or heterocyclic containing one, two or three ring heteroatoms selected from N, O and $S(O)_p$;

each $R^4$ or $R^5$ is independently H or $C_1$-$C_6$ alkyl;

each m is independently 0, 1, 2 or 3;

each n is independently 0, 1, 2 or 3; and each p is independently 0, 1 or 2.

In one embodiment of this aspect of the invention, $X^1$ is N and $X^2$ is CH. In one embodiment of this aspect of the invention, $X^1$ is CH and $X^2$ is N. In some embodiments, $X^1$ is CH and $X^2$ is CH.

In one embodiment of this aspect of the invention, $R^1$ is 5- or 6-membered heteroaryl containing 1, 2 or 3 heteroatoms independently selected from O, N and S, and optionally substituted with one, two or three $R^3$ groups. In one embodiment of this aspect of the invention, $R^1$ is thiazolyl, oxazolyl, pyrazolyl, imidazolyl, triazolyl, 1,2,4-thiadiazolyl, pyridinyl or pyrimidinyl, optionally substituted with one, two or three $R^3$ groups. In one embodiment of this aspect of the invention, $R^1$ is $C_6$-$C_{10}$ aryl optionally substituted with one, two or three $R^3$ groups. In one embodiment of this aspect of the invention, $R^1$ is phenyl optionally substituted with one, two or three $R^3$ groups. In one embodiment of this aspect of the invention, $R^1$ is 4-6-membered heterocycle containing 1, 2 or 3 heteroatoms independently selected from O, N and $S(O)_p$ optionally substituted with one, two or three $R^3$ groups.

In one embodiment of this aspect of the invention, $R^2$ is selected from —$OCH_3$, F, Cl, Br and CN. In some embodiments, $R^2$ is $OCH_3$. In one embodiment of this aspect of the invention, $R^2$ is a 5-membered heteroaryl containing 1, 2 or 3 heteroatoms independently selected from O, N and S. In one embodiment of this aspect of the invention, $R^2$ is a 5-membered heteroaryl containing 1, 2 or 3 nitrogen atoms. In one embodiment of this aspect of the invention, $R^2$ is selected from pyrazolyl, imidazolyl and triazolyl. In one embodiment of this aspect of the invention, $R^2$ is triazolyl.

In one embodiment of this aspect of the invention, $X^1$ is N and $R^2$ is —$OCH_3$.

In one embodiment of this aspect of the invention, $X^1$ is N and $R^2$ is a 5-membered heteroaryl containing 1, 2 or 3 heteroatoms independently selected from O, N and S.

In one embodiment of this aspect of the invention, $X^1$ is CH and $R^2$ is —$OCH_3$.

In one embodiment of this aspect of the invention, $X^1$ is CH and $R^2$ is a 5-membered heteroaryl containing 1, 2 or 3 heteroatoms independently selected from O, N and S.

In one embodiment of this aspect of the invention, $X^1$ is N and $R^2$ is a 5-membered heteroaryl containing 1, 2 or 3 nitrogen atoms.

In one embodiment of this aspect of the invention, $X^1$ is CH and $R^2$ is a 5-membered heteroaryl containing 1, 2 or 3 nitrogen atoms.

In one embodiment of this aspect of the invention, $X^1$ is N and $R^2$ is selected from pyrazolyl, imidazolyl and triazolyl.

In one embodiment of this aspect of the invention, $X^1$ is CH and $R^2$ is selected from pyrazolyl, imidazolyl and triazolyl.

In one embodiment of this aspect of the invention, $X^1$ is N and $R^2$ is triazolyl.

In one embodiment of this aspect of the invention, $X^1$ is CH and $R^2$ is triazolyl.

In one embodiment of this aspect of the invention, $X^1$ is N, $R^1$ is 5- or 6-membered heteroaryl containing 1, 2 or 3 heteroatoms independently selected from O, N and S, and optionally substituted with one, two or three $R^3$ groups and $R^2$ is —OCH$_3$.

In one embodiment of this aspect of the invention, $X^1$ is CH, $R^1$ is 5- or 6-membered heteroaryl containing 1, 2 or 3 heteroatoms independently selected from O, N and S, and optionally substituted with one, two or three $R^3$ groups, and $R^2$ is —OCH$_3$.

In one embodiment of this aspect of the invention, $X^1$ is N, $R^1$ is 5- or 6-membered heteroaryl containing 1, 2 or 3 heteroatoms independently selected from O, N and S, and optionally substituted with one, two or three $R^3$ groups and $R^2$ is a 5-membered heteroaryl containing 1, 2 or 3 heteroatoms independently selected from O, N and S.

In one embodiment of this aspect of the invention, $X^1$ is CH, $R^1$ is 5- or 6-membered heteroaryl containing 1, 2 or 3 heteroatoms independently selected from O, N and S, and optionally substituted with one, two or three $R^3$ groups and $R^2$ is a 5-membered heteroaryl containing 1, 2 or 3 heteroatoms independently selected from O, N and S.

In one embodiment of this aspect of the invention, $X^1$ is N, $R^1$ is thiazolyl, oxazolyl, pyrazolyl, imidazolyl, triazolyl, 1,2,4-thiadiazolyl, pyridinyl or pyrimidinyl, optionally substituted with one, two or three $R^3$ groups, and $R^2$ is a 5-membered heteroaryl containing 1, 2 or 3 heteroatoms independently selected from O, N or S.

In one embodiment of this aspect of the invention, $X^1$ is CH, $R^1$ is thiazolyl, oxazolyl, pyrazolyl, imidazolyl, triazolyl, 1,2,4-thiadiazolyl, pyridinyl or pyrimidinyl, optionally substituted with one, two or three $R^3$ groups, and $R^2$ is a 5-membered heteroaryl containing 1, 2 or 3 heteroatoms independently selected from O, N or S.

In one embodiment of this aspect of the invention, $X^1$ is N, $R^1$ is thiazolyl, oxazolyl, pyrazolyl, imidazolyl, triazolyl, 1,2,4-thiadiazolyl, pyridinyl or pyrimidinyl, optionally substituted with one, two or three $R^3$ groups, and $R^2$ is —OCH$_3$.

In one embodiment of this aspect of the invention, $X^1$ is CH, $R^1$ thiazolyl, oxazolyl, pyrazolyl, imidazolyl, triazolyl, 1,2,4-thiadiazolyl, pyridinyl or pyrimidinyl, optionally substituted with one, two or three $R^3$ groups, and $R^2$ is —OCH$_3$.

In one embodiment of this aspect of the invention, $R^1$ is 5- or 6-membered heteroaryl containing 1, 2 or 3 heteroatoms independently selected from O, N and S, and optionally substituted with one, two or three $R^3$ groups and $R^2$ is —OCH$_3$.

In one embodiment of this aspect of the invention, $R^1$ is 5- or 6-membered heteroaryl containing 1, 2 or 3 heteroatoms independently selected from O, N and S, and optionally substituted with one, two or three $R^3$ groups and $R^2$ is a 5-membered heteroaryl containing 1, 2 or 3 heteroatoms independently selected from O, N and S.

In one embodiment of this aspect of the invention, $X^1$ is CH, and $R^1$ is 5- or 6-membered heteroaryl containing 1, 2 or 3 heteroatoms independently selected from O, N and S, and optionally substituted with one, two or three $R^3$ groups.

In one embodiment of this aspect of the invention, $X^1$ is N, and $R^1$ is 5- or 6-membered heteroaryl containing 1, 2 or 3 heteroatoms independently selected from O, N and S, and optionally substituted with one, two or three $R^3$ groups.

In one embodiment of this aspect of the invention, $X^1$ is N, $R^1$ is $C_6$-$C_{10}$ aryl optionally substituted with one, two or three $R^3$ groups, and $R^2$ is —OCH$_3$.

In one embodiment of this aspect of the invention, $X^1$ is CH, $R^1$ is $C_6$-$C_{10}$ aryl optionally substituted with one, two or three $R^3$ groups, and $R^2$ is —OCH$_3$.

In one embodiment of this aspect of the invention, $X^1$ is N, $R^1$ is phenyl optionally substituted with one, two or three $R^3$ groups, and $R^2$ is —OCH$_3$.

In one embodiment of this aspect of the invention, $X^1$ is CH, $R^1$ is phenyl optionally substituted with one, two or three $R^3$ groups, and $R^2$ is —OCH$_3$.

In one embodiment of this aspect of the invention, $X^1$ is N, $R^1$ is $C_6$-$C_{10}$ aryl optionally substituted with one, two or three $R^3$ groups, and $R^2$ is a 5-membered heteroaryl containing 1, 2 or 3 heteroatoms independently selected from O, N and S.

In one embodiment of this aspect of the invention, $X^1$ is CH, $R^1$ is $C_6$-$C_{10}$ aryl optionally substituted with one, two or three $R^3$ groups, and $R^2$ is a 5-membered heteroaryl containing 1, 2 or 3 heteroatoms independently selected from O, N and S.

In one embodiment of this aspect of the invention, $X^1$ is N, $R^1$ is phenyl optionally substituted with one, two or three $R^3$ groups, and $R^2$ is a 5-membered heteroaryl containing 1, 2 or 3 heteroatoms independently selected from O, N and S.

In one embodiment of this aspect of the invention, $X^1$ is CH, $R^1$ is phenyl optionally substituted with one, two or three $R^3$ groups, and $R^2$ is a 5-membered heteroaryl containing 1, 2 or 3 heteroatoms independently selected from O, N and S.

In one embodiment of this aspect of the invention, $R^1$ is selected from the group consisting of

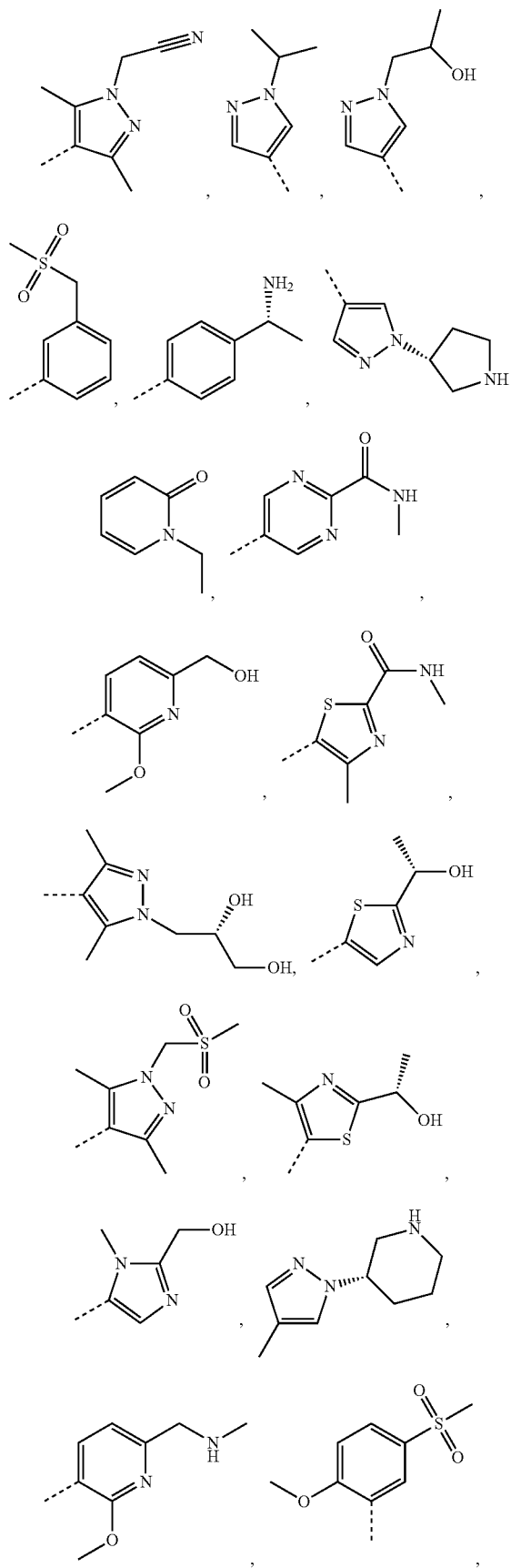
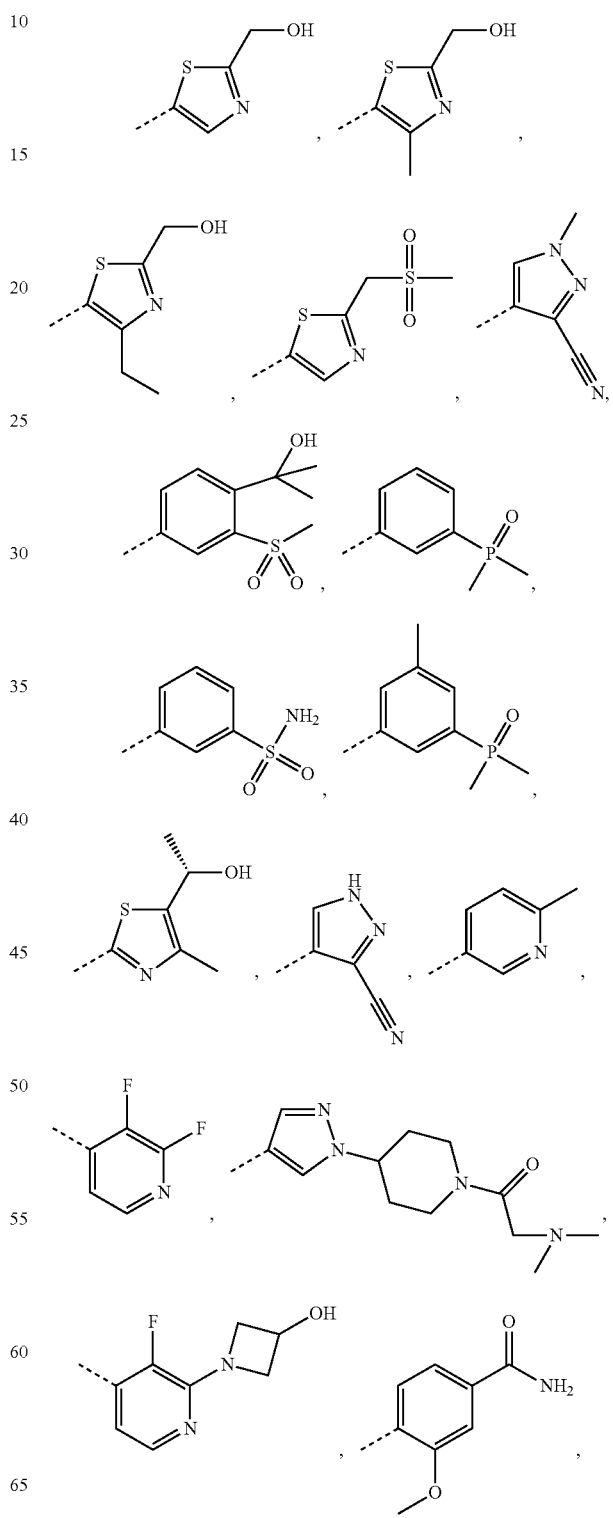

-continued

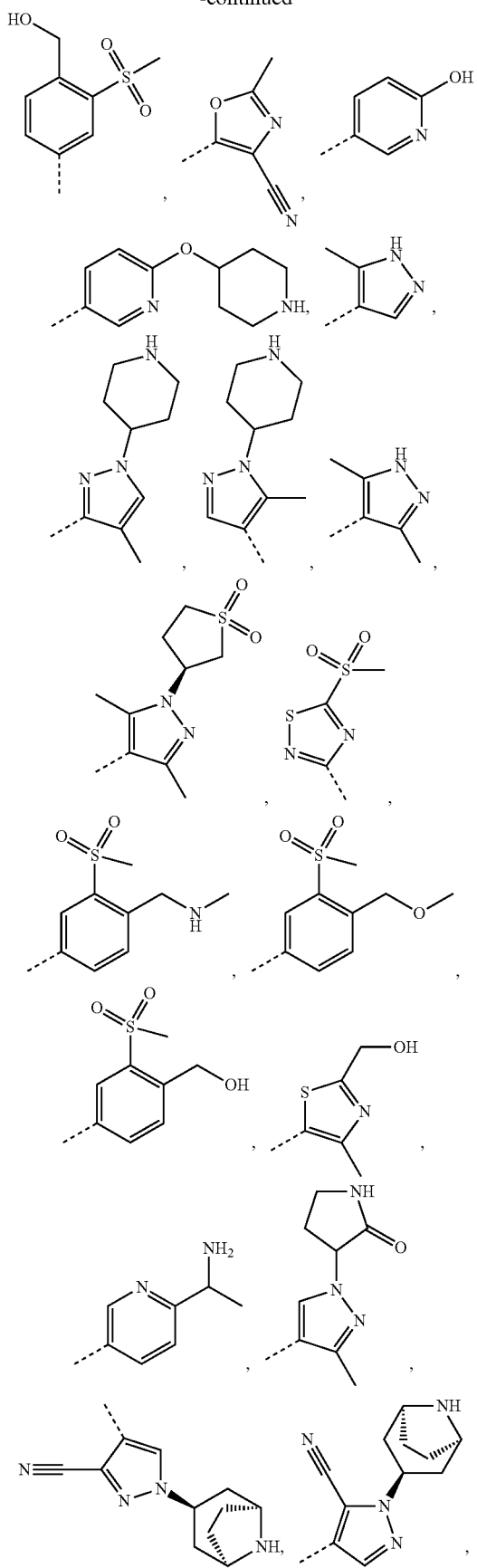

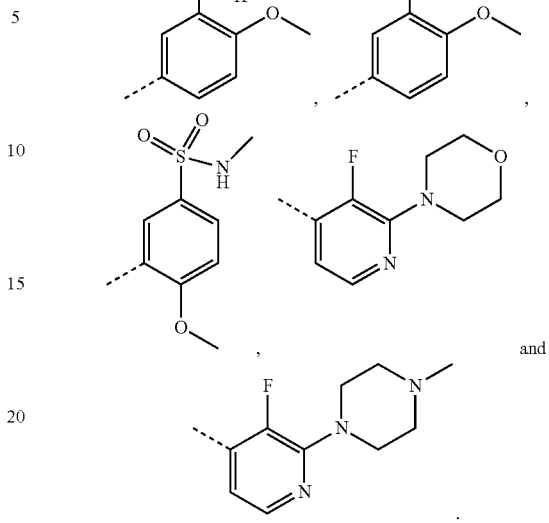

and

In one embodiment, the invention provides a compound selected from the group consisting of 2-[4-(6-amino-5-{(1R)-1-[5-fluoro-2-(2H-1,2,3-triazol-2-yl)phenyl]ethoxy}pyridin-3-yl)-2-(methylsulfonyl)phenyl]propan-2-ol; 5-{(1R)-1-[5-fluoro-2-(2H-1,2,3-triazol-2-yl)phenyl]ethoxy}-6'-(piperidin-4-yloxy)-3,3'-bipyridin-6-amine; 3-[4-(6-amino-5-{(1R)-1-[5-fluoro-2-(2H-1,2,3-triazol-2-yl)phenyl]ethoxy}pyridin-3-yl)-3,5-dimethyl-1H-pyrazol-1-yl]propane-1,2-diol; 5-{4-[(1R)-1-aminoethyl]phenyl}-3-{(1R)-1-[5-fluoro-2-(2H-1,2,3-triazol-2-yl)phenyl]ethoxy}pyridin-2-amine; 3-{(1R)-1-[5-fluoro-2-(2H-1,2,3-triazol-2-yl)phenyl]ethoxy}-5-[2-(4-methyl piperazin-1-yl)pyridin-4-yl]pyrazin-2-amine; 3-{(1R)-1-[5-fluoro-2-(2H-1,2,3-triazol-2-yl)phenyl]ethoxy}-5-[3-methyl-1-(piperidin-4-yl)-1H-pyrazol-4-yl]pyridin-2-amine; [4-(6-amino-5-{(1R)-1-[5-fluoro-2-(2H-1,2,3-triazol-2-yl)phenyl]ethoxy}pyridin-3-yl)-2-(methylsulfonyl)phenyl]methanol; 2-[5-(6-amino-5-{(1R)-1-[5-fluoro-2-(2H-1,2,3-triazol-2-yl)phenyl]ethoxy}pyridin-3-yl)-4-methyl-1,3-thiazol-2-yl]propan-2-ol; 3-{(1R)-1-[5-fluoro-2-(2H-1,2,3-triazol-2-yl)phenyl]ethoxy}-5-{2-[(methylsulfonyl)methyl]-1,3-thiazol-5-yl}pyridin-2-amine; 3-{(1R)-1-[5-fluoro-2-(2H-1,2,3-triazol-2-yl)phenyl]ethoxy}-5-[5-methyl-1-(piperidin-4-yl)-1H-pyrazol-4-yl]pyridin-2-amine; and 1-(6-amino-3'-fluoro-5-{(1R)-1-[5-fluoro-2-(2H-1,2,3-triazol-2-yl)phenyl]ethoxy}-3,4'-bipyridin-2'-yl)azetidin-3-ol; or a pharmaceutically acceptable salt thereof.

In one embodiment, the invention provides a pharmaceutical composition comprising an effective amount of a compound of the invention or a pharmaceutically acceptable salt thereof. In another embodiment, the pharmaceutical composition further comprises one or more pharmaceutically acceptable excipients.

In one embodiment, the invention provides a pharmaceutically acceptable salt thereof, for use as a medicament. In one embodiment, the invention provides a compound or a pharmaceutically acceptable salt thereof, for use in the treatment of abnormal cell growth in a mammal mediated by a EML4-ALK fusion protein having at least one mutation. In another embodiment, the mutation is L1196M. In another embodiment, the mutation is C1156Y.

In one embodiment, the invention provides a method of treating cancer in a mammal, comprising administering a compound of the invention or a pharmaceutically acceptable salt thereof, wherein said cancer is mediated by a EML4-ALK fusion protein having at least one mutation. In one embodiment, the mutation is L1196M. In one embodiment, the mutation is C1156Y.

In another embodiment, the abnormal cell growth is cancer. In another embodiment, the cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and combinations thereof. In another embodiment, the cancer is selected from the group consisting of non-small cell lung cancer (NSCLC), squamous cell carcinoma, hormone-refractory prostate cancer, papillary renal cell carcinoma, colorectal adenocarcinoma, neuroblastomas, anaplastic large cell lymphoma (ALCL) and gastric cancer.

In a further embodiment, the invention provides compounds of general formula (1):

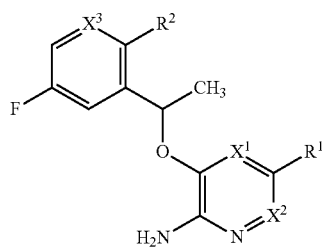

(1)

or a pharmaceutically acceptable salt or solvate thereof, wherein $R^1$ is a 5 or 6-membered heteroaryl containing 1, 2 or 3 heteroatoms independently selected from O, N or S and optionally substituted with one, two or three groups independently selected from $C_1$-$C_4$ alkyl, $C_2$-$C_4$ alkenyl, O—$C_1$-$C_4$ alkyl, halogen, amino, $SO_2CH_3$, oxo or hydroxy; wherein said $C_1$-$C_4$ alkyl and O—$C_1$-$C_4$ alkyl are optionally substituted with one or two hydroxy;

$X^1$ is N or CH and $X^2$ is N or CH, provided that when $X^2$ is N then $X^1$ is CH;

$X^3$ is N or CH; and, $R^2$ is $OCH_3$, F, Cl, Br, CN or a 5-membered heteroaryl containing 1, 2 or 3 heteroatoms independently selected from O, N or S; or, $X^3$ is N or C, and $R^2$ and $X^3$ form together with the carbon atom to which they are bound, a 5 or 6-membered heteroaryl containing 1, 2 or 3 heteroatoms independently selected from O, N or S. In a one embodiment, $X^1$ is N and $X^2$ is CH. In a one embodiment, $X^1$ is CH and $X^2$ is N. In a one embodiment, $X^1$ is CH and $X^2$ is CH.

In a preferred embodiment, $R^2$ is selected from $OCH_3$, F, Cl, Br and CN. In a preferred embodiment, $R^2$ is $OCH_3$. In one embodiment, $R^2$ is a 5-membered heteroaryl containing 1, 2 or 3 heteroatoms independently selected from O, N or S. In a preferred embodiment, $R^2$ is a 5-membered heteroaryl containing 1, 2 or 3 nitrogen atoms, preferably 2 or 3 nitrogen atoms. In a preferred embodiment, $R^2$ is selected from oxazolyl, pyrazolyl, imidazolyl or triazolyl. In a preferred embodiment, $R^2$ is selected from pyrazolyl, imidazolyl or triazolyl.

In one embodiment, $R^2$ and $X^3$ form, together with the carbon atom to which they are bound, a 5 or 6-membered heteroaryl containing 1, 2 or 3 heteroatoms independently selected from O, N or S. Preferably, at least one of the heteroatom is nitrogen. Preferably said 5 or 6-membered heteroaryl is a pyridine or a thiazole.

In one embodiment, $X^3$ is nitrogen. In a preferred embodiment, $X^3$ is nitrogen and $R^2$ is $OCH_3$. In one embodiment, $X^3$ is CH. In a preferred embodiment, $X^3$ is CH and $R^2$ is $OCH_3$.

In one embodiment, $R^1$ is 5-membered heteroaryl containing 1, 2 or 3 heteroatoms independently selected from O, N or S, preferably thiazolyl, oxazolyl, pyrazolyl, imidazolyl or triazolyl, and optionally substituted with one, two or three groups independently selected from $C_1$-$C_4$ alkyl, $C_2$-$C_4$ alkenyl, O—$C_1$-$C_4$ alkyl, halogen, amino, $SO_2CH_3$, oxo or hydroxy; wherein said $C_1$-$C_4$ alkyl and O—$C_1$-$C_4$ alkyl are optionally substituted with one or two hydroxy. In one embodiment, $R^1$ is pyrazolyl, imidazolyl or triazolyl, optionally substituted with one or two methyl.

In one embodiment, $R^1$ is 6-membered heteroaryl containing 1, 2 or 3 heteroatoms independently selected from O, N or S, preferably pyridyl, pyridazinyl or pyrimidinyl, and optionally substituted with one, two or three groups independently selected from $C_1$-$C_4$ alkyl, $C_2$-$C_4$ alkenyl, O—$C_1$-$C_4$ alkyl, halogen, amino, $SO_2CH_3$, oxo or hydroxy; wherein said $C_1$-$C_4$ alkyl and O—$C_1$-$C_4$ alkyl are optionally substituted with one or two hydroxy.

In one embodiment, the compound of formula (1) has the following configuration (S-isomer):

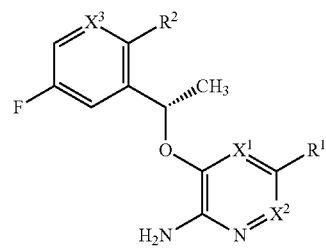

In a preferred embodiment, the compound of formula (1) has the following configuration (R-isomer):

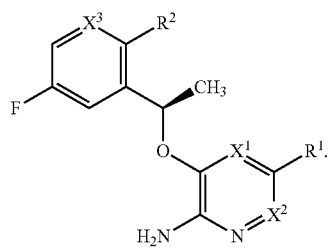

The compounds of formula (1) are ALK inhibitors that are particularly useful for the treatment of disorders in which ALK receptor or an ALK fusion protein is involved or in which inhibition of ALK activity may induce benefit. ALK fusion protein refers to a fusion protein comprising a portion of the ALK receptor comprising the ALK kinase domain and a portion of a different protein. Examples of such fusion proteins are EML4-ALK (Soda et Al, Nature, Vol. 448, 561-566) or NPM-ALK. Further examples such as TPM3-ALK, $TFG_{XL}$-ALK, $TFG_L$-ALK, TFGs-ALK, ATIC-ALK, CLTC-ALK, MSN-ALK, TPM4-ALK, MYH9-ALK, RANBP2-ALK, ALO17-ALK, and CARS-ALK are disclosed in the literature (see for example Pulford. K et al, Journal of Cellular Physiology, 199:330-358 (2004)).

DEFINITIONS

As used herein, "$C_1$-$C_4$ alkyl" denote a straight-chain or branched group containing 1, 2, 3 or 4 carbon atoms. As used herein, "$C_1$-$C_6$ alkyl" denote a straight-chain or branched group containing 1, 2, 3, 4, 5 or 6 carbon atoms. This also applies if they carry substituents or occur as substituents of other radicals, for example in O—($C_1$-$C_4$)alkyl radicals or O—($C_1$-$C_6$)alkyl radicals. Examples of suitable $C_1$-$C_6$ alkyl radicals are methyl, ethyl, n-propyl, iso-propyl, n-butyl, iso-butyl, sec-butyl, tert-buty, n-pentyl, sec-pentyl, neopentyl, n-hexyl, sec-hexyl, and the like. Examples of suitable O—($C_1$-$C_6$)alkyl radicals are methoxy, ethoxy, n-propyloxy, iso-propyloxy, n-butyloxy, iso-butyloxy, sec-butyloxy and tert-butyloxy, n-pentyloxy, neopentyloxy, hexyloxy, and the like.

Halo denotes a halogen atom selected from the group consisting of fluoro, chloro, bromo or iodo.

As used herein, "5- or 6-membered heteroaryl" refers to a monocyclic group of 5 or 6 ring atoms containing one, two or three ring heteroatoms selected from N, O, and S, the remaining ring atoms being C, and, in addition, having a completely conjugated pi-electron system. Substituents on adjacent ring atoms of a 5- or 6-membered heteroaryl may combine to form a fused 5- or 6-membered carbocyclic ring optionally substituted by one or more substituents, such as oxo, $C_1$-$C_6$ alkyl, hydroxyl, animo and halogen, or a fused 5- or 6-membered heterocyclic ring containing one, two or three ring heteroatoms selected from N, O and $S(O)_p$ (where p is 0, 1 or 2) optionally substituted by one or more substituents, such as oxo, $C_1$-$C_6$ alkyl, hydroxyl, animo and halogen. A pharmaceutically acceptable heteroaryl is one that is sufficiently stable to be attached to a compound of the invention, formulated into a pharmaceutical composition and subsequently administered to a patient in need thereof.

Examples of typical monocyclic heteroaryl groups include, but are not limited to:

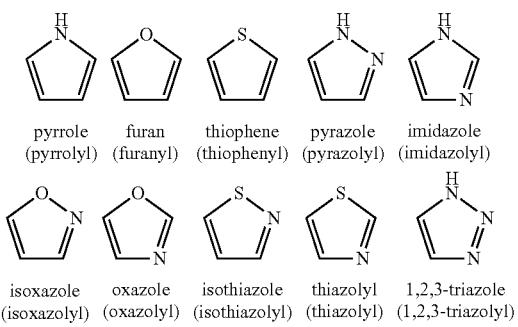

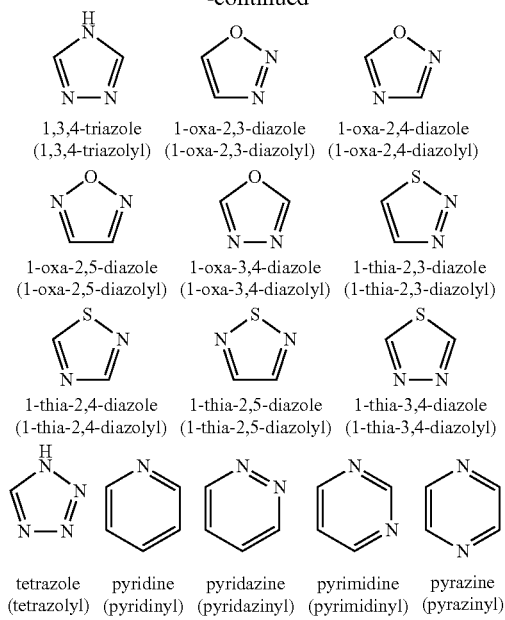

Examples of 6-membered heteroaryl groups having adjacent ring atoms that form a fused heterocyclic ring or a carbocyclic ring include, but are not limited to

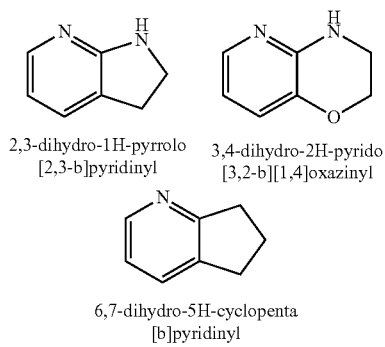

Preferred 5-membered heteroaryl containing 1, 2 or 3 heteroatoms independently selected from O, N and S comprise pyrrolyl, thienyl, furanyl, pyrazolyl, imidazolyl, oxazolyl, isoxazolyl, thiazolyl, isothiazolyl, triazolyl, oxadiazolyl and thiadiazolyl. Preferred 6-membered heteroaryl contain 1 or 2 nitrogen atoms. Examples of preferred 6-membered heteroaryl are pyridyl, pyridazinyl, pyrimidinyl and pyrazinyl.

As used herein, "4-6-membered heterocyclic" refers to a monocyclic group having 4 to 6 ring atoms, in which one or two ring atoms are heteroatoms selected from N, O and $S(O)_p$ (where p is 0, 1, 2) the remaining ring atoms being C. The ring may also have one or more double bonds. However, the ring does not have a completely conjugated pi-electron system. Substituents on two ring carbon atoms may combine to form a 5- or 6-membered bridged ring that is either carbocyclic or heterocyclic containing one, two or three ring heteroatoms selected from N, O and $S(O)_p$ (where p is 0, 1 or 2). The heterocyclic group is optionally substituted by oxo, hydroxyl, amino, $C_1C_6$-alkyl and the like. Examples of suitable partially unsaturated heteroalicyclic groups include, but are not limited to:

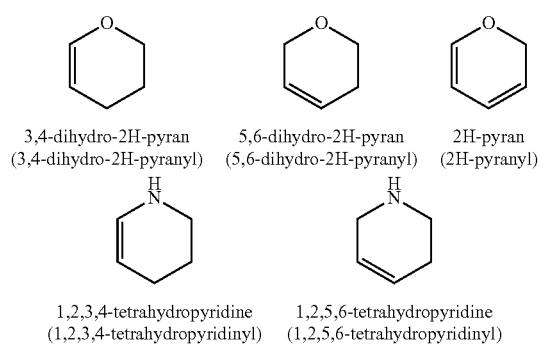

Examples of suitable saturated heteroalicyclic groups include, but are not limited to:

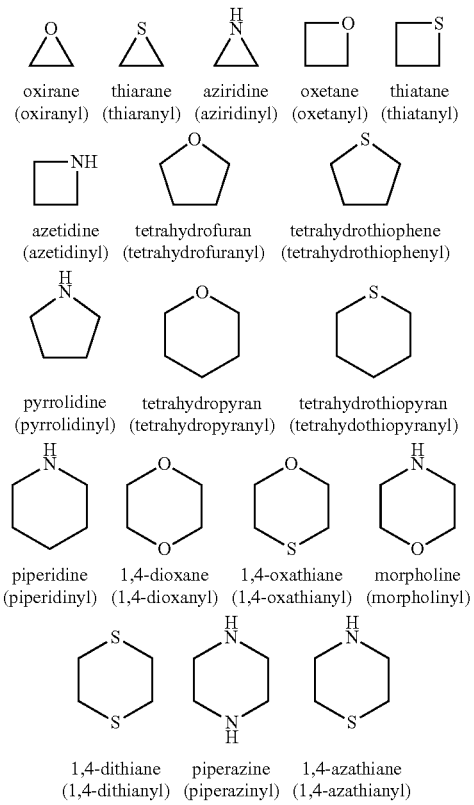

Examples of 4-6-membered heterocyclic rings having substituents on two ring carbon atoms that combine to form a 5-membered carbocyclic bridged ring include but are not limited to

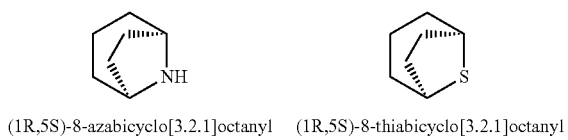 [SMILES: C1C[C@@H]2CC[C@H](C1)N2 ; C1C[C@@H]2CC[C@H](C1)S2]

As used herein, "$C_6$-$C_{10}$ aryl" refers to an all-carbon monocyclic or fused-ring polycyclic groups of 6 to 10 carbon atoms having a completely conjugated pi-electron system. Examples of aryl groups are phenyl and naphthalenyl. The aryl group may be substituted or unsubstituted. Substituents on adjacent ring carbon atoms of a $C_6$-$C_{10}$ aryl may combine to form a 5- or 6-membered carbocyclic ring optionally substituted by one or more substituents, such as oxo, $C_1$-$C_6$ alkyl, hydroxyl, animo and halogen, or a 5- or 6-membered heterocyclic ring containing one, two or three ring heteroatoms selected from N, O and $S(O)_p$ (where p is 0, 1 or 2) optionally substituted by one or more substituents, such as oxo, $C_1$-$C_6$ alkyl, hydroxyl, amino and halogen. Examples of $C_6$-$C_{10}$ aryl having two ring carbon atoms that form a fused heterocyclic or carbocyclic ring include but are not limited to

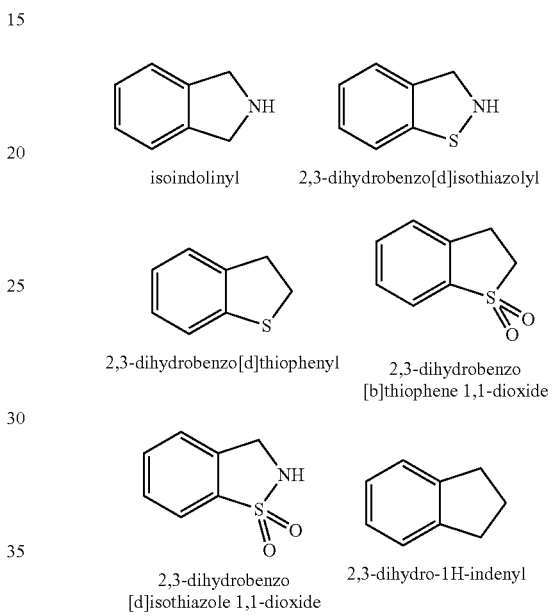

As used herein, the symbol "⁓" and "⁄" when used in connection with structural formulas of the compounds of the invention denote points of attachment of the substituents or moieties to which they are attached to the compounds of the invention.

DETAILED DESCRIPTION OF THE INVENTION

The following schemes illustrate the preparation of compounds of the invention throughout which groups $R^1$, $R^2$ and $X^1$, $X^2$ and $X^3$ are as defined above unless otherwise stated.

Scheme 1.1

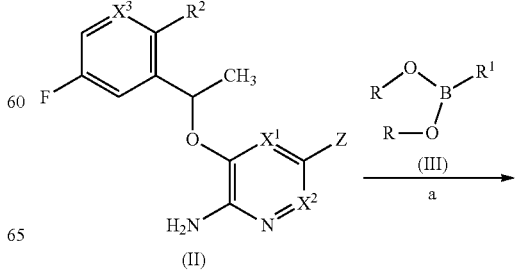

-continued

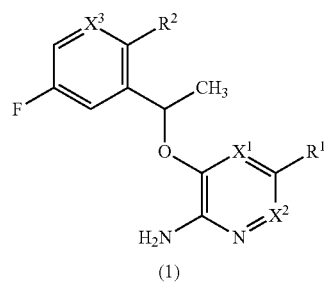

(1)

Z represents halo (typically I, Br or Cl).

R represents an alkyl group (typically Me, Et or iPr) or the two R groups are joined to form a cycle (typically pinacol) or H.

Compounds suitable for use as compound (III) are commercially available, are known in the literature or can be prepared as outlined in scheme 7.1.

Step (a):

Halide (II) is reacted with a boronic heteroaryl (III) to give the compound of the invention. Typically the reaction is carried out by a palladium catalysed cross-coupling reaction using a suitable additive such as cesium fluoride or sodium hydrogen carbonate, a suitable palladium catalyst such as tetrakis(triphenylphosphine)palladium(0) or 1,1'-bis(diphenylphosphino)ferrocene palladium dichloride, heating the starting materials to elevated temperatures, such as 60° C.-140° C., for 1 to 48 hours, under an inert atmosphere, using a solvent such as 1,4-dioxane, dimethyl acetamide or dimethyl ethylene glycol, optionally with the addition of water.

Preferred conditions are:

Halide (II) and boronic heteroaryl (III), with catalytic tetrakis(triphenylphosphine)palladium(0) and sodium hydrogen carbonate in aqueous 1,4-dioxane at 120° C. for 16 hrs, or, halide (II) and boronic heteroaryl (III), with catalytic 1,1'-bis(diphenylphosphino)ferrocene palladium dichloride and cesium fluoride in anhydrous dimethyl ethylene glycol at 100° C. for 16 hrs.

Alternatively, when $R^2$ is Br and $X^1$, $X^2$ and $X^3$ are CH, compounds (1) can be prepared as outlined in scheme 1.2.

-continued

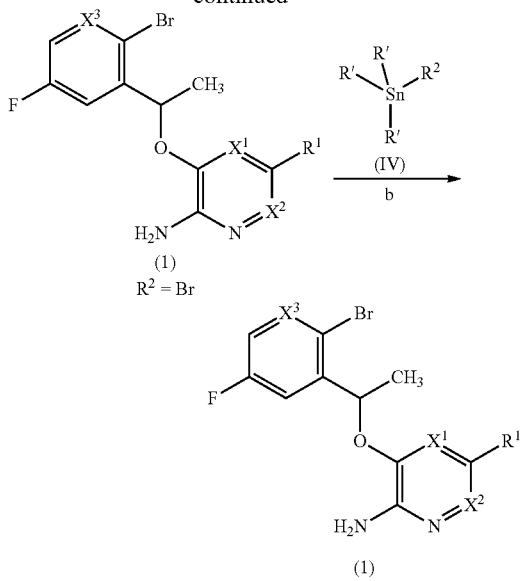

R' represents an alkyl group (typically nBu).

Compounds suitable for use as compound (IV) are commercially available or are known in the literature.

Step (b):

Bromide (1) where $R^2$ is Br is reacted with a stannic heteroaryl (IV) to give the compound of the invention. Typically the reaction is carried out by a palladium catalysed cross-coupling reaction using a suitable additive such as cesium fluoride, a suitable palladium catalyst such as tetrakis(triphenylphosphine)palladium(0) or 1,1'-bis(diphenylphosphino)ferrocene palladium dichloride, heating the starting materials to elevated temperatures, such as 80° C.-140° C., for 1 to 48 hours, under an inert atmosphere, using a solvent such as 1,4-dioxane, toluene or dimethyl ethylene glycol, optionally with the addition of water.

Preferred conditions are:

Halide (II) and stannic heteroaryl (IV), with catalytic tetrakis(triphenylphosphine)palladium(0) and sodium hydrogen carbonate in aqueous 1,4-dioxane at 120° C. for 16 hrs, or, halide (II) and stannic heteroaryl (IV), with catalytic 1,1'-bis(diphenylphosphino)ferrocene palladium dichloride and cesium fluoride in anhydrous dimethyl ethylene glycol at 100° C. for 16 hrs.

Alternatively, compound (1) can be prepared as outlined in scheme 1.3.

Scheme 1.2

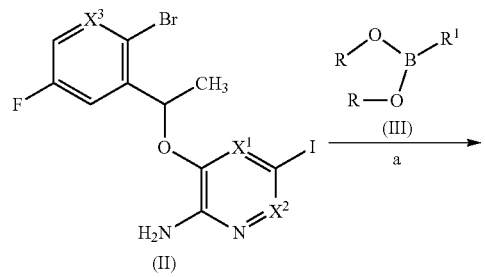

Scheme 1.3

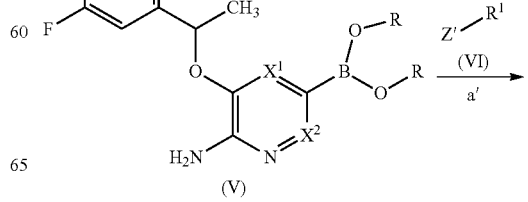

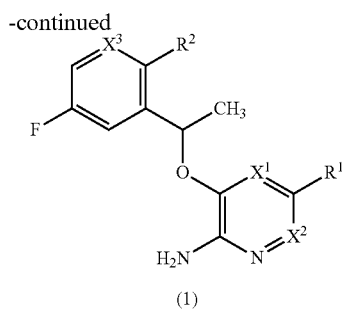

Z' represent halo (typically I, Br or Cl).

R represents an alkyl group (typically Me, Et or iPr) or the two R groups are joined to form a cycle (typically pinacol).

Compounds suitable for use as compound (V) can be prepared as outlined in scheme 1.4.

Compounds suitable for use as compound (VI) are commercially available, are known in the literature or can be prepared as outlined in Schemes 8.1, 8.2 and 8.3.

Step (a'):

Same as step (a) except that the coupling partners are reversed.

Alternatively, compound (1) can be prepared as outlined in scheme 1.4.

Compounds suitable for use as compound (VII) are commercially available or are known in the literature.

Step (c):

Halide (II) is reacted with a diboron ester (VII) (typically bis(pinacolato)diboron) to give the intermediate compound of formula (V). Typically the reaction is carried out by a palladium catalysed cross-coupling reaction using a suitable base such as potassium acetate, a suitable palladium catalyst such as 1,1'-bis(diphenylphosphino)ferrocene palladium dichloride, under an inert atmosphere, heating the starting materials to elevated temperatures, such as 80° C.-140° C., optionally using microwave heating, for 1 to 48 hours, under an inert atmosphere, using a solvent such as 1,4-dioxane or dimethyl sulphoxide.

Preferred conditions are:

Halide (II) and bis(pinacolato)diboron (VII), with catalytic (0.02 eq.) 1,1'-bis(diphenylphosphino)ferrocene palladium dichloride and potassium acetate in dimethyl sulphoxide at 80° C. 16 hr.

Alternatively, compounds (1) where $R^1$ is 2-(pyridin-2-yloxy)-ethanol can be prepared as outlined in scheme 1.5.

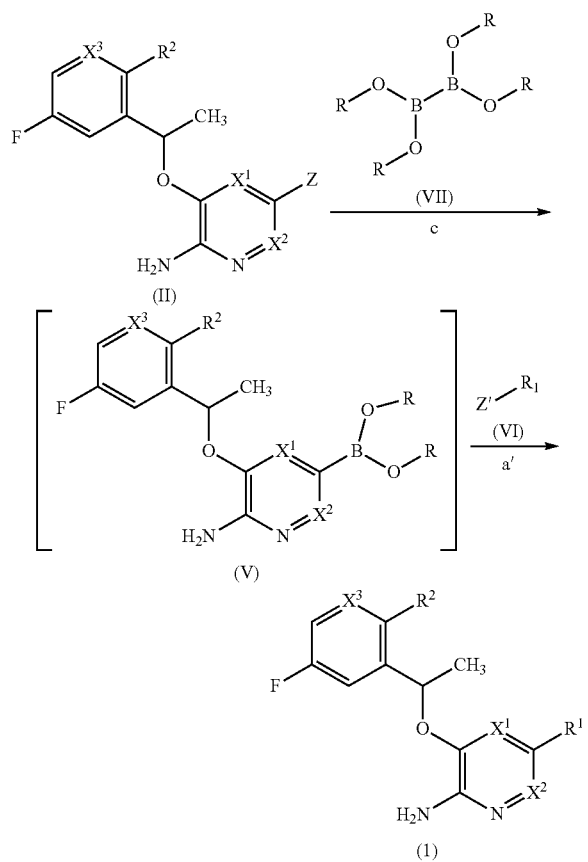

Scheme 1.4

Z and Z' represent halo (typically I, Br or Cl).

R represents an alkyl group (typically Me, Et or iPr) or the two R groups are joined to form a cycle (typically pinacol).

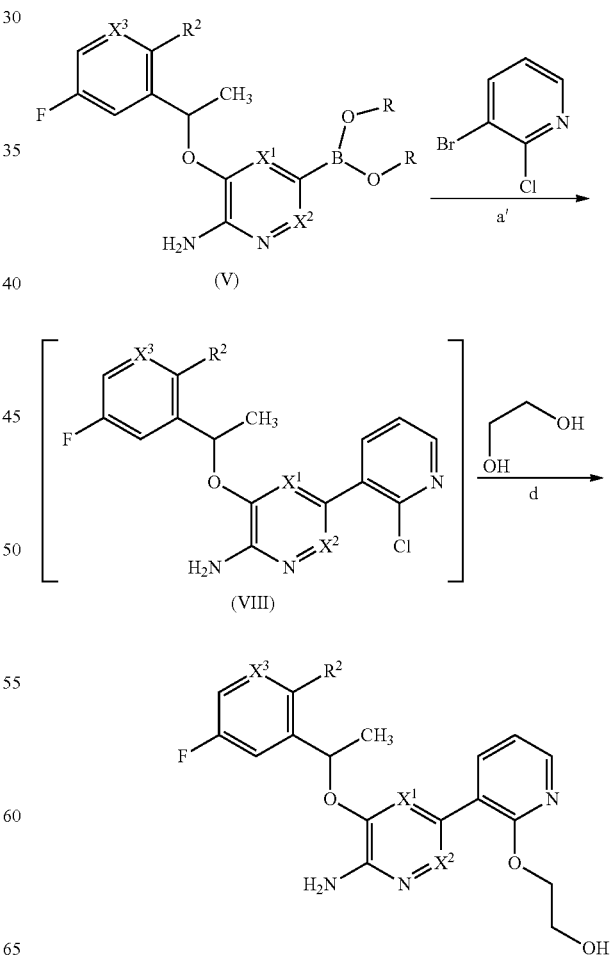

Scheme 1.5

R represents an alkyl group (typically Me, Et or iPr) or the two R groups are joined to form a cycle (typically pinacol).

Step (d):

Chloro pyridine (VIII) is reacted with excess ethylene glycol to give the compound of the invention where $R^1$ is 2-(pyridin-2-yloxy)-ethanol. Typically the reaction is carried out by heating chloro pyridine (VIII) with ethylene glycol and a strong base such as potassium hydroxide to elevated temperatures, such as 60° C.-140° C., for 1 to 72 hours, under an inert atmosphere, optionally in a solvent such as dimethyl sulphoxide.

Preferred conditions are:

Chloro pyridine (VIII), ethylene glycol (10 eq.) with potassium hydroxide in dimethyl sulphoxide at 60° C. for 72 hrs.

Alternatively, compounds (1) where $R^1$ is (1-methyl-1H-pyrazol-4-yl)-methanol can be prepared as outlined in scheme 1.6.

R represents an alkyl group (typically Me, Et or iPr) or the two R groups are joined to form a cycle (typically pinacol).

Step (e):

Aldehyde (IX) is reacted with a reducing agent such as sodium borohydride to give the compound of the invention where $R^1$ is (1-methyl-1H-pyrazol-4-yl)-methanol. Typically the reaction is carried out by stirring a alcoholic solution of aldehyde (IX) with sodium borohydride at room temperature for 1 to 24 hours, under an inert atmosphere, optionally in a co-solvent such as tetrahydrofuran or 1,4-dioxane.

Preferred conditions are:

Aldehyde (IX), in methanol and tetrahydrofuran with sodium borohydride at room temperature for 18 hrs.

Alternatively, when $X^1$ and $X^2$ are CH, compounds (1) can be prepared as outlined in scheme 1.7.

Scheme 1.6

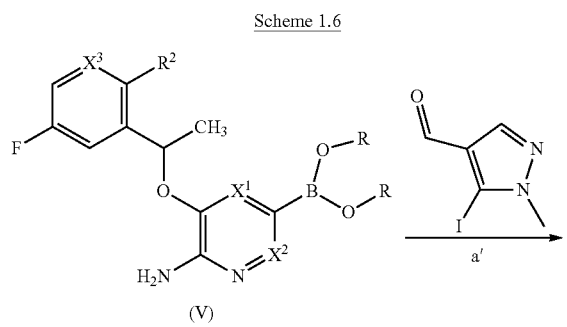

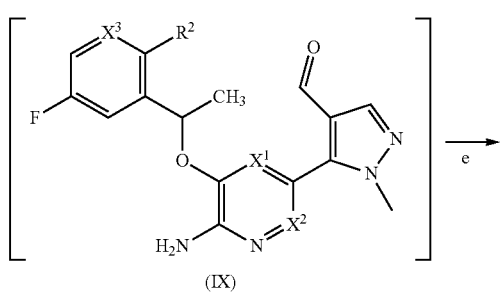

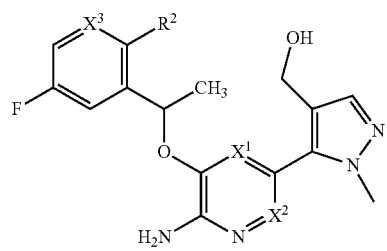

Scheme 1.7

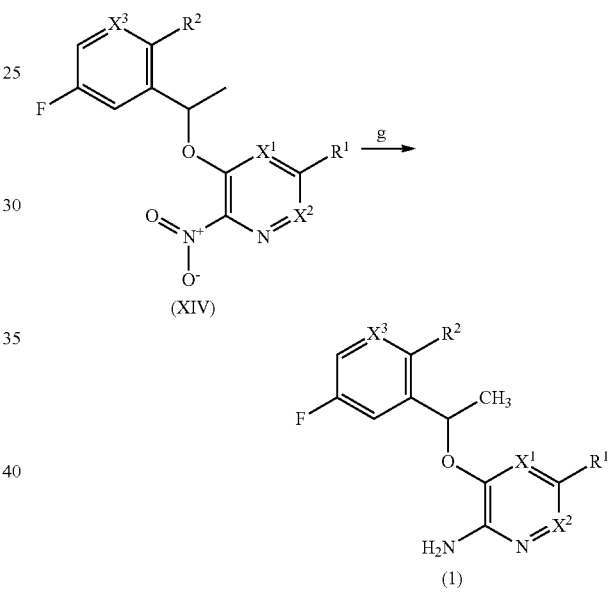

Compounds (XIV) can be prepared as outlined in scheme 3.1.

Step (g):

Nitro pyridine (XIV) is reduced in the presence of a suitable reducing agent give the compound of the invention. Typically the reaction is carried out by heating, typically 40° C. to 70° C., the nitro pyridine (XIV) in a suitable solvent like acetic acid, tetrahydrofuran, ethanol, dioxane or toluene for 1 to 24 hours in the presence of a reducing agent, typically iron, tin tetrachloride, sodium dithionite under an inert atmosphere or using raney Nickel in the presence of hydrogen.

Preferred conditions are:

Nitro pyridine (XIV), in acetic acid and 1,4-dioxane with iron powder at 40° C. for 1 hr, or, nitro pyridine (XIV), in ethanol with raney nickel at 40° C. under an atmosphere of hydrogen for 1 hr.

When $X^1$ and $X^2$ are CH, compounds suitable for use as compounds (II) can be prepared as outlined in scheme 2.1.

Scheme 2.1

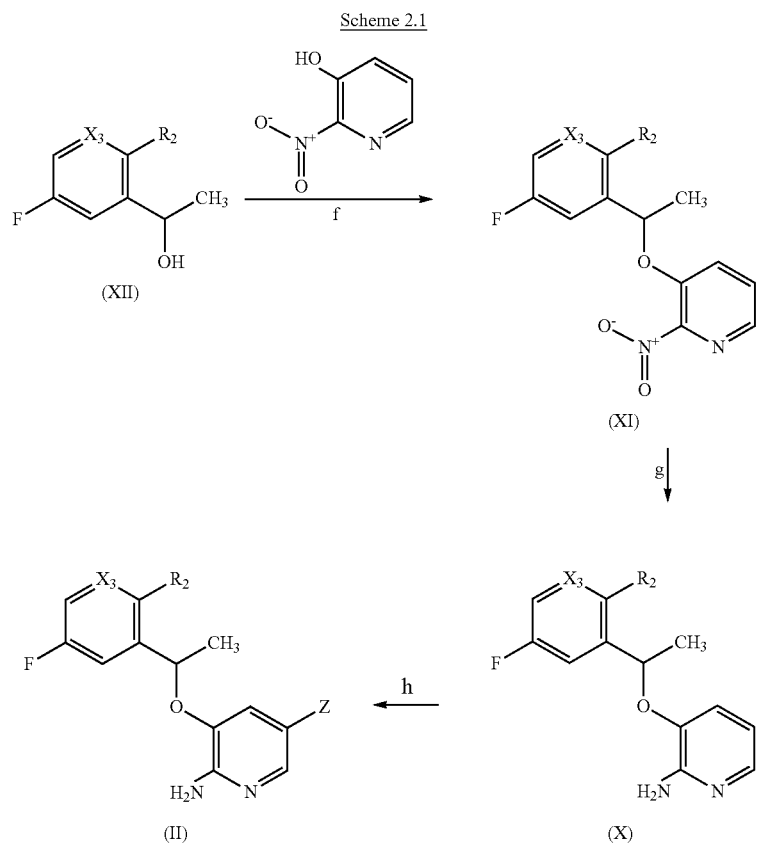

Compounds suitable for use as alcohols (XII) are commercially available, known in the literature or can be prepared as described in scheme 4.1.

Step (f):

Alcohol (XII) is reacted with 2-nitro-3-hydroxy pyridine to give the compound of formula (XI). Typically the reaction is carried out by adding alcohol (XII) to a solution of diazodicarboxylate ester, 2-nitro-3-hydroxy pyridine and triphenylphosphine in a suitable solvent like tetrahydrofuran or toluene at 0° C. to room temperature for 1 to 24 hours, under an inert atmosphere.
Preferred conditions are:

Alcohol (XII), in toluene with diisopropyl azodicarboxylate, 2-nitro-3-hydroxy pyridine and triphenyl phosphine at 10° C. to room temperature for 5 hrs.

Step (g):
Same conditions as previously disclosed.

Step (h):
Amino pyridine (X) is reacted with a halogenating reagent to give the compound of formula (II). Typically the reaction is carried out by adding a halogenating agent, typically N-bromosuccinamide, to a solution of amino pyridine (X) in a suitable solvent like acetonitrile or acetic acid at 0° C. to room temperature for 1 to 24 hours, under an inert atmosphere.
Preferred conditions are:

Amino pyridine (X), in acetonitrile with N-bromosuccinamide at 10° C. to room temperature for 1 hr, or, amino pyridine (X), in acetonitrile with N-iodoosuccinamide at 10° C. to room temperature for 1 hr.

Alternatively, when $X^1$ and $X^2$ are CH, compounds suitable for use as compounds (II) can be prepared as outlined in scheme 2.2

Scheme 2.2

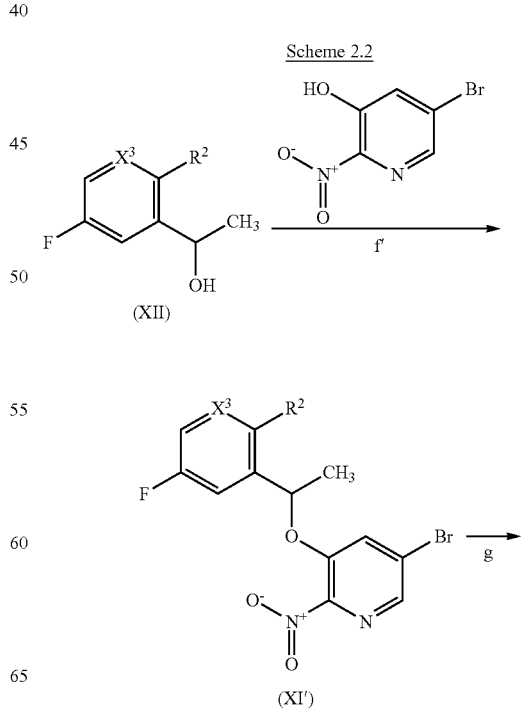

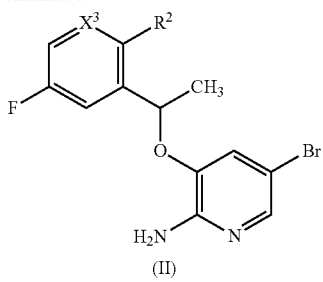

Step (f'):

Same conditions as step (f) except that 2-nitro-3-hydroxy-5-bromo-pyridine is used instead of 2-nitro-3-hydroxy pyridine.

Alternatively, when $X^1$ and $X^2$ are CH and Z is Br, compounds (II) can be prepared as outlined in scheme 2.3.

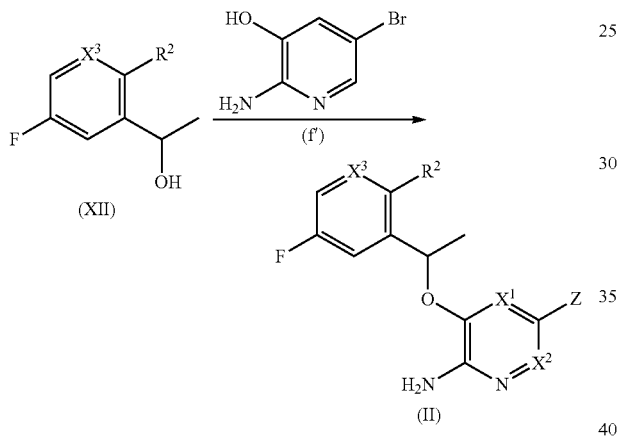

Alternatively, when $X^1$ and $X^2$ are CH and Z is Br compounds (II) can be prepared as outlined in scheme 2.4

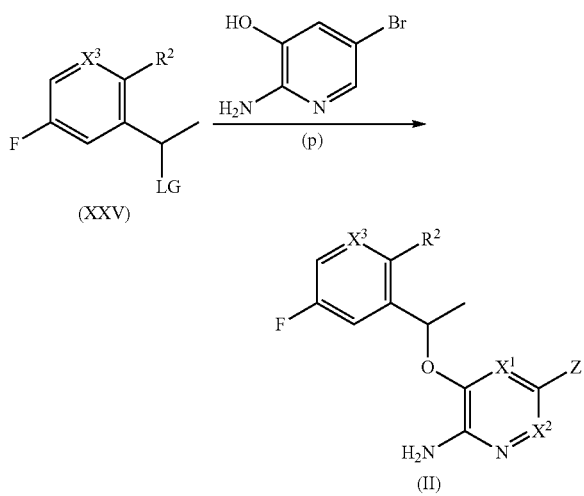

LG is a leaving group (typically bromo, chloro or OMs)

Compounds suitable for use as (XXV) are known in the literature, commercially available or can be prepared as outlined in scheme 6.1.

Step (p):

Compound (XXV) is reacted with a phenolic residue, for example 2-amino-3-hydroxy-bromo-pyridine to give the compound of formula (II). Typically the reaction is carried out by adding compound (XXV) to a solution of 2-amino-3-hydroxy-bromo-pyridine and base, typically cesium carbonate or potassium carbonate in a solvent like tetrahydrofuran, DMF or acetone at room temperature to elevated temperature for 1 to 24 hours, under an inert atmosphere.

Preferred conditions are:

Compound (XXV), in actone with cesium carbonate and 2-amino-3-hydroxy-5-bromo-pyridine at 50° C. for 18 hrs.

Alternatively, when $X^1$ or $X^2$ are N, compounds (II) can be prepared as outlined in scheme 2.5.

When $X^1$ is N, Z is Cl and when $X^2$ is N, Z is Br.

Compounds suitable for use as compounds (XVII) are either commercially available or known in the literature.

Step (i):

Alcohol (XII) is reacted with a bromide (XVII) to give the compound of formula (II). Typically the reaction is carried out by adding a strong base, typically sodium hydride or sodium hexamethyl disilazide, to a solution the alcohol (XII) and then adding the bromide (XVII) in a suitable solvent like tetrahydrofuran or toluene and heating at elevated temperature for 1 to 24 hours, under an inert atmosphere.

Preferred conditions are:

Alcohol (XII), in tetrahydrofuran with sodium hexamethyl disilazide and heating to 60° C. with bromide (XVII) for 4 hr, under an atmosphere of nitrogen.

When $X^1$ and $X^2$ are CH, compounds suitable for use as (XIV) can be obtained as outlined in scheme 3.1.

Scheme 3.1

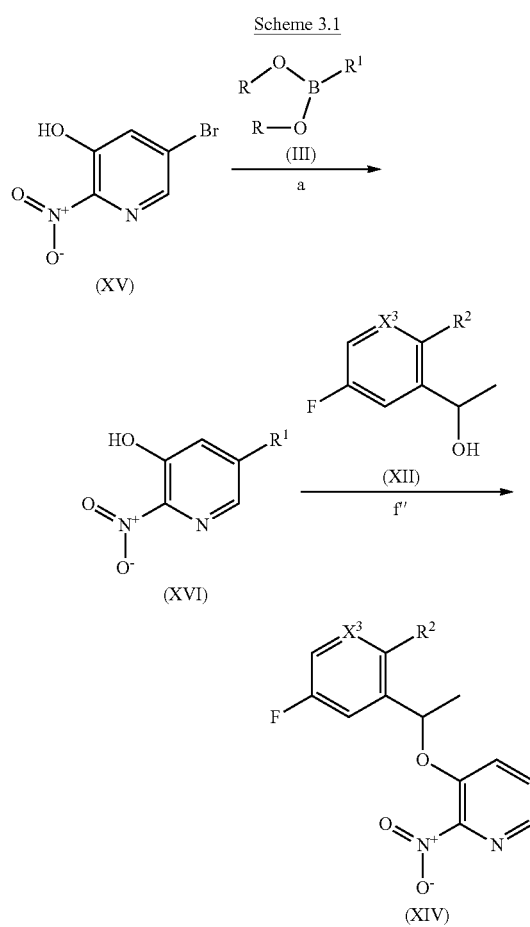

R represents an alkyl group (typically Me, Et or iPr) or the two R groups are joined to form a cycle (typically pinacol).

Compound (XV) is commercially available.

Compounds suitable for use as compound (III) are commercially available, are known in the literature or can be prepared as outlined in scheme 7.1.

Step (a):
Same conditions as previously disclosed.

Step (f″):
Same conditions as step (f) except that 3-hydroxy-pyridine is used instead of 2-nitro-3-hydroxy pyridine.

Compounds suitable for use as alcohols (XII) can be prepared as outlined in scheme 4.1

Scheme 4.1

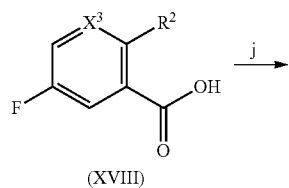

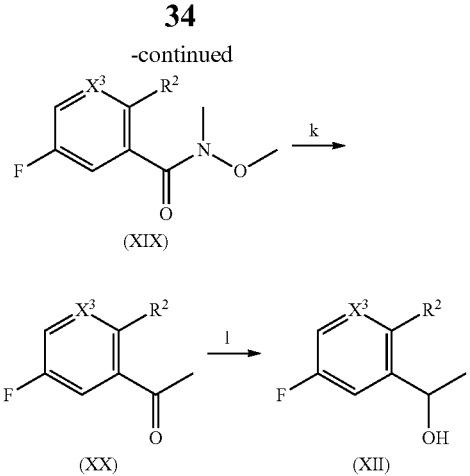

Suitable compounds for use as (XVIII) are commercially available or are known in the literature.

Step (j):

Acid (XVIII) is reacted with O, N-Dimethyl-hydroxylamine to form the Weinreb amide (XIX). Typically the acid (XVIII) is activated by reaction with amide coupling reagent, typically HATU, thionyl chloride, oxalyl chloride or CDI, the activated acid is then treated with O,N-Dimethyl-hydroxylamine in the presence of a base, typically triethyl amine or Hunig's base, at room temperature for 1 to 72 hr, in a suitable solvent like tetrahydrofuran or 1,4-dioxane.

Preferred conditions are,

Acid (XVIII) in tetrahydrofuran with CDI followed by O, N-Dimethyl-hydroxylamine and Hunig's base at room temperature for 72 hrs.

Step (k):

Weinreb Amide (XIX) is reacted with a methyl organometallic to form the methyl ketone (XX). Typically the amide (XIX) is reacted with methyl Grignard or methyl lithium at low temperature, in a suitable solvent, typically tetrahydrofuran, under an inert atmosphere, for 1 to 5 hrs.

Preferred conditions are,

Amide (XIX), in tetrahydrofuran at −78° C., with methyl magnesium chloride for 3 hr.

Step (l):

Methyl ketone (XX) is reduced to form the methyl alcohol (XII). Typically the ketone (XX) is reacted with a suitable reducing agent, typically sodium borohydride, (−)-Dip Chloride® or borane, at low temperature to elevated temperature, typically −30° C. to +50° C., in a suitable solvent, typically tetrahydrofuran, under an inert atmosphere, for 1 to 24 hrs.

Preferred conditions are,

Ketone (XX), in tetrahydrofuran at −30° C. to room temperature, with (−)-Dip Chloride® for 5 hr, or, Ketone (XX), in tetrahydrofuran and methanol at room temperature, with sodium borohydride for 1 hr.

Compounds suitable for use as ketone (XX) are commercially available or known in the literature or can be prepared as outlined in scheme 5.1.

Scheme 5.1

(XXI) → (XX)

Z is halo (typically bromo or iodo).

Compounds suitable for use as halo aryl (XXI) are commercially available or known in the literature.

Step (m):

Halo aryl (XXI) is coupled to an alkyl ether under palladium catalysis to give the ketone (XX). Typically the Halo aryl (XXI) is reacted with an alkyl vinyl ether, typically butyl vinyl ether, with catalytic palladium (II), typically palladium acetate, and a ligand with a base, typically triethylamine, and the starting materials are heated to elevated temperature for 1 to 72 hr in a solvent, typically acetonitrile, toluene or dimethyl formamide.

Preferred conditions are,

Halo aryl (XXI) with butyl vinyl ether, palladium acetate, 1,3-bis(diphenylphosphino)propane, triethylamine in acteonitrile at 90° C. for 18 hr.

Alternatively, methyl ketone (XX) can be prepared as outlined in scheme 5.2,

Scheme 5.2

(XX') + (XXIV) → (XX)

Z is a halo (typically iodo bromo or fluoro).

$X^4$ and $X^5$ are independently selected from CH or N.

Suitable compounds for use as (XX') and (XXIV) are either commercially available or known in the literature.

Step (o):

Halo methyl ketone (XX') is reacted with a 1H-azole (XXIV) to give the ketone (XX). Typically the fluoro aryl (XX') is reacted with an alkyl 1H-azole (XXIV), with a base such as potassium carbonate, cesium carbonate, potassium butoxide or sodium hydride and the starting materials are heated to elevated temperature, typically 120° C. to 160° C. for 1 to 24 hr, optionally in a solvent like NMP or dimethyl formamide, Alternatively, typically the iodo aryl (XX') is reacted with an alkyl 1H-azole (XXIV), with a base such as potassium carbonate, cesium carbonate, and a copper (I) catalyst, typically Copper (I) iodide. The starting materials are heated to elevated temperature, typically 120° C. to 150° C. for 1 to 24 hr, optionally in a solvent like NMP or dimethyl formamide.

Preferred conditions are,

Fluoro aryl (XX') and 1H-azole (XXIV) with potassium carbonate at 140° C., NMP for 3 hr, or, Iodo aryl (XX') and 1H-azole (XXIV) with cesium carbonate and catalytic CuI at 140° C., NMP for 3 hr.

Compounds suitable for use as compounds (XXV) are known in the literature, commercially available or can be prepared as outlined in scheme 6.1.

Scheme 6.1

(XXVI) → (XXV)

LG is Cl or Br

Compounds suitable for use as (XXVI) are known in the literature or are commercially available.

Step (q):

Ethyl aryl (XXVI) is reacted with a radical halogenating reagent to give compound (XXV). Typically the ethyl aryl (XXVI) is reacted with N-halosuccinamide with a radical initiator, and the reaction is heated to elevated temperature, typically 80° C. to 100° C. for 1 to 24 hr, under an inert atmosphere, in a solvent like carbon tetrachloride or trifluoromethyl benzene.

Preferred conditions are,

Ethyl aryl (XXVI) and N-bromosuccinamide in trifluoromethyl benzene with catalytic azobisisobutyronitrile at 100° C. for 18 hr.

Compounds suitable for use as compounds (III) are known in the literature, commercially available or can be prepared as outlined in scheme 7.1.

Scheme 7.1

(XXVII) → (III)

LG is a leaving group (typical halo or OMs).

Compounds suitable for use as (XXVII) are known in the literature or are commercially available.

Step (s):

Compound (XXVII) is reacted with a 3,5-dimethyl-4-(4,4,5,5-tetramethyl-1,3,2-dioxaborolan-2-yl)-1H-pyrazole to give boronic heteroaryl (III). Typically the compound (XXVII) is reacted with 3,5-dimethyl-4-(4,4,5,5-tetramethyl-1,3,2-dioxaborolan-2-yl)-1H-pyrazole with a base, typically potassium carbonate and the reaction is heated to elevated temperature, typically 60° C. to 100° C. for 1 to 24 hr, under an inert atmosphere, in a solvent like acetonitrile, optionally in the presence of an iodide source.

Preferred conditions are,

Compound (XXVII) and 3,5-dimethyl-4-(4,4,5,5-tetramethyl-1,3,2-dioxaborolan-2-yl)-1H-pyrazole in acetonitrile with potassium carbonate and sodium iodide at 80° C. for 5 hr.

Compounds suitable for use as compounds (VI) are known in the literature, commercially available or can be prepared as outlined in scheme 8.1.

Scheme 8.1

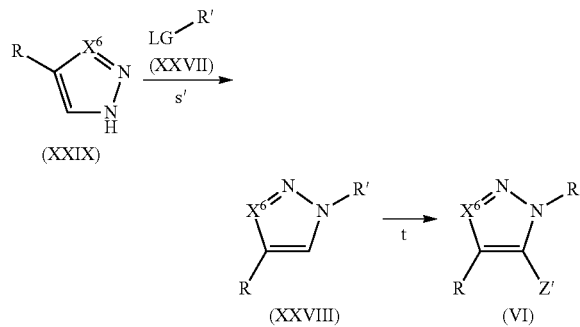

LG is a leaving group (typical halo or OMs), $X^6$ is N or CH, R is OMe, Me, CHO, F or H, R' is $C_1$-$C_4$ alkyl or hydroxy ethyl, and Z' is a halogen typically iodo or bromo Compounds suitable for use as (XXVII) and (XXIX) are known in the literature or are commercially available.

Step (s'):

Compound (XXVII) is reacted with an azole (XXIX) to give compound (XXVIII). Typically the compound (XXVII) is reacted with azole (XXIX) with a base, typically potassium carbonate and the reaction is heated to elevated temperature, typically 60° C. to 100° C. for 1 to 24 hr, under an inert atmosphere, in a solvent like acetonitrile, optionally in the presence of an iodide source.

Preferred conditions are,

Compound (XXVII) and azole (XXIX) in acetonitrile with potassium carbonate and sodium iodide at 80° C. for 5 hr.

Step (t):

Compound (XXVIII) is deprotonated and reacted with a halogenating reagent to give halo heteroaryl (VI). Typically the compound (XXVIII) is reacted with an organolithium at low temperature, typically −78° C. for 1 to 3 hr, then anion formed is quenched with a halogenating reagent, typically iodine, under an inert atmosphere, in a solvent like tetrahydrofuran or diethyl ether.

Preferred conditions are,

Compound (XXVIII) and n-Butyl lithium in tetrahydrofuran at −78° C. for 30 mins then quenched with iodine.

Alternatively, compounds (VI) can be prepared by the method outlined by scheme 8.2.

Scheme 8.2

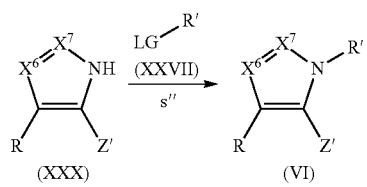

$X^6$ and $X^7$ are independently selected from CH or N, R' is alkyl or hydroxy ethyl, Z' is a halo (typically iodo, bromo or chloro), and LG is a leaving group.

Suitable compounds for use as Compounds (XXVII) and (XXX) are known in the literature or commercially available.

Step (s"):

Compound (XXVII) is reacted with an azole (XXX) to give halo heteroaryl (VI). Typically the compound (XXVII) is reacted with azole (XXX) with a base, typically potassium carbonate and the reaction is heated to elevated temperature, typically 60° C. to 100° C. for 1 to 24 hr, under an inert atmosphere, in a solvent like acetonitrile, optionally in the presence of an iodide source.

Preferred conditions are,

Compound (XXVII) and azole (XXX) in acetonitrile with potassium carbonate and sodium iodide at 80° C. for 5 hr.

Alternatively, compounds (VI) can be prepared by the method outlined by scheme 8.3.

Scheme 8.3

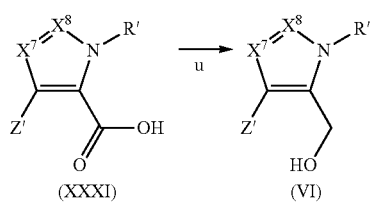

$X^7$ and $X^8$ are independently selected from CH or N; R' is alkyl or hydroxy ethyl; and, Z' is a halo, typically iodo, bromo or chloro.

Suitable compounds for use as halo acid (XXXI) are known in the literature or commercially available.

Step (u):

The acid (XXXI) is activated and reduced to the alcohol (VI). Typically the acid (XXXI) is activated with thionyl chloride, CDI or amide coupling agent then the intermediate active ester is treated with a reducing agent, typically sodium borohydride, in a solvent like methanol at room temperature for 1 to 18 hr, optionally with a co solvent like tetrahydrofuran.

Alternatively the acid is esterified typically using acid catalysis in methanol, but not exclusively. Then the ester intermediate is reduced with lithium borohydride in methanol, at room temperature, optionally with a co solvent.

Preferred conditions are,

The acid (XXXI) in tetrahydrofuran with CDI for 2 hr at room temperature followed by sodium borohydride in methanol for 3 hr at room temperature. Or, the acid (XXXI) is esterified using methanol and catalytic sulphuric acid followed by reduction with lithium borohydride in methanol.

Alternatively, compounds (VI) can be prepared by the method outlined by scheme 8.3.

Scheme 8.4

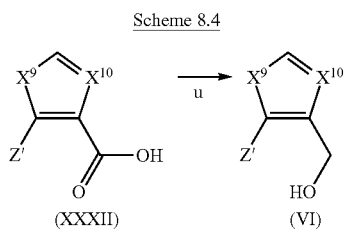

Z' is a halo, typically iodo, bromo or chloro; $X^9$ is S and then $X^{10}$ is N, or, $X^9$ is N then $X^{10}$ is S.

Suitable compounds for use as halo acid (XXXII) are known in the literature or commercially available.

For some of the steps of the here above described process of preparation of the compounds of the invention, it may be necessary to protect potential reactive functions that are not wished to react, and to cleave said protecting groups in consequence. In such a case, any compatible protecting radical can be used. In particular methods of protection and deprotection such as those described by T. W. GREENE (*Protective Groups in Organic Synthesis*, A. Wiley-Interscience Publication, 1981) or by P. J. Kocienski (*Protecting groups*, Georg Theme Verlag, 1994), can be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the invention as well as intermediate for the preparation thereof can be purified according to various well-known methods, such as for example crystallization or chromatography.

Pharmaceutically acceptable salts of the compounds of the invention preferably include the base salts thereof.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by one or more of three methods:
(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of the invention include references to salts, solvates and complexes thereof and to solvates and complexes of salts thereof.

The compounds of the invention include compounds of the invention as hereinbefore defined, including all polymorphs and crystal habits thereof, prodrugs and isomers thereof (including optical, geometric and tautomeric isomers) as hereinafter defined and isotopically-labeled compounds of the invention.

As indicated, so-called 'pro-drugs' of the compounds of the invention are also within the scope of the invention. Thus certain derivatives of compounds of the invention which may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of the invention with certain moieties known to those skilled in the art as 'pro-moieties' as described, for example, in "Design of Prodrugs" by H. Bundgaard (Elsevier, 1985).

Some examples of prodrugs in accordance with the invention include:
(i) where the compound of the invention contains a carboxylic acid functionality (—COOH), an ester thereof, for example, a compound wherein the hydrogen of the carboxylic acid functionality of the compound of the invention is replaced by $(C_1-C_8)$alkyl;
(ii) where the compound of the invention contains an alcohol functionality (—OH), an ether thereof, for example, a compound wherein the hydrogen of the alcohol functionality of the compound of the invention is replaced by $(C_1-C_6)$alkanoyloxymethyl; and
(iii) where the compound of the invention contains a primary or secondary amino functionality (—$NH_2$ or —NHR where R≠H), an amide thereof, for example, a compound wherein, as the case may be, one or both hydrogens of the amino functionality of the compound of the invention is/are replaced by $(C_1-C_{10})$alkanoyl.

Further examples of replacement groups in accordance with the foregoing examples and examples of other prodrug types may be found in the aforementioned references.

Moreover, certain compounds of the invention may themselves act as prodrugs of other compounds of the invention.

Also included within the scope of the invention are metabolites of compounds of the invention, that is, compounds formed in vivo upon administration of the drug. Some examples of metabolites in accordance with the invention include
(i) where the compound of the invention contains a methyl group, an hydroxymethyl derivative thereof (—$CH_3$→—$CH_2OH$):
(ii) where the compound of the invention contains an alkoxy group, an hydroxy derivative thereof (—OR→—OH);
(iii) where the compound of the invention contains a tertiary amino group, a secondary amino derivative thereof (—$NR^1R^2$→—$NHR^1$ or —$NHR^2$);
(iv) where the compound of the invention contains a secondary amino group, a primary derivative thereof (—$NHR^1$→—$NH_2$);
(v) where the compound of the invention contains a phenyl moiety, a phenol derivative thereof (-Ph→-PhOH); and
(vi) where the compound of the invention contains an amide group, a carboxylic acid derivative thereof (—$CONH_2$→COOH).

Compounds of the invention containing one or more asymmetric carbon atoms can exist as two or more stereoisomers. Where a compound of the invention contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, New York, 1994).

The present invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (1), a film-forming polymer, a binder, a solvent, a humectant, a plasticiser, a stabiliser or emulsifier, a viscosity-modifying agent and a solvent. Some components of the formulation may perform more than one function.

The compound of the invention may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of the invention may be in the form of multi particulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by a prefilled capsule, blister or pocket or by a system that utilises a gravimetrically fed dosing chamber. Units in accordance with the invention are typically arranged to administer a metered dose or "puff" containing from 0.001 to 5 mg of (compound name here), or a salt thereof. The overall daily dose will typically be in the range 0.001 mg to 20 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the invention, or pharmaceutically acceptable salts, derived forms or compositions thereof, can also be used as a combination with one or more additional therapeutic agents to be co-administered to a patient to obtain some particularly desired therapeutic end result such as the treatment of central nervous system diseases, cancer and pain. The second and more additional therapeutic agents may also be a compound of the formula (1), or a pharmaceutically acceptable salt, derived forms or compositions thereof, or may be selected from a different class of therapeutic agents.

As used herein, the terms "co-administration", "co-administered" and "in combination with", referring to the compounds of the invention and one or more other therapeutic agents, is intended to mean, and does refer to and include the following:

simultaneous administration of such combination of compound(s) of the invention and therapeutic agent(s) to a patient in need of treatment, when such components are formulated together into a single dosage form which releases said components at substantially the same time to said patient, substantially simultaneous administration of such combination of compound(s) of the invention and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of the invention and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of the invention, or pharmaceutically acceptable salts, derived forms or compositions thereof, include, but are by no means limited to:

Selective Serotonin Reuptake Inhibitor such as citalopram, dapoxetine, escitalopram, fluoxetine, fluvoxamine, indalpine, paroxetine, sertraline, or zimelidine;

a phosphodiesterase inhibitor, preferably PDE4 inhibitor, PDE5 inhibitor (eg sildenafil), PDE9 inhibitor, or PDE10 inhibitor;

an acetylcholinesterase inhibitor such as donepezil, rivastigmine or galantamine;

an antipsychotic such as ziprasidone, aripiprazole or clozapine;

an anti-angiogenesis agent (e.g., an agent that stops tumors from developing new blood vessels), a signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors.

a classical antineoplastic agents. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins.

It is to be appreciated that all references herein to treatment include curative, palliative and prophylactic treatment. The description, which follows, concerns the therapeutic applications to which the compounds of the invention may be put.

The compounds of the invention, their pharmaceutically acceptable salts and/or derived forms or composition thereof, are valuable pharmaceutically active compounds, which are suitable for the therapy and prophylaxis of numerous disorders in which ALK receptor or an ALK fusion protein is involved or in which inhibition of ALK activity may induce benefit, in particular, central nervous system diseases, cancer and pain.

The compounds of formula (1) are useful for the stimulation of neurogenesis. The neurogenesis can be required in various locations, including but not limited to, the brain, CNS, ear or any other location containing neurons therein and can result in increasing neurological and/or cognitive function. By "stimulation of neurogenesis" as used herein, it is meant that neural growth is promoted or enhanced. This can include, but is not limited to, new neuronal growth or enhanced growth of existing neurons, as well as growth and proliferation of parenchymal cells and cells that promote tissue plasticity. Neurogenesis also encompasses, but is not limited to, neurite and dendritic extension and synaptogenesis. This can also include increasing production of brain cells that facilitate improved cognition and/or augmenting the production of neurons in a site in need of augmentation. Patients suffer neurological and functional deficits after stroke, CNS injury and neurodegenerative disease. In an embodiment, the compound of the present invention promotes an improved outcome from ischemic cerebral injury, or other neuronal injury, by inducing neurogenesis and cellular changes that promote functional improvement. In an embodiment, the compounds of formula (1) also provide a means to enhance brain compensatory mechanism to improve function after CNS damage or degeneration The compounds of formula (1) are suitable for the therapy or the prophylaxis of central nervous system diseases and in particular neurodegenerative diseases. The compounds of formula (1) are particularly useful for the therapy or the prophylaxis of Alzheimers disease, mild cognitive impairment, age-related cognitive decline, dementia, in particular HIV related dementia, schizophrenia, stroke, Parkinson's disease, Huntington's disease, anxiety, depression and addiction such as psychoactive substance addiction (alcohol, tobacco . . . ).

As used herein "cancer" refers to any malignant and/or invasive growth or tumor caused by abnormal cell growth.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous). This includes the abnormal growth of: (1) tumor cells (tumors) that proliferate by expressing ALK or an ALK fusion protein; (2) benign and malignant cells of other proliferative diseases in which ALK or an ALK fusion protein occurs; (3) any tumors that proliferate by aberrant ALK or ALK fusion protein activation; and (4) benign and malignant cells of other proliferative diseases in which aberrant ALK or ALK fusion protein activation occurs. The ALK fusion proteins of particular interest for the present invention are the mutated forms of EML4-ALK. Specifically, the L1196M mutant EML4-ALK fusion protein and the C1156Y mutant EML4-ALK fusion protein.

As used herein "cancer" refers to solid tumors named for the type of cells that form them, cancer of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one. The compounds of the invention, are potent inhibitors of ALK, and thus are all adapted to therapeutic use as antiproliferative agents (e.g., cancer), antitumor (e.g., effect against solid tumors) in mammals, particularly in humans. In particular, the compounds of the invention are useful in the prevention and treatment of a variety of human hyperproliferative disorders including both malignant and benign abnormal cell growth.

The compounds, compositions and methods provided herein are useful for the treatment of cancers including but not limited to cancers of the circulatory system, respiratory tract, gastrointestinal system, genitourinary tract, liver, bone, nervous system, reproductive system, hematologic system, oral cavity, skin, adrenal glands, and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of "cancer" when used herein in connection with the present invention include cancer selected from lung cancer, preferably non small cell lung carcinoma (NSCLC), lymphoma, preferably Anaplastic large cells lymphoma, neuroblastoma or soft tissue cancer such as inflammatory myofibroblastic tumor.

As used herein "pain" refers in particular to acute pain; chronic pain; neuropathic pain; inflammatory pain; visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

A further aspect of the invention relates to a compound of the invention, or pharmaceutically acceptable salts, derived forms or compositions thereof, for use as a medicament, and in particular for use in the treatment of diseases where the inhibition of ALK activity may induce benefit, such central nervous system diseases, cancer or pain.

In a preferred embodiment, the invention relate to a compound of the invention for use in the treatment of diseases, disorders, and conditions selected from Alzheimers disease, mild cognitive impairment, age-related cognitive decline, dementia in particular HIV related dementia, schizophrenia, stroke, anxiety, depression, addiction, Parkinson's disease, Huntington's disease, pain, non small cell lung carcinoma, anaplastic large cells lymphoma, neuroblastoma or inflammatory myofibroblastic tumor.

In a preferred embodiment, the invention relate to a compound of the invention for use in the treatment of Alzheimers disease. In a preferred embodiment, the invention relate to a compound of the invention for use in the stimulation of neurogenesis. In a preferred embodiment, the invention relate to a compound of the invention for use in the treatment of non small cell lung carcinoma.

A still further aspect of the present invention also relates to the use of the compounds of the invention, or pharmaceutically acceptable salts, derived forms or compositions thereof, for the manufacture of a drug having an ALK inhibitory activity for the treatment of ALK-mediated diseases and/or conditions, in particular the diseases and/or conditions listed above.

As a consequence, the present invention provides a particularly interesting method to treat a mammal, including a human being, with an effective amount of a compound of the invention, or a pharmaceutically acceptable salt, derived form or composition thereof. More precisely, the present invention provides a particularly interesting method for the treatment of a ALK-mediated diseases and/or conditions in a mammal, including a human being, in particular the diseases and/or conditions listed above, comprising administering said mammal with an effective amount of a compound of the invention, its pharmaceutically acceptable salts and/or derived forms.

Another embodiment of the present invention of particular interest relates to a method for the treatment of lung cancer in a human in need of such treatment, comprising administering to said human an amount of a compound of the invention, in combination with one or more (preferably one to three) anticancer agents selected from the group consisting of capecitabine (Xeloda), bevacizumab (Avastin), gemcitabine (Gemzar), docetaxel (Taxotere), paclitaxel, premetrexed disodium (Alimta), Tarceva, Iressa, Vinorelbine, Irinotecan, Etoposide, Vinblastine, and Paraplatin (carboplatin), wherein the amounts of the active agent together with the amounts of the combination anticancer agents is effective in treating lung cancer.

Preferably, the compounds of the invention are able to cross the blood brain barrier. The potential of the compound of the invention to cross the blood brain barrier can be assessed using standard permeability assays well known to the man skilled in the art, such as Caco-2 or Madine-Darby Canine Kidney (MDCK) cells assay (see for example Journal of Pharmaceutical Sciences, vol. 98, No. 12, 2009, p. 4429 to 4468).

Preferably, the compounds of the invention are selective ALK inhibitors. Preferably, the compounds of the invention are selective inhibitors of the EML4-ALK mutant L1196M. Preferably, the compounds of the invention are selective inhibitors of the EML4-ALK mutant C1156Y. Preferably, the compounds of the invention are ALK inhibitors or EML4-ALK mutant inhibitors selective over cMet. Preferably, the compounds of the invention are ALK inhibitors or EML4-ALK mutant inhibitors selective over TrkA. Preferably, the compounds of the invention are ALK inhibitors or EML4-ALK mutant inhibitors selective over cMet and TrkA.

The endogenous activator for cMet is hepatic growth factor (HGF). Data from the literature indicates that HGF plays an important role in synaptogenesis, synaptic plasticity and synaptic function (see for example Lim et al, Cell Signal 2008 20, 825-35; Tyndall et al. Cell Cycle. 2006 5, 1560-8; Akimoto et al, Neuroscience 2004; 128, 155-62). Since synaptic function is known to be critical for learning and memory, it is preferable, in particular for compounds able to cross the blood brain barrier not to inhibit normal cMet function.

The endogenous activator for TrkA is nerve growth factor (NGF). This growth factor signalling system is known to important for maintaining the nucleus basalis cholinergic cortical projection neurons, a neural system which has an important role in cognitive functioning and which degenerates in Alzheimer's disease (Lad S P, et al. Curr Drug Targets CNS Neurol Disord. 2003 2, 315-34). In addition, this signalling system is known to play an important role in synaptic plasticity; this includes the modulation of neurotransmitter release at the synapse (eg Blochl A and Sirrenberg C J Biol Chem 1996, 271, 21100-21107). Therefore, it is preferable, in particular for compounds able to cross the blood brain barrier not to inhibit normal TrkA function.

The Preparations and Examples that follow illustrate the invention but do not limit the invention in any way. All starting materials are available commercially or are described in the literature. All temperatures are in ° C. Flash column chromatography was carried out using Merck silica gel 60 (9385). Thin layer chromatography (TLC) was carried out on Merck silica gel 60 plates (5729). "$R_f$" represents the distance travelled by a compound divided by the distance travelled by the solvent front on a TLC plate. Melting points were determined using a Gallenkamp MPD350 apparatus and are uncorrected. NMR was carried out using a Varian-Unity Inova 400 MHz NMR spectrometer or a Varian Mercury 400 MHz NMR spectrometer. Mass spectroscopy was carried out using a Finnigan Navigator single quadrupole electrospray mass spectrometer or a Finnigan aQa APCI mass spectrometer.

Where it is stated that compounds were prepared in the manner described for an earlier Preparation or Example, the skilled person will appreciate that reaction times, number of equivalents of reagents and reaction temperatures may be modified for each specific reaction, and that it may nevertheless be necessary or desirable to employ different work-up or purification conditions.

The invention is illustrated by the following non-limiting examples in which the following abbreviations and definitions are used:

"Et" means ethyl, "Ac" means acetyl, "Me" means methyl, "Ph" means phenyl, "Boc" means tert-butoxycarbonyl, "EtOAc" means ethyl acetate, "TEA", "NEt$_3$" or "Et$_3$N" means triethylamine, "THF" means tetrahydrofuran, "MeTHF" means methyltetrahydrofuran, "MeOH" means methanol, "DMSO" means dimethylsulfoxide, "CDCl$_3$" means deuterated chloroform, "TBME" or "MTBE" means methyl t-butyl ether, "DMF" means dimethyl formamide, "DMAP" means 4-dimethylaminopyridine, "dppf" means diphenylphosphino ferrocene, "DME" means ethylene glycol dimethyl ether, "TLC" means thin layer chromatography, "h", "hr" or "hrs" means hours, "min." or "mins." means minutes, "DCM" or "CH$_2$Cl$_2$" means methylene chloride, "Et$_2$O" means diethyl ether, "LC-MS" or "LCMS" means liquid chromatography-mass spectrometry, "MS" means mass spectrometry, "rt" or "RT" means room temperature, "NBS" means N-bromosuccinimide, "MeCN" or "CH$_3$CN" means acetonitrile, "brine" means saturated aqueous sodium chloride, "HATU" means 2-(7-Aza-1H-benzotriazole-1-yl)-1,1,3,3-tetramethyluronium hexafluoro-phosphate, "APCI" means atmospheric pressure chemical ionization, "CD$_3$OD" means deuterated methanol, "(CD$_3$)$_2$SO" means deuterated dimethyl sulphoxide, "δ" means chemical shift, "d" means doublet, "DAD" means diode array detector, g means grams, "ESCI" means electrospray chemical ionization, "HPLC" means high pressure liquid chromatography, "LRMS" means low resolution mass spectrum, "M" means molar, "m" means multiplet, "mg" or "mgs" means milligrams, "MHz" means mega hertz, "mL" means milliliters, "µL" means microliters, "mmol" means millimoles, "mol" means moles, "NMR" means nuclear magnetic resonance, "q" means quartet, "Rt" means retention time, "s" means singlet, "t" means triplet, "TFA" means trifluoroacetic acid, "SFC" means supercritrital fluid chromatography, "MeMgBr" means methyl magnesium bromide, "DMSO-d$_6$" means dueterated dimethylsulfoxide, "DIBAL-H" means diisobutylaluminium hydride, "CH$_3$I" means methyl iodide, "ppm" means parts per million, "mCPBA" means meta-chloroperoxybenzoic acid, "DIPCl" means β-chlorodiisopinocamphenylborane (DIP-Chloride®), "N$_2$" means nitrogen gas, "MeI" means methyl iodide, Where compounds have been analysed by LCMS, there are six methods used. These are illustrated below and will be referred to by system number.

Mass Spectrometer Model: Agilent 1956A
Ionization Mode: API-ES

Polarity: Positive
System 1: 6 minute basic run:
A: 0.1% ammonium hydroxide in water
B: 0.1% ammonium hydroxide in acetonitrile
Column: C18 phase Fortis 50×4.6 mm with 5 micron particle size
Gradient: 95-5% A over 3 min, 1 min hold, 1 mL/min
UV: 210 nm-450 nm DAD
Temperature: 50° C.
System 2: 2 minute acidic run:
A: 0.1% formic acid in water
B: 0.1% formic acid in acetonitrile
Column: C18 phase Fortis Pace 20×2.1 mm with 3 micron particle size
Gradient: 70-2% A over 1.8 min, 0.2 min hold, 1.8 mL/min
UV: 210 nm-450 nm DAD
Temperature: 75° C.
System 3: Mass Spec:
ESCI: MS
Solvent 20 mM Ammonia 1 minute run
System 4: 6 minute acidic run:
A: 0.1% formic acid in water
B: 0.1% formic acid in acetonitrile
Column: C18 phase Phenomenex Luna 50×4.6 mm with 5 micron particle size
Gradient: 95-5% A over 3 min, 1 min hold, 1 mL/min
UV: 210 nm-450 nm DAD
Temperature: 50° C.
System 5: 5 minute acidic run:
A: 0.0375% TFA in water
B: 0.01875% TFA in acetonitrile
Column: Ymc ODS-AQ 50 mm×2 mm with 5 micron particle size
Gradient: 90-10% A over 4.7 min, 1 min hold, 0.8 mL/min
Temperature: 50° C.
System 6: 5 minute acidic run:
A: 0.0375% TFA in water
B: 0.01875% TFA in acetonitrile
Column: Ymc ODS-AQ 50 mm×2 mm with 5 micron particle size
Gradient: 99-0% A over 4.7 min, 1 min hold, 0.8 mL/min
Temperature: 50° C.

Where Example compounds have been purified by High Performance Liquid Chromatography (HPLC), unless otherwise stated, one of two preparative methods was used. These preparative methods are outlined below and are referred to as Acidic Conditions or Basic Conditions. These same compounds were then analysed using one of two analytical HPLC methods. These analytical methods are outlined below and are referred to as Acidic Analytical (QC) and Basic Analytical (QC).

| HPLC Separation conditions | |
| --- | --- |
| Preparative | |
| Acidic conditions | Basic conditions |
| Column: SunFire C18, 5 um 19 × 100 mm<br>Temperature: Ambient<br>Detection: ELSD-MS<br>Fractionlynx 3<br>Injection Volume: 1000 uL<br>Flow Rate: 18 mL/min<br>Mobile Phase: A: H$_2$O + 0.1% formic, B: Acetonitrile + 0.1% formic acid<br>Gradient (Time (mins), % B): (0-1, 5), (1-7, 5-98), (7-9, 98), (9-9.1, 98-5), (9.1-10, 5) | Column: XTerra C18, 5 um 19 × 100 mm<br>Temperature: Ambient<br>Detection: ELSD-MS<br>Fractionlynx 3<br>Injection Volume: 1000 uL<br>Flow Rate: 18 mL/min<br>Mobile Phase: A: H$_2$O + 0.1% Diethylamine, B: Acetonitrile + 0.1% Diethylamine<br>Gradient (Time (mins), % B): (0-1, 5), (1-7, 5-98), (7-9, 98), (9-9.1, 98-5), (9.1-10, 5) |
| Analytical | |
| Acidic Analytical (QC) | Basic Analytical (QC) |
| Column: SunFire C18, 5 um 4.6 × 50 mm<br>Temperature: Ambient<br>Detection: UV 225 nm-ELSD-MS<br>Injection volume: 5 uL<br>Flow rate: 1.5 mL/min<br>Mobile phase: A: H$_2$O + 0.1% formic acid, B: acetonitrile + 0.1% formic acid<br>Gradient (Time (mins), % B): (0, 5), (3, 95), (4, 95), (4.1, 5), (5, 5) | Column: XTerra C18, 5 um 4.6 × 50 mm<br>Temperature: Ambient<br>Detection: UV 225 nm-ELSD-MS<br>Injection volume: 5 uL<br>Flow rate: 1.5 mL/min<br>Mobile phase: A: H$_2$O + 0.1% ammonia, B: acetonitrile + 0.1% ammonia<br>Gradient (Time (mins), % B): (0, 5), (3, 95), (4, 95), (4.1, 5), (5, 5) |

Preparation 1

1-(5-Fluoro-2-[1,2,3]triazol-2-yl-phenyl)-ethanone

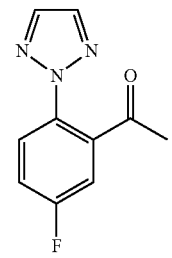

To a solution of 2',5'-difluoroacetophenone (10.0 g, 64 mmol) in 1-methyl-2-pyrrolidinone (10 mL) was added potassium carbonate (8.84 g, 64 mmol) and 1H-1,2,3-triazole (6.64 g, 96 mmol). This mixture was heated to 140° C. for 3 hr, under an atmosphere of nitrogen. After this time, the reaction was cooled and then partitioned between ethyl acetate (300 mL) and aqueous ammonium chloride solution (1M, 100 mL). The organic phase was washed with water (3×200 mL) and then dried over magnesium sulphate, filtered and concentrated under reduced pressure. The residue was purified by chromatography on silica gel eluting with ethyl acetate in heptane (10:90 by volume) to produce the title compound as a brown oil (4.6 g, 35%).

$^1$H NMR (400 MHz, CDCl$_3$): δ ppm 2.17 (s, 3H), 7.20-7.28 (m, 2H), 7.8-7.85 (m, 3H).

Preparations 2 to 3

The compounds of the following tabulated preparations of the general formula:

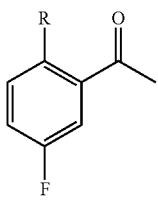

were prepared by a similar method to that of preparation 1 using the appropriate azole material and 2',5'-difluoroacetophenone.

| Prep. No. | R | Name | Form, yield | Data |
|---|---|---|---|---|
| 2[1] | 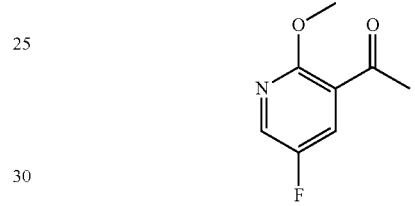 | 1-(5-Fluoro-2-[1,2,3]triazol-1-yl-phenyl)-ethanone | Brown oil, 30% | $^1$H NMR (400 MHz, CDCl$_3$): δ ppm 2.15 (s, 3H), 7.44 (m, 1H), 7.74 (m, 2H), 7.87 (d, 2H, J = 5.2 Hz). |
| 3[2] | | 1-(5-Fluoro-2-pyrazol-1-yl-phenyl)-ethanone | Brown oil, 69% | $^1$H NMR (400 MHz, CDCl$_3$): δ ppm 1.95 (s, 3 H) 6.42-6.56 (m, 1 H) 7.18-7.33 (m, 2 H) 7.43 (dd, J = 8.59, 4.69 Hz, 1 H) 7.70 (dd, J = 9.76, 1.95 Hz, 2 H). |

Footnotes
[1]Reaction heated 16 hr. Chromatography solvent was ethyl acetate in heptane (25:75, by volume).
[2]Chromatography solvent was ethyl acetate in heptane (30:70, by volume).

Preparation 4

5-Fluoro-2,N-dimethoxy-N-methyl-nicotinamide

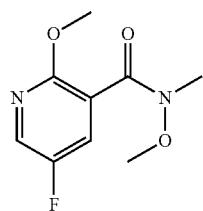

To a solution of 5-fluoro-2-methoxynicotinic acid (1 g, 5.8 mmol) in tetrahydrofuran (10 mL) was added 1,1'-carbonyl-diimidazole (1.4 g, 8.77 mmol, 1.5 eq.) portionwise over a 5 min period. The resulting solution was stirred at room temperature for 20 min before adding O,N-Dimethyl-hydroxy-lamine hydrochloride (0.63 g, 6.43 mmol, 1.1 eq.) and then stirred for a further 72 hr. The resulting mixture was then partitioned between ethyl acetate (30 mL) and 2M aqueous hydrochloric acid (30 mL). The organic phase was washed with 1M aqueous sodium hydrogen carbonate (30 mL), followed by brine (30 mL) and then dried over magnesium sulphate. The resulting mixture was filtered and concentrated under reduced pressure to produce the title compound as a colourless oil (0.53 g, 43%). $^1$H NMR (400 MHz, CDCl$_3$): δ ppm 3.36 (br. s., 3H) 3.55 (br. s., 3H) 3.97 (s, 3H) 7.33-7.44 (m, 1H) 8.06 (d, J=2.73 Hz, 1H).

LRMS: APCI, m/z=215 [M+H]$^+$

Preparation 5

1-(5-Fluoro-2-methoxy-pyridin-3-yl)-ethanone

To a solution of the amide from preparation 4 (0.53 g, 2.47 mmol) in tetrahydrofuran (10 mL), cooled to −70° C. under nitrogen, was added methyl magnesium chloride solution (3M in tetrahydrofuran, 1.0 mL, 3.09 mmol, 1.25 eq) dropwise over a 5 min period. The resulting solution was stirred at −70° C. for 15 min before warming to room temperature over a period of 2 hr. The resulting mixture was carefully quenched with aqueous ammonium chloride solution (1M, 5 mL) and then partitioned between tert-butyl methyl ether (30 mL) and water (10 mL). The organic phase was washed with brine (30 mL) and then dried over magnesium sulphate. The resulting mixture was filtered and concentrated under reduced pressure. The residue was purified by chromatography on silica gel eluting with a gradient of tert-butyl methyl ether in pentane (0:100 to 50:50 by volume) to produce the title compound as a colourless solid (0.195 g, 47%).

$^1$H NMR (400 MHz, CDCl$_3$): δ ppm 2.66 (s, 3H) 4.05 (s, 3H) 7.88 (dd, J=8.20, 3.12 Hz, 1H) 8.16 (d, J=3.12 Hz, 1H).
LRMS: APCI, m/z=170 [M+H]$^+$ Preparation 6

6-Fluoro-benzothiazole-4-carboxylic acid

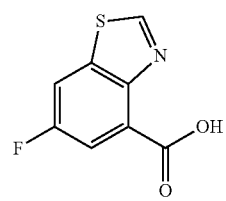

To a solution of 6-fluoro-benzothiazole-4-carboxylic acid methyl ester (1.97 g, 9.33 mmol) in tetrahydrofuran (30 mL) was added aqueous lithium hydroxide solution (2M, 14.0 mL, 28 mmol, 3 eq.) and then stirred, at room temperature, for 4 hr. The reaction mixture was quenched with aqueous hydrochloric acid (2M, 30 mL) and stirred for 15 min. The resulting suspension was filtered and the solid produced was washed with water and air dried to give the title compound as a grey solid (1.51 g, 82%).

$^1$H NMR (400 MHz, DMSO-d6): δ ppm 7.71 (dd, J=10.15, 2.73 Hz, 1H) 8.03 (dd, J=8.20, 2.73 Hz, 1H) 9.39 (s, 1H).

LRMS: ESI, m/z=198 [M+H]$^+$

Preparation 7

6-Fluoro-benzothiazole-4-carboxylic acid methoxy-methyl-amide

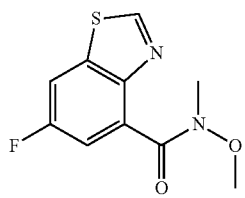

The title compound was prepared by a similar method to that of preparation 4 using the acid from preparation 6 except that the tetrahydrofuran was replaced with N,N-dimethyl formamide and reaction heated to 80° C. for 72 hr to give the title compound as a brown oil (1.15 g, 55%).

$^1$H NMR (400 MHz, CDCl$_3$): δ ppm 3.09 (s, 3H) 3.68 (s, 3H) 7.32-7.40 (m, 1H) 7.68-7.73 (m, 1H) 9.02 (s, 1H)

LRMS: ESI, m/z=241 [M+H]$^+$

Preparation 8

1-(6-Fluoro-benzothiazol-4-yl)ethanone

The title compound was prepared by a similar method to that of preparation 5 using the amide from preparation 7 to give an orange solid (0.81 g, 84%).

$^1$H NMR (400 MHz, DMSO-d6): δ ppm 2.94 (s, 3H) 7.60-7.83 (m, 1H) 8.39 (dd, J=8.20, 2.73 Hz, 1H) 9.58 (s, 1H)

LRMS: ESI, m/z=196 [M+H]$^+$

Preparation 9

1-(6-Fluoro-quinolin-8-yl)-ethanone

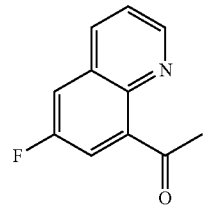

To a solution of 6-fluoro-8-bromo-quinoline (1.53 g, 6.8 mmol) in acetonitrile (35 mL) was added palladium(II) acetate (0.31 g, 1.36 mmol, 0.2 eq.), butyl vinyl ether (2.04 g, 20 mmol, 3.0 eq.), and 1,3-bis(diphenylphosphino)propane (0.70 g, 1.7 mmol, 0.25 eq) was added triethylamine (1.1 g, 11 mmol, 1.6 eq). The resulting mixture was heated to 90° C. for 17 hr and then evaporated under reduced pressure. The residue was dissolved in aqueous hydrochloric acid (2M, 15 mL) and stirred, at room temperature, for 1.5 hr. This mixture was then diluted with water (35 mL) and the pH adjusted with solid sodium hydrogen carbonate until neutral. The mixture was then extracted with ethyl acetate (100 mL); the organic phase was dried over magnesium sulphate. The resulting mixture was filtered and concentrated under reduced pressure to give a brown oil. This crude product was purified by chromatography on silica gel eluting with 10% ethyl acetate in pentane (by volume) to produce the title compound as a pale yellow solid (0.91 g, 71%).

$^1$H NMR (400 MHz, CDCl$_3$): δ ppm 2.96 (s, 3H), 7.48 (dd, 1H), 7.56 (dd, 1H), 7.74 (dd, 1H), 8.16 (dd, 1H), 8.95 (dd, 1H)

Preparation 10

1-(5-Fluoro-2-[1,2,3]triazol-2-yl-phenyl)-ethanol

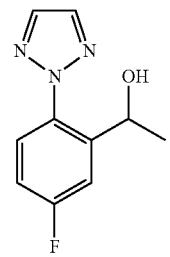

To a solution of ketone from preparation 1 (1.5 g, 7.3 mmol) in methanol (25 mL) was added sodium borohydride (0.36 g, 9.5 mmol, 1.3 eq.) portionwise over a period of 20 min [CAUTION: vigorous effervescence observed]. The mixture was stirred for 2 hr, at room temperature, before removing the methanol by evaporation under reduced pressure. The residue was quenched with aqueous hydrochloric acid (2M, 20 mL) and then the mixture made basic with aqueous ammonia (0.880, 5 mL) and partitioned with ethyl acetate (100 mL). The organic phase was washed with brine and dried over magnesium sulphate. The resulting mixture was filtered and concentrated under reduced pressure to give the title compound as a pale yellow oil (1.5 g, 99%).

¹H NMR (400 MHz, CDCl₃): δ ppm 1.43 (d, J=6.64 Hz, 3H) 4.85 (dd, J=6.64, 1.17 Hz, 1H) 7.09 (ddd, J=8.79, 7.62, 3.12 Hz, 1H) 7.38 (dd, J=9.57, 2.93 Hz, 1H) 7.59 (dd, J=8.98, 5.08 Hz, 1H) 7.86 (s, 2H)

Preparations 11 to 15

The compounds of the following tabulated preparations of the general formula,

were prepared by a similar method to that of preparation 10 using the appropriate ketone starting material.

| Prep. No. | R | Name | Form, yield | Data |
|---|---|---|---|---|
| 11 | | 1-(5-Fluoro-2-[1,2,3]triazol-1-yl-phenyl)-ethanol | Yellow solid, 78% | ¹H NMR (400 MHz, CHLOROFORM-d) δ ppm 1.39 (d, J = 6.64 Hz, 3 H) 3.24 (m, 1 H) 4.55-4.70 (m, 1 H) 7.06-7.16 (m, 1 H) 7.27 (s, 1 H) 7.47 (dd, J = 9.37, 2.73 Hz, 1 H) 7.77-7.87 (m, 2 H) |
| 12 | | 1-(5-Fluoro-2-pyrazol-1-yl-phenyl)-ethanol | Yellow oil, 99% | ¹H NMR (400 MHz, CDCl₃): δ ppm 1.39 (d, J = 6.64 Hz, 3 H) 3.01-3.68 (br s, 1 H) 4.65 (dd, J = 6.64, 1.17 Hz, 1 H) 6.32-6.63 (m, 1 H) 6.91-7.15 (m, 1 H) 7.20-7.40 (m, 2 H) 7.52-7.90 (m, 2 H) |
| 13 | | 1-(5-Fluoro-2-methoxy-pyridin-3-yl)-ethanol | Clear oil, 97% | ¹H NMR (400 MHz, CDCl₃): δ ppm 1.49 (d, J = 6.25 Hz, 3 H) 3.97 (s, 3 H) 5.01 (q, 1 H) 7.41-7.52 (m, 1 H) 7.90 (d, J = 3.12 Hz, 1 H) |
| 14 | | 1-(6-Fluoro-benzothiazol-4-yl)-ethanol | Orange oil, 86% | ¹H NMR (400 MHz, CDCl₃): δ ppm 1.69 (d, J = 6.64 Hz, 3 H) 4.04 (d, 1 H) 5.38-5.52 (m, 1 H) 7.21-7.27 (m, 2 H) 7.49-7.59 (m, 1 H) 8.97 (s, 1 H) |
| 15 | | 1-(6-Fluoro-quinolin-8-yl)-ethanol | Yellow oil, 90% | ¹H NMR (400 MHz, CDCl₃): δ 1.74 (d, 3H), 5.49 (q, 1H), 5.74 (br s, 1H, OH), 7.35 (dd, 1H), 7.41 (dd, 1H), 7.46 (dd, 1H), 8.16 (dd, 1H), 8.83 (dd, 1H) |

Preparation 16

1-(2-Bromo-5-fluoro-phenyl)ethanol

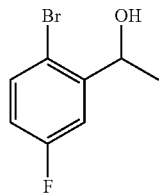

To a solution of 2-bromo-5-fluoro-benzaldehyde (17.0 g, 83.7 mmol) in tetrahydrofuran (100 mL), cooled to 0° C. under nitrogen, was added methyl magnesium chloride solution (3M in tetrahydrofuran, 31.0 mL, 93.0 mmol, 1.1 eq.) dropwise over a 20 min period. The resulting solution was stirred at 0° C. for 45 min before quenching with aqueous ammonium chloride solution (1M, 17 mL). The resulting mixture was partitioned between pentane (300 mL) and water (100 mL). The organic phase was washed with brine (50 mL) and then dried over magnesium sulphate. This mixture was filtered and concentrated under reduced pressure. The residue was purified by chromatography on silica gel eluting with a gradient of toluene in pentane (50:50 to 100:0 by volume) to produce the title compound as a colourless oil (13.8 g, 75%).

$^1$H NMR (400 MHz, CDCl$_3$): δ ppm 1.47 (d, J=6.25 Hz, 3H) 5.18 (ddd, J=6.25, 3.51, 1.17 Hz, 1H) 6.75-6.97 (m, 1H) 7.34 (dd, J=9.76, 3.12 Hz, 1H) 7.42-7.56 (m, 1H)

Preparation 17

(S)-1-(5-Fluoro-2-[1,2,3]triazol-2-yl-phenyl)-ethanol

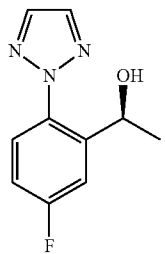

To a solution of (−)-DIP-Chloride™ (21.3 g, 66.4 mmol, 1.25 eq) in tetrahydrofuran (60 mL), at −35° C., was added a solution of the ketone from preparation 1 in tetrahydrofuran (20 mL) dropwise at such a rate as to maintain the temperature below −27° C. The resulting mixture was stirred at −35° C. 3 hr and then warmed slowly to room temperature over 18 hr. The mixture was evaporated under reduced pressure to remove most of the tetrahydrofuran and the resulting residue dissolved in tert-butyl methyl ether (150 mL) and rapidly stirred with an overhead stirrer whilst diethanolamine (15.1 g, 2.7 eq.) was added, allowing the temperature to rise to 50° C. during the addition. The resulting mixture was stirred for 1 hr before filtering. The filter cake was washed with tert-butyl methyl ether (2×100 mL) and discarded. The combined filtrate was evaporated under reduced pressure and resulting crude product purified by chromatography on silica gel (300 g) eluting with toluene in heptane (50:50) followed by a gradient of tert-butyl methyl ether in heptane (50:50 to 100:0) to produce the title compound as a colourless oil (10.9 g, 99%).

$^1$H NMR (400 MHz, CDCl$_3$): δ ppm 1.43 (d, J=6.64 Hz, 3H) 4.85 (dd, J=6.64, 1.17 Hz, 1H) 7.09 (ddd, J=8.79, 7.62, 3.12 Hz, 1H) 7.38 (dd, J=9.57, 2.93 Hz, 1H) 7.59 (dd, J=8.98, 5.08 Hz, 1H) 7.86 (s, 2H)

Preparation 18

3-[(R)-1-(5-Fluoro-2-methoxy-phenyl)-ethoxy]-2-nitro-pyridine

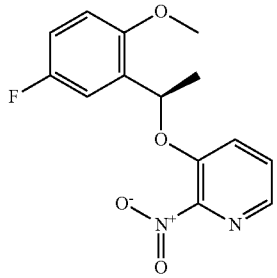 [SMILES: COc1ccc(F)cc1[C@@H](C)Oc1cccnc1[N+](=O)[O-]]

To an ice cooled solution (0° C.) of (S)-1-(5-fluoro-2-methoxy-phenyl)-ethanol (see H. C. Brown, *Tet. Letts.*, 35 (14), 2141-4, 1994. Optical purity of alcohol: >99.5% e.e. (based on SFC on a chiral column: Chiralpak IA (250*4.6 mm i.d.), eluent 5% methanol alcohol in carbon dioxide, Flow rate 4 mL/min, temp. 40° C., back pressure 150 bar, Rt=2.16 min (opposite enantiomer Rt=2.35 min))) (2.00 g, 11.7 mmol), triphenylphosphine (3.54 g, 13.5 mmol, 1.15 eq.) and 3-hydroxy-2-nitro-pyridine (1.81 g, 12.9 mmol, 1.1 eq) in toluene (100 mL) was added a solution of diisopropyl azodicarboxylate (2.73 g, 13.5 mmol, 1.15 eq.) in toluene (20 mL) at such a rate as to maintain the temperature below 10° C. The resulting mixture was stirred at room temperature for 18 hr. The crude reaction mixture was extracted with aqueous potassium hydroxide solution (2M, 2×50 mL). The organic phase was washed with brine and dried over magnesium sulphate before filtering. The filtrate was evaporated under reduced pressure to give an orange semi solid material. This material was suspended in diethyl ether and heptane (80:20 by volume) and filtered. This filtrate was evaporated under reduced pressure. The residue was purified by chromatography on silica gel eluting with a gradient of diethyl ether in heptane (50:50 to 80:20 by volume) to produce the title compound as a pale yellow oil (3.48 g, 86%).

$^1$H NMR (400 MHz, CDCl$_3$): δ ppm 1.63 (d, J=6.24 Hz, 3H) 3.90 (s, 3H) 5.81 (q, J=6.63 Hz, 1H) 6.85 (dd, J=9.17, 4.10 Hz, 1H) 6.95 (m, 1H) 7.13 (dd, J=8.58, 3.12 Hz, 1H) 7.22-7.30 (m, 1H) 7.31-7.38 (m, 1H) 8.01 (dd, J=4.68, 1.17 Hz, 1H)

Optical purity: 84.0% e.e. (chiral column conditions Chiralpak IC, eluent 30% isopropyl alcohol in heptane, 1 mL/min, Rt=17.9 min (opposite enantiomer Rt=8.5 min))

Preparations 19 to 27

The compounds of the following tabulated preparations of the general formula:

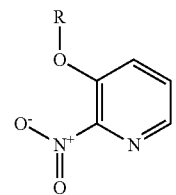

were prepared by a similar method to that of preparation 18 using the appropriate alcohol starting material.

| Prep. No. | R | Name | Form, yield | Data |
|---|---|---|---|---|
| 19 | (1,2,3-triazol-2-yl attached to 5-fluoro-phenyl) | 3-[1-(5-Fluoro-2-[1,2,3]triazol-2-yl-phenyl)-ethoxy]-2-nitro-pyridine | White solid, 83% | ¹H NMR (400 MHz, CDCl₃): δ ppm 1.61 (d, 3H), 5.90 (q, 1H), 7.14 (ddd, 1H), 7.36 (dd, 1H), 7.39-7.44 (m, 2H), 7.64 (dd, 1H), 7.93 (s, 2H), 8.03 (dd, 1H) |
| 20 | (1,2,3-triazol-2-yl attached to 5-fluoro-phenyl, R config) | 3-[(R)-1-(5-Fluoro-2-[1,2,3]triazol-2-yl-phenyl)-ethoxy]-2-nitro-pyridine | Brown oil, 78% | ¹H NMR (400 MHz, CDCl₃): δ ppm 1.61 (d, 3H), 5.90 (q, 1H), 7.14 (ddd, 1H), 7.36 (dd, 1H), 7.39-7.44 (m, 2H), 7.64 (dd, 1H), 7.93 (s, 2H), 8.03 (dd, 1H) |
| 21 | (pyrazol-1-yl attached to 5-fluoro-phenyl) | 3-[1-(5-Fluoro-2-pyrazol-1-yl-phenyl)-ethoxy]-2-nitro-pyridine | Yellow gum, 63% | ¹H NMR (400 MHz, CDCl₃): δ ppm 1.52 (d, 3H), 5.78 (q, 1H), 6.53 (dd, 1H), 7.09 (m, 1H), 7.30 (dd, 1H), 7.37-7.41 (m, 2H), 7.64-7.69 (m, 2H), 7.80 (d, 1H), 8.03 (dd, 1H) |
| 22 | (5-fluoro-2-methoxy-pyridin-3-yl) | 5-Fluoro-2-methoxy-3-[1-(2-nitro-pyridin-3-yloxy)-ethyl]-pyridine | Brown oil | 1H NMR (400 MHz, CDCl₃): δ ppm 1.64 (d, J = 6.64 Hz, 3 H) 4.02 (s, 3 H) 5.72 (q, 1 H) 7.28-7.34 (m, 1 H) 7.38-7.45 (m, 1 H) 7.47-7.56 (m, 1 H) 7.95 (s, 1 H) 8.07 (dd, 1 H) LCMS (System 4) Rt @ 3.14 min APCI m/z 294 [M + H]+ |
| 23 | (6-fluoro-benzothiazol-4-yl) | 6-Fluoro-4-[1-(2-nitro-pyridin-3-yloxy)-ethyl]-benzothiazole | Brown oil | LRMS: ESI, m/z = 318 [M + H]⁺ |
| 24 | (6-fluoro-quinolin-8-yl) | 6-Fluoro-8-[1-(2-nitro-pyridin-3-yloxy)-ethyl]-quinoline | White solid, 79% | ¹H NMR (400 MHz, CDCl₃): δ ppm 1.81 (d, 3H), 6.87 (q, 1H), 7.26 (dd, 1H), 7.36-7.42 (m, 2H), 7.52 (dd, 1H), 7.69 (dd, 1H), 8.00 (dd, 1H), 8.17 (dd, 1H), 8.94 (dd, 1H) |

| Prep. No. | R | Name | Form, yield | Data |
|---|---|---|---|---|
| 25 | 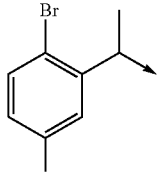 | 3-[1-(2-Bromo-5-fluoro-phenyl)-ethoxy]-2-nitro-pyridine | White solid, 70% | $^1$H NMR (400 MHz, CDCl$_3$): δ ppm 1.68 (d, J = 6.25 Hz, 3 H) 5.73 (dd, J = 6.25, 1.17 Hz, 1 H) 6.92 (ddd, J = 8.79, 7.62, 3.12 Hz, 1 H) 7.18 (dd, J = 8.59, 1.17 Hz, 1 H) 7.23-7.30 (m, 1 H) 7.37-7.43 (m, 1 H) 7.55 (dd, J = 8.59, 5.08 Hz, 1 H) 8.01-8.10 (m, 1 H) |
| 26 | 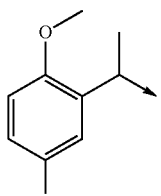 | 3-[1-(5-Fluoro-2-methoxy-phenyl)-ethoxy]-2-nitro-pyridine | White solid, 65% | $^1$H NMR (400 MHz, CDCl$_3$): δ ppm 1.63 (d, J = 6.24 Hz, 3 H) 3.90 (s, 3 H) 5.81 (q, J = 6.63 Hz, 1 H) 6.85 (dd, J = 9.17, 4.10 Hz, 1 H) 6.95 (m, 1H) 7.13 (dd, J = 8.58, 3.12 Hz, 1 H) 7.22-7.30 (m, 1 H) 7.31-7.38 (m, 1 H) 8.01 (dd, J = 4.68, 1.17 Hz, 1 H) |
| 27 |  | 3-[1-(2,5-Difluoro-phenyl)-ethoxy]-2-nitro-pyridine | Yellow gum, 78% | $^1$H NMR (400 MHz, CDCl$_3$): δ ppm 1.70 (d, J = 6.25 Hz, 3 H) 5.76 (d, J = 6.64 Hz, 1 H) 6.94-7.02 (m, 1 H) 7.06 (dt, J = 9.27, 4.54 Hz, 1 H) 7.19 (ddd, J = 8.49, 5.57, 3.12 Hz, 1 H) 7.31-7.37 (m, 1 H) 7.39-7.46 (m, 1 H) 8.03-8.10 (m, 1 H) |

Preparation 28

3-[(R)-1-(5-Fluoro-2-methoxy-phenyl)ethoxy]-pyridin-2-ylamine

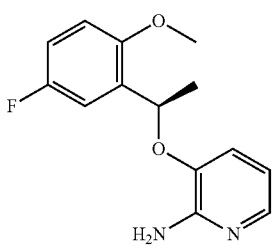 [SMILES: COc1ccc(F)cc1[C@@H](C)Oc1cccnc1N]

To a solution of the nitro compound from preparation 18 (93.0 g, 320 mmol) in a mixture of acetic acid (250 mL) and 1,4-dioxane (250 mL) was added 325 mesh iron powder (90 g, 5 eq.) in portions with external cooling from a water bath [Caution: exothermic]. The resulting mixture was heated to 40° C. for 30 min before filtering through a pad of Arbocel™ and washing the pad with 1,4-dioxane (3×200 mL). The filtrate was evaporated under reduced pressure. The crude mixture was partitioned between 10% (wt/vol) aqueous citric acid solution (3000 mL) and tert-butyl methyl ether (1000 mL). The aqueous phase was then made basic with aqueous ammonia (0.880, 500 mL) and extracted with tert-butyl methyl ether (2×1000 mL). These organic phases were combined and washed with brine (200 mL) and dried over magnesium sulphate. This mixture was filtered through a small plug of silica (50 g) and the filtrate evaporated under reduced pressure. The resulting pink solid (53 g) was suspended in acetonitrile (400 mL) and resulting mixture filtered to give a white solid (7.7 g, racemate). The filtrate was evaporated under reduced pressure to give the title compound as a brown solid (45.0 g, 54%).

$^1$H NMR (400 MHz, CDCl$_3$): δ ppm 1.59 (d, J=6.25 Hz, 3H) 3.88 (s, 3H) 4.78 (br. s., 2H) 5.63 (d, J=6.25 Hz, 1H) 6.44 (dd, J=7.81, 5.08 Hz, 1H) 6.65 (dd, J=7.81, 1.56 Hz, 1H) 6.76-6.96 (m, 2H) 7.03 (dd, J=8.98, 3.12 Hz, 1H) 7.60 (dd, J=5.08, 1.56 Hz, 1H)

Preparations 29 to 37

The compounds of the following tabulated preparations of the general formula:

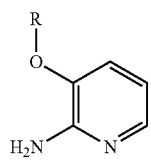

were prepared by a similar method to that of preparation 28 using the appropriate nitro starting material.

| Prep. No. | R | Name | Form, yield | Data |
|---|---|---|---|---|
| 29 | [1,2,3-triazol-2-yl-(4-fluorophenyl) structure with isopropyl] | 3-[1-(5-Fluoro-2-[1,2,3]triazol-2-yl-phenyl)-ethoxy]-pyridin-2-ylamine | White solid, 87% | $^1$H NMR (400 MHz, CDCl$_3$): δ ppm 1.58 (d, 3H), 4.73 (bs, 2H, NH$_2$), 5.67 (dq, 1H), 6.44 (dd, 1H), 6.68 (dd, 1H), 7.10 (ddd, 1H), 7.29 (dd, 1H), 7.61 (d, 1H), 7.62 (dd, 1H), 7.91 (s, 2H) |
| 30 | [1,2,3-triazol-2-yl-(4-fluorophenyl) structure with (R)-isopropyl] | 3-[(R)-1-(5-Fluoro-2-[1,2,3]triazol-2-yl-phenyl)-ethoxy]-pyridin-2-ylamine | Brown solid, 77% | $^1$H NMR (400 MHz, CDCl$_3$): δ ppm 1.58 (d, 3H), 4.73 (bs, 2H, NH$_2$), 5.67 (dq, 1H), 6.44 (dd, 1H), 6.68 (dd,1H), 7.10 (ddd, 1H), 7.29 (dd, 1H), 7.61 (d, 1H), 7.62 (dd, 1H), 7.91 (s, 2H) |
| 31 | [pyrazol-1-yl-(4-fluorophenyl) structure] | 3-[1-(5-Fluoro-2-pyrazol-1-yl-phenyl)-ethoxy]-pyridin-2-ylamine | brown solid, 87% | $^1$H NMR (400 MHz, CDCl$_3$): δ ppm 1.54 (d, 3H), 4.70 (bs, 2H, NH$_2$), 5.48 (q, 1H), 6.46 (dd, 1H), 6.50 (m, 1H), 6.75 (dd, 1H), 7.05 (m, 1H), 7.25-7 31 (m, 2H), 7.60 (dd, 1H), 7.63 (d, 1H), 7.78 (d, 1H) |
| 32 | [2-methoxy-5-fluoropyridin-3-yl structure] | 3-[1-(5-Fluoro-2-methoxy-pyridin-3-yl)-ethoxy]-pyridin-2-ylamine | Yellow solid, 61% | $^1$H NMR (400 MHz, CDCl$_3$): δ ppm 1.62 (d, J = 6.25 Hz, 3 H) 4.02 (s, 3H) 4.89 (br. s., 2H) 5.52 (q, 1 H) 6.47 (dd, J = 7.81, 5.08 Hz, 1 H) 6.65 (d, J = 6.64 Hz, 1 H) 7.36 (dd, 1 H) 7.62 (dd, J = 5.08, 1.56 Hz, 1 H) 7.92 (d, J = 3.12 Hz, 1 H) |
| 33 | [6-fluorobenzothiazol-4-yl structure] | 3-[1-(6-Fluoro-benzothiazol-4-yl)-ethoxy]-pyridin-2-ylamine | Brown oil, 63% | $^1$H NMR (400 MHz, CDCl$_3$): δ ppm 1.80 (d, J = 6.64 Hz, 3 H) 4.83 (br. s., 2 H) 6.27 (q, 1 H) 6.40 (dd, J = 7.81, 5.08 Hz, 1 H) 6.73 (dd, J = 7.81, 1.56 Hz, 1 H) 7.29 (dd, J = 9.57, 2.54 Hz, 1 H) 7.56 (dd, J = 7.62, 2.54 Hz, 1 H) 7.61 (d, 1 H) 9.02 (s, 1 H) |
| 34 | [6-fluoroquinolin-8-yl structure] | 3-[1-(6-Fluoro-quinolin-8-yl)-ethoxy]-pyridin-2-ylamine | Yellow solid, 80% | $^1$H NMR (400 MHz, CDCl$_3$): δ ppm 1.79 (d, 3H), 4.99 (bs, 2H, NH2), 6.35 (dd, 1H), 6.64 (q, 1H), 6.68 (dd, 1H), 7.36 (dd, 1H), 7.49 (dd, 1H), 7.54 (dd, 1H), 7.57 (dd, 1H), 8.15 dd, 1H), 8.93 (dd, 1H) |

-continued

| Prep. No. | R | Name | Form, yield | Data |
|---|---|---|---|---|
| 35 | Br, F (phenyl) | 3-[1-(2-Bromo-5-fluoro-phenyl)-ethoxy]-pyridin-2-ylamine | Pink solid, 70% | ¹H NMR (400 MHz, CDCl₃): δ ppm 1.65 (d, J = 6.64 Hz, 3 H) 4.76 (br. s., 2 H) 5.45-5.62 (m, 1 H) 6.47 (dd, J = 7.81, 5.08 Hz, 1 H) 6.56 (dd, J = 8.01, 1.37 Hz, 1 H) 6.83-6.94 (m, 1 H) 7.13 (dd, J = 9.18, 2.93 Hz, 1 H) 7.53 (dd, J = 8.79, 5.27 Hz, 1 H) 7.63 (dd, J = 5.08, 1.17 Hz, 1 H) |
| 36 | O(Me), F (phenyl) | 3-[1-(5-Fluoro-2-methoxy-phenyl)-ethoxy]-pyridin-2-ylamine | Brown solid, 85% | ¹H NMR (400 MHz, CDCl₃): δ ppm 1.59 (d, J = 6.25 Hz, 3 H) 3.88 (s, 3H) 4.78 (br. s, 2 H) 5.63 (d, J = 6.25 Hz, 1 H) 6.44 (dd, J = 7.81, 5.08 Hz, 1 H) 6.65 (dd, J = 7.81, 1.56 Hz, 1 H) 6.76-6.96 (m, 2 H) 7.03 (dd, J = 8.98, 3.12 Hz, 1 H) 7.60 (dd, J = 5.08, 1.56 Hz, 1 H) |
| 37¹ | F, F (phenyl) | 3-[1-(2,5-Difluoro-phenyl)-ethoxy]-pyridin-2-ylamine | Yellow solid, 83% | ¹H NMR (400 MHz, CDCl₃): δ ppm 1.68 (d, J = 6.25 Hz, 3 H) 4.71-5.12 (m, 2 H) 5.58 (d, J = 6.64 Hz, 1 H) 6.49 (dd, J = 7.81, 5.08 Hz, 1 H) 6.74 (dd, J = 8.01, 1.37 Hz, 1 H) 6.89-6.98 (m, 1 H) 7.00-7.13 (m, 2 H) 7.62 (dd, J = 5.08, 1.56 Hz, 1 H) |

Footnote
¹Purified by automated flash chromatography ISCO ™, 40 g silica cartridge, gradient elution of ethyl acetate in heptane (0:100 to 50:50) over 30 min.

Preparation 38

5-Bromo-3-[(R)-1-(2,5-difluoro-phenyl)ethoxy]-2-nitro-pyridine

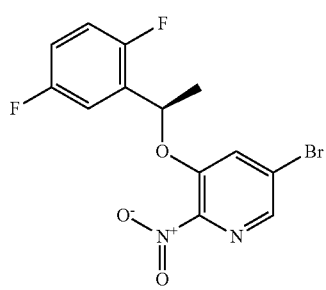 [SMILES: C[C@@H](Oc1cc(Br)cnc1[N+](=O)[O-])c1cc(F)ccc1F]

The title compound was prepared by a similar method to that of preparation 18 using commercially available 5-bromo-3-hydroxy-2-nitro-pyridine and (S)-1-(2,5-difluoro-phenyl)-ethanol except the reaction time was 1 hr and crude reaction purified by chromatography on silica gel eluting with ethyl acetate in heptane (50:50) to give a yellow oil (21.0 g, 93%).

¹H NMR (400 MHz, CDCl₃): δ ppm 1.71 (d, 3H), 5.75 (q, 1H), 7.02 (m, 1H), 7.10 (m, 1H), 7.18 (m, 1H), 7.50 (d, 1H), 8.12 (d, 1H)

Preparation 39

5-Bromo-3-[1-(2-chloro-5-fluoro-phenyl)-ethoxy]-pyridin-2-ylamine

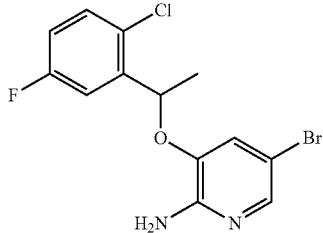

The title compound was prepared by a similar method to that of preparation 18 using commercially available 5-bromo-3-hydroxy-2-amino-pyridine and 1-(2-chloro-5-fluoro-phenyl)-ethanol (prepared according to WO 2009087305 A1) except the reaction time was 18 hr and the crude reaction was purified by chromatography on silica gel eluting initially with ethyl acetate in dichloromethane (2:98) followed by a second purification on silica gel eluting with tert-butyl methyl ether in heptane (45:55) to give a white solid (3.82 g, 49%).

¹H NMR (400 MHz, DMSO-d₆): δ ppm 1.57 (d, J=6.24 Hz, 3H) 5.74 (q, J=6.24, 1.17 Hz, 1H) 6.18 (s, 2H) 6.93 (d, J=1.95 Hz, 1H) 7.21 (td, J=8.39, 3.12 Hz, 1H) 7.45-7.59 (m, 3H)

Preparation 40

2-(1-Bromo-ethyl)-4-fluoro-benzonitrile

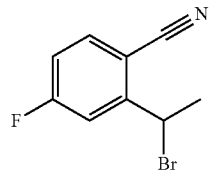

To a solution of 2-ethyl-4-fluoro-benzonitrile (prepared according to WO 07039178, page 116) (1.14 g, 7.6 mmol) in trifluoromethyl-benzene (30 mL) was added N-bromosuccinimide (1.63 g, 9.1 mmol, 1.2 eq.) followed by azobisisobutyronitrile (0.025 g, 0.15 mmol, 0.02 eq.). The mixture was heated to 100° C. for 18 hr under an atmosphere of nitrogen and then cooled to room temperature. The mixture was filtered and filtrate partitioned with aqueous sodium sulphite solution (1M, 20 mL). The organic phase was washed with water (20 mL) and then evaporated under reduced pressure to give the title compound as a beige solid (1.62 g, 93%).

$^1$H NMR (400 MHz, CDCl$_3$): δ ppm 2.05 (d, 3H), 5.5 (q, 1H), 7.1 (m, 1H), 7.4 (m, 1H), 7.6 (m, 1H)

Preparation 41

2-[1-(2-Amino-5-bromo-pyridin-3-yloxy)-ethyl]-4-fluoro-benzonitrile

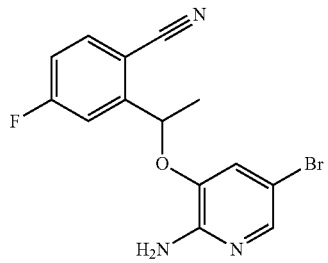 [SMILES: CC(Oc1cc(Br)cnc1N)c1cc(F)ccc1C#N]

To a rapidly stirred mixture of 5-bromo-3-hydroxy-2-amino-pyridine (1.03 g, 5.46 mmol) and tetrabutylammonium bromide (0.026 g, 0.08 mmol, 0.015 eq.) in dichloromethane (6 mL) was added an aqueous solution of sodium hydroxide (7.7M, 4.0 mL, 5.6 eq.). The mixture was stirred for 15 min before a solution of the bromide from preparation 40 (1.37 g, 6.0 mmol, 1.1 eq.) in dichloromethane (6 mL) was added and stirring continued for a further 18 hr. The resulting mixture was diluted with dichloromethane (50 mL) and partitioned with water. The organic phase was dried over magnesium sulphate and this mixture filtered. The filtrate was evaporated under reduced pressure. The residue was purified by chromatography on silica gel (300 g) eluting with a gradient of ethyl acetate in heptane (10:90 to 50:50) to give the title compound as a beige solid (1.62 g, 87%).

$^1$H NMR (400 MHz, CDCl$_3$): δ ppm 1.75 (d, 3H), 4.8 (br s, 2H), 5.6 (q, 1H), 6.8 (s, 1H), 7.1 (m, 1H), 7.2 (m, 1H), 7.7 (m, 2H)

Preparation 42

5-Bromo-3-[(R)-1-(2,5-difluoro-phenyl)ethoxy]-pyridin-2-ylamine

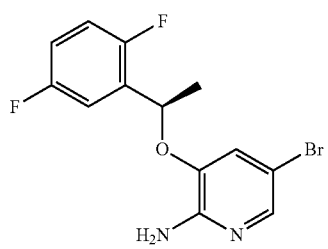 [SMILES: C[C@@H](Oc1cc(Br)cnc1N)c1cc(F)ccc1F]

The title compound was prepared by a similar method to that of preparation 28 using the nitro compound from preparation 38, except that 2M aqueous hydrochloric acid used in the work up instead of 10% aqueous citric acid, to give a white solid. (13.8 g, 92%)

$^1$H NMR (400 MHz, CDCl$_3$): δ ppm 1.70 (d, 3H), 5.15 (br s, 2H, NH2), 5.58 (q, 1H), 6.87 (d, 1H), 6.96-7.12 (m, 3H), 7.67 (d, 1H)

LRMS: APCI, m/z=329, 331 [MH]$^+$

Optical purity: 94.8% e.e. (chiral column conditions Chiralpak AD-H (250*4.6 mm i.d.), eluent 30% isopropyl alcohol in heptane, 1 mL/min, Rt=6.54 min (opposite enantiomer Rt=5.35 min)).

Preparation 43

5-Bromo-3-[(R)-1-(5-fluoro-2-methoxy-phenyl)-ethoxy]-pyridin-2-ylamine

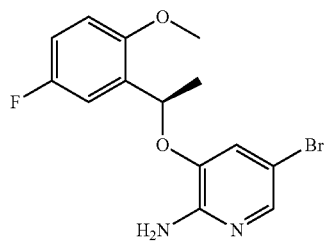 [SMILES: COc1ccc(F)cc1[C@@H](C)Oc1cc(Br)cnc1N]

To cooled (5° C.) solution of the pyridin-2-ylamine of preparation 28 (45.0 g, 172 mmol) in acetonitrile (500 mL) was added a solution of N-bromo-succinimide (30.5 g, 172 mmol, 1.0 eq.) in acetonitrile (400 mL) at such a rate as to maintain the temperature below 10° C. The resulting mixture was stirred for 5 min before evaporating under reduced pressure. The residue was dissolved in tert-butyl methyl ether (1000 mL) and washed with aqueous sodium hydroxide (2M, 3×50 mL) and aqueous sodium thiosulphate (2M, 100 mL). The organic phase was dried over magnesium sulphate and this mixture filtered. The filtrate was evaporated under reduced pressure and the resulting residue purified by chromatography on silica gel (900 g) eluting with a gradient of ethyl acetate in heptane (20:80 to 30:70) to give the title compound as a brown oil which slowly crystallizes to give a brown solid (46.0 g, 79%).

$^1$H NMR (400 MHz, CDCl$_3$): δ ppm 1.59 (d, J=6.25 Hz, 3H) 3.89 (s, 3H) 4.87 (br. s., 2H) 5.62 (m, 1H) 6.80-6.86 (m, 2H) 6.89-6.97 (m, 1H) 6.98-7.04 (m, 1H) 7.64 (d, J=1.95 Hz, 1H)

Optical purity: 98.8% e.e. (Chiral column conditions: Chiralpak IC (250*4.6 mm i.d.), eluent 30% isopropyl alcohol in heptane, 1 mL/min, Rt=6.2 min (opposite enantiomer Rt=5.0 min)).

Preparations 44 to 51

The compounds of the following tabulated preparations of the general formula:

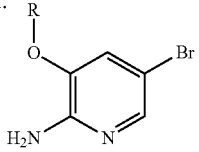

were prepared by a similar method to that of preparation 43 using the appropriate pyridin-2-ylamine starting material.

| Prep. No. | R | Name | Form, yield | Data |
|---|---|---|---|---|
| 44[1] | (1-aryl-1,2,3-triazol-2-yl group: 5-fluoro-2-[1,2,3]triazol-2-yl-phenyl) | 5-Bromo-3-[1-(5-fluoro-2-[1,2,3]triazol-2-yl-phenyl)-ethoxy]-pyridin-2-ylamine | Orange solid, 77% | $^1$H NMR (400 MHz, CDCl$_3$): δ ppm 1.57 (d, 3H), 4.75 (bs, 2H, NH2), 5.73 (q, 1H), 6.87 (d, 1H), 7.14 (ddd, 1H), 7.27 (dd, 1H), 7.63-7.67 (m, 2H), 7.92 (s, 2H) |
| 45[2] | (same as above, R-enantiomer) | 5-Bromo-3-[(R)-1-(5-fluoro-2-[1,2,3]triazol-2-yl-phenyl)-ethoxy]-pyridin-2-ylamine | Brown solid, 73% | $^1$H NMR (400 MHz, CDCl$_3$): δ ppm 1.57 (d, 3H), 4.75 (bs, 2H, NH2), 5.73 (q, 1H), 6.87 (d, 1H), 7.14 (ddd, 1H), 7.27 (dd, 1H), 7.63-7.67 (m, 2H), 7.92 (s, 2H) Optical purity: 96.1% e.e. |
| 46 | (5-fluoro-2-pyrazol-1-yl-phenyl) | 5-Bromo-3-[1-(5-fluoro-2-pyrazol-1-yl-phenyl)-ethoxy]-pyridin-2-ylamine | Orange solid, 93% | $^1$H NMR (400 MHz, CDCl$_3$): δ ppm 1.61 (d, 3H), 4.71 (bs, 2H, NH$_2$), 5.45 (q, 1H), 6.54 (m, 1H), 6.81 (d, 1H), 7.08 (m, 1H), 7.24-7.32 (m, 2H), 7.65 (d, 1H), 7.68 (d, 1H), 7.80 (d, 1H). |
| 47[3] | (5-fluoro-2-methoxy-pyridin-3-yl) | 5-Bromo-3-[1-(5-fluoro-2-methoxy-pyridin-3-yl)-ethoxy]-pyridin-2-ylamine | Yellow solid, 48% | $^1$H NMR (400 MHz, CDCl$_3$): δ ppm 1.65 (d, J = 6.25 Hz, 3 H) 4.05 (s, 3 H) 5.43 (br. s., 2 H) 5.56 (q, 1 H) 6.89 (d, J = 1.95 Hz, 1 H) 7.35 (dd, 1 H) 7.64 (d, J = 1.95 Hz, 1 H) 7.98 (d, J = 2.73 Hz, 1 H) LRMS: ESI, m/z = 360 [M + H]$^+$ |
| 48[4] | (6-fluoro-benzothiazol-4-yl) | 5-Bromo-3-[1-(6-fluoro-benzothiazol-4-yl)-ethoxy]-pyridin-2-ylamine | Pink solid, 51% | $^1$H NMR (400 MHz, CDCl$_3$): δ ppm 1.80 (d, J = 6.64 Hz, 3 H) 4.84 (br. s., 2 H) 6.25 (q, J = 6.38 Hz, 1 H) 6.91 (s, 1 H) 7.27 (m, 1 H) 7.60 (dd, J = 7.81, 2.34 Hz, 1 H) 7.67 (d, J = 1.95 Hz, 1 H) 9.04 (s, 1 H) LRMS: ESI, m/z = 368 [M + H]+ |
| 49 | (6-fluoro-quinolin-8-yl) | 5-Bromo-3-[1-(6-fluoro-quinolin-8-yl)-ethoxy]-pyridin-2-ylamine | Orange solid, 99% | $^1$H NMR (400 MHz, CDCl$_3$): δ ppm 1.72 (d, 3H), 4.77 (bs, 2H, NH$_2$), 6.57 (q, 1H), 6.81 (s, 1H), 7.31 (dd, 1H), 7.39-7.46 (m, 2H), 7.59 (s, 1H), 8.07 (dd, 1H), 8.87 (dd, 1H) |

-continued

| Prep. No. | R | Name | Form, yield | Data |
|---|---|---|---|---|
| 50 | (4-fluoro-2-methoxyphenyl with ethyl substituent) | 5-Bromo-3-[1-(5-fluoro-2-methoxy-phenyl)-ethoxy]-pyridin-2-ylamine | Brown solid, 89% | $^1$H NMR (400 MHz, CDCl$_3$): δ ppm 1.59 (d, J = 6.25 Hz, 3 H) 3.89 (s, 3 H) 4.87 (br. s., 2 H) 5.62 (m, 1 H) 6.80-6.86 (m, 2 H) 6.89-6.97 (m, 1 H) 6.98-7.04 (m, 1 H) 7.64 (d, J = 1.95 Hz, 1 H) |
| 51 | (2,5-difluorophenyl with ethyl substituent) | 5-Bromo-3-[1-(2,5-difluoro-phenyl)-ethoxy]-pyridin-2-ylamine | White solid, 61% | $^1$H NMR (400 MHz, CDCl$_3$) δ ppm 1.70 (d, 3H), 5.15 (br s, 2H, NH$_2$), 5.58 (q, 1H), 6.87 (d, 1H), 6.96-7.12 (m, 3H), 7.67 (d, 1H) |

Footnote
$^1$Purified by chromatography on silica eluting with ethyl acetate in heptane (50:50).
$^2$Chiral column conditions: Chiralpak IC (250*4.6 mm i.d.), eluent 20% isopropyl alcohol in heptane, 1 mL/min, Rt = 7.32 min (opposite enantiomer Rt = 6.13 min)).
$^3$Purified by automated flash chromatography ISCO ™, 40 g silica cartridge, gradient elution of tert-butyl methyl ether in heptane (0:100 to 60:40) over 30 min.
$^4$Purified by automated flash chromatography ISCO ™, 12 g silica cartridge, gradient elution of ethyl acetate in heptane (0:100 to 70:30) over 30 min.

Preparation 52

3-[1-(2-Bromo-5-fluoro-phenyl)-ethoxy]-5-iodo-pyridin-2-ylamine

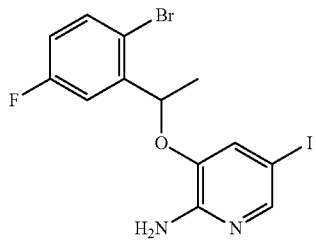 [SMILES: CC(Oc1cc(I)cnc1N)c1cc(F)ccc1Br]

To a solution of the pyridin-2-ylamine of preparation 35 (4.1 g, 13.2 mmol) in acetic acid (30 mL) was added a solution of N-iodo-succinimide (3.91 g, 16.0 mmol, 1.3 eq.). The resulting mixture was stirred at room temperature for 4 hr before evaporating under reduced pressure. The residue was dissolved in tert-butyl methyl ether (100 mL) and washed with aqueous sodium hydroxide (2M, 3×50 mL) and aqueous sodium sulphite (2M, 2×30 mL). The organic phase was dried over magnesium sulphate and this mixture filtered. The filtrate was evaporated under reduced pressure and the resulting residue purified by chromatography on silica gel (150 g) eluting with a gradient of ethyl acetate in heptane (10:90 to 30:70) to give the title compound as a brown solid (2.75 g, 47%).

$^1$H NMR (400 MHz, CDCl$_3$): δ ppm 1.59-1.69 (m, 3H) 4.79 (br. s., 2H) 5.54 (dd, J=6.25, 1.17 Hz, 1H) 6.82 (d, J=1.56 Hz, 1H) 6.87-6.97 (m, 1H) 7.10 (dd, J=9.37, 3.12 Hz, 1H) 7.56 (dd, J=8.79, 5.27 Hz, 1H) 7.81 (d, J=1.56 Hz, 1H)

Preparation 53

(R)-1-(5-Fluoro-2-methoxy-phenyl)-ethanol

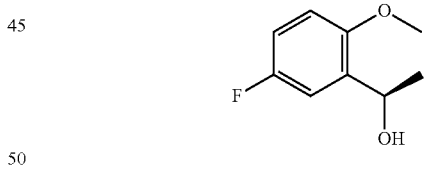

The title compound was prepared, according to the method used to make (S)-1-(5-fluoro-2-methoxy-phenyl)-ethanol from 1-(5-fluoro-2-methoxy-phenyl)-ethanone (see H. C. Brown, Tet. Letts., 35 (14), 2141-4, 1994) except that (+)-DIP-Chloride™ was used instead of (−)-DIP-Chloride™, as a white crystalline solid (63%).

$^1$H NMR (400 MHz, DMSO-d6): δ 1.25 (d, 3H), 3.78 (s, 3H), 4.94 (m, 1H), 5.11 (d, 1H), 6.94 (m, 2H), 7.19 (m, 1H)

Optical purity: >99.5% e.e. (based on SFC on a chiral column: Chiralpak IA (250*4.6 mm i.d.), eluent 5% methanol alcohol in carbon dioxide, Flow rate 4 mL/min, temp. 40° C., back pressure 150 bar, Rt=2.35 min (opposite enantiomer Rt=2.16 min))

Preparation 54

6-Chloro-4-[(R)-1-(5-fluoro-2-methoxy-phenyl)-ethoxy]-pyridazin-3-ylamine

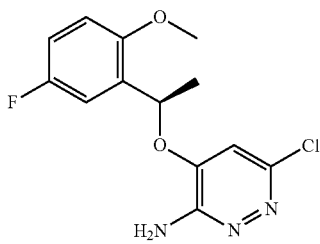 [SMILES: COc1ccc(F)cc1[C@@H](C)Oc1cc(Cl)nnc1N]

To a solution of (R)-1-(5-fluoro-2-methoxy-phenyl)-ethanol (4.78 g, 28 mmol, 1.5 eq.) in tetrahydrofuran (40 mL) was added 2-amino-4-bromo-6-chloro-pyridazine (3.9 g, 18.7 mmol) followed by a solution of sodium hexamethyldisilazide (1M in tetrahydrofuran, 28.1 mL, 1.5 eq.). This mixture was then heated to 66° C. for 18 hr before cooling and evaporating under reduced pressure. The residue was purified by chromatography on silica gel (150 g) eluting with a gradient of ethyl acetate in heptane (10:90 to 50:50) to give the title compound as a yellow solid (3.0 g, 54%).

$^1$H NMR (400 MHz, CDCl$_3$): δ ppm 1.65 (d, 3H), 3.9 (s, 3H), 5.1 (br s, 2H), 5.75 (q, 1H), 6.45 (s, 1H), 6.9-7.05 (m, 3H)

Preparation 55

6-Chloro-4-[1-(5-fluoro-2-pyrazol-1-yl-phenyl)-ethoxy]-pyridazin-3-ylamine

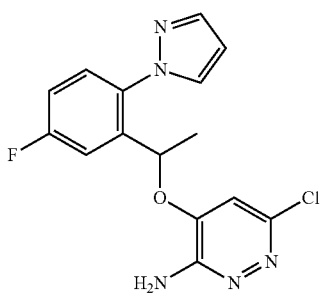 [SMILES: CC(Oc1cc(Cl)nnc1N)c1cc(F)ccc1-n1cccn1]

The title compound was prepared, by a similar method to that of preparation 54 using the alcohol from preparation 12, as a yellow solid (67%).

$^1$H NMR (400 MHz, CDCl$_3$): δ ppm 1.63 (d, 3H), 5.27 (br s, 2H); 5.72 (q, 1H); 6.55 (m, 1H), 6.71 (s, 1H), 7.13 (ddd, 1H), 7.20 (dd, 1H), 7.33 (dd, 1H), 7.69 (d, 1H), 7.82 (d, 1H)

Preparation 56

5-Bromo-3-[1-(5-fluoro-2-methoxy-phenyl)-ethoxy]-pyrazin-2-ylamine

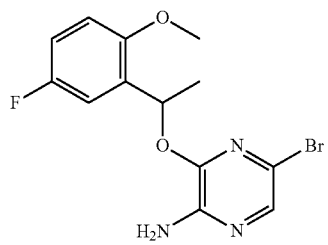 [SMILES: COc1ccc(F)cc1C(C)Oc1nc(Br)cnc1N]

To a solution of 1-(5-fluoro-2-methoxy-phenyl)-ethanol (33.6 g, 197 mmol, 1.5 eq.) in tetrahydrofuran (140 mL) was added 2-amino-3,5-dibromo-pyrazine (39.9 g, 158 mmol) followed by a solution of sodium hexamethyldisilazide (1M in tetrahydrofuran, 200 mL, 1.5 eq.). This mixture was then heated to 66° C. for 4 hr before cooling and evaporating under reduced pressure. The residue was purified by chromatography on silica gel (100 g) eluting with tert-butyl methyl ether to give an orange solid after evaporating under reduced pressure. This solid was slurried in ice cold methanol and filtered to give the title compound as a beige solid (28.4 g, 42%).

$^1$H NMR (400 MHz, CDCl$_3$): δ ppm 1.62 (d, 3H), 3.88 (s, 3H), 4.84 (br s, 2H), 6.46 (q, 1H), 6.84 (m, 1H), 6.93 (m, 1H), 7.08 (m, 1H), 7.61 (s, 1H).

LRMS: API, m/z=344.12 [MH]+

Preparation 57

5-Bromo-3-[1-(2-chloro-5-fluoro-phenyl)-ethoxy]-pyrazin-2-ylamine

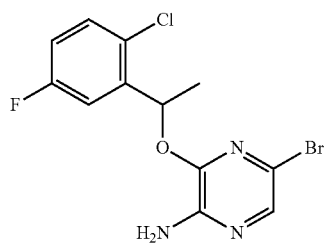 [SMILES: CC(Oc1nc(Br)cnc1N)c1cc(F)ccc1Cl]

The title compound was prepared, by a similar method to that of preparation 56 using 1-(2-chloro-5-fluoro-phenyl)-ethanol (prepared according to WO 2009087305 A1 20090716), except reaction heated to 66° C. for 16 hr and crude reaction mixture purified by automated flash chromatography ISCO™, 80 g silica cartridge, gradient elution of tert-butyl methyl ether in heptane (0:100 to 50:50) to give a yellow solid (67%).

$^1$H NMR (400 MHz, CDCl$_3$): δ ppm 1.67 (d, 3H) 4.82 (br. s., 2H) 6.42 (q, 1H) 6.95 (d t, 1H) 7.15 (dd, 1H) 7.35 (dd, 1H) 7.63 (s, 1H)

LRMS: ESI, m/z 348 [M+H]+

Preparation 58

3-[1-(5-Fluoro-2-methoxy-phenyl)-ethoxy]-5-(4,4,5,5-tetramethyl-[1,3,2]dioxaborolan-2-yl)-pyridin-2-ylamine

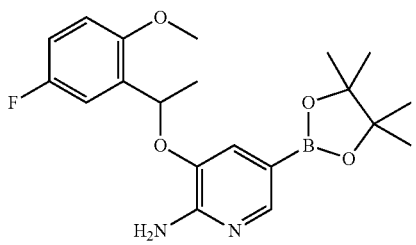 [SMILES: COc1ccc(F)cc1C(C)Oc1cc(B2OC(C)(C)C(C)(C)O2)cnc1N]

To a solution of the bromide from preparation 50 (5.89 g, 17.3 mmol) in anhydrous dimethyl sulphoxide (40 mL) was added bis(pinacolato)diboron (4.82 g, 19.0 mmol, 1.1 eq.), potassium acetate (5.08 g, 51.8 mmol, 3.0 eq.) and [1,1'-bis(diphenylphosphino)ferrocene]dichloropalladium(II) (0.63 g, 0.86 mmol, 0.05 eq.). The mixture was thoroughly degassed before heating under nitrogen at 80° C. for 16 hr. The reaction mixture was cooled, diluted with ethyl acetate (250 mL) and filtered. The filtrate was washed with water (2×250 mL) and then dried over magnesium sulphate. This mixture was filtered and the filtrate evaporated under reduced pressure to give a brown solid. This solid was triturated with diethyl ether (20 mL) and filtered to give the title compound as a brown solid (5.4 g, 80%).

$^1$H NMR (400 MHz, CDCl$_3$): δ ppm 1.29 (d, 12H), 1.60 (d, 3H), 3.92 (s, 3H), 5.06 (br s, 2H), 5.78 (q, 1H), 6.83 (dd, 1H), 6.92 (m, 1H), 7.09 (dd, 1H), 7.17 (m, 1H), 8.00 (d, 1H)

Preparation 59

1-[2-(tert-Butyl-dimethyl-silanyloxy)-ethyl]-4-methyl-1H-[1,2,3]triazole

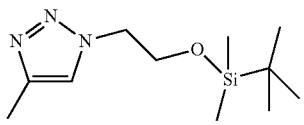 [SMILES: Cc1cn(CCO[Si](C)(C)C(C)(C)C)nn1]

To a suspension of N'-[(1Z)-2,2-dichloro-1-methylethylidene]-4-methylbenzenesulfonohydrazide (prepared according to WO2007088478 example 13) (5.0 g, 16.9 mmol) in methanol (100 mL), at 0° C. under an atmosphere of nitrogen, was added triethylamine (11.8 mL, 84.7 mmol, 5.0 eq.) over a period of 2 min. To the resulting orange solution was added a solution of 2-{[tert-butyl-(dimethyl)silyl]oxy}ethanamine (prepared according to J.O.C. 74(4), 1791-1793, 2009) (3.3 g, 18.8 mmol, 1.1 eq.) in methanol (70 ml). The reaction mixture was stirred at room temperature for 18 hr. The mixture was then evaporated under reduced pressure and the residue partitioned between tert-butyl methyl ether (250 mL) and aqueous citric acid (10% wt/vol, 100 mL). The organic phase was washed with aqueous sodium hydrogen carbonate (1M, 100 mL), saturated brine (20 mL) and dried over sodium sulphate. The resulting mixture was filtered and the filtrate concentrated under reduced pressure to give a crude brown oil. The crude oil was purified by chromatography on silica gel (200 g) eluting with a gradient of tert-butyl methyl ether in toluene (10:90 to 40:60) to give the title compound as a yellow oil (3.07 g, 75%).

$^1$H NMR (400 MHz, CDCl$_3$): δ ppm 0.00 (s, 6H), 0.90 (s, 9H), 2.39 (s, 3H), 3.99 (t, 2H), 4.43 (t, 2H), 7.39 (s, 1H)

Preparation 60

5-Iodo-4-methyl-1-vinyl-1H-[1,2,3]triazole

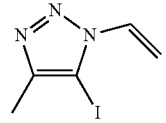

To a cold (−78° C.) solution of the triazole from preparation 59 (3.0 g, 12.4 mmol) in tetrahydrofuran (70 mL), under an atmosphere of nitrogen, was added n-butyllithium (2.5M in hexane, 5.5 ml, 14 mmol, 1.1 eq.) at such a rate as to maintain the temperature below −70° C. The resulting yellow solution was stirred at −78° C. for 2 hr before adding a solution of iodine (3.47 g, 13.7 mmol, 1.1 eq.) in tetrahydrofuran (10 mL). The resulting mixture was allowed to slowly warm to room temperature over 2 hr before concentrating the mixture by evaporation under reduced pressure. The residue was partition between tert-butyl methyl ether (150 mL) and a mixture of aqueous sodium hydrogen carbonate (1M, 50 mL) and aqueous sodium sulphite (1M, 100 ml). The organic phase was washed with saturated brine (20 mL) and dried over sodium sulphate. The resulting mixture was filtered and the filtrate concentrated under reduced pressure to give an orange solid. The crude solid was purified by chromatography on silica gel (100 g) eluting with a gradient of ethyl acetate in heptane (10:90 to 50:50) to give the title compound as a white solid (1.6 g, 55%).

$^1$H NMR (400 MHz, CDCl$_3$): δ ppm 2.37 (s, 3H), 5.27 (d, 1H), 6.18 (d, 1H), 7.11 (dd, 1H)

Preparation 61

1-[2-(tert-Butyl-dimethyl-silanyloxy)-ethyl]-4-methyl-1H-[1,2,3]triazole

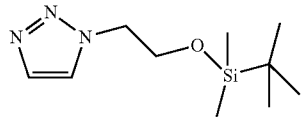

To a suspension of 1H-[1,2,3]triazole (2.0 g, 29 mmol), potassium carbonate (4.6 g, 33.4 mmol, 1.15 eq.) and sodium iodide (4.3 g, 29 mmol, 1.0 eq.) in acetonitrile (50 mL) was added a solution of (2-bromo-ethoxy)-tert-butyl-dimethylsilane (7.80 g, 33 mmol) in acetonitrile (7 mL). The resulting mixture was heated to 80° C. for 5 hr under an atmosphere of nitrogen. The mixture was cooled and filtered. The filtrate was evaporated under reduced pressure and the resulting residue partitioned between heptane (200 mL) and water (100 mL). The organic phase was washed with saturated brine solution (30 mL) and dried over sodium sulphate. The resulting mixture was filtered and the filtrate evaporated under reduced pressure to give an oil. This oil was was purified by chromatography on silica gel (100 g) eluting with a gradient of ethyl acetate in heptane (0:100 to 50:50) to give the title compound as a colourless oil (2.9 g, 44%).

¹H NMR (400 MHz, CDCl₃): δ=0.00 (s, 6H), 0.89 (s, 9H), 3.96 (t, 2H), 4.48 (t, 2H), 7.64 (s, 1H), 7.66 (s, 1H).

Preparation 62

1-[2-(tert-Butyl-dimethyl-silanyloxy)-ethyl]-5-iodo-1H-[1,2,3]triazole

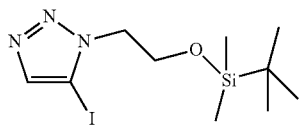 [SMILES: CC(C)(C)[Si](C)(C)OCCn1nncc1I]

The title compound was prepared, by a similar method to that of preparation 60 using the triazole of preparation 61, except that the reaction mixture was purified by chromatography on silica gel (30 g) gradient elution of diethyl ether in heptane (0:100 to 50:50) to give a white solid (59%).

¹H NMR (400 MHz, CDCl₃): δ ppm 0.00 (s, 6H), 0.87 (s, 9H), 4.16 (t, 2H), 4.62 (t, 2H), 7.83 (s, 1H)

Preparation 63

5-Iodo-1,4-dimethyl-1H-[1,2,3]triazole

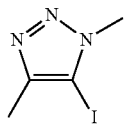

The title compound was prepared, by a similar method to that of preparation 60 using 1,4-dimethyl-1H-[1,2,3]triazole (prepared according to *bulletin des Societes Chimiques Belges*, 105(1), 45-51; 1996) (0.660 g, 6.8 mmol), except that the reaction mixture was purified by chromatography on silica gel (40 g) gradient elution of diethyl ether in heptane (0:100 to 40:60) to give a white solid (1.14 g, 75%).

¹H NMR (400 MHz, CD₃OD): δ=2.27 (s, 3H), 4.05 (s, 3H) LRMS: APCI+, m/z [MH⁺] 224.14

Preparation 64

2-(5-Iodo-pyrazol-1-yl)-ethanol

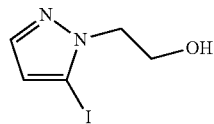

To a cold (0° C.) solution of 2-pyrazol-1-yl-ethanol (0.5 g, 4.46 mmol) in tetrahydrofuran (15 mL), under an atmosphere of nitrogen, was added N,N,N',N'-tetramethyl-ethylenenediamine (1.34 ml, 8.92 mmol, 2.0 eq.) followed by n-butyl-lithium (2.5M in hexane, 4.0 ml, 10 mmol, 2.2 eq.) at such a rate as to maintain the temperature below 5° C. The resulting yellow solution was stirred at 0° C. for 0.5 hr before adding a solution of iodine (1.36 g, 5.35 mmol, 1.2 eq.) in tetrahydrofuran (10 mL). The resulting mixture was stirred for 20 min before concentrating the mixture by evaporation under reduced pressure. The residue was partition between ethyl acetate (50 mL) and aqueous citric acid (1M, 100 ml). The organic phase was washed with 10% aqueous sodium thiosulphate solution, saturated brine (20 mL) and dried over sodium sulphate. The resulting mixture was filtered and the filtrate concentrated under reduced pressure to give a brown oil. The crude oil was purified by chromatography on silica gel (60 g) eluting with a gradient of ethyl acetate in heptane (50:50) to give the title compound as a white solid (0.4 g, 38%).

¹H NMR (400 MHz, CDCl₃): δ=3.24 (t, 1H), 4.02-4.06 (m, 2H), 4.31 (t, 2H), 6.48 (d, 1H), 7.55 (d, 1H)

Preparation 65

(4-Iodo-2-methyl-2H-pyrazol-3-yl)methanol

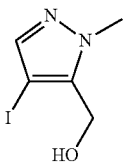

To a solution of 4-iodo-2-methyl-2H-pyrazole-3-carboxylic acid (1.0 g, 3.96 mmol) in tetrahydrofuran (10 mL), under an atmosphere of nitrogen, was added carbonyl diimidazole (0.78 g, 4.36 mmol, 1.1 eq.). The resulting mixture was stirred at room temperature for 1.5 hr before adding sodium borohydride (0.75 g, 19.8 mmol, 3.0 eq.) followed by a solution of methanol in tetrahydrofuran (5 mL), dropwise over a period of 10 min. The resulting mixture was stirred for 3 hr before quenching with 2M aqueous hydrochloric acid (30 mL). This mixture was partition with ethyl acetate (50 mL). The organic phase was washed with 1M aqueous sodium hydrogen carbonate (20 mL), saturated brine (20 mL) and dried over sodium sulphate. The resulting mixture was filtered and the filtrate concentrated under reduced pressure to give the title compound as a brown oil (0.56 g, 60%).

¹H NMR (400 MHz, DMSO-d6) δ ppm 3.87 (s, 3H) 4.48 (d, J=5.47 Hz, 2H) 5.30 (t, 1H) 7.42 (s, 1H)

Preparation 66

5-Iodo-1-methyl-1H-pyrazole-4-carbaldehyde

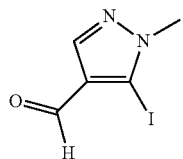

To a cooled (0° C.) solution of 5-iodo-1-methyl-1H-pyrazole (1.3 g, 6.3 mmol) in dimethyl formamide (2 mL), under an atmosphere of nitrogen, was added phosphorus oxychloride (1.72 mL, 18.8 mmol, 3.0 eq.). The resulting mixture was

Preparation 67

(5-Iodo-thiazol-4-yl)-methanol

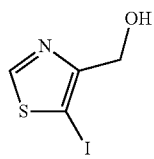

To a solution of 5-iodo-thiazole-4-carboxylic acid methyl ester (0.50 g, 2.25 mmol) in tetrahydrofuran (5 mL), under an atmosphere of nitrogen, was added lithium borohydride (358 mg, 4.5 mmol, 6.0 eq.) followed by methanol (5 mL) [caution: vigorous effervescence ocurrs]. The reaction mixture was stirred at room temperature for 18 hr before partitioning between ethyl acetate (80 mL) and water (80 mL). The organic phase was dried over magnesium sulphate. The resulting mixture was filtered and the filtrate evaporated under reduced pressure to give a yellow oil. The crude oil was purified by chromatography on silica gel (30 g) eluting with a gradient of ethyl acetate in heptane (10:90 to 50:50) to give the title compound as a white waxy solid (0.185 g, 42%).

$^1$H NMR (400 MHz, CDCl$_3$): δ ppm 4.80 (s, 2H), 8.80 (2, 1H)

Preparation 68

4-Methoxy-1-methyl-1H-pyrazole

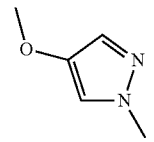

To a solution of 4-hydroxy-1H-pyrazole (0.20 g, 2.37 mmol) in 1-methyl-2-pyrrolidone (2 mL), under an atmosphere of nitrogen, was added sodium hydride (60% wt/wt in mineral oil, 210 mg, 5.23 mmol, 2.2 eq.) [Caution: vigorous effervescence ocurrs]. The reaction mixture was stirred at room temperature for 20 min before adding methyl iodide (0.37 mL, 5.95 mmol, 2.5 eq.). The resulting mixture was stirred for a further 4 hr before partitioning between ethyl acetate (80 mL) and water (80 mL). The organic phase was dried over magnesium sulphate. The resulting mixture was filtered and the filtrate evaporated under reduced pressure to give a yellow oil (680 mg). The crude oil was purified by chromatography on silica gel (30 g) eluting with a gradient of ethyl acetate in heptane (10:90 to 50:50) to give the title compound as a colourless oil (60 mg, 22%).

stirred at room temperature for 4 hr before partitioning between ethyl acetate (80 mL) and 2M aqueous potassium carbonate (80 mL). The aqueous layer was extracted again with ethyl acetate (80 mL). The organic extracts were combined and washed with water (3×50 mL) and then dried over magnesium sulphate. The resulting mixture was filtered and the filtrate evaporated under reduced pressure to give the title compound as an orange solid (0.58 g, 39%).

LRMS: ESI, m/z 337 [M+H]$^+$ $^1$H NMR (400 MHz, CD$_3$OD): δ ppm 3.72 (s, 3H) 3.78 (s, 3H) 7.17 (s, 1H) 7.30 (d, J=1.17 Hz, 1H)

Preparation 69

5-Iodo-4-methoxy-1-methyl-1H-pyrazole

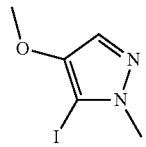

The title compound was prepared, by a similar method to that of preparation 60 using the triazole of preparation 68, except that the reaction mixture was purified by chromatography on silica gel (40 g) gradient elution of diethyl ether in heptane (0:100 to 40:60) to give a yellow solid (1.79 g, 84%).

$^1$H NMR (400 MHz, CD$_3$OD): δ ppm 3.79 (s, 3H) 3.83 (s, 3H) 7.33 (s, 1H)

Preparation 70

5-Bromo-1,4-dimethyl-1H-imidazole

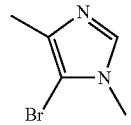

To a cooled (0° C.) suspension of sodium hydride (60% wt/wt in mineral oil, 149 mg, 3.73 mmol, 1.2 eq.) in anhydrous tetrahydrofuran (10 mL), under an atmosphere of nitrogen, was added a solution of 5-bromo-4-methyl-1H-imidazole (500 mg, 3.11 mmol) in tetrahydrofuran (5 mL). The resulting mixture was stirred at room temperature for 30 min before adding methyl iodide (661 mg, 4.66 mmol, 1.5 eq.). The reaction mixture was stirred for 30 min before partitioning between ethyl acetate (100 mL) and water (20 mL). The organic phase was dried over magnesium sulphate and the resulting mixture filtered. The filtrate was evaporated under reduced pressure and the resulting residue purified by chromatography on silica gel (40 g) eluting with a gradient of methanol in dichloromethane (0:100 to 5:95) to give the title compound as a clear oil (80 mg, 15%).

$^1$H NMR (400 MHz, CDCl$_3$): δ=2.10 (s, 3H), 3.59 (s, 3H), 7.53 (s, 1H)

MS: APCI+ m/z=174, 176 [MH+]

Preparation 71

3-(4-Bromo-3,5-dimethyl-pyrazol-1-yl)-propane-1,2-diol

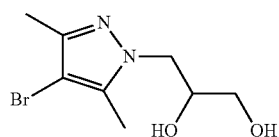

To a solution of 1-allyl-4-bromo-3,5-dimethyl-1H-pyrazole (3.07 g, 14.2 mmol) in a mixture of acetone (20 mL) and water (11 mL) was added pyridine (1 mL), potassium osmate (VI) dihydrate (0.105 g, 0.28 mmol, 0.02 eq.) and 1-methyl morpholine N-oxide (3.88 g, 28 mmol, 2.0 eq.). The resulting mixture was heated to 50° C. for 5 hr before evaporating under reduced pressure to give a brown solid. This solid was slurried with hot toluene (25 mL) and filtered, the filtrate was allowed to cool and resulting crystals filtered off and washed with toluene: isopropyl alcohol (2:1 by volume, 2×5 mL). The resulting crystals were air dried to give the title compound as tan crystals (1.78 g, 50%).

$^1$H NMR (400 MHz, CD$_3$OD): δ ppm 2.14 (s, 3H), 2.27 (s, 3H), 3.44-3.53 (m, 2H), 3.93 (m, 1H), 4.02 (dd, 1H), 4.13 (dd, 1H)

MS: APCI+, m/z=249.16 [MH$^+$]

Preparation 72

1-(2-{[tert-butyl (di methyl)silyl]oxy}ethyl)-3,5-di methyl-4-(4,4,5,5-tetramethyl-1,3,2-dioxaborolan-2-yl)-1H-pyrazole

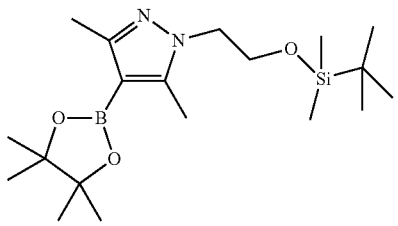 [SMILES: Cc1nn(CCO[Si](C)(C)C(C)(C)C)c(C)c1B1OC(C)(C)C(C)(C)O1]

The title compound was prepared, by a similar method to that of preparation 61 using 3,5-dimethyl-4-(4,4,5,5-tetramethyl-1,3,2-dioxaborolan-2-yl)-1H-pyrazole, except that the reaction mixture was purified by chromatography on silica gel (75 g) eluting with a gradient of tert-butyl methyl ether in heptane (10:90 to 50:50) followed by 10% ethyl acetate to give a yellow solid (865 mg, 50%).

$^1$H NMR (400 MHz, CDCl$_3$): δ ppm 0.00 (s, 6H), 0.90 (s, 9H), 1.38 (s, 12H), 2.39 (s, 3H), 2.48 (s, 3H), 3.98 (t, 2H), 4.15 (t, 2H)

Preparation 73

4-Fluoro-5-iodo-1-methyl-1H-pyrazole

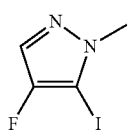

The title compound was prepared, by a similar method to that of preparation 60 using 4-fluoro-1-methyl-1H-pyrazole, except that the reaction mixture was purified by chromatography on silica gel (30 g) gradient elution of diethyl ether in heptane (0:100 to 50:50) to give an orange solid (52%).

$^1$H NMR (400 MHz, CDCl$_3$): δ ppm 3.87 (d, J=0.78 Hz, 3H) 7.37 (d, J=4.69 Hz, 1H)

Preparation 74

6-Bromo-1-benzothiophen-3(2H)-one 1,1-dioxide

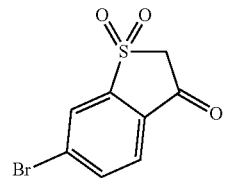 [SMILES: O=C1CS(=O)(=O)c2cc(Br)ccc21]

To a solution of methyl 4-bromo-2-(methylsulfonyl)benzoate (774 mg, 2.64 mmol) in anhydrous THF (10 mL) was added NaH (60% in mineral, 111 mg, 2.77 mmol). The mixture was stirred at room temperature for 5 hr. The reaction was monitored by LCMS for completion. H$_2$O (1 mL) was added to quench the reaction followed by the addition of aqueous hydrochloric acid (1N, 50 mL) and EtOAc (50 mL). The organic layer was separated, and the water layer was extracted with 2×EtOAc. The combined organic layers were washed with brine, dried over sodium sulfate, filtered, and concentrated to give the title compound (689 mg, 100%) as a white solid.

$^1$H NMR (400 MHz, DMSO-d$_6$) δ ppm 4.62 (s, 2H), 7.92 (d, J=8.34 Hz, 1H), 8.14 (dd, J=8.21, 1.14 Hz, 1H), 8.53 (s, 1H).

Preparation 75

6-Bromo-2,3-dihydrobenzo[b]thiophen-3-ol-1,1 dioxide

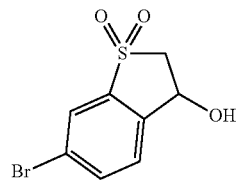

To a suspension of preparation 74 (427 mg, 1.64 mmol) in MeOH (15 mL) and DCM (7 mL) was added NaBH$_4$ (30.9 mg, 0.818 mmol) at 0° C. The mixture was stirred at 0° C. to room temperature for 1.5 hr. The reaction was quenched with H$_2$O at 0° C., extracted with EtOAc (2×30 mL), dried over sodium sulfate, filtered, and concentrated to provide the title compound (391 mg, 90.9%) as a white solid.

$^1$H NMR (400 MHz, DMSO-d$_6$) δ ppm 3.37 (dd, J=13.64 Hz, 5.05 Hz, 1H), 4.05 (d, J=7.07 Hz, 1H), 5.38 (q, J=6.23 Hz, 1H), 6.38 (d, J=6.06 Hz, 1H), 7.63 (d, J=8.08 Hz, 1H), 7.94 (dd, J=8.08, 1.77 Hz, 1H), 8.05 (d, J=1.77 Hz, 1H). MS: ESI+ m/z 263 [M+H]+.

Preparation 76

2-(4-bromo-2-(methylsulfonyl)phenyl)propan-2-ol

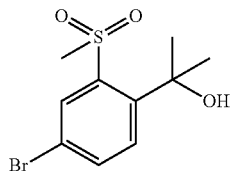

To a cooled (0° C.) solution of 4-bromo-2-(methylsulfonyl)benzoate (603 mg, 2.06 mmol) in THF (12 mL) was added a THF solution of MeMgBr (3M, 2.06 mL, 6.17 mmol). The reaction was stirred at room temperature for overnight. LCMS showed the starting material was consumed completely. The reaction was quenched with the slow addition of saturated aqueous NH$_4$Cl (10 mL), diluted with EtOAc (50 mL) and water (25 mL), extracted twice more with EtOAc (35 mL), dried over sodium sulfate, filtered, concentrated, and purified with a silica gel column by ISCO CombiFlash® chromatography eluting with 0%-30% EtOAc/Heptane to give the title compound (327 mg, 54.2%) as a white solid.

$^1$H NMR (400 MHz, DMSO-d$_6$) δ ppm 1.62 (s, 6H), 3.44 (s, 3H), 5.51 (s, 1H), 7.58 (d, J=8.59 Hz, 1H), 7.84 (dd, J=8.59, 2.27 Hz, 1H), 8.20 (d, J=2.27 Hz, 1H).

Preparation 77

(5-Bromo-6-methoxypyridin-2-yl)methanol

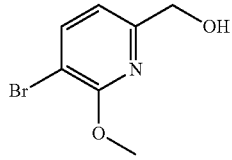

To a solution of methyl 5-bromo-6-methoxypicolinate (249 mg, 1.01 mmol) in dichloromethane (10 mL) added DIBAL-H in CH$_2$Cl$_2$ (1M, 3.04 mL) at −78° C. The reaction was immediately warmed to room temperature then stirred at room temperature for 1 hr. LCMS indicated that the reaction was complete. To the reaction mixture was added saturated aqueous NaK tartrate. It was stirred for 30 min. The reaction mixture was extracted with CH$_2$Cl$_2$ (3×20 mL). The combined organic layers were dried over sodium sulfate, filtered, and concentrated under reduced pressure to afford the title compound as a white solid (205 mg, 93.3%).

$^1$H NMR (400 MHz, CHLOROFORM-d) δ ppm 3.21 (br. s., 1H), 4.01 (s, 3H), 4.62 (s, 2H), 6.75 (d, J=7.58 Hz, 1H), 7.76 (d, J=7.83 Hz, 1H). MS: ESI+ m/z 218 [MH]+.

Preparation 78

5-Bromo-6-methoxypicolinaldehyde

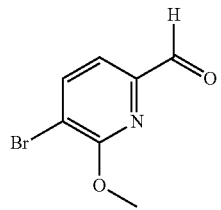

(5-Bromo-6-methoxypyridin-2-yl)methanol of preparation 77 (92 mg, 0.42 mmol) was dissolved in DCM (5 ml). MnO$_2$ (477 mg, 5.49 mmol) was added. The reaction was stirred under nitrogen at room temperature for overnight. LCMS showed ~30% of the starting material remained, and the reaction continued for another 5 hr at which time ~15% of the starting material remained by LCMS. The reaction mixture was filtered and the filtrate was evaporated to dryness in vacuo. A brownish solid was obtained (69 mg) which was used in the next step without further purification.

Preparation 79

(5-Bromo-6-methoxypyridin-2-yl)-N-methylmethanamine

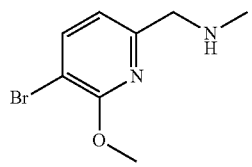

5-Bromo-6-methoxypicolinaldehyde of preparation 78 (69 mg, 0.32 mmol) in a solution of NH$_2$CH$_3$ in THF (2M, 3 mL) was stirred under nitrogen at room temperature for 45 mins, and LCMS showed a mass of 230 which indicated the presence of the iminium ion. Sodium borohydride (36.2 mg, 0.957 mmol) was added, and the reaction was stirred at room temperature overnight. The desired product was detected by LCMS, and the reaction was quenched with MeOH (0.5 mL) and water (10 ml), then partitioned with EtOAc (10 mL). The organic layer was dried over sodium sulfate, filtered and evaporated to give the title compound as a yellow oil (47 mg), which was taken into the next step without further purification.

MS: ESI+ m/z 231 [MH]+.

Preparation 80

2-Bromo-1-methoxy-4-(methylsulfonyl)benzene

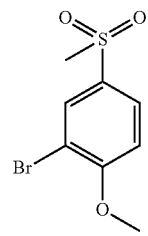

To a solution of 2-bromo-4-(methylsulfonyl)phenol (243 mg, 0.968 mmol) and K₂CO₃ (201 mg, 1.45 mmol) in DMF (2 mL) was added CH₃I (0.0660 mL, 1.06 mmol). The reaction was stirred at room temperature for overnight, diluted reaction with EtOAc (10 mL) and water (10 mL). The organic layer was separated, and the aqueous layer extracted again with EtOAc (15 mL). The combined organic layers were washed with brine, dried over sodium sulfate, filtered, concentrated, and purified with a silica gel column by ISCO CombiFlash® chromatography eluting with 10%-40% EtOAc/Heptane to afford the desired product (168 mg, 65.5%) as a white solid.

$^1$H NMR (400 MHz, CHLOROFORM-d) δ ppm 3.02 (s, 3H), 3.95 (s, 3H), 7.00 (d, J=8.84 Hz, 1H), 7.83 (dd, J=8.84, 2.27 Hz, 1H), 8.06 (d, J=2.27 Hz, 1H). MS: ESI+ m/z 265 [MH]+.

Preparation 81

5-Bromo-N-methylpyrimidine-2-carboxamide

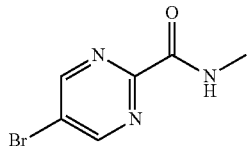

Methyl 5-bromopyrimidine-2-carboxylate (94 mg, 0.43 mmol) was dissolved in a mixture of methanol (1 mL) and tetrahydrofuran (2 mL). An aqueous solution of methylamine (40%, 0.5 mL) was added. The reaction was stirred at room temperature for three days, and was evaporated to dryness in vacuo. The title compound was obtained as a white solid (94 mg).

$^1$H NMR (400 MHz, DMSO-d₆) δ ppm 2.81 (d, J=4.80 Hz, 3H), 8.89 (br. s., 1H), 9.13 (s, 2H). MS: ESI+ m/z 216 [MH]+.

Preparation 82

(R)-1-(4-(4,4,5,5-tetramethyl-1,3,2-dioxaborolan-2-yl)phenyl)ethanamine HCl salt

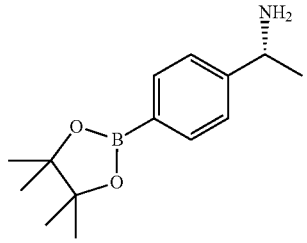 [SMILES: C[C@@H](N)c1ccc(B2OC(C)(C)C(C)(C)O2)cc1]

(R)-tert-butyl 1-(4-(4,4,5,5-tetramethyl-1,3,2-dioxaborolan-2-yl)phenyl)ethylcarbamate (727 mg, 2.09 mmol) was dissolved in CH₂Cl₂ (4 mL) and a solution of HCl in dioxane (4M, 4 mL). The mixture was stirred at room temperature for overnight. LCMS indicated the reaction was complete. The reaction solution was concentrated in vacuo to afford the title compound as a white solid (1.00 g).

$^1$H NMR (400 MHz, DMSO-d₆) δ ppm 1.29 (s, 12H), 1.49 (d, J=6.82 Hz, 3H), 4.34-4.43 (m, 1H), 7.51 (d, J=8.08 Hz, 2H), 7.71 (d, J=8.08 Hz, 2H), 8.54 (br. s., 2H).

Preparation 83

Ethyl 4-methylthiazole-2-carboxylate

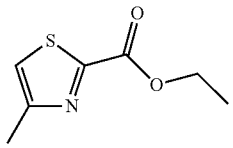

1-Chloropropan-2-one (0.334 mL, 4.20 mmol) and methyl 2-amino-2-thioxoacetate (500 mg, 4.20 mmol) was dissolved in EtOH. The reaction solution was heated to 80° C. for overnight, cooled to RT, concentrated and purified with a silica gel column by ISCO CombiFlash® chromatography eluting with 10%-35% EtOAc/Haptane to give the title compound as a yellowish oil (243 mg, 33.8%) as the ethyl ester. A methyl ester product was isolated as a yellow solid (104 mg, 15.8%).

$^1$H NMR (400 MHz, CHLOROFORM-d) δ ppm 1.36 (t, J=7.07 Hz, 3H), 2.47 (s, 3H), 4.40 (q, J=7.24 Hz, 2H), 7.14 (d, J=0.76 Hz, 1H). MS: ESI+ m/z 172 [MH]+.

Preparation 84

Ethyl 5-bromo-4-methylthiazole-2-carboxylate

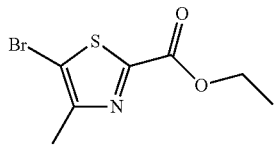

The reaction solution of ethyl 4-methylthiazole-2-carboxylate of preparation 83 (240 mg, 1.40 mmol), NBS (277 mg, 1.14 mmol) in CH₃CN (5 mL) was heated at 50° C. for overnight under nitrogen. ~20% starting material was present by LCMS. Additional portion of NBS (70 mg) was added. The reaction solution was heated at 60° C. for 4 hr, diluted with EtOAc (30 ml), washed with water (2×20 mL), brine, dried over sodium sulfate and purified with a silica gel column by ISCO CombiFlash® chromatography eluting with 0%-20% EtOAc/Heptane to give the title compound as a yellowish oil (177 mg, 50.5%).

$^1$H NMR (400 MHz, CHLOROFORM-d) δ ppm 1.37-1.44 (m, 3H), 2.49 (s, 3H), 4.38-4.50 (m, 2H). MS: ESI+ m/z 250 [MH]+.

Preparation 85

5-bromo-N,4-dimethylthiazole-2-carboxamide

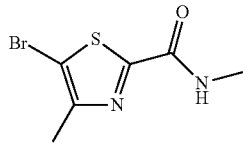

Ethyl 5-bromo-4-methylthiazole-2-carboxylate of preparation 84 (177 mg, 0.708 mmol) was dissolved in a mixture of methanol (2 mL) and tetrahydrofuran (2 mL). Methylamine (40% in water, 1.0 mL) was added. The reaction was stirred at room temperature for 72 hours. The reaction judged to be complete by LCMS. It was evaporated to dryness in vacuo. A white solid (180 mg) was obtained which contained ~40% of the title compound based on LCMS, and was taken into the next step without further purification.

MS: ESI+ m/z 235 [MH]+.

Preparation 86

2-(5-Bromo-4-methylthiazol-2-yl)propan-2-ol

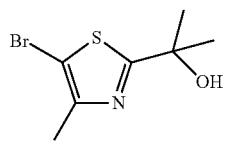

2-(4-Methylthiazol-2-yl)propan-2-ol (321 mg 2.04 mmol) and NBS (404 mg 2.25 mmol) was stirred in DMF (10 mL) at room temperature for 2 hours under nitrogen. The mixture was diluted with EtOAc (50 mL) and washed with water (2×20 ml), then brine, dried over sodium sulfate and concentrated to give an oil which was purified by ISCO CombiFlash® chromatography eluting with Heptane:EtOAc (100:0 to 0:100 over 20 CV) to the product as a pale yellow oil (296 mg 61%).

$^1$H-NMR (400 MHz, CDCl$_3$): δ ppm 1.64 (s, 6H), 2.37 (s, 3H), 2.74 (s, 1H). MS: m/z 235/237 [MH]$^+$.

Preparation 87

(4-Ethylthiazol-2-yl)methanol

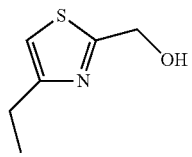

Ethyl 4-ethylthiazole-2-carboxylate (500 mg 2.27 mmol) was stirred in methanol (20 mL) under nitrogen. Sodium borohydride (230 mg 6.07 mmol) was added in portions and the resulting solution stirred for a further 3 hours. The methanol was removed under vacuum and the residue dissolved in ethyl acetate (40 mL), washed with water, dried over sodium sulfate and concentrated to give the title product as a colorless oil (350 mg, 91%).

$^1$H-NMR (400 MHz, CDCl$_3$): δ ppm 1.30 (t, 3H), 2.79 (q, J=7.41 Hz, 2H), 3.44 (br. s., 1H), 4.92 (d, J=2.27 Hz, 2H), 6.86 (s, 1H).

Preparation 88

(5-Bromo-4-ethylthiazol-2-yl)methanol

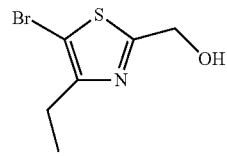

(4-Ethylthiazol-2-yl)methanol of preparation 87 (350 mg 2.44 mmol) was brominated as for the methyl analogue of preparation 86 to give the title compound as a white solid (428 mg, 79%). $^1$H-NMR (400 MHz, CDCl$_3$): δ ppm 1.26 (t, J=7.58 Hz, 3H), 2.61 (t, J=6.19 Hz, 1H), 2.74 (q, J=7.58 Hz, 2H), 4.87 (d, J=6.06 Hz, 2H). MS: m/z 221.9/223.9 [MH]$^+$.

Preparation 89

5-Bromo-2-(methylthiomethyl)thiazole

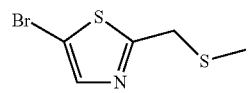

5-Bromo-2-(chloromethyl)thiazole (177 mg, 0.833 mmol) was stirred in DMF (10 mL) under nitrogen at room temperature and sodium thiomethoxide (117 mg, 1.67 mmol) was added. The mixture was stirred overnight and concentrated. The residue was slurried in ethyl acetate (30 ml), washed with water, dried over sodium sulfate, and concentrated to give a brown oil which was purified by ISCO CombiFlash® chromatography with Heptane:DCM (100:0 to 0:100 over 10 column volume and held for a further 10 CV to give the product as a brown oil (53 mg 28%).

$^1$H-NMR (400 MHZ, CDCL$_3$): δ PPM 2.16 (S, 3H), 3.94 (S, 2H), 7.56 (S, 1H). MS: M/Z 223.9/226.0 [MH]$^+$.

Preparation 90

5-Bromo-2-(methylsulfonylmethyl)thiazole

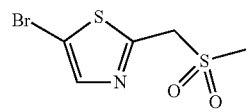

5-Bromo-2-(methylthiomethyl)thiazole of preparation 89 (53 mg, 0.24 mmol) was stirred in DCM (10 mL) under nitrogen. mCPBA (122 mg 0.543 mmol) was added and the clear solution was stirred for 3 hours, washed with NaHCO$_3$, water and brine, and dried over sodium sulfate. The solvent was removed in vacuo to provide the title compound as a white solid (78 mg, 130%) which was used without further purification.

¹H-NMR (400 MHZ, CDCL₃): δ 2.98 (S, 3H), 4.58 (S, 2H), 7.76 (S, 1H). MS: M/Z 255.85/257.80 [MH]⁺.

Preparation 91

1-(5-Bromo-thiazol-2-yl)-ethanol

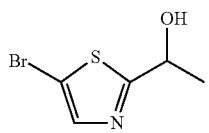

To an ice cold solution of 5-bromothiazole-2-carbaldehyde (3 g, 15.6 mmol) in diethyl ether (20 mL) was added a THF solution of MeMgBr (3M, 50 ml, 150 mmol). Solid was produced rapidly. LCMS showed a new product with desired mass. The reaction was quenched with saturated aqueous ammonium chloride solution, extracted with ethyl acetate, dried over sodium sulfate, filtered and concentrated under reduced pressure. The residue was purified by ISCO Combi-Flash® chromatography eluting 10-40% ethyl acetate in heptanes. The title compound was obtained as a viscous yellow oil (3.25 g, 62% yield).

Preparation 92

4-Bromo-3,5-dimethyl-1-(methylthiomethyl)-1H-pyrazole

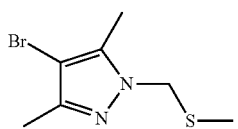

To a solution of 4-bromo-3,5-dimethyl-1H-pyrazole (2.10 g, 14.3 mmol) in acetone (20 mL) was added K₂CO₃ (2.37 g, 17.1 mmol) followed by chloromethyl methyl sulfide (1.3 mL, 5.7 mmol). The light yellow suspension was stirred at room temperature for 96 hr. At this time the reaction was thick with white precipitate. The reaction mixture was stripped off volatiles, diluted with methylene chloride and filtered. The filtrate was concentrated under reduced pressure to give the title compound as a light yellow oil which was used without further purification.

Preparation 93

4-bromo-3,5-dimethyl-1-(methylsulfonyl methyl)-1H-pyrazole

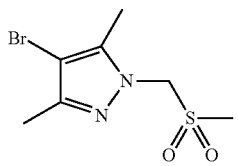

Oxone (9.25 g, 14 mmol) was added portion-wise to a solution of 4-bromo-3,5-dimethyl-1-(methylthiomethyl)-1H-pyrazole of preparation 91 (2.56 g, 10.9 mmol) in methanol/water at 0° C. The reaction solution was stirred at 0° C. for 30 min, then slowly warmed to room temperature overnight. The reaction was thick with white precipitate, which was concentrated to roughly 20 mL, poured into water and filtered the white solid. The solid was washed with water and air dried to give the title compound as a white solid (1.2 g, 41% yield)
¹H-NMR (400 MHz, CDCl₃) δ ppm 5.16 (s, 2H), 2.95 (s, 3H), 2.37 (s, 3H), 2.23 (s, 3H).

Preparation 94

4-Methylthiazole-2-carbaldehyde

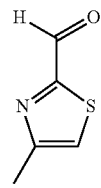

To a solution of 4-methylthiazole (9 g, 90.9 mmol) in dry THF (200 mL) was added n-BuLi (2.5 M, 54.5 mL, 136.4 mmol) drop-wise at −70° C., and the mixture was stirred at −70° C. for 1.5 hour, DMF (11 mL) was added to the slurry over 15 min, and the mixture was slowly warmed to room temperature and stirred overnight. TLC (petroleum ether: EtOAc 10:1) indicated the reaction was completed. The mixture was warmed to 0° C., and quenched by saturated NH₄Cl solution (100 mL). The mixture was acidified by 2N HCl to pH~4, and extracted with EtOAc (100 mL×3). The combined organic layers were washed with brine (150 mL), dried over sodium sulfate, and concentrated in vacuum to give the title compound as a brown oil (7.0 g, 60.8%).

Preparation 95

1-(4-Methylthiazol-2-yl)ethanol

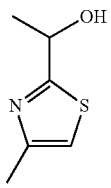

To a solution of 4-methylthiazole-2-carbaldehyde of preparation 94 (5.8 g, 45.6 mmol) in anhydrous THF (100 mL) was added a THF solution of MeMgBr (3M, 30.4 mL, 91.3 mmol) drop-wise at −60° C. under N₂, and the mixture was warmed to room temperature and stirred for another 2 hours. TLC (petroleum ether:EtOAc 2:1) showed the reaction was completed. The mixture was quenched by saturated NH₄Cl solution (120 mL), and extracted with EtOAc (100 mL×3). The combined organic extracts were washed with brine (50 mL), dried over sodium sulfate and concentrated in vacuum to give the residue which was purified by a silica gel column eluting with petroleum ether:EtOAc=20:1-8:1 to give the title compound as a yellow oil (3.4 g, 50%).

Preparation 96

1-(5-Bromo-4-methylthiazol-2-yl)ethanol

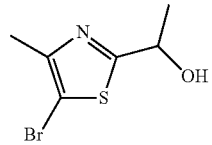

To a solution of 1-(4-methylthiazol-2-yl)ethanol of preparation 95 (3.3 g, 22.9 mmol) in DMF (80 mL) was added NBS (4.47 g, 25.2 mmol), and the mixture was stirred at 50° C. for 2 hours. TLC (petroleum ether:EtOAc 3:1) indicated the reaction was completed. The mixture was diluted with H$_2$O (100 mL) and extracted with EtOAc (80 mL×3). The combined organic extracts were washed with brine (80 mL×3), dried over sodium sulfate, and concentrated in vacuum to give the residue which was purified by a silica gel column eluting with petroleum ether:EtOAc=25:1-5:1 to give the title compound as a yellow solid (3.7 g, 74%).

$^1$H-NMR (400 MHz, CDCl$_3$): δ ppm 4.93-4.97 (q, 1H), 2.29 (m, 1H), 7.04-7.07 (s, 3H), 1.51-1.53 (d, 3H). MS: m/z 223.7 [MH]+.

Preparation 97

(2-Bromo-4-methylthiazol-5-yl)methanol

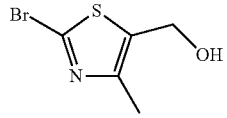

To a solution of ethyl 2-bromo-4-methylthiazole-5-carboxylate (7 g, 28 mmol) in EtOH (120 mL) and H$_2$O (20 mL) was added portion-wise NaBH$_4$ (3.2 g, 84 mmol). After the addition, the mixture was stirred at room temperature overnight. TLC (petroleum ether/EtOAc=5:1) showed the reaction was complete. The reaction mixture was carefully concentrated in vacuum. The residue was separated between EtOAc (50 mL) and H$_2$O (50 mL). The inorganic layer was extracted with EtOAc (50 mL×2). The combined organic layers were washed with brine (100 mL), dried over sodium sulfate and concentrated in vacuum to give the title compound as a colorless oil (3.8 g, 65%).

Preparation 98

2-Bromo-4-methylthiazole-5-carbaldehyde

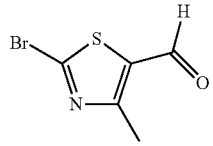

A mixture of (2-bromo-4-methylthiazol-5-yl)methanol of preparation 97 (3.8 g, 18.4 mmol) and MnO$_2$ (16.5 g, 0.18 mmol) in CHCl$_3$ (180 mL) was stirred at room temperature overnight. TLC (petroleum ether/EtOAc=3:1) showed the reaction was complete. The reaction mixture was filtered and the filtrate was concentrated in vacuum. The residue was purified by a Biotage silica gel cartridge (EA/PE=30%, Rf=0.5) to give the title compound as a white solid (1.8 g, 47%) as a white solid, and as well as impure 2-bromo-4-methylthiazole-5-carbaldehyde (1.3 g, 34%) as an off-white solid.

Preparation 99

1-(2-Bromo-4-methylthiazol-5-yl)ethanol

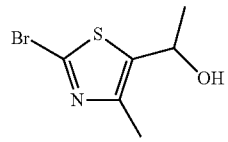

To a mixture of 2-bromo-4-methylthiazole-5-carbaldehyde of preparation 98 (1.8 g, 8.8 mmol) in dry THF (50 mL) was added dropwise MeMgBr in Et$_2$O (3M, 2.9 mL, 8.8 mmol) at −40° C. under N$_2$. After the addition, the mixture was stirred at room temperature for 1 hr. TLC (petroleum ether/EtOAc=5:1) showed most of the starting material was consumed. To the reaction mixture was added saturated NH$_4$Cl (60 mL). The mixture was extracted with EtOAc (50 mL×2). The combined organic layers were washed with brine (80 mL), dried over sodium sulfate and concentrated in vacuum. The residue was purified by a Biotage silica gel cartridge (EA/PE 48%, Rf=0.5) to give the title compound as a yellow oil (1.7 g, 87%).

$^1$H NMR (400 MHz, CDCl$_3$): δ ppm 5.09-5.06 (q, 1H), 2.29-2.28 (d, 4H), 1.46-1.45 (d, 3H). MS: m/z 223.6 [MH]+.

Preparation 99a (4-Bromo-2-(methylsulfonyl)phenyl)methanol

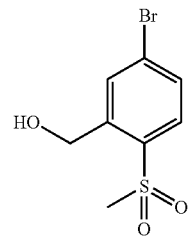

To a stirring solution of methyl 4-bromo-2-(methylsulfonyl)benzoate (1000 mg, 3.41 mmol) in THF (20 mL) at −78° C. was added DIBAL-H solution (1.0 M in hexanes, 7.50 ml, 2.20 equiv.) dropwise. The mixture was stirred for 15 min and then gradually warmed to room temperature and stirred for another 4 hour. LCMS indicated clean conversion of the starting material to the product. The reaction was quenched with sodium bicarbonate, and then concentrated to dryness. The resulting solids were stirred with DCM (100 ml) for 1 hour and then filtered. The solids were rinsed with EtOAc until the rinse was free of product. The combined filtrate were dried over sodium sulfate, concentrated to dryness to give the desired product (788 mg)

¹H NMR (400 MHz, CDCl₃) δ ppm 8.19 (d, J=2.02 Hz, 1H), 7.78 (dd, J=8.08, 2.02 Hz, 1H), 7.47 (d, J=8.08 Hz, 1H), 4.93 (d, J=6.57 Hz, 2H), 3.20 (s, 3H), 2.90 (t, J=6.69 Hz, 1H).

Preparation 100

4-(tert-butoxycarbonyl)-2-methyl-3,4-dihydro-2H-pyrido[3,2-b][1,4]oxazin-7-ylboronic acid

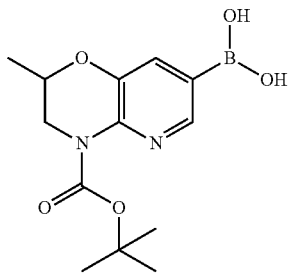 [SMILES: CC1CN(C(=O)OC(C)(C)C)c2ncc(B(O)O)cc2O1]

Butyl lithium (2.5 M in THF, 6.08 mL, 2.5 equiv.) was added dropwise into a stirring solution of 7-bromo-2-methyl-2,3-dihydro-pyrido[3,2-b][1,4]oxazine-4-carboxylic acid tert-butyl ester (2.0 g, 6.08 mmol, 1.0 equiv.) and triisopropylborate (2.86 g, 15.19 mmol, 2.5 equiv.) in anhydrous THF (20 mL) at −78° C. under nitrogen. The reaction was stirred at −78° C. and monitored with LCMS. After 2 hr, LCMS indicated the reaction complete. The reaction was quenched with water (20 mL) and concentrated under reduced pressure. The residue was washed with ether (2×10 mL) and the aqueous layer was placed in an ice-water bath. While stirring, 10 N HCl aqueous solution was carefully added dropwise until pH~7. Filtration and washing with ice-water (3×5 mils) gave the desired product as a white solid (923 mg).

MS: m/z 295.20 [MH]+

Preparation 101

1-(4-(4,4,5,5-Tetramethyl-1,3,2-dioxaborolan-2-yl)-1H-pyrazol-1-yl)propan-2-ol

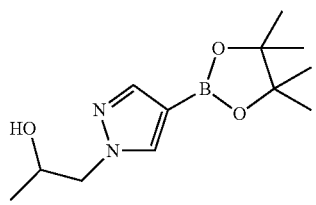 [SMILES: CC(O)Cn1cc(B2OC(C)(C)C(C)(C)O2)cn1]

A mixture of 4-(4,4,5,5-Tetramethyl-[1,3,2]dioxaborolan-2-yl)-1H-pyrazole (500 mg, 2.58 mmoles, 1.0 equiv.), 1-bromopropan-2-ol (358 mg, 2.58 mmoles, 1.0 equiv.), and cesium carbonate (1010 mg, 3.09 mmoles, 1.20 equiv.) in DMF (10 mL) was heated in an oil bath at 80° C. for 16 hours. LCMS indicated the reaction complete. The reaction was filtered and concentrated to dryness under high vacuum to give the desired product (520 mg).

MS: m/z 253.2 [MH]+

Preparation 102

1-Isopropyl-4-(4,4,5,5-tetramethyl-1,3,2-dioxaborolan-2-yl)-1H-pyrazole

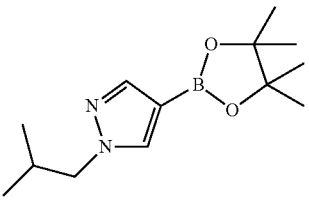

The procedure of preparation 101 was followed to provide the desired product (582 mg).

MS: m/z 237.2 [MH]+,

Preparation 102a

Tert-butyl 3-fluoro-4-(4-(4,4,5,5-tetramethyl-1,3,2-dioxaborolan-2-yl)-1H-pyrazol-1-yl)piperidine-1-carboxylate

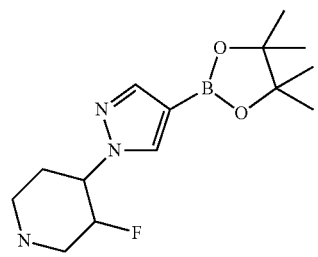 [SMILES: CC1(C)OB(c2cnn(C3CCNCC3F)c2)OC1(C)C]

The procedure of preparation 101 was followed to provide the desired product (1360 mg).

MS: m/z 340.2 [MH]+.

Preparation 103

(R)-1-(5-Fluoro-2-[1,2,3]triazol-2-yl-phenyl)-ethanol

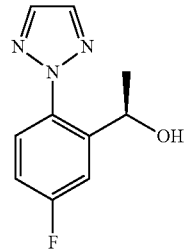

(+)-DIPCl (28.12 g, 87.7 mmol, 1.5 eq.) was dissolved at room temperature in THF (50 mL). The solution was cooled at −30° C. and a solution of the acetophenone of preparation 1 (12.03 g, 58.5 mmol, 1.0 eq.) in THF (40 mL) was added dropwise over 70 min (final temperature: −10° C.). The solution was slowly raised to 10° C. during 3.5 hr. The crude mixture was concentrated then TBME (300 mL) was added. A solution of diethanolamine (14 mL, 146.2 mmol, 2.5 eq.) in EtOH (7 mL) and THF (15 mL) was added dropwise (observe formation of white solids). The mixture was heated at reflux for 1.5 hr then stirred at RT for 18 hr. The white solids were then filtered and rinsed with TBME (400 mL). The mother liquor obtained was concentrated to afford an orange oil which was purified by column chromatography (eluants: from 100% heptane to heptane/AcOEt 7:3). The desired title compound was obtained as a yellow oil (10.65 g, 87% yield, 98% purity, 95% ee).

¹H NMR (400 MHz, CDCl₃) δ ppm 1.45 (d, 3H); 3.93 (d, 1H); 4.83-4.89 (m, 1H); 7.08-7.13 (m, 1H); 7.38 (dd, 1H); 7.62 (dd, 1H); 7.88 (s, 2H). MS: m/z 190 [MH]+. HPLC: 95% ee (Rt (major)=3.70 min; Rt (minor)=4.30 min (Chiralpak IA, 4.6×250 mm, heptane/EtOH 50/50, 1 mL/min, 25° C., 275 nm).

Preparation 104

5-Bromo-3-[(R)-1-(5-fluoro-2-[1,2,3]triazol-2-yl-phenyl)-ethoxy]-pyrazin-2-ylamine

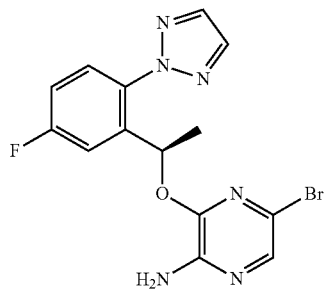 [SMILES: C[C@@H](Oc1nc(Br)cnc1N)c1cc(F)ccc1-n1nccn1]

NaH (2.46 g, 102.8 mmol, 60% in mineral oil) was suspended in THF (50 mL) under a nitrogen atmosphere. The suspension was cooled down to 0° C. and a solution of the alcohol of preparation 103 (10.64 g, 51.4 mmol) in THF (50 mL) was added dropwise over 30 min. The suspension was stirred at 0° C. during 30 min then a solution of 3,5-dibromo-pyrazin-2-ylamine (13.05 g, 51.4 mmol) in THF (80 mL) was added dropwise over 40 min. The solution was heated to reflux for 17 hrs; the reaction was then cooled down to 0° C. and 2-propanol (50 mL) and MeOH (50 mL) were added carefully. The suspension was concentrated under vacuum to provide a dark brown oil which was purified by column chromatography (eluants: heptane/AcOEt 1:0 to 3.3:1). The title compound was obtained as a yellow oil (10.10 g, 64% yield, 98% purity, 97% ee).

¹H NMR (400 MHz, CDCl₃) δ ppm 1.73 (d, 3H); 4.74 (br s, 2H); 6.44 (qd, 1H); 7.08-7.13 (m, 1H); 7.32 (dd, 1H); 7.54 (s, 1H); 7.64 (dd, 1H); 7.86 (s, 2H). MS m/z 379/381 (1:1) [MH]+. HPLC: 97% ee (Rt (minor)=7.55 min; Rt (major)=8.31 min, chiralpak IA, 4.6×250 mm, heptane/EtOH/MeOH/DEA 94/3/3/0.1, 1 mL/min, 25° C., 275 nm).

Preparation 105

1-(2-Acetyl-4-fluoro-phenyl)-pyrrolidin-2-one

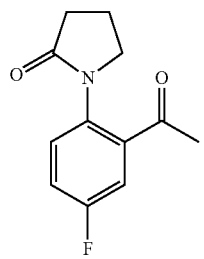 [SMILES: CC(=O)c1cc(F)ccc1N1CCCC1=O]

1,4-Dioxane (50 mL) was degassed by heating briefly to reflux and bubbling nitrogen gas through the solvent for 10 minutes, whilst it cooled to room temperature. CuI (180 mg, 5 mol %), glycine (284 mg, 20 mol %), 2-pyrrolidinone (1.73 mL, 22.73 mmol), K₃PO₄ (10.05 g, 47.35 mmol) and 1-(5-fluoro-2-iodo-phenyl)-ethanone (5.0 g, 18.94 mmol) were added sequentially to the solvent and the reaction mixture was heated at 100° C. under N₂ for 10 hours. The reaction mixture was filtered through a celite plug, eluting with EtOAc and the filtrate was concentrated. The crude product was purified by flash chromatography (5% MeOH in DCM) to give the title compound (2.02 g, 48% yield) as a yellow oil ¹H NMR (400 MHz, CDCl₃): δ ppm 2.20 (2H, pentet), 2.47 (2H, t), 2.54 (3H, s), 3.83 (2H, t), 7.17-7.21 (2H, m), 7.28-7.32 (1H, m). MS: m/z 222 [MH]+.

Preparation 106

1-[4-Fluoro-2-(1-hydroxy-ethyl)-phenyl]-pyrrolidin-2-one

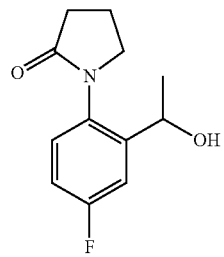 [SMILES: CC(O)c1cc(F)ccc1N1CCCC1=O]

The acetophenone of preparation 105 (2.00 g, 9.04 mmol) was dissolved in MeOH (30 mL) and cooled to 0° C. NaBH₄ (684 mg, 18.08 mmol) was added portionwise over 5 minutes and the reaction stirred for 1 hour. Water and 10% citric acid were added and the reaction mixture extracted with DCM and the organic extracts washed with water and brine, dried over magnesium sulfate and concentrated. The crude product was purified by flash chromatography (5% MeOH in DCM) to give the title compound (1.73 g, 86% yield) as a yellow oil.

¹H NMR (400 MHz, CDCl₃): δ 1.45 (3H, d), 2.20-2.28 (2H, m), 2.59 (2H, t), 3.59-3.67 (1H, m), 3.81-3.90 (1H, m), 4.75-4.82 (1H, m), 7.01 (1H, ddd), 7.09 (1H, dd), 7.30 (1H, dd). MS: m/z 206 [MH+–18].

Preparation 107

1-{2-[1-(3-Amino-6-bromo-pyrazin-2-yloxy)-ethyl]-4-fluoro-phenyl}-pyrrolidin-2-one

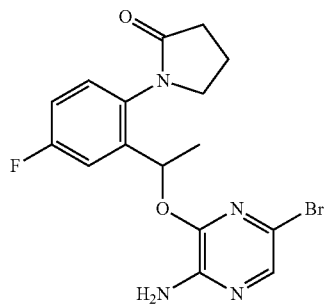 [SMILES: CC(Oc1nc(Br)cnc1N)c1cc(F)ccc1N1CCCC1=O]

The alcohol of preparation 106 (2.40 g, 10.75 mmol) was dissolved in MeTHF (30 mL) and cooled to 0° C. under $N_2$. NaH (0.43 g, 10.75 mmol, 60% dispersion in mineral oil) was added portionwise over 5 minutes and the reaction stirred for one hour. 3,5-Dibromo-pyrazin-2-ylamine (2.72 g, 10.75 mmol) was then added portionwise and a thick yellow suspension formed, which was difficult to stir. Additional MeTHF (40 mL) was added and the reaction heated at 70° C. overnight. TLC analysis indicated that a new product had formed but some starting material remained. The reaction was cooled to room temperature and additional NaH (75 mg) was added, and the reaction was heated at 70° C. for another 7 hours. The reaction was cooled to room temperature, quenched with water and then diluted with EtOAc. The phases were separated and the aqueous phase extracted three times with DCM. All the organic phases were combined, dried over magnesium sulfate and concentrated. The crude product was purified by flash chromatography (1:1 EtOAc: heptane, then 5% MeOH in DCM) to give an orange solid, which still contained ~15% of alcohol starting material by $^1$H NMR. The solid was recrystallised from MeOH (125 mL) to obtain the title compound (1.64 g, 39% yield, 92% purity) as an orange solid.

$^1$H NMR (400 MHz, CDCl$_3$): δ ppm 1.72 (3H, d), 2.17-2.42 (2H, m), 2.52-2.68 (2H, m), 3.77 (1H, q), 4.21 (1H, td), 4.84 (2H, s), 6.09 (1H, q), 7.19 (1H, dd), 7.02 (1H, td), 7.13 (1H, dd), 7.58 (1H, s). MS: m/z 395/397 [MH]+.

Preparation 108

[1-(5-Bromo-pyridin-2-yl)-ethyl]-carbamic acid tert-butyl ester

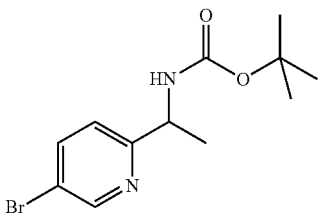 [SMILES: CC(NC(=O)OC(C)(C)C)c1ccc(Br)cn1]

To a stirred solution of 5-bromo-pyridine-2-carbonitrile (1 g, 5.46 mmol) in dry THF (10 mL) was added dropwise MeMgBr (2.03 mL, 6.09 mmol, 3M in THF) at −20° C. under $N_2$ atmosphere. After the addition, the reaction mixture was stirred at room temperature for 30 mins. The suspension was then treated with methanol (20 mL) and NaBH$_4$ (0.4 g, 13.3 mmol). The reaction was stirred at room temperature for 10 hrs and then poured into H$_2$O (10 mL) and aqueous NaOH (2M, 10 mL), extracted with EtOAc (50 mL×2). The combined organic layers were washed with brine (50 mL×3), dried over Na$_2$SO$_4$ and concentrated in vacuum. The residue was purified by a silica gel column chromatography (petroleum:EtOAc 3:1) to give 1-(5-bromo-pyridin-2-yl)-ethylamine (0.65 g, 59%) as a yellow liquid.

To a solution of 1-(5-bromo-pyridin-2-yl)-ethylamine (500 mg, 2.48 mmol) and Et$_3$N (300 mg, 2.98 mmol) in DCM (10 mL) was added Boc$_2$O (650 mg, 2.98 mmol) at room temperature. After the addition, the reaction mixture was stirred at room temperature for 5 hrs. TLC (petroleum ether:EtOAc 5:1) indicated the reaction was completed. Then the mixture was poured into brine (10 mL) and extracted with DCM (50 mL×3), washed with brine (10 mL×3), dried over Na$_2$SO$_4$, concentrated in vacuum to give the residue, which was purified by Biotage (petroleum ether/EtOAc 3:1, Rf~0.6) to give the title compound (450 mg, 60%) as a yellow solid.

Preparation 109

3-[(R)-1-(5-Fluoro-2-[1,2,3]triazol-2-yl-phenyl)-ethoxy]-5-(4,4,5,5-tetramethyl-[1,3,2]dioxaborolan-2-yl)-pyridin-2-ylamine

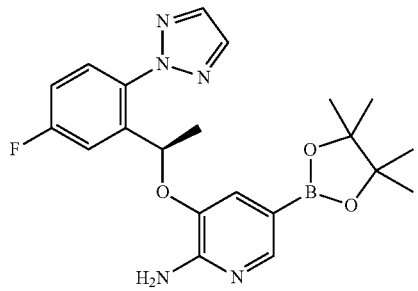 [SMILES: C[C@@H](Oc1cc(B2OC(C)(C)C(C)(C)O2)cnc1N)c1cc(F)ccc1-n1nccn1]

DMSO (15 mL) was bubbled with argon gas for about 15 min. and added to a mixture of 4,4,4',4',5,5,5',5'-octamethyl-2,2'-bi(1,3,2-dioxaborolane) (332 mg, 1.31 mmol), (R)-5-bromo-3-(1-(5-fluoro-2-(2H-1,2,3-triazol-2-yl)phenyl)ethoxy)pyridin-2-amine (preparation 45) (291 mg, 0.769 mmol) and potassium acetate (264 mg, 2.69 mmol) under argon atmosphere. 1,1'-Bis(diphenylphosphino)ferrocene-palladium (II) dichloride dichloromethane complex (31 mg, 0.038 mmol) was added to the mixture which was further bubbled with argon gas for about 5 min. and then placed in an 80° C. oil bath for 3 h. After cooling to room temperature, ethyl acetate, aqueous NaH$_2$PO$_4$ (1 M) and brine were added. The mixture was extracted three times with EtOAc, and the combined extractions were dried over sodium sulfate, filtered, and evaporated to a black tar which was then resuspended in EtOAc. The product was extracted into water (10 mL) containing HCl (0.8 mmol). To the product in water was added aqueous Na$_2$HPO$_4$ (0.25 M, 0.75 mmol, 3 mL). The pH was then further adjusted to about 5 by the addition of aqueous NaH$_2$PO$_4$ (1M). The cream colored product precipitated, and EtOAc and brine were added. Dissolving the product, the aqueous layer was extracted three times with EtOAc. The combined EtOAc extractions were dried over sodium sulfate, filtered, and evaporated to afford the title compound (250 mg, 0.59 mmol, 77% yield) as cream solids which was used without further purification.

$^1$H NMR (400 MHz, DMSO-d$_6$): δ ppm 8.23 (s, 2H), 7.77-7.65 (m, 3H), 7.36 (m, 1H), 6.72 (s, 1H, partially obscured), 6.70 (br s, 2H, partially obscured), 5.70 (q, J=6.63 Hz, 1H), 1.58 (d, J=6.15 Hz, 3H), 1.23 (s, 12H).

Preparation 110

1-Chloro-3-di methyl phosphoryl-5-methylbenzene

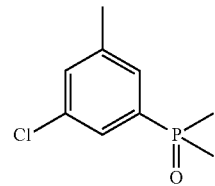

A solution of 3-chloro-5-methyl phenyl magnesium bromide in THF (0.5 M, 15 ml, 7.5 mmol) was added to the flask containing anhydrous 2-methyl THF (3 mL) at 0° C. under nitrogen. To the solution was added a solution of dimethylphosphinic chloride (465 mg, 4.13 mmol) in 2-methyl THF (7 mL) dropwise via a syringe while maintaining internal temperature below 10° C. At the end of the addition, the reaction mixture was left stirring in the ice bath without recharging the ice. After 16 hours, the reaction mixture was cooled to 0° C. and quenched with the addition of saturated NH$_4$Cl (10 mL), which resulted in the formation of a white precipitate. The reaction mixture was diluted with water (2 mL) and extracted with ethyl acetate (40 mL). The organic layer was washed once with brine, dried over MgSO$_4$, filtered and concentrated to give the title compound as a brown solid (890 mg, 98% yield).

$^1$H NMR (400 MHz, CDCl$_3$) δ ppm 1.74 (s, 3H) 1.77 (s, 3H) 3.89 (s, 3H) 6.84-6.91 (m, 1H) 7.46 (dd, J=8.59, 2.53 Hz, 1H) 7.95 (dd, J=12.88, 2.78 Hz, 1H). MS: m/z 219 [MH]+.

Preparation 111

3-Bromo-5-methanesulfonyl-pyridine

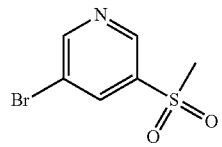

To a stirred solution of 3,5-dibromopyridine (1 g, 4.22 mmol) in dry Et$_2$O (10 mL) was added dropwise n-BuLi in hexane (2.5 M, 2 mL, 4.64 mmol) at −70° C. under N$_2$ atmosphere. After the addition, the reaction mixture was stirred at −70° C. for 3 hrs, at which time methyldisulfanylmethane (0.5 mL, 4.22 mmol) was added. The reaction was stirred at room temperature for 30 mins. TLC (petroleum ether:EtOAc 5:1) showed the reaction was complete. The reaction was quenched with H$_2$O (10 mL), and extracted with EtOAc (20 mL×2). The combined organic layers were washed with brine (50 mL×3), dried over sodium sulfate and concentrated in vacuum. The residue was purified by a Biotage silica gel cartridge (petroleum ether/EtOAc 5:1, Rf~0.6) to give the title compound (0.45 g, 53%) as a yellow liquid.

Preparation 112

2-Bromo-4-methanesulfonyl-1-methyl-benzene

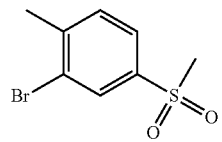

To a solution of elemental iron (67 mg, 1.2 mmol) in Br$_2$ (2.05 mL, 39.9 mmol) was added 4-methanesulfonyl-1-methyl-benzene (340 mg, 2.0 mmol) at 0° C. The reaction mixture was stirred at room temperature for 2 hrs. TLC (petroleum ether:EtOAc 3:1) indicated the reaction was completed. Then the mixture was poured into an ice-cold aqueous Na$_2$S$_2$SO$_3$ (1M, 10 mL) and extracted with EtOAc (20 mL×3), washed with brine (10 mL×3), dried over sodium sulfate, concentrated in vacuum, and the residue was purified by a Biotage silica gel cartridge (petroleum ether/EtOAc 3:1, Rf~0.6) to give the title compound (300 mg, 80%) as a white solid.

Preparation 112a (4-Bromo-2-methanesulfonyl-phenyl)-methanol

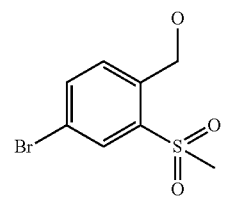

To a stirred solution of 4-bromo-2-fluoro-1-methyl-benzene (3 mL, 26.3 mmol) in DMF (15 mL) was added MeSNa (1.84 g, 26.3 mmol). After the addition, the reaction mixture was stirred at 90° C. overnight. TLC (petroleum) showed the reaction was complete. Then the mixture was poured into aq. NaHCO$_3$ (10 mL), extracted with EtOAc (20 mL×2). The combined organic layers were washed with brine (50 mL×3), dried over sodium sulfate and concentrated in vacuum. The residue was purified by a silica gel column chromatography (petroleum) to give 4-Bromo-1-methyl-2-methylsulfanyl-benzene (4 g, 68%) as a yellow liquid.

To a stirred solution of 4-bromo-1-methyl-2-methylsulfanyl-benzene (4 g, 36.9 mmol) in H$_2$O (80 mL) was added KMnO$_4$ (28 g, 177.2 mmol). After the addition, the reaction mixture was refluxed for 2 hrs. Then the mixture was filtered and the cake was washed with hot water, the aq. layer was acidified to pH=1-2 with aq. HCl, and extracted with EtOAc (30 mL×2). The combined organic layers were washed with brine (50 mL×3), dried over sodium sulfate and concentrated in vacuum to give 4-bromo-2-methanesulfonyl-benzoic acid (4 g, 40%) as a white solid.

To a stirred solution of 4-Bromo-2-methanesulfonyl-benzoic acid (4 g, 14.2 mmol) and Et$_3$N (1.6 g, 15.8 mmol) in dry THF (20 mL) was added dropwise isobutylchloroformate (2.06 g, 15.8 mmol) at −5° C. under N$_2$ atmosphere. After the addition, the resulting solution was stirred at −5° C. for 1 hour. Then the mixture was filtered to remove the salt to give a solution of the isobutyl mixed anhydride in THF, which was carried on directly. To a stirred solution of the isobutyl mixed anhydride (5.6 g, 14.3 mmol) in dry THF (30 mL) was added dropwise a solution of NaBH$_4$ (1.84 g, 42.9 mmol) in H$_2$O (10 mL) at −5° C. under N$_2$ atmosphere. After the addition, the resulting solution was stirred at room temperature overnight. TLC (petroleum ether:EtOAc 1:1) indicated the reaction was completed. The reaction mixture was concentrated in vacuo to give a residue which was extracted with EtOAc (20 mL×3), washed with brine (10 mL×3), dried over sodium sulfate, concentrated in vacuum to give the residue which was purified by a silica gel Biotage cartridge (petroleum ether/EtOAc 1:1, Rf~0.4) to give the title compound (3.5 g, 80%) as a white solid.

Preparation 113

4-Bromo-2-methanesulfonyl-1-methoxymethyl-benzene

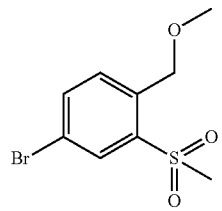

To a solution of (4-bromo-2-methanesulfonyl-phenyl)-methanol (preparation 112) (500 mg, 1.89 mmol) in DMF (10 mL) was added NaH (226 mg, 5.66 mmol, 60% in oil) at room temperature. After stirring at room temperature for 30 minutes, to above mixture was added MeI (230 mg, 10 mmol) at room temperature. The resulting mixture was stirred at room temperature for 3 hrs. TLC (petroleum ether:EtOAc 1:1) showed the reaction was complete. Then the mixture was poured into $H_2O$ (10 mL) and extracted with EtOAc (50 mL×3), washed with brine (10 mL×3), dried over sodium sulfate, concentrated in vacuo to give the residue, which was purified by a Biotage silica gel cartridge (petroleum ether/EtOAc 1:1, Rf~0.5) to give the title compound (200 mg, 40%) as yellow oil.

Preparation 114

(4-Bromo-2-methanesulfonyl-benzyl)-methyl-amine

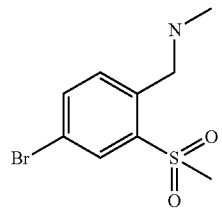

To a solution of (4-bromo-2-methanesulfonyl-phenyl)-methanol (preparation 112) (100 mg, 0.38 mmol) in $POBr_3$ (542 mg, 1.89 mmol) was added $PBr_3$ (511 mg, 1.89 mmol). After the addition, the reaction mixture was stirred at 130° C. overnight. TLC (petroleum ether:EtOAc 1:1) showed the reaction was complete. The reaction was cooled to room temperature and then poured into brine (10 mL) and extracted with EtOAc (10 mL×2). The combined organic layers were washed with brine (10 mL×2), dried over sodium sulfate and concentrated in vacuo to give crude 4-bromo-1-bromomethyl-2-methanesulfonyl-benzene (200 mg, 80%) as a white solid.

A solution of 4-bromo-1-bromomethyl-2-methanesulfonyl-benzene (300 mg, 0.9 mmol) in ~40% $MeNH_2$/MeOH (10 mL) was stirred at room temperature for 3 hours. TLC (petroleum ether:EtOAc 3:1) showed the reaction was complete. The reaction mixture was concentrated in vacuo to give crude title compound (200 mg, 80%) as a yellow oil, which was used for next step without further purification.

Preparation 115

(5-Bromo-4-methyl-thiazol-2-yl)-methanol

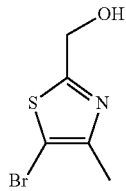

To a solution of 4-methyl-thiazole (10 g, 100 mmol) in dry THF (300 mL) was added n-BuLi in hexane (60 mL, 150 mmol, 2.5 M) dropwise at −70° C., and the mixture was stirred at −70° C. for 1.5 hour, DMF (12 mL) was added to the slurry over 15 min, and the mixture was stirred at −70° C. for 3 hours. TLC (petroleum ether:EtOAc 10:1) indicated the reaction was completed. The mixture was warmed to 0° C., and poured onto wet-ice. The mixture was acidified by 2N HCl to pH~4, and extracted with EtOAc (100 mL×3). The combined organic layers were washed with brine (100 mL), dried over sodium sulfate, and concentrated in vacuum to give 4-methyl-thiazole-2-carbaldehyde (10 g, 78.7%) as brown oil.

To a solution of 4-methyl-thiazole-2-carbaldehyde (10.0 g, 78 mmol) in dry THF (80 mL) was added $NaBH_4$ (1.49 g, 39 mmol), and the mixture was stirred at room temperature for 2 hours. TLC (petroleum ether:EtOAc 2:1) indicated the reaction was completed. The mixture was diluted with $NH_4Cl$ solution (50 mL) and the mixture was filtered. The filtrate was extracted with EtOAc (50 mL×3). The combined organic layers were washed with brine (50 mL), dried over sodium sulfate, and concentrated in vacuum to give the residue which was purified by a silica gel column eluting with petroleum ether:EtOAc 3:1 to give (4-Methyl-thiazol-2-yl)-methanol (7 g, 70%) as a yellow oil.

To a solution of (4-methyl-thiazol-2-yl)-methanol (7.0 g, 54.3 mmol) in DMF (80 mL) was added NBS (10.6 mg, 59.6 mmol), and the mixture was stirred at 50° C. overnight. TLC (petroleum ether:EtOAc 2:1) indicated the reaction was completed. The mixture was diluted with $H_2O$ (50 mL) and extracted with EtOAc (50 mL×3). The combined organic layers were washed with brine (50 mL×3), dried over sodium sulfate, and concentrated in vacuum to give the residue which was purified by a silica gel column (petroleum ether:EtOAc 10:1) to give the title compound (11.2 g, 99%) as a brown solid.

Preparation 115a

3-Bromo-5-methanesulfonyl-[1,2,4]thiadiazole

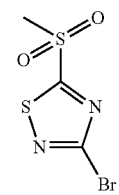

A mixture of cyanamide (10.6 g, 0.25 mol) and $CS_2$ (21.0 g, 0.276 mol) was stirred at room temperature for 30 minutes. Then KOH (28.1 g, 0.5 mol) in 95% EtOH (90 mL) was added dropwise to the mixture at 0° C. After addition, the resulting mixture was stirred at room temperature overnight. The reaction mixture filtered and the wet cake washed with EtOH (10 mL) to give potassium cyanocarbonimidodithioate (20 g, 41.2%) as a white solid.

To a solution of potassium cyanocarbonimidodithioate (10 g, 51.5 mmol) in acetone (40 mL) and water (45 mL) was added dropwise MeI (7.31 g, 51.5 mmol) at 0° C. After addition, the resulting mixture was stirred at room temperature for 2 hours. TLC (Petroleum ether:EtOAc 0:1) indicated the reaction was completed. The reaction mixture was concentrated in vacuum and to the was added acetone (100 mL) and then stirred at room temperature for 0.5 hour. The mixture was filtered and the filtrate was concentrated in vacuo to give crude potassium methyl cyanocarbonimidodithioate, which was crystallized from MTBE (20 mL) to give potassium methyl cyanocarbonimidodithioate (6.5 g, 74%) as a white solid.

To a solution of potassium methyl cyanocarbonimidodithioate (5 g, 29.4 mmol) in dichloromethane (100 mL) was added dropwise $Br_2$ (5.2 g, 32.9 mmol) at 0° C. After addition, the resulting mixture was stirred at room temperature overnight. TLC (Petroleum ether:EtOAc 0:1) indicated the reaction was completed. The reaction mixture was added excess $Na_2SO_3$ and water (50 mL) to decompose the excess $Br_2$. The mixture was separated and the separated organic layer was washed with brine (50 mL×3), dried over $Na_2SO_4$ and concentrated in vacuo to yield 3-bromo-5-methylsulfanyl-[1,2,4]thiadiazole (1.2 g, 19.2%) as an off-white solid.

To a solution of 3-bromo-5-methylsulfanyl-[1,2,4]thiadiazole (0.8 g, 3.8 mmol) in dichloromethane (20 mL) was added dropwise mCPBA (1.97 g, 11.4 mmol) in DCM (10 mL) at 0° C. After addition, the resulting mixture was stirred at room temperature overnight. TLC (Petroleum ether:EtOAc 10:1) indicated the reaction was completed. The reaction mixture was added excess sodium sulfite and water (50 mL) to decompose the excess mCPBA. The mixture was separated and the separated organic layer was washed with brine (50 mL×3), dried over sodium sulfate and concentrated in vacuo to give residue, which was purified by a silica gel column to yield the title compound (0.58 g, 63.2%) as a white solid.

Preparation 116

5-Bromo-3-(1-(5-fluoro-2-methoxyphenyl)ethoxy)-N-bis(tert-butoxycarbonyl)pyridin-2-ylamine

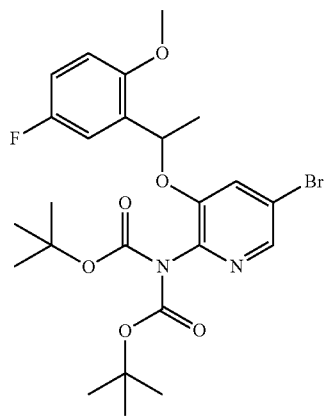 [SMILES: COc1ccc(F)cc1C(C)Oc1cc(Br)cnc1N(C(=O)OC(C)(C)C)C(=O)OC(C)(C)C]

A mixture of di-tert-butyl dicarbonate (64.6 g, 0.299 mol), DMAP (3.12 g, 0.025 mol) and preparation 50 (17.0 g, 0.050 mol) in DMF (100 mL) was stirred at room temperature overnight. TLC (petroleum ether:EtOAc 6:1) indicated complete consumption of preparation 50. Water (200 mL) was added to the reaction mixture and the mixture was extracted with EtOAc (3×100 mL). The organic layers were combined, dried over sodium sulfate, filtered, and evaporated to give residue, which was purified via column chromatography (silica gel, petroleum ether:EtOAc 6:1) to yield the title compound (22 g, 81.7%) as a yellow solid.

Preparation 117

3-(1-(5-Fluoro-2-methoxyphenyl)ethoxy)-5-(4,4,5,5-tetramethyl-1,3,2-dioxaborolan-2-yl)-N-bis(tert-butoxycarbonyl)pyridin-2-amine

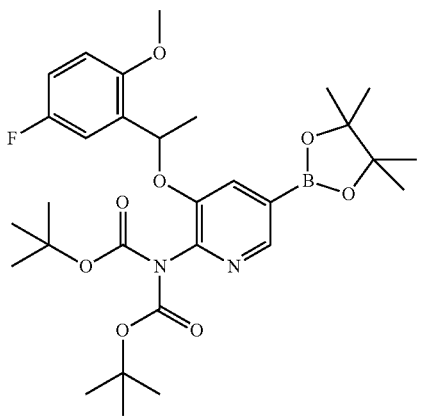 [SMILES: COc1ccc(F)cc1C(C)Oc1cc(B2OC(C)(C)C(C)(C)O2)cnc1N(C(=O)OC(C)(C)C)C(=O)OC(C)(C)C]

A mixture of bis(pinacilato)diboron (5.7 g, 0.022 mol) and potassium acetate (3.6 g, 0.037 mol) were added to a solution of preparation 116 (10 g, 0.018 mol) in dioxane (200 mL). The mixture was purged with nitrogen several times and then Pd(dppf)$Cl_2$ (0.7 g, 0.55 mmol) was added. The resulting mixture was heated at 80° C. for 3 hours and TLC (petroleum ether:EtOAc 6:1) indicated complete consumption of preparation 116. The reaction mixture was cooled to room temperature, filtered through a bed of celite and rinsed with EtOAc. The filtrate was washed with brine (2×500 mL), dried over sodium sulfate, filtered and concentrated. The residue was purified via column chromatography (silica gel, petroleum ether:EtOAc 6:1) to yield the title compound (4.4 g, 40.5%) as a brown solid.

Preparation 118

3-[1-(5-Fluoro-2-methoxy-phenyl)-ethoxy]-5-trimethylstannanyl-pyridin-2-ylamine

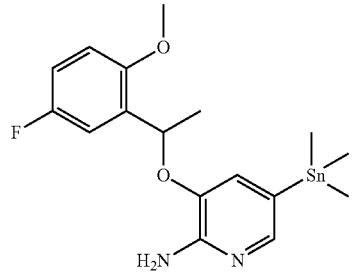 [SMILES: COc1ccc(F)cc1C(C)Oc1c[c]([Sn]([CH3])([CH3])[CH3])cnc1N]

To a solution of preparation 50 (5 g, 14.63 mmol), 1,1,1,2,2,2-hexamethyl-distannane (14.38 g, 43.9 mmol), 2,6-di-tert-butyl-4-methyl-phenol (170 mg, 1.46 mmol) and LiCl (2.3 g, 53.4 mmol) in dioxane (150 mL) was added Pd(PPh$_3$)$_4$ (1.7 g, 1.46 mmol) under N$_2$. The resulting solution was refluxed overnight. TLC (Petroleum ether:EtOAc 3:1) indicated the reaction was completed. The mixture was poured into water (100 mL) and then extracted with EtOAc (100 mL×3). The combined extracts were washed with brine (50 mL×3), dried over sodium sulfate and concentrated in vacuo, the residue was purified via column chromatography (silica gel, petroleum ether:EtOAc 4:1) to yield the title compound (4.0 g, 67%) as a yellow solid.

Preparation 119

5-Bromo-2-methyl-oxazole-4-carbonitrile

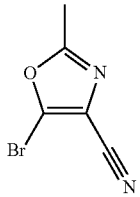

A solution of 5-amino-2-methyl-oxazole-4-carbonitrile (4.0 g, 1.0 eq), CuBr$_2$ (2.0 eq) and tBuONO (2.0 eq) in MeCN was stirred at room temperature for 1 hr when starting material was completely consumed. After workup and purification, the title compound was obtained as a tan solid (3.54 g, 58%).

Preparation 120

5-Bromo-2-(chloromethyl)-4-ethylthiazole

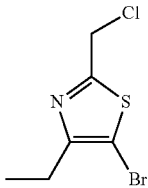

To a solution of (5-bromo-4-ethylthiazol-2-yl)methanol (313 mg 1.41 mmol) in THF (15 ml) under nitrogen at room temperature was added thionyl chloride (0.206 ml 2.82 mmol) and stirred overnight. LCMS indicated the completion of the reaction. A saturated ice cold aqueous NaHCO$_3$ solution was added to the reaction solution with gas evolution. The mixture was extracted with EtOAc (4×20 ml), dried over sodium sulfate and concentrated to give a brown oil 301 mg, 89% which was used for the next step without further purification.

MS: m/z=239.9/241.85 [MH]+.

Preparation 121

5-Bromo-4-ethyl-2-((methylthio)methyl)thiazole

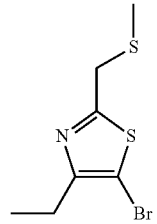

The title compound was prepared from 5-bromo-2-(chloromethyl)-4-ethylthiazole (preparation 120) (301 mg 1.25 mmol) using the same procedure as for the preparation 89 as a yellow oil (72 mg 23%).

$^1$H-NMR (400 MHz, CDCl$_3$): δ 1.25 (t, J=7.58 Hz, 3H), 2.17 (s, 3H), 2.66-2.77 (m, 2H) 3.90 (s, 2H). MS: m/z 251.95/253.95 [MH]+.

Preparation 122

5-Bromo-4-ethyl-2-((methylsulfonyl)methyl)thiazole

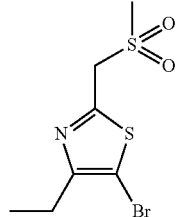

The title compound was prepared from 5-bromo-4-ethyl-2-((methylthio)methyl)thiazole (preparation 121) (72 mg 0.28 mmol) using the same procedure as for preparation 90 to give the required product as a yellow solid (55 mg, 68%).

LC-MS: m/z=283.90/285.90 [MH]+.

Example 1

3-[1-(5-Fluoro-2-methoxyphenyl)ethoxy]-5-(4-methyl-1-vinyl-1H-1,2,3-triazol-5-yl)pyridin-2-amine

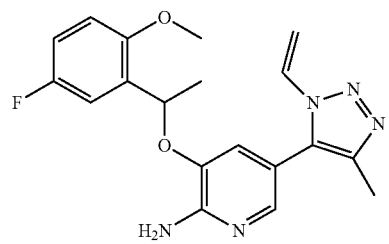 [SMILES: C=Cn1nnc(C)c1-c1cnc(N)c(OC(C)c2cc(F)ccc2OC)c1]

To a solution of the boronate ester of preparation 58 (300 mg, 0.77 mmol) in 1,4-dioxane (5 mL) was added the iodide of preparation 60 (200 mg, 0.85 mmol, 1.1 eq.) followed by tetrakis(triphenylphosphine)palladium(0) (89 mg, 0.077 mmol, 0.1 eq.) and aqueous sodium hydrogen carbonate (1M, 2.36 mL, 3.05 eq.). The resulting mixture was heated to 110° C., under an atmosphere of nitrogen, for 18 hr. The reaction mixture was cooled to room temperature and acetic acid (8 mL) added before evaporating under reduced pressure. The resulting brown resin was dissolved in methanol (5 mL) passed through an Isolute® flash SCX-2 (10 g) cartridge eluting with methanol (10 mL), ethyl acetate (10 mL), dichloromethane (10 mL) and finally 2M ammonia in methanol. The basic eluent was evaporated under reduced pressure. The resulting brown gum was purified using preparative high pressure liquid chromatography under acidic conditions to give the title compound as a white solid (18 mg, 6.3%).

$^1$H NMR (400 MHz, CD$_3$OD): δ ppm 1.64 (d, 3H), 2.10 (s, 3H), 3.84 (s, 3H), 5.07 (d, 1H), 5.76 (q, 1H), 5.85 (d, 1H), 6.61 (s, 1H), 6.70 (dd, 1H), 7.0-7.06 (m, 3H), 7.46 (s, 1H)

LRMS: APCI, m/z=370.22 [MH]$^+$

Example 2 to 17

The compounds of the following tabulated Examples of the general formula:

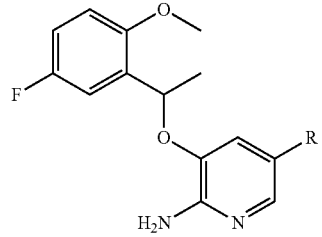

were prepared by a similar method to that of example 1 using the appropriate halo-heterocycle stating material.

| Ex. No. | R | Name | Form, yield | Data |
|---|---|---|---|---|
| 2[4] | | 2-(5-{6-amino-5-[1-(5-fluoro-2-methoxyphenyl)ethoxy]-pyridin-3-yl}-1H-1,2,3-triazol-1-yl)ethanol | White solid, 22% | MS: ESI+, m/z = 374.155 [MH]+ HPLC: Acidic Analytical (QC) Rt = 2.46 min |
| 3[4] | | 3-[1-(5-fluoro-2-methoxyphenyl)ethoxy]-5-(1-methyl-1H-1,2,3-triazol-5-yl)pyridin-2-amine | White solid, 50% | MS: ESI+, m/z = 344.144 [MH]+ HPLC: Acidic Analytical (QC) Rt = 3.05 min |
| 4[1] | | 5-[1-(5-fluoro-2-methoxyphenyl)ethoxy]-5'-(methylsulfonyl)-3,3'-bipyridin-6-amine | Library | LRMS: ESI+, m/z = 418 [MH]+ HPLC$^2$: Rt = 2.537 min |
| 5[1] | | 5-{6-amino-5-[1-(5-fluoro-2-methoxyphenyl)ethoxy]-pyridin-3-yl}-4-methylpyrimidin-2-amine | Library | LRMS: ESI+, m/z = 370 [MH]+ HPLC$^2$: Rt = 2.303 min |
| 6[1] | | 5-(3,5-dimethyl-1H-pyrazol-4-yl)-3-[1-(5-fluoro-2-methoxyphenyl)ethoxy]-pyridin-2-amine | Library | LRMS: ESI+, m/z = 357 [MH]+ HPLC$^2$: Rt = 2.418 min |
| 7[1] | | 3-[1-(5-fluoro-2-methoxyphenyl)ethoxy]-5-(1,3,5-trimethyl-1H-pyrazol-4-yl)pyridin-2-amine | Library | LRMS: ESI+, m/z = 371 [MH]+ HPLC$^2$: Rt = 2.543 min |
| 8[5] | | 6'-amino-5'-[1-(5-fluoro-2-methoxyphenyl)ethoxy]-3,3'-bipyridin-2-ol | Brown solid, 10% | MS: ESI+, m/z = 356.133 [MH]+ HPLC: Basic Analytical (QC) Rt = 2.23 min |

| Ex. No. | R | Name | Form, yield | Data |
|---|---|---|---|---|
| 9[5] | 1-methyl-1H-imidazol-5-yl (attached via 5-position) | 3-[1-(5-fluoro-2-methoxyphenyl)ethoxy]-5-(1-methyl-1H-imidazol-4-yl)pyrazin-2-amine | White foam, 53% | MS: ESI+, m/z = 343.149 [MH]+ HPLC: Basic Analytical (QC) Rt = 1.93 min |
| 10[3] | 1,4-dimethyl-1H-1,2,3-triazol-5-yl | 5-(1,4-dimethyl-1H-1,2,3-triazol-5-yl)-3-[1-(5-fluoro-2-methoxyphenyl)ethoxy]-pyridin-2-amine | White foam, 73% | $^1$H NMR (400 MHz, CD$_3$OD): δ ppm = 1.65 (d, 3H), 2.04 (s, 3H), 3.73 (s, 3H), 3.85 (s, 3H), 5.78 (q, 1H), 6.66 (s, 1H), 6.97-7.08 (m, 3H), 7.50 (s, 1H) MS: APCI+, m/z = 358.29 [MH]+ |
| 11[5] | 2-hydroxyethyl-pyrazol-1-yl | 2-(5-{6-amino-5-[1-(5-fluoro-2-methoxyphenyl)ethoxy]-pyridin-3-yl}-1H-pyrazol-1-yl)ethanol | White foam, 30% | MS: ESI+, m/z = 373.16 [MH]+ HPLC: Basic Analytical (QC) Rt = 2.76 min |
| 12 | (hydroxymethyl)-1-methyl-1H-pyrazol-5-yl | (4-{6-amino-5-[1-(5-fluoro-2-methoxyphenyl)ethoxy]-pyridin-3-yl}-1-methyl-1H-pyrazol-5-yl)methanol | Off white powder, 30% | $^1$H NMR (400 MHz, DMSO-d6) δ ppm 1.55 (d, J = 6.25 Hz, 3 H) 3.82 (s, 3 H) 3.83 (s, 3 H) 4.35 (d, J = 5.86 Hz, 2 H) 5.19 (t, 1 H) 5.72 (q, 1 H) 5.78 (s, 2 H) 6.85 (s, 1 H) 6.99-7.11 (m, 2 H) 7.23 (dd, J = 9.18, 2.93 Hz, 1 H) 7.34 (s, 1 H) 7.57 (s, 1 H) MS: ESI+, m/z = 373 [MH]+ |
| 13[4] | (hydroxymethyl)-1,3-thiazol-5-yl | (4-{6-amino-5-[1-(5-fluoro-2-methoxyphenyl)ethoxy]-pyridin-3-yl}-1,3-thiazol-5-yl)methanol | White foam, 33% | MS: ESI+, m/z = 376.105 [MH]+ HPLC: Acidic Analytical (QC) Rt = 2.52 min |
| 14[5] | (hydroxymethyl)-1,3-thiazol-4-yl | (5-{6-amino-5-[1-(5-fluoro-2-methoxyphenyl)ethoxy]-pyridin-3-yl}-1,3-thiazol-4-yl)methanol | White solid, 35% | MS: ESI+, m/z = 376.105 [MH]+ HPLC: Basic Analytical (QC) Rt = 2.92 min |
| 15[5] | 1-methyl-2-oxo-1,2-dihydropyridin-3-yl | 6'-amino-5'-[1-(5-fluoro-2-methoxyphenyl)ethoxy]-1-methyl-3,3'-bipyridin-2(1H)-one | White foam, 45% | MS: ESI+, m/z = 370.149 [MH]+ HPLC: Basic Analytical (QC) Rt = 3.12 min |
| 16[4] | 4-methoxy-1-methyl-1H-pyrazol-5-yl | 3-[1-(5-fluoro-2-methoxyphenyl)ethoxy]-5-(4-methoxy-1-methyl-1H-pyrazol-5-yl)pyridin-2-amine | White solid, 21% | MS: ESI+, m/z = 373.160 [MH]+ HPLC: Basic Analytical (QC) Rt = 3.04 min |

-continued

| Ex. No. | R | Name | Form, yield | Data |
|---|---|---|---|---|
| 17[4] | 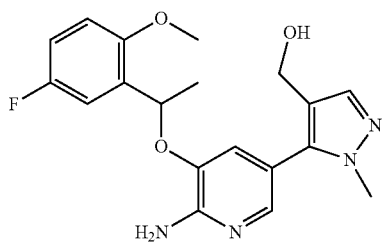 | 4-{6-amino-5-[1-(5-fluoro-2-methoxyphenyl)ethoxy]-pyridin-3-yl}-6-chloropyridazin-3-amine | White foam, 38% | MS: ESI+, m/z = 390.105 [MH]+ HPLC: Acidic Analytical (QC) Rt = 2.38 min |

Footnotes:
[1]Made as part of parallel array (library) using 1,1'-bis(di-t-butylphosphino) ferrocene palladium (II) dichloride as catalyst and potassium phosphate as base. Purified by HPLC (Agilent 1200 HPLC/1956 MSD/SEDEX 75 ELSD, ionization mode API-ES, polarity positive) [column: Phenomenex Gemini C18 250 × 21.2 mm × 10 μm, mobile phase A: acetonitrile, mobile phase B: 0.1% ammonium hydroxide in water, gradient elution of A:B (0:100 to 100:0) over 11 min. Flow rate 25 mL/min.
[2]Compound analysed by HPLC (Agilent 1200 HPLC/1956 MSD/SEDEX 75 ELSD, ionization mode API-ES, polarity positive) [column: Welch XB-C18 2.1 × 50 mm × 5 μm, temperature: 50° C., mobile phase A: 0.0375% TFA in water, mobile phase B: 0.0188% TFA in acetonitrile, Gradient: initial 1% B, T = 0 min 1% B, T = 0.6 min 5% B, T = 4.0 min 100% B, T = 4.3 min 1% B, T = 4.7 min 1% B, Flow rate: 0.8 ml/min, injection volume 2 μL].
[3]Purified by chromatography on silica eluting with a gradient of dichloromethane:methano:0.880 ammonia (100:0:0 to 90:10:1).
[4]Purified by preparative HPLC under Acidic conditions.
[5]Purified by preparative HPLC under Basic conditions.

Example 18

(5-{6-amino-5-[1-(5-fluoro-2-methoxyphenyl)ethoxy]pyridin-3-yl}-1-methyl-1H-pyrazol-4-yl)methanol

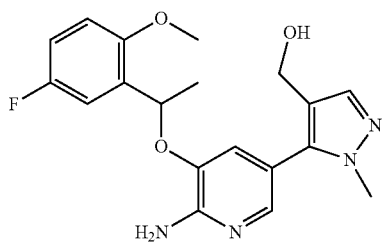 [SMILES: COc1ccc(F)cc1C(C)Oc1cc(-c2c(CO)cnn2C)cnc1N]

To a solution of the boronate ester of preparation 58 (750 mg, 1.93 mmol) in 1, 4 dioxane (15 mL) was added the iodide of preparation 66 (502 mg, 2.12 mmol, 1.1 eq.) followed by tetrakis (triphenylphosphine) palladium (0) (225 mg, 0.193 mmol, 0.1 eq.) and aqueous sodium hydrogen carbonate (1M, 6.7 mL, 3.5 eq.). The resulting mixture was heated to 110° C., under an atmosphere of nitrogen, for 18 hr. The reaction mixture was cooled to room temperature and diluted with diethyl ether (50 mL). This mixture was extracted with 10% aqueous citric acid (wt/vol, 2×50 mL). The combined citric layer were made basic with aqueous ammonium hydroxide (0.880, 5 mL) and then extracted with ethyl acetate (2×100 mL). The combined ethyl acetate phases were dried over magnesium sulphate. The resulting mixture was filtered and the filtrate evaporated under reduced pressure to give an intermediate beige solid (380 mg). To a solution of the intermediate beige solid (40 mg) in tetrahydrofuran (3 mL) was added sodium borohydride (16 mg) followed by methanol (1 mL). The resulting mixture was stirred at room temperature for 18 hr before partitioning between ethyl acetate (40 mL) and water (20 mL). The organic phase was dried over magnesium sulphate and the resulting mixture filtered and the filtrate evaporated under reduced pressure to give an oily residue. The oily residue was purified using preparative high pressure liquid chromatography under acidic conditions to give the title compound as a white solid (23 mg, 59%).

MS: ESI+, m/z=373.16 [MH]+
HPLC: Acidic Analytical (QC), Rt=2.22 min

Example 19

2-{6'-Amino-5'-[1-(5-fluoro-2-methoxy-phenyl)-ethoxy]-[3,3]bipyridinyl-2-yloxy}-ethanol

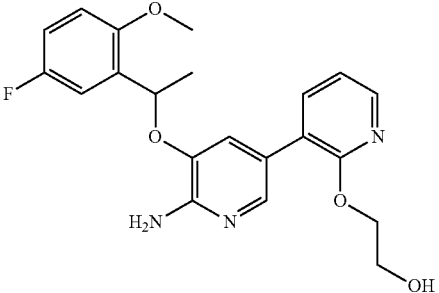 [SMILES: COc1ccc(F)cc1C(C)Oc1cc(-c2cccnc2OCCO)cnc1N]

To a solution of the boronate ester of preparation 58 (155 mg, 0.4 mmol) in 1, 4 dioxane (2 mL) was added the 3-bromo-2-chloropyridine (84 mg, 0.44 mmol, 1.1 eq.) followed by tetrakis(triphenylphosphine)palladium(0) (46 mg, 0.04 mmol, 0.1 eq.) and aqueous sodium hydrogen carbonate (1M, 2.36 mL, 3.05 eq.). The resulting mixture was heated to 110° C., under an atmosphere of nitrogen, for 18 hr. The reaction mixture was cooled to room temperature and acetic acid (8 mL) added before evaporating under reduced pressure. The resulting brown resin was dissolved in methanol (5 mL) passed through an Isolute® flash SCX-2 (10 g) cartridge eluting with methanol (10 mL), ethyl acetate (10 mL), dichloromethane (10 mL) and finally 2M ammonia in methanol. The basic eluent was evaporated under reduced pressure. The resulting brown gum was purified by chromatography on a Biotage™ Redisep silica cartridge (12 g) eluting with a gradient of ethyl acetate in heptane (30:70 to 90:10) to an intermediate yellow gum (70 mg). To a solution of the intermediate yellow gum (35 mg, 0.093 mmol) in dimethyl sulphoxide (0.4 mL) was added potassium hydroxide (13 mg, 0.23 mmol, 2.5 eq.) and ethylene glycol (58 mg, 0.93 mmol, 10.0 eq.).

This mixture was heated to 60° C. for 72 hr before partitioning between water (3 mL) and dichloromethane (3 mL). The aqueous phase was extracted with ethyl acetate (3×3 mL). The combined organic phases were dried over magnesium sulphate. The resulting mixture was filtered and the filtrate evaporated under reduced pressure. The residue was purified using preparative high pressure liquid chromatography under basic conditions to give the title compound as a white solid (14.5 mg, 62%).

MS: ESI+, m/z=400.159 [MH]+
HPLC: Basic Analytical (QC) Rt=2.29 min

Example 20

3-[(R)-1-(5-Fluoro-2-methoxy-phenyl)-ethoxy]-5-(3-methyl-3H-[1,2,3]triazol-4-yl)-pyridin-2-ylamine

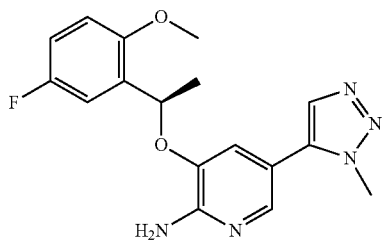 [SMILES: COc1ccc(F)cc1[C@@H](C)Oc1cc(-c2cnnn2C)cnc1N]

To a solution of the bromide of preparation 43 (3.5 g, 10.2 mmol) in dimethyl sulphoxide (40 ML) were added potassium acetate (3.47 g, 35.3 mmol, 3.5 eq.), bis(pinacolato) diboron (2.83 g, 11.1 mmol, 1.1 eq.) and 1,1'-bis(diphenylphosphino)ferrocene palladium dichloride (148 mg, 0.202 mmol, 0.02 eq.). The resulting mixture was thoroughly degassed before heating, under an atmosphere of nitrogen, to 80° C. for 16 hr. The reaction mixture was cooled, diluted with 1,4-dioxane (300 mL) and sodium hydrogen carbonate (2.54 g, 30.3 mmol, 3.0 eq.), 5-iodo-1-methyl-[1,2,3]-triazole (4.22 g, 20.2 mmol, 2.0 eq.) and tetrakis(triphenylphosphine) palladium(0) (582 mg, 0.505 mmol, 0.05 eq.) were added. This mixture was degassed and heated to 110° C. for 5 hr. The reaction mixture was evaporated under reduced pressure to a brown oily residue. The oily residue was partitioned between tert-butyl methyl ether (200 mL) and aqueous citric acid (20% wt/vol, 500 mL). The aqueous layer was washed with tert-butyl methyl ether (2×100 mL), then made basic with aqueous ammonium hydroxide (0.880, 200 mL) and extracted with ethyl acetate (3×300 mL). The combined ethyl acetate phases were washed with water (5×100 mL) and dried over magnesium sulphate. The mixture was filtered and the filtrate evaporated under reduced pressure. The resulting residue was purified by chromatography on silica (200 g) eluting with a gradient of ethyl acetate in heptane (60:40 to 100:0) followed by methanol in ethyl acetate (5:95). Clean fractions were combined and evaporated under reduced pressure. The resulting gum was azeotroped with diethyl ether (3×200 mL) to give the title compound as a white solid. (2.17 g, 62%)

$^1$H NMR (400 MHz, CDCl$_3$): δ 1.65 (d, 3H), 3.80 (s, 3H), 3.87 (s, 3H), 5.24 (br s, 2H), 5.69 (q, 1H), 6.63 (d, 1H), 6.85 (dd, 1H), 6.93-7.03 (m, 2H), 7.54 (s, 1H), 7.65 (d, 1H)

MS: ESI+, m/z=344.2 [MH]+

Optical purity: 99.0% e.e. (Chiral column conditions: Chiralpak AD-H (250*4.6 mm i.d.), eluent 30% isopropyl alcohol in heptane, 1 mL/min, Rt=9.92 min (opposite enantiomer Rt=11.35 min)).

Example 21 to 29

The compounds of the following tabulated Examples of the general formula:

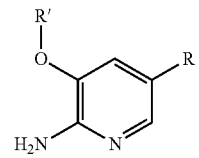

were prepared by a similar method to that of example 20 using the appropriate 5-bromo-pyridin-2-amine and halo-heterocycle starting materials.

| Ex No. | R' | R | Name | Form, yield | Data |
|---|---|---|---|---|---|
| 21 |  |  | 3-{(1R)-1-[5-fluoro-2-(2H-1,2,3-triazol-2-yl)phenyl]-ethoxy}-5-(1-methyl-1H-1,2,3-triazol-5-yl)pyridin-2-amine | White solid, 36% | $^1$H NMR (400 MHz, CDCl$_3$): δ ppm 1.62 (d, J = 6.25 Hz, 3 H) 3.86 (s, 2 H) 4.92-5.33 (m, 2 H) 5.59-5.78 (m, 1 H) 6.80 (d, J = 1.95 Hz, 1 H) 7.13 (s, 1 H) 7.27 (dd, J = 9.18, 2.93 Hz, 1 H) 7.54-7.66 (m, 2 H) 7.70 (d, J = 1.56 Hz, 1 H) 7.88 (s, 1 H) MS: ESI+, m/z = 381 [MH]+ |
| 22[1] |  |  | 3-[(1R)-1-(5-fluoro-2-methoxyphenyl)-ethoxy]-5-(1-methyl-1H-imidazol-5-yl)pyridin-2-amine | Beige foam, 35% | $^1$H NMR (400 MHz, CDCl$_3$): δ = 1.62-1.65 (d, 3H), 3.42 (s, 3H), 3.86 (s, 3H), 5.17 (bs, 2H), 5.64-5.70 (q, 1H), 6.64-6.65 (m, 1H), 6.81-6.85 (m, 1H), 6.90-6.96 (m, 2H), 6.99-7.03 (m, 1H), 7.59-7.61 (m, 1H), 7.70 (s, 1H) MS: APCI+, m/z = 343 [MH]+ |

| Ex No. | R' | R | Name | Form, yield | Data |
|---|---|---|---|---|---|
| 23[2] | 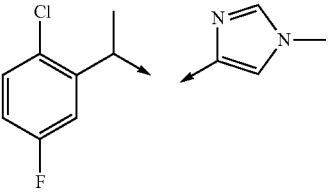 | 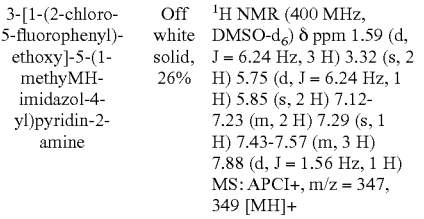 | 3-[1-(2-chloro-5-fluorophenyl)-ethoxy]-5-(1-methyMH-imidazol-4-yl)pyridin-2-amine | Off white solid, 26% | $^{1}$H NMR (400 MHz, DMSO-d$_{6}$) δ ppm 1.59 (d, J = 6.24 Hz, 3 H) 3.32 (s, 2 H) 5.75 (d, J = 6.24 Hz, 1 H) 5.85 (s, 2 H) 7.12-7.23 (m, 2 H) 7.29 (s, 1 H) 7.43-7.57 (m, 3 H) 7.88 (d, J = 1.56 Hz, 1 H) MS: APCI+, m/z = 347, 349 [MH]+ |
| 24[3,4] | 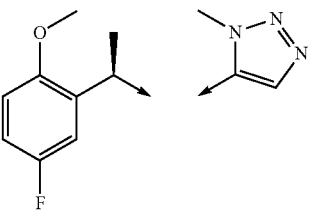 | 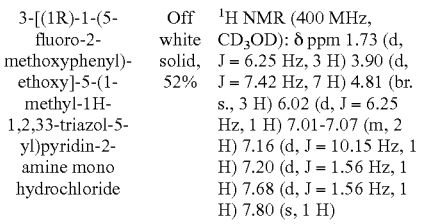 | 3-[(1R)-1-(5-fluoro-2-methoxyphenyl)-ethoxy]-5-(1-methyl-1H-1,2,33-triazol-5-yl)pyridin-2-amine mono hydrochloride | Off white solid, 52% | $^{1}$H NMR (400 MHz, CD$_{3}$OD): δ ppm 1.73 (d, J = 6.25 Hz, 3 H) 3.90 (d, J = 7.42 Hz, 7 H) 4.81 (br. s., 3 H) 6.02 (d, J = 6.25 Hz, 1 H) 7.01-7.07 (m, 2 H) 7.16 (d, J = 10.15 Hz, 1 H) 7.20 (d, J = 1.56 Hz, 1 H) 7.68 (d, J = 1.56 Hz, 1 H) 7.80 (s, 1 H) MS: APCI+, m/z = 343 [MH]+ Microanalysis: Observed 51.47% C, 5.18% H, 17.86% N (calculated for HCl, mono hydrate 51.32 % C, 5.32% H, 17.60% N) Optical purity: >99.5% e.e. (Rt = 10.0 min (opposite enantiomer Rt = 11.2 min)) |
| 25 | 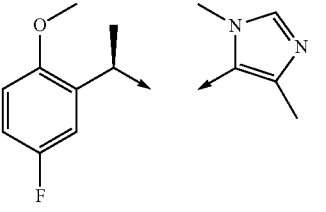 | 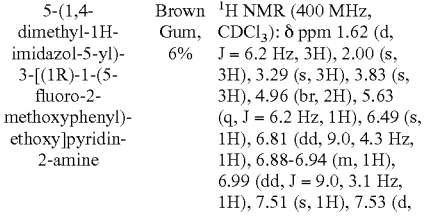 | 5-(1,4-dimethyl-1H-imidazol-5-yl)-3-[(1R)-1-(5-fluoro-2-methoxyphenyl)-ethoxy]pyridin-2-amine | Brown Gum, 6% | $^{1}$H NMR (400 MHz, CDCl$_{3}$): δ ppm 1.62 (d, J = 6.2 Hz, 3H), 2.00 (s, 3H), 3.29 (s, 3H), 3.83 (s, 3H), 4.96 (br, 2H), 5.63 (q, J = 6.2 Hz, 1H), 6.49 (s, 1H), 6.81 (dd, 9.0, 4.3 Hz, 1H), 6.88-6.94 (m, 1H), 6.99 (dd, J = 9.0, 3.1 Hz, 1H), 7.51 (s, 1H), 7.53 (d, J = 2.0 Hz, 1H) MS: APCI+, m/z = 357.3 [MH]+ |
| 26[6] | 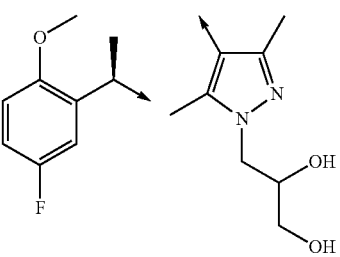 | 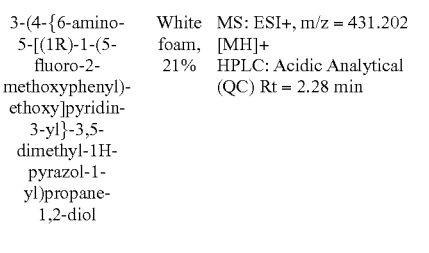 | 3-(4-{6-amino-5-[(1R)-1-(5-fluoro-2-methoxyphenyl)-ethoxy]pyridin-3-yl}-3,5-dimethyl-1H-pyrazol-1-yl)propane-1,2-diol | White foam, 21% | MS: ESI+, m/z = 431.202 [MH]+ HPLC: Acidic Analytical (QC) Rt = 2.28 min |
| 27[1] | 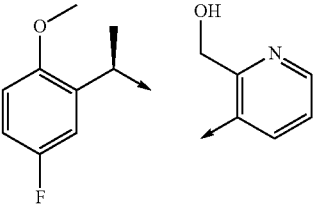 | 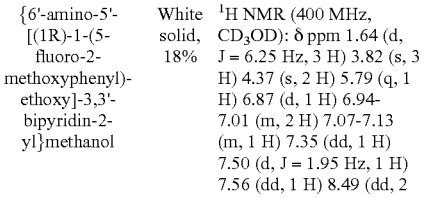 | {6'-amino-5'-[(1R)-1-(5-fluoro-2-methoxyphenyl)-ethoxy]-3,3'-bipyridin-2-yl}methanol | White solid, 18% | $^{1}$H NMR (400 MHz, CD$_{3}$OD): δ ppm 1.64 (d, J = 6.25 Hz, 3 H) 3.82 (s, 3 H) 4.37 (s, 2 H) 5.79 (q, 1 H) 6.87 (d, 1 H) 6.94-7.01 (m, 2 H) 7.07-7.13 (m, 1 H) 7.35 (dd, 1 H) 7.50 (d, J = 1.95 Hz, 1 H) 7.56 (dd, 1 H) 8.49 (dd, 2 H) MS: ESI+, m/z = 370 [MH]+ |

-continued

| Ex No. | R' | R | Name | Form, yield | Data |
|---|---|---|---|---|---|
| 28[5] | 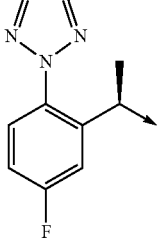 | 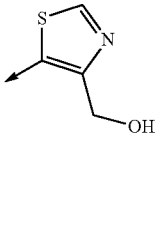 | [5-(6-amino-5-{(1R)-1-[5-fluoro-2-(2H-1,2,3-triazol-2-yl-phenyl]ethoxy}-pyridin-3-yl)-1,3-thiazol-4-yl]methanol | White foam, 17% | MS: ESI+, m/z = 413.112 [MH]+ HPLC: Acidic Analytical (QC) Rt = 2.36 min |
| 29[5,7] | 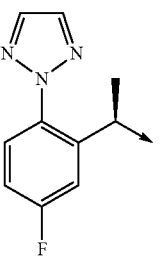 | 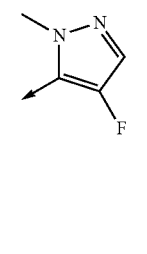 | 5-(4-fluoro-1-methyl-1H-pyrazol-5-yl)-3-{(1R)-1-[5-fluoro-2-(2H-1,2,3-triazol-2-yl-phenyl]ethoxy}-pyridin-2-amine | White foam, 6% | MS: ESI+, m/z = 398.146 [MH]+ HPLC: Acidic Analytical (QC) Rt = 2.52 min |

Footnotes:
[1]Purified by chromatography on silica (20 g) eluting with a gradient of ethyl acetate:methanol:ammonium hydroxide (100:0:0 to 92:7.5:2.5).
[2]Purified by automated flash chromatography Biotage ™, 12 g silica cartridge, gradient elution of methanol in dichloromethane (0:100 to 10:90).
[3]The compound of example 20 was dissolved in ethyl acetate and treated with 2M hydrogen chloride in diethyl ether. The resulting mixture was evaporated and the residue dissolved in ethyl acetate and isopropyl alcohol and evaporated. The reulting off white solid was filtered off and air dried.
[4]Analysed by analytical chiral HPLC (Chiral column conditions: Chiralpak AD-H (250*4.6 mm i.d.), eluent 30% isopropyl alcohol in heptane, 1 mL/min).
[5]Purified by preparative HPLC under Acidic conditions.
[6]Purified by preparative HPLC under Basic conditions.
[7]Except 5,5,5',5'-tetramethyl-2,2'-bi-1,3,2-dioxaborinane used instead of bis(pinacolato)diboron.

Example 30

3-{(1R)-1-[5-fluoro-2-(2H-1,2,3-triazol-2-yl)phenyl]ethoxy}-5-(1-methyl-1H-pyrazol-5-yl)pyridin-2-amine

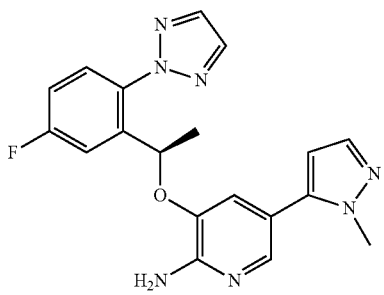 [SMILES: C[C@@H](Oc1cc(-c2ccnn2C)cnc1N)c1cc(F)ccc1-n1nccn1]

To a solution of the bromide of preparation 45 (690 mg, 1.82 mmol) in 1,4-dioxane (100 mL) was added 1-methyl-5-(4,4,5,5-tetramethyl-1,3,2-dioxaborolan-2-yl)-1H-pyrazole (949 mg, 4.56 mmol, 2.5 eq.) followed by tetrakis(triphenylphosphine)palladium(0) (105 mg, 0.091 mmol, 0.05 eq.) and aqueous sodium hydrogen carbonate (1M, 4.6 mL, 2.5 eq.). The resulting mixture was heated to 110° C., under an atmosphere of nitrogen, for 2 hr. The reaction mixture was cooled to room temperature and evaporated under reduced pressure to a brown oily residue. The oily residue was partitioned between tert-butyl methyl ether (100 mL) and aqueous hydrochloric acid (4M, 100 mL). The aqueous layer was washed with tert-butyl methyl ether (3×100 mL), then made basic with aqueous ammonium hydroxide (0.880, 100 mL) and extracted with ethyl acetate (3×50 mL). The combined ethyl acetate phases were washed with water (5×20 mL) and dried over magnesium sulphate. The mixture was filtered and the filtrate evaporated under reduced pressure. The resulting residue was purified by chromatography on silica (50 g) eluting with ethyl acetate. The clean fractions were combined and evaporated under reduced pressure. The resulting gum was azeotroped with diethyl ether (3×100 mL) to give the title compound as a white foam. (220 mg, 32%)

$^1$H NMR (400 MHz, CDCl$_3$): δ ppm 1.61 (d, 3H), 3.67 (s, 3H), 4.92 (bs, 2H, NH$_2$), 5.78 (q, 1H), 6.16 (d, 1H), 6.80 (d, 1H), 7.12 (ddd, 1H), 7.29 (dd, 1H), 7.44 (d, 1H), 7.62 (dd, 1H), 7.71 (d, 1H), 7.87 (s, 2H)

Optical purity: 97.0% e.e. (Chiral column conditions: Chiralpak AD-H (250*4.6 mm i.d.), eluent 100% methyl alcohol, 1 mL/min, Rt=4.77 min (opposite enantiomer Rt=4.17 min)).

Example 31 to 54

The compounds of the following tabulated Examples of the general formula:

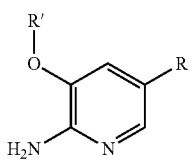

were prepared by a similar method to that of example 30 using the appropriate 5-bromo-pyridin-2-amine and heterocycle-boronate ester stating materials.

| Ex No | R' | R | Name | Form, yield | Data |
|---|---|---|---|---|---|
| 31[1] | 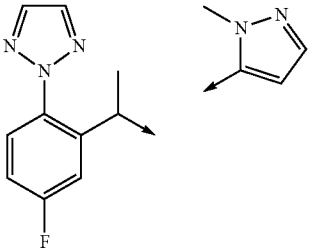 | 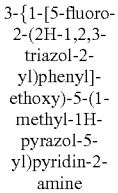 | 3-{1-[5-fluoro-2-(2H-1,2,3-triazol-2-yl)phenyl]-ethoxy)-5-(1-methyl-1H-pyrazol-5-yl)pyridin-2-amine | White solid, 33% | MS: ESI+, m/z = 380 [MH]+<br>HPLC: Acidic Analytical (QC)<br>Rt = 2.3 min |
| 32 | 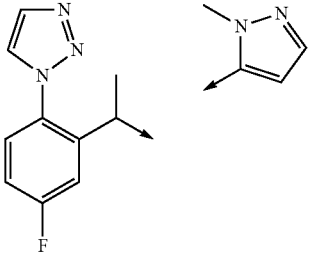 | 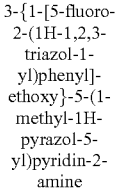 | 3-{1-[5-fluoro-2-(1H-1,2,3-triazol-1-yl)phenyl]-ethoxy}-5-(1-methyl-1H-pyrazol-5-yl)pyridin-2-amine | Brown solid, 46% | $^1$H NMR (400 MHz, CDCl$_3$): δ ppm 1.60 (d, J = 6.25 Hz, 3 H) 3.70-3.81 (m, 3 H) 4.89 (s, 2 H), 5.37-5.47 (m, 1 H), 6.15 (d, J = 1.95 Hz, 1 H), 6.77 (d, J = 1.56 Hz, 1 H), 7.11-7.19 (m, 1 H), 7.31 (dd, J = 8.59, 4.69 Hz, 1 H), 7.36 (dd, J = 8.98, 2.73 Hz, 1 H), 7.46 (d, J = 1.95 Hz, 1 H), 7.71 (d, J = 1.95 Hz, 1 H), 7.73 (d, J = 1.17 Hz, 1 H), 7.90 (d, J = 0.78 Hz, 1 H)<br>MS: ESI+, m/z = 380 [MH]+ |
| 33[3] | 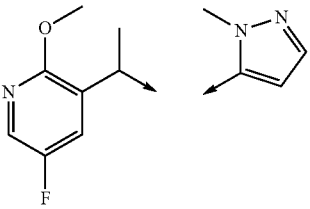 | 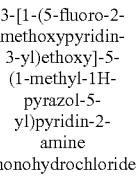 | 3-[1-(5-fluoro-2-methoxypyridin-3-yl)ethoxy]-5-(1-methyl-1H-pyrazol-5-yl)pyridin-2-amine monohydrochloride | White foam, 40% | $^1$H NMR (400 MHz, DMSO-d6): δ ppm 1.61 (d, J = 6.25 Hz, 3 H), 3.74 (s, 3 H), 3.90 (s, 3 H), 5.75 (s, 1 H), 5.90 (q, 1 H), 6.40 (d, J = 1.95 Hz, 1 H), 7.38-7.55 (m, 2 H), 7.76 (d, J = 1.56 Hz, 1 H), 7.97 (dd, 1 H), 8.13 (d, J = 2.73 Hz, 1 H), 8.39 (br. s., 1 H)<br>MS: APCI, m/z 344 [M + H]+ |
| 34[4] | 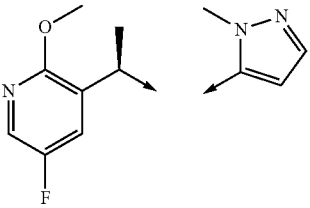 | 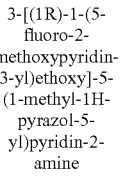 | 3-[(1R)-1-(5-fluoro-2-methoxypyridin-3-yl)ethoxy]-5-(1-methyl-1H-pyrazol-5-yl)pyridin-2-amine | White foam, 20% | $^1$H NMR (400 MHz, DMSO-d6) d ppm 1.61 (d, J = 6.25 Hz, 3 H), 3.74 (s, 3 H), 3.90 (s, 3 H), 5.75 (s, 1 H), 5.90 (q, 1 H), 6.40 (d, J = 1.95 Hz, 1 H), 7.38-7.55 (m, 2H), 7.76 (d, J = 1.56 Hz, 1 H), 7.97 (dd, 1 H), 8.13 (d, J = 2.73 Hz, 1 H), 8.39 (br. s., 1 H)<br>MS: APCI, m/z 344 [M + H]+<br>Optical purity: >98% e.e. (Rt = 10.843 min (opposite enantiomer Rt = 9.712 min)). |
| 35 | 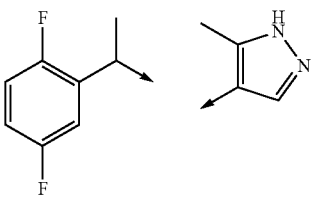 | 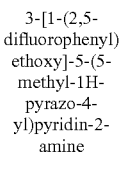 | 3-[1-(2,5-difluorophenyl)ethoxy]-5-(5-methyl-1H-pyrazo-4-yl)pyridin-2-amine | White foam, 51% | $^1$H NMR (400 MHz, CDCl$_3$): δ ppm 1.74 (d, 3H), 2.22 (s, 3H), 5.12 (br s, 1H), 5.66 (q, 1H), 5.73 (br s, 2H), 6.86 (d, 1H), 6.99 (m, 1H), 7.04-7.12 (m, 2H), 7.49 (s, 1H), 7.57 (d, 1H)<br>MS: APCI, m/z 331 [M + H]+ |
| 36[5] | 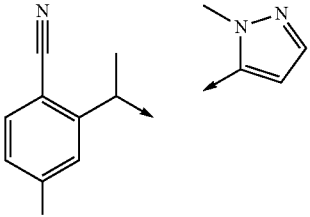 | 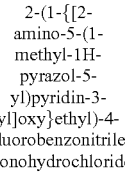 | 2-(1-{[2-amino-5-(1-methyl-1H-pyrazol-5-yl)pyridin-3-yl]oxy}ethyl)-4-fluorobenzonitrile monohydrochloride | White solid, 88% | $^1$H NMR (400 MHz, METHANOL-d4) δ ppm 1.85 (d, J = 6.64 Hz, 3 H) 3.77 (s, 3 H) 4.90 (br. s., 2 H) 6.04 (q, J = 6.25 Hz, 1 H) 6.43 (d, J = 1.95 Hz, 1 H) 7.32 (td, J = 8.30, 2.54 Hz, 1 H) 7.39 (d, J = 1.56 Hz, 1 H) 7.54 (d, J = 1.95 Hz, 1 H) 7.59 (dd, J = 9.37, 2.73 Hz, 1 H) 7.66 (d, J = 1.56 Hz, 1 H) 7.90 (dd, J = 8.59, 5.47 Hz, 1 H)<br>MS: APCI, m/z 338 [M + H]+ |

| Ex No | R' | R | Name | Form, yield | Data |
|---|---|---|---|---|---|
| 37[6] | 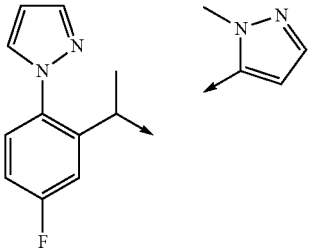 |  | 3-{1-[5-fluoro-2-(1H-pyrazol-1-yl)phenyl]-ethoxy}-5-(1-methyl-1H-pyrazol-5-yl)pyridin-2-amine | Cream waxy solid, 76% | $^1$H NMR (400 MHz, CDCl$_3$): δ ppm 1.58 (d, 3H), 3.72 (s, 3H), 4.90 (bs, 2H, NH$_2$), 5.64 (q, 1H), 6.16 (d, 1H), 6.47 (dd, 1H), 6.91 (d, 1H), 7.06 (ddd, 1H), 7.25-7.30 (m, 2H), 7.46 (d,1H), 7.57 (dd, 1H), 7.69 (d, 1H), 7.73 (d, 1H) MS: APCI, m/z 379.1 [M + H]+ |
| 38[2] | 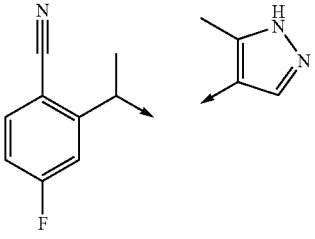 |  | 2-(1-{[2-amino-5-(3-methyl-1H-pyrazol-4-yl)pyridin-3-yl]oxy}ethyl)-4-fluorobenzonitrile | White foam, 53% | MS: ESI+, m/z = 338.134 [MH]+ HPLC: Acidic Analytical (QC) Rt = 2.16 min |
| 39[6] | 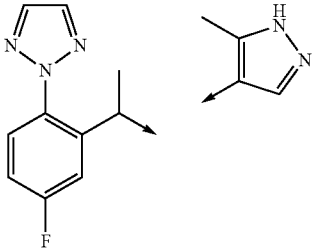 |  | 3-{1-[5-fluoro-2-(2H-1,2,3-triazol-2-yl)phenyl]-ethoxy}-5-(3-methyl-1H-pyrazol-4-yl)pyridin-2-amine | White foam, 48% | $^1$H NMR (400 MHz, CDCl$_3$): δ ppm 1.61 (d, 3H), 2.21 (s, 3H), 4.77 (bs, 2H, NH$_2$), 5.73 (q, 1H), 6.80 (d, 1H), 7.10 (ddd, 1H), 7.31 (dd, 1H), 7.52 (s, 1H), 7.61 (dd, 1H), 7.68 (d, 1H), 7.89 (s, 2H) MS: ESI+, m/z = 380.1 [MH]+ |
| 40[7] | 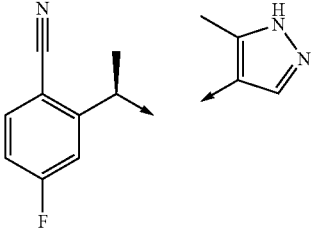 |  | 2-[(1R)-1-{[2-amino-5-(3-methyl-1H-pyrazol-4-yl)pyridin-3-yl]oxy}ethyl]-4-fluorobenzonitrile | White foam, 32% | $^1$H NMR (400 MHz, CDCl$_3$): δ ppm 1.78 (d, J = 6.25 Hz, 2 H) 2.25 (s, 3 H) 4.70-5.10 (m, 2 H) 5.58-5.79 (m, 1 H) 6.73 (d, J = 1.95 Hz, 1 H) 7.03-7.21 (m, 1 H) 7.25-7.31 (m, 1 H) 7.51 (s, 1 H) 7.63-7.79 (m, 2 H) MS: ESI+, m/z = 338.04 [MH]+ Optical purity = 99.8% e.e. (Rt = 9.534 min (opposite enantiomer Rt = 13.453 min)). |
| 41[8] | 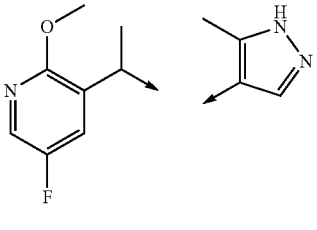 |  | 3-[1-(5-fluoro-2-methoxypyridin-3-yl)ethoxy]-5-(3-methyl-1H-pyrazol-4-yl)pyridin-2-amine | White foam, 26% | $^1$H NMR (400 MHz, CDCl$_3$): δ ppm 1.65 (d, J = 6.25 Hz, 3 H) 2.20 (s, 3 H) 4.00 (s, 3 H) 4.78 (br. s., 2 H) 5.57 (q, 1 H) 6.70 (d, J = 1.56 Hz, 1 H) 7.39 (dd, 1 H) 7.48 (s, 1 H) 7.69 (d, J = 1.56 Hz, 1 H) 7.93 (d, J = 2.73 Hz, 1 H) MS: ESI+, m/z = 344 [MH]+ |
| 42[8] | 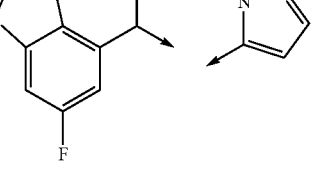 |  | 3-[1-(6-fluoro-1,3-benzothiazol-4-yl)ethoxy]-5-(1-methyl-1H-pyrazol-5-yl)pyridin-2-amine | Off white solid, 51% | $^1$H NMR (400 MHz, CDCl$_3$): δ ppm 1.83 (d, J = 6.25 Hz, 3 H) 3.44 (s, 3 H) 5.01 (br. s., 2 H) 6.04 (d, J = 1.95 Hz, 1 H) 6.33 (q, 1 H) 6.75 (d, J = 1.95 Hz, 1 H) 7.30 (dd, J = 9.57, 2.54 Hz, 1 H) 7.39 (d, J = 1.56 Hz, 1 H) 7.58 (dd, J = 7.81, 2.34 Hz, 1 H) 7.68 (d, J = 1.95 Hz, 1 H) 9.01 (s, 1 H) MS: ESI+, m/z = 370 [MH]+ |

| Ex No | R' | R | Name | Form, yield | Data |
|---|---|---|---|---|---|
| 43[5] | 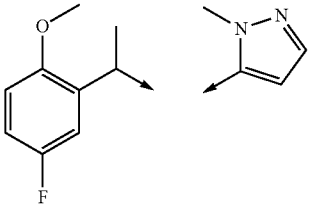 | 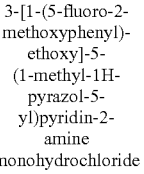 | 3-[1-(5-fluoro-2-methoxyphenyl)-ethoxy]-5-(1-methyl-1H-pyrazol-5-yl)pyridin-2-amine monohydrochloride | Beige solid, 39% | $^1$H NMR (400 MHz, CD$_3$OD): δ ppm 1.72 (d, J = 6.64 Hz, 3 H) 3.62 (s, 3 H) 3.89 (s, 3H) 4.90 (br. s., 3 H) 6.00 (q, J = 6.25 Hz, 1 H) 6.35 (s, 1 H) 7.03 (m, 2 H) 7.19 (m, 2 H) 7.54 (s, 1 H) 7.59 (s, 1 H) MS: APCI+, m/z = 343 [MH]+ |
| 44[7] | 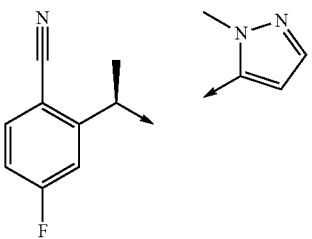 | 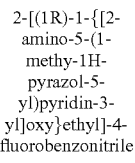 | 2-[(1R)-1-{[2-amino-5-(1-methy-1H-pyrazol-5-yl)pyridin-3-yl]oxy}ethyl]-4-fluorobenzonitrile | White solid, 43% | $^1$H NMR (400 MHz, CD$_3$OD): δ ppm 1.79 (d, J = 6.64 Hz, 3 H) 3.70 (s, 3 H) 4.87 (s, 2 H) 5.78-5.91 (m, 1 H) 6.24 (d, J = 1.95 Hz, 1 H) 6.98 (d, J = 1.56 Hz, 1 H) 7.21-7.31 (m, 1 H) 7.45 (d, J = 1.95 Hz, 1 H) 7.50-7.57 (m, 1 H) 7.63 (d, J = 1.56 Hz, 1 H) 7.80-7.92 (m, 1 H) MS: ESI+, m/z = 338 [MH]+ Optical purity: 99.8% e.e. (Rt = 14.93 min (opposite enantiomer Rt = 10.51 min)). |
| 45[1] | 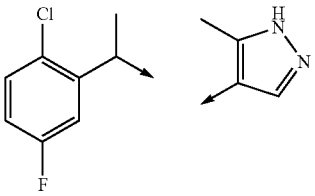 | 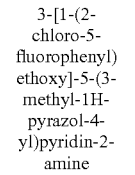 | 3-[1-(2-chloro-5-fluorophenyl)ethoxy]-5-(3-methyl-1H-pyrazol-4-yl)pyridin-2-amine | White foam, 64% | MS: ESI+, m/z = 347.1 [MH]+ HPLC: Acidic Analytical (QC) Rt = 2.30 min |
| 46[2,9] | 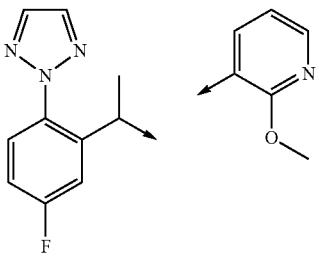 | 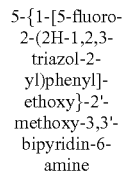 | 5-{1-[5-fluoro-2-(2H-1,2,3-triazol-2-yl)phenyl]-ethoxy}-2'-methoxy-3,3'-bipyridin-6-amine | White solid, 35% | MS: ESI+, m/z = 407.155 [MH]+ HPLC: Acidic Analytical (QC) Rt = 2.37 min |
| 47[1] | 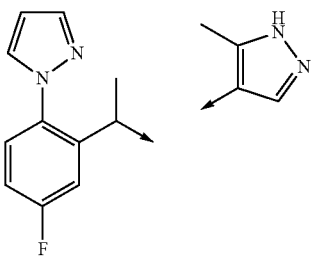 | 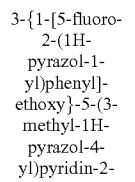 | 3-{1-[5-fluoro-2-(1H-pyrazol-1-yl)phenyl]-ethoxy}-5-(3-methyl-1H-pyrazol-4-yl)pyridin-2-amine | White foam, 17% | MS: ESI+, m/z = 379.3 [MH]+ HPLC: Acidic Analytical (QC) Rt = 2.14 min |
| 48[1] | 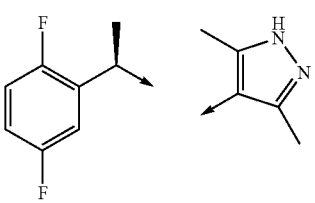 | 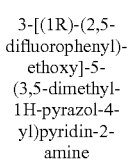 | 3-[(1R)-(2,5-difluorophenyl)-ethoxy]-5-(3,5-dimethyl-1H-pyrazol-4-yl)pyridin-2-amine | White solid, 41% | MS: ESI+, m/z = 345.145 [MH]+ HPLC: Acidic Analytical (QC) Rt = 2.15 min |

| Ex No | R' | R | Name | Form, yield | Data |
|---|---|---|---|---|---|
| 49[6] | 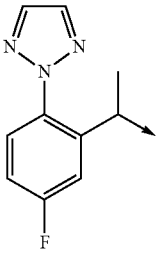 | 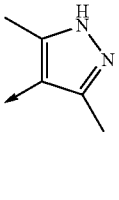 | 5-(3,5-dimethyl-1H-pyrazol-4-yl)-3-{1-[5-fluoro-2-(2H-1,2,3-triazol-2-yl)phenyl]-ethoxy}pyridin-2-amine | Cream solid, 26% | $^1$H NMR (400 MHz, CDCl$_3$): δ 1.59 (d, 3H), 2.08 (s, 6H), 4.78 (bs, 2H, NH$_2$), 5.79 (q, 1H), 6.66 (d, 1H), 7.10 (ddd, 1H), 7.31 (dd, 1H), 7.54 (d, 1H), 7.62 (dd, 1H), 7.85 (s, 2H) MS: ESI+, m/z = 394.2 [MH]+ |
| 50[10] | 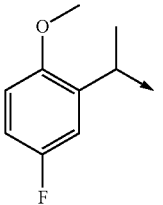 | 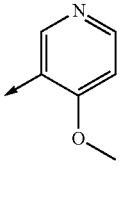 | 5-[1-(5-fluoro-2-methoxyphenyl)-ethoxy]-4'-methoxy-3,3'-bipyridin-6-amine | Library | LRMS: ESI+, m/z = 370 [MH]+ HPLC[11]: Rt = 1.77 min |
| 51 | 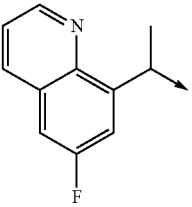 | 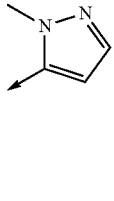 | 3-[1-(6-fluoroquinolin-8-yl)ethoxy]-5-(1-methyl-1H-pyrazol-5-yl)pyridin-2-amine | Beige solid, 10% | $^1$H NMR (400 MHz, CDCl$_3$): δ 1.82 (d, 3H), 3.32 (s, 3H), 5.02 (bs, 2H, NH$_2$), 5.99 (d, 1H), 6.71 (s, 1H), 6.72 (q, 1H), 7.35 (d, 1H), 7.38 (dd, 1H), 7.50 (dd, 1H), 7.56 (dd, 1H), 7.66 (d, 1H), 8.15 (dd, 1H), 8.91 (dd, 1H) MS: ESI+, m/z = 363.9 [MH]+ |
| 52[6] | 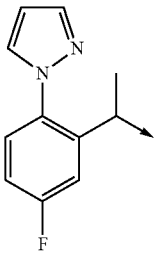 | 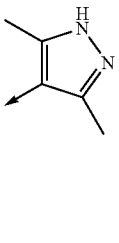 | 5-(3,5-dimethyl-1H-pyrazol-4-yl)-3-{1-[5-fluoro-2-(1H-pyrazol-1-yl)phenyl]-ethoxy}pyridin-2-amine | Pale yellow solid, 68% | $^1$H NMR (400 MHz, CDCl$_3$): δ 1.55 (d, 3H), 2.11 (s, 6H), 4.75 (bs, 2H, NH$_2$), 5.62 (q, 1H), 6.45 (m, 1H), 6.76 (d, 1H), 7.05 (ddd, 1H), 7.24-7.31 (m, 2H), 7.53 (d, 1H), 7.55 (d, 1H), 7.71 (d, 1H) MS: ESI+, m/z = 393.2 [MH]+ |
| 53[1,12] | 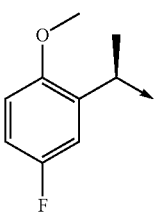 | 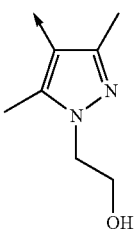 | 2-(4-{6-amino-5-[(1R)-1-(5-fluoro-2-methoxyphenyl)-ethoxy]pyridin-3-yl}-3,5-dimethyl-1H-pyrazol-1-yl)ethanol | White foam, 31% | MS: ESI+, m/z = 401.191 [MH]+ HPLC: Acidic Analytical (QC) Rt = 2.22 min |

131
-continued

| Ex No | R' | R | Name | Form, yield | Data |
|---|---|---|---|---|---|
| 54[10] | 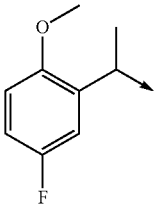 | 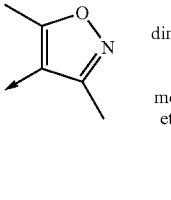 | 5-(3,5-dimethylisoxazol-4-yl)-3-[1-(5-fluoro-2-methoxyphenyl)-ethoxy]pyridin-2-amine | Library | LRMS: ESI+, m/z = 358 [MH]+ HPLC[11]: Rt = 2.543 min |

Footnotes:

[1] Purified by preparative HPLC under Acidic conditions.

[2] Purified by preparative HPLC under Basic conditions.

[3] Purified by chromatography on silica (20 g) eluting with a gradient of ethyl acetate in heptane (20:80 to 70:30). The hydrochloride salt was formed by dissolving ethyl acetate, treating with 2M hydrogen chloride in diethyl ether and evaporating.

[4] Racemic material prepared and then enantiomers produced by sperating by preparative chiral HPLC.(Chiral column conditions: Chiralpak AD-H (250*4.6 mm i.d.), eluent 30% isopropyl alcohol in heptane, 0.75 mL/min)

[5] Purified by partitioning with 2M HCl instead of citric acid. The crude product was treated with 2M hydrogen chloride in diethyl ether and evaporated to give the crude salt. The crude salt was triturated with diethyl ether and filtered.

[6] Purified by automated flash chromatography ISCO ™, 12 g silica cartridge, gradient elution of ethyl acetate in heptane (50:50 to 100:0) over 25 min.

[7] Racemic material prepared and then enantiomers produced by sperating by preparative chiral HPLC (Chiral column conditions: Chiralpak AD-H (250*4.6 mm i.d.), eluent 50% methyl alcohol in ethanol, 0.5 mL/min).

[8] Purified by automated flash chromatography ISCO ™, 12 g silica cartridge, gradient elution of ethyl acetate in heptane (0:100 to 100:0) over 25 min then dichloromethane:methanol:0.880 ammonia (95:5:0.5).

[9] (2-methoxypyridin-3-yl)boronic acid used instead of boronic ester, reaction time 16 hr.

[10] Made as part of parallel array (library) using 1,1'-bis (di-t-butylphosphino) ferrocene palladium (II) dichloride as catalyst and cesium carbonate as base in mixture of 1,4 dioxane, dimethyl acetamide and water.

[11] Compound purified by HPLC (Agilent 1200 HPLC/1956 MSD/SEDEX 75 ELSD, ionization mode API-ES, polarity positive) [column: Welch XB-C18 2.1 x 50 mm 5 μm, temperature: 50° C., mobile phase A: 0.0375% TFA in water, mobile phase B: 0.0188% TFA in acetonitrile, Gradient: initial 1% B, T = 0 min 1% B, T = 0.6 min 5% B, T = 4.0 min 100%B, T = 4.3 min 1% B, T = 4.7 min 1% B, Flow rate: 0.8 ml/min, injection volume 2 μL].

[12] Using the boronate ester of preparation 72. Deprotected by stirring crude reaction mixture in dimethyl fomamide (1 mL) with Cesium fluoride (excess) for 5 hr.

Example 55

4-{1-[5-fluoro-2-(1H-pyrazol-1-yl)phenyl]ethoxy}-6-(1-methyl-1H-pyrazol-5-yl)pyridazin-3-amine

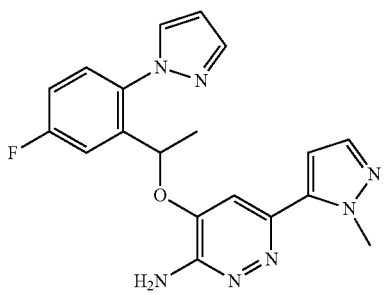 [SMILES: CC(Oc1cc(-c2ccnn2C)nnc1N)c1cc(F)ccc1-n1cccn1]

To a solution of the chloride of preparation 55 (100 mg, 0.3 mmol) in dimethyl ethylene glycol (4 mL) were added 1-methyl-5-(4,4,5,5-tetramethyl-1,3,2-dioxaborolan-2-yl)-1H-pyrazole (125 mg, 0.6 mmol, 2.0 eq.), 1,1'-bis(diphenylphosphino)ferrocene palladium dichloride (44 mg, 0.06 mmol, 0.2 eq.) and cesium fluoride (160 mg, 1.05 mmol, 3.5 eq.). The resulting mixture was thoroughly degassed before heating, under an atmosphere of nitrogen, to 100° C. for 3 hr. The crude reaction mixture was partitioned between ethyl acetate (40 mL) and water (40 mL). The organic phase was dried over magnesium sulphate and the mixture filtered and the filtrate evaporated under reduced pressure. The resulting residue was purified by chromatography on silica (50 g) eluting with ethyl acetate. Clean fractions were combined and evaporated under reduced pressure to give the title compound as a purple solid. (35 mg, 31%)

$^1$H NMR (400 MHz, CDCl$_3$): δ ppm 1.62 (d, 3H), 4.20 (s, 3H), 5.27 (br s, 2H), 5.77 (q, 1H), 6.56 (m, 1H), 6.57 (d, 1H), 7.10 (m, 1H), 7.22 (dd, 1H), 7.26 (m, 1H), 7.32 (dd, 1H), 7.46 (d, 1H), 7.66 (d, 1H), 7.83 (d, 1H)

MS: ESI+, m/z=380.1 [MH]+

Example 56

4-[(1R)-1-(5-fluoro-2-methoxyphenyl)ethoxy]-6-(1-methyl-1H-pyrazol-5-yl)pyridazin-3-amine

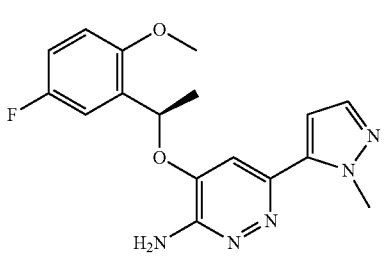 [SMILES: COc1ccc(F)cc1[C@@H](C)Oc1cc(-c2ccnn2C)nnc1N]

The title compound was prepared by a similar method to that of example 55 using the chloride of preparation 54. The titled compound was isolated as an off white foam (52%).

$^1$H-NMR (400 MHz, CDCl$_3$): δ ppm 1.69 (d, 3H), 3.94 (s, 3H), 4.15 (s, 3H), 5.06 (s, 2H), 5.83 (q, 1H), 6.24 (d, 1H), 6.70 (s, 1H), 6.88 (dd, 1 h), 6.95-7.02 (m, 2H), 7.45 (d, 1H)

MS: ESI+, m/z=366 [MNa]+

Example 57

5-(1,2-dimethyl-1H-imidazol-4-yl)-3-[1-(5-fluoro-2-methoxyphenyl)ethoxy]pyrazin-2-amine

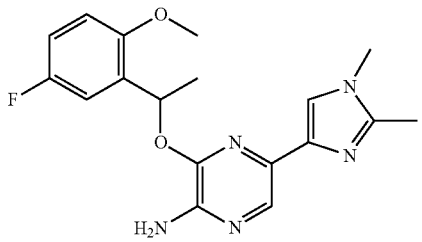 [SMILES: COc1ccc(F)cc1C(C)Oc1nc(-c2cn(C)c(C)n2)cnc1N]

To a solution of the bromide of preparation 56 (50 mg, 0.15 mmol) in dimethyl sulphoxide (3 mL) were added 1,1'-bis(diphenylphosphino)ferrocene palladium dichloride (11 mg, 0.015 mmol, 0.1 eq.) and potassium acetate (21 mg, 0.22 mmol, 1.5 eq.). The resulting mixture was thoroughly degassed before heating, under an atmosphere of nitrogen, in a microwave vial to 120° C. for 15 min (Biotage Initiator™ 400 W). The crude intermediate reaction mixture was cooled and 4-bromo-1,2-dimethyl-1H-imidazole (50 mg, 0.3 mmol, 2 eq.) added followed by potassium phosphate (160 mg, 0.75 mmol, 5 eq.). The vial was sealed and reheated to 150° C. for 30 min under μWave heating. The black reaction mixture was partitioned between ethyl acetate (20 mL) and water (20 mL). The organic phase was dried over magnesium sulphate and the mixture filtered and the filtrate evaporated under reduced pressure. The resulting residue was purified by automated chromatography on an ISCO™ silica cartridge (12 g) eluting with ethyl acetate in heptane (50:50) followed by a gradient of methanol in ethyl acetate (0:100 to 5:95). The clean fractions were combined and evaporated under reduced pressure to give the title compound as a brown oil. (7 mg, 10%)

$^1$H NMR (400 MHz, CDCl$_3$): δ ppm 1.62 (d, 3H) 2.39 (s, 3H) 3.57 (s, 3H) 3.88 (s, 3H) 4.79 (br. s., 2H) 6.51 (q, 1H) 6.77-6.85 (m, 1H) 6.86-6.95 (m, 1H) 7.07 (s, 1H) 7.12 (dd, 1H) 8.13 (s, 1H)

MS: ESI+, m/z=358 [MH]+

Example 58

3-[1-(5-fluoro-2-methoxyphenyl)ethoxy]-5-(1-methyl-1H-imidazol-4-yl)pyrazin-2-amine

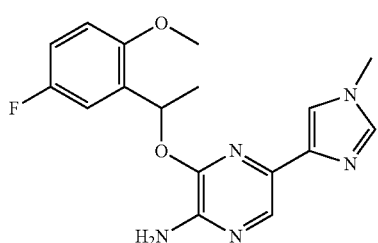

The title compound was prepared by a similar method to that of example 20 except using the bromide of preparation 56 and 4-iodo-1-methyl-1H-imidazole. The reaction mixture was purified by HPLC under basic conditions to isolate the title compound as a white foam (25%).

MS: ESI+, m/z=342.144 [MH]+

HPLC: Basic Analytical (QC) Rt=2.87 min

Example 59

3-[1-(2-chloro-5-fluorophenyl)ethoxy]-5-(1-methyl-1H-imidazol-4-yl)pyrazin-2-amine

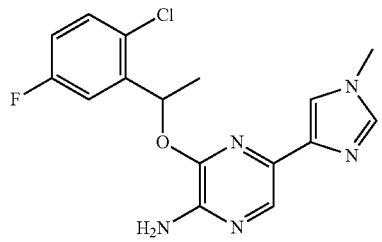 [SMILES: CC(Oc1nc(-c2cn(C)cn2)cnc1N)c1cc(F)ccc1Cl]

The title compound was prepared by a similar method to that of example 57 except using 4-iodo-1-methyl-1H-imidazole and the bromide of preparation 57 and cesium carbonate used instead of potassium phosphate. The reaction mixture was purified by HPLC under basic conditions to isolate the title compound as a white foam (10%).

MS: ESI+, m/z=348.095 [MH]+

HPLC: Basic Analytical (QC) Rt=3.05 min

Example 60

3-[1-(5-fluoro-2-methoxyphenyl)ethoxy]-5-(1-methyl-1H-imidazol-2-yl)pyrazin-2-amine

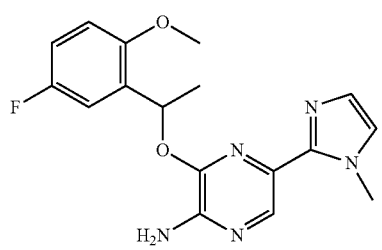 [SMILES: COc1ccc(F)cc1C(C)Oc1nc(-c2nccn2C)cnc1N]

The title compound was prepared by a similar method to that of example 20 except using the bromide of preparation 56 and 2-iodo-1-methyl-1H-imidazole. The reaction mixture was purified by chromatography on silica (5 g) eluting with a gradient of dichloromethane: methanol: ammonium hydroxide (100:0:0 to 90:10:1) to isolate the title compound as a white foam (42%).

$^1$H NMR (400 MHz, CDCl$_3$): δ ppm 1.63 (d, 3H), 3.61 (s, 3H), 3.83 (s, 3H), 5.03 (s, 2H), 6.38 (q, 1H), 6.77-6.81 (m 2H), 6.87-6.92 (m, 1H), 6.99-7.01 (m, 2H), 8.38 (s, 1H)

MS: APCI+, m/z=344 [MH]+

Example 61

3-[1-(2-Bromo-5-fluoro-phenyl)-ethoxy]-5-(2-methyl-2H-pyrazol-3-yl)-pyridin-2-ylamine

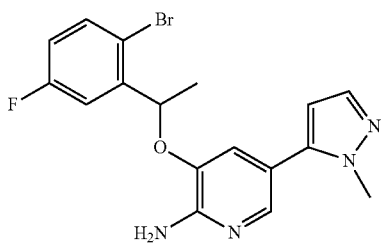 [SMILES: CC(Oc1cc(-c2ccnn2C)cnc1N)c1cc(F)ccc1Br]

The title compound was prepared by a similar method to that of example 30 using the iodide of preparation 52, except the reaction was heated to 60° C. for 4 hr and then purified by chromatography on silica eluting with a gradient of ethyl acetate in heptane (50:50 to 100:0). The titled compound was isolated as a brown solid (100%).

$^1$H NMR (400 MHz, CDCl$_3$): δ ppm 1.69 (d, J=6.25 Hz, 3H) 3.65 (s, 3H) 4.94 (s, 2H) 5.48-5.72 (m, 1H) 6.15 (d, J=1.95 Hz, 1H) 6.57 (d, J=1.95 Hz, 1H) 6.83-6.97 (m, 1H) 7.09-7.19 (m, 1H) 7.45 (d, J=1.95 Hz, 1H) 7.54 (dd, J=8.79, 5.27 Hz, 1H) 7.72 (d, J=1.95 Hz, 1H)

MS: ESI+, m/z=391.24, 393.20 [MH]+

Example 62

3-{1-[5-fluoro-2-(1,3-oxazol-2-yl)phenyl]ethoxy}-5-(1-methyl-1H-pyrazol-5-yl)pyridin-2-amine

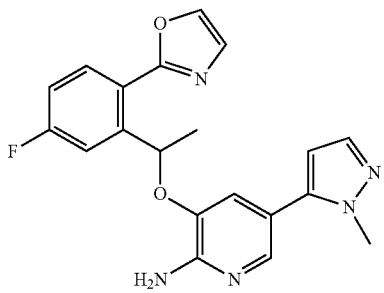 [SMILES: CC(Oc1cc(-c2ccnn2C)cnc1N)c1cc(F)ccc1-c1ncco1]

The title compound was prepared by a similar method to that of example 30 using the bromide of example 61, except 2-tributylstannanyl-oxazole used instead of 1-methyl-5-(4,4,5,5-tetramethyl-1,3,2-dioxaborolan-2-yl)-1H-pyrazole. The reaction mixture was purified by HPLC under acidic conditions to isolate the title compound as a white foam (41%).

MS: ESI+, m/z=380.144 [MH]+

HPLC: Basic Analytical (QC) Rt=3.07 min

Example 63

3-{1-[5-Fluoro-2-(1-methyl-1H-imidazol-2-yl)-phenyl]ethoxy}-5-(2-methyl-2H-pyrazol-3-yl)-pyridin-2-ylamine

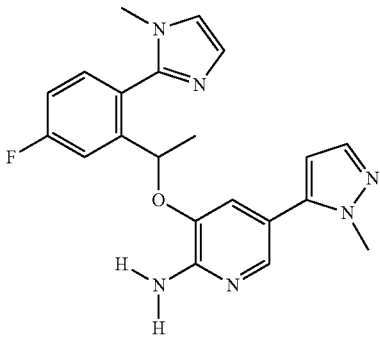 [SMILES: CC(Oc1cc(-c2ccnn2C)cnc1N)c1cc(F)ccc1-c1nccn1C]

To a solution of example 61 (100 mg, 0.256 mmol) was added MeOH (2 mL) and 2-butylstannanyl-1-methyl-1H-imidazole (114 mg, 0.307 mmol). The reaction solution was degassed and charged with nitrogen for 5 mins, then added CsF (117 mg, 0.77 mol) in water (0.1 mL) and bis(tri-t-butyphosphine)palladium (13 mg, 0.03 mmol). The reaction was degassed and heated at 100° C. for 30 mins, cooled to room temperature, filtered to remove the solid. The filtrate was concentrated and purified with a reversed phase preparative HPLC eluting with water/methanol containing 0.1% formic acid to provide the title compound as a white amorphous solid after lyophilization (15 mg, 15% yield).

$^1$H NMR (400 MHz, CDCl$_3$) δ ppm 1.68 (br. s., 3H) 3.12 (s, 3H) 3.64 (s, 3H) 5.02 (br. s., 2H) 5.43 (q, J=6.40 Hz, 1H) 6.08 (s, 1H) 6.26 (s, 1H) 7.09 (td, J=8.15, 2.65 Hz, 2H) 7.18 (dd, J=8.34, 5.56 Hz, 1H) 7.34 (dd, J=9.47, 2.40 Hz, 1H) 7.48 (s, 1H) 7.53 (s, 1H) 7.63 (s, 1H)

Example 64

5-(5-amino-6-{(1R)-1-[5-fluoro-2-(2H-1,2,3-triazol-2-yl)phenyl]ethoxy}pyrazin-2-yl)pyridine-2-carboxamide

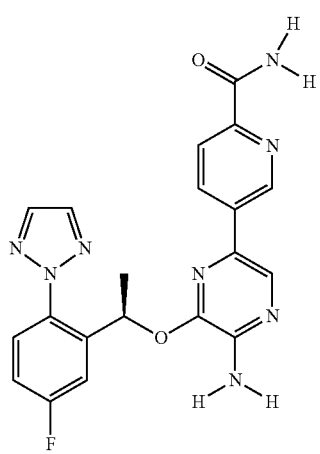 [SMILES: C[C@@H](Oc1nc(-c2ccc(C(N)=O)nc2)cnc1N)c1cc(F)ccc1-n1nccn1]

The pyrazine starting material of preparation 104 (100 mg, 0.264 mmol, 1.0 eq) and 4-(4,4,5,5-tetramethyl-[1,3,2]dioxaborolan-2-yl)-benzamide (150 mg, 0.6046 mmol, 1.7 eq) were dissolved in DME (3 mL), which then was added freshly prepared $Na_2CO_3$ aqueous solution (3.0 eq, 84 mg/0.4 mL $H_2O$) and $PdCl_2(dppf)CH_2Cl_2$ (10 mg, 0.05 eq). The suspension was degassed for three times and was heated up via microwave at 120° C. for 1 hr. The reaction was monitored by LCMS for completion. The crude product was filtered and concentrated. The residue was purified with a reverse phase preparative HPLC under acidic condition to provide the title compound as a white amorphous solid after lyophilization (64 mg, 57.6% yield)

$^1$H NMR (600 MHz, DMSO-$D_6$): δ ppm 8.77 (d, J=1.89 Hz, 1H), 8.33 (s, 2H), 8.23 (s, 1H), 8.07 (br. s., 1H), 7.93-7.96 (m, 1H), 7.89 (dd, J=8.12, 2.08 Hz, 1H), 7.80 (dd, J=9.82, 3.02 Hz, 1H), 7.69 (dd, J=8.88, 5.10 Hz, 1H), 7.62 (br. s., 1H), 7.31 (td, J=8.31, 3.02 Hz, 1H), 6.93 (s, 2H), 6.49 (q, J=6.42 Hz, 1H), 1.73 (d, J=6.42 Hz, 3H).

MS: m/z 421.20 [MH]+.

Examples 65 to 84

Examples 65-84 were prepared by a similar method to that of example 64 using the appropriate 5-bromo-pyridin-2-amine or 5-bromo-pyrazin-2-amine and aryl or heteroaryl boronate ester stating materials. Examples 71, 73-74 and 79-81 used Boc-protected boronic ester. After Suzuki coupling reaction, the Boc-protecting group was removed with 4M HCl/dioxane and methanol as exemplified with example 71.

Example 71

3-{(1R)-1-[5-fluoro-2-(2H-1,2,3-triazol-2-yl)phenyl]
ethoxy}-5-[1-(piperidin-4-yl)-1H-pyrazol-4-yl]
pyrazin-2-amine

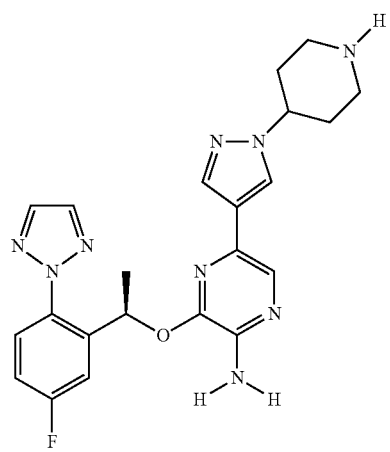 [SMILES: C[C@@H](Oc1nc(-c2cnn(C3CCNCC3)c2)cnc1N)c1cc(F)ccc1-n1nccn1]

4-(3-{5-Amino-6-[(R)-1-(5-fluoro-2-[1,2,3]triazol-2-yl-phenyl)-ethoxy]-pyrazin-2-yl}-pyrazol-1-yl)-piperidine-1-carboxylic acid tert-butyl ester (80 mg, 0.15 mmol) was dissolved in MeOH (6 mL), then added a solution of HCl (4M, 1 mL, 4 mmol) in dioxane. The mixture was stirred at room temperature for 2 hours at which time the starting material was disappeared by LCMS. The reaction solvent was removed to give 76 mg of the crude desired product as HCl salt which was purified with a revered phase preparative HPLC under acidic condition to provide the title product (62.8 mg, 95% yield).

| Ex No. | Structure | NAME | $^1$H NMR, δ ppm |
|---|---|---|---|
| 65 | 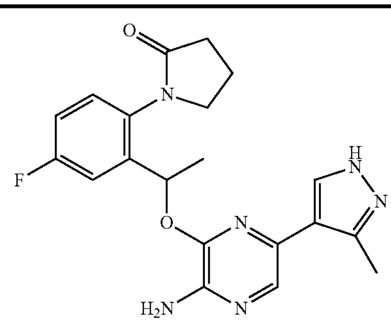 | 1-[2-(1-{[3-amino-6-(3-methyl-1H-pyrazol-4-yl)pyrazin-2-yl]oxy}ethyl)-4-fluorophenyl]pyrrolidin-2-one | 400 MHz, MeOH-$d_4$): 1.69 (3H, d), 1.80-1.94 (1H, m), 2.02-2.12 (1H, m), 2.30-2.51 (5H, m), 3.65-3.75 (2H, m), 6.40 (1H, q), 7.13 (1H, td), 7.26 (1H, dd), 7.49 (1H, dd), 7.63 (1H, s), 7.73 (1H, s). |
| 66 | ABS | 3-{(1R)-1-[5-fluoro-2-(2H-1,2,3-triazol-2-yl)phenyl]ethoxy}-5-(2-methoxypyridin-3-yl)pyrazin-2-amine | 400 MHz, MeOH-$d_4$: 8.22 (s, 1H), 8.01-8.04 (m, 3H), 7.69-7.74 (m, 2H), 7.54 (dd, 1H), 7.17 (td, 1H), 6.96 (dd, 1H), 6.55 (q, 1H), 3.98 (s, 3H), 1.85 (d, 3H). |

| Ex No. | Structure | NAME | $^1$H NMR, δ ppm |
|---|---|---|---|
| 67 | ABS | 3-{(1R)-1-[5-fluoro-2-(2H-1,2,3-triazol-2-yl)phenyl]ethoxy}-5-(3-methyl-1H-pyrazol-4-yl)pyrazin-2-amine | 400 MHz, CDCl$_3$: 7.84 (s, 2H), 7.71 (s, 1H), 7.65-7.68 (m, 2H), 7.35 (dd, 1H), 7.05-7.10 (m, 1H), 6.58 (q, 1H), 4.84 (br s, 1H), 2.29 (s, 3H), 1.69 (d, 3H). |
| 68 | ABS | 5-{4-[(1S)-1-aminoethyl]phenyl}-3-[(1R)-1-(5-fluoro-2-methoxyphenyl)ethoxy]pyrazin-2-amine | 400 MHz, DMSO-d$_6$: 8.03 (s, 1H), 7.71-7.70 (d, 2H), 7.36-7.34 (d, 3H), 7.03-7.02 (d, 2H), 6.53-6.52 (m, 3H), 3.99-3.98 (q, 1H), 3.90 (s, 3H), 1.56-1.55 (d, 3H), 1.25-1.24 (d, 3H) |
| 69 | 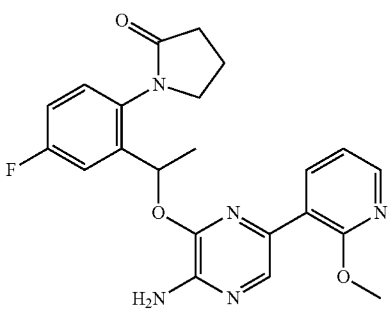 | 1-[2-(1-{[3-amino-6-(2-methoxypyridin-3-yl)pyrazin-2-yl]oxy}ethyl)-4-fluorophenyl]pyrrolidin-2-one | 400 MHz, CDCl$_3$: 1.71 (3H, d), 1.84-1.96 (1H, m), 1.97-2.10 (1H, m), 2.42-2.49 (2H, m), 3.49-3.52 (1H, m), 3.62-3.71 (1H, m), 4.00 (3H, s), 4.90 (2H, s), 6.27-6.34 (1H, m), 6.93 (1H, dd), 7.01-7.07 (1H, m), 7.13 (1H, dd), 7.25-7.30 (1H, m), 7.85 (1H, dd), 8.11 (1H, dd), 8.32 (1H, s). |
| 70 | ABS | 3-{(1R)-1-[5-fluoro-2-(2H-1,2,3-triazol-2-yl)phenyl]ethoxy}-5-[2-(4-methylpiperazin-1-yl)pyridin-4-yl]pyrazin-2-amine | 600 MHz, DMSO-d$_6$: 8.25 (s, 2 H) 8.21 (s, 1 H) 8.00 (d, J = 4.91 Hz, 1 H) 7.69-7.75 (m, 2 H) 7.30-7.34 (m, 1 H) 7.00 (s, 1 H) 6.87 (s, 2 H) 6.68 (d, J = 5.29 Hz, 1 H) 6.57 (q, J = 6.40 Hz, 1 H) 2.54 (s, 2 H) 2.36 (t, J = 4.72 Hz, 4 H) 2.21 (s, 3 H) 1.90 (s, 2 H) 1.62 (d, J = 6.42 Hz, 3 H) |

| Ex No. | Structure | NAME | $^1$H NMR, δ ppm |
|---|---|---|---|
| 71 | ABS | 3-{(1R)-1-[5-fluoro-2-(2H-1,2,3-triazol-2-yl)phenyl]ethoxy}-5-[1-(piperidin-4-yl)-1H-pyrazol-4-yl]pyrazin-2-amine | 600 MHz, DMSO-d$_6$: 8.21-8.26 (m, 2 H) 7.66-7.71 (m, 2 H) 7.63 (dt, J = 8.78, 4.48 Hz, 2 H) 7.51 (s, 1 H) 7.20-7.25 (m, 1H) 6.32 (br. s., 2 H) 6.19 (d, J = 6.42 Hz, 1 H) 4.29 (br. s., 1 H) 3.24 (d, J = 11.71 Hz, 2 H) 2.90 (d, J = 11.71 Hz, 2 H) 2.07 (br. s., 2 H) 1.93-2.02 (m, 2 H) 1.67 (d, J = 6.42 Hz, 3 H) |
| 72 | ABS | 3-{(1R)-1-[5-fluoro-2-(2H-1,2,3-triazol-2-yl)phenyl]ethoxy}-5-[3-(methylsulfonyl)phenyl]pyrazin-2-amine | 600 MHz, DMSO-d$_6$: 8.21 (s, 2 H) 8.16 (br. s., 2 H) 7.71-7.81 (m, 2 H) 7.61-7.68 (m, 2 H) 7.52-7.59 (m, 1 H) 7.24 (t, J = 6.99 Hz, 1 H) 6.82 (br. s., 2 H) 6.52 (d, J = 6.42 Hz, 1 H) 3.20 (s, 3 H) 1.64 (d, J = 6.04 Hz, 3 H) |
| 73 | ABS | 5-{(1R)-1-[5-fluoro-2-(2H-1,2,3-triazol-2-yl)phenyl]ethoxy}-2'-(4-methylpiperazin-1-yl)-3,4'-bipyridin-6-amine | 400 MHz, DMSO-d$_6$: 8.23 (s, 2 H) 8.03 (d, J = 5.56 Hz, 1 H) 7.93 (d, J = 1.52 Hz, 1 H) 7.58-7.68 (m, 2 H) 7.30-7.37 (m, 1 H) 6.90 (d, J = 1.52 Hz, 1 H) 6.67-6.70 (m, 2 H) 6.26 (s, 2 H) 5.56 (q, 1 H) 3.42-3.50 (m, 4 H) 2.39 (t, J = 4.93 Hz, 4 H) 2.22 (s, 3 H) 1.61 (d, J = 6.32 Hz, 3 H) |
| 74 | 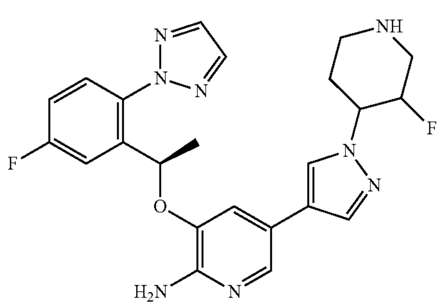 | 5-[1-(3-fluoropiperidin-4-yl)-1H-pyrazol-4-yl]-3-{(1R)-1-[5-fluoro-2-(2H-1,2,3-triazol-2-yl)phenyl]ethoxy}pyridin-2-amine | 400 MHz, DMSO-d$_6$: 8.30 (s, 2 H) 7.91 (s, 1 H) 7.72 (d, J = 1.77 Hz, 1 H) 7.59-7.69 (m, 3 H) 7.33 (td, J = 8.34, 3.03 Hz, 1 H) 6.72 (d, J = 1.52 Hz, 1 H) 5.86 (s, 2 H) 5.36-5.47 (m, 1 H) 4.55-4.92 (m, 1 H) 4.18-4.39 (m, 1 H) 3.25-3.30 (m, 1 H) 2.94 (d, J = 12.63 Hz, 1 H) 2.53-2.61 (m, 2 H) 1.87-2.32 (m, 3 H) 1.61 (d, 3 H) |

| Ex No. | | Structure | NAME | ¹H NMR, δ ppm |
|---|---|---|---|---|
| 75 | ABS | 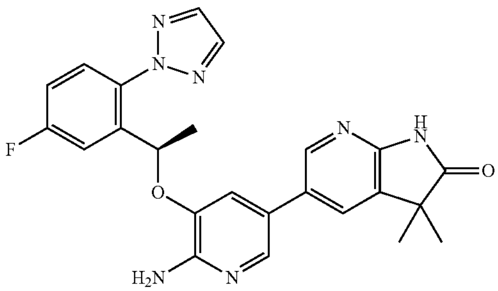 | 5-(6-amino-5-{(1R)-1-[5-fluoro-2-(2H-1,2,3-triazol-2-yl)phenyl]ethoxy}pyridin-3-yl)-3,3-dimethyl-1,3-dihydro-2H-pyrrolo[2,3-b]pyridin-2-one | 400 MHz, DMSO-d₆: 10.95 (s, 1 H) 8.21 (s, 2 H) 8.08 (d, J = 2.27 Hz, 1 H) 7.78 (d, J = 1.77 Hz, 1 H) 7.57-7.70 (m, 3 H) 7.33 (td, J = 8.27, 2.91 Hz, 1 H) 6.81 (d, J = 1.52 Hz, 1 H) 6.07 (s, 2 H) 5.51 (q, J = 6.32 Hz, 1 H) 1.63 (d, J = 6.32 Hz, 3 H) 1.31 (d, 6 H) |
| 76 | ABS | 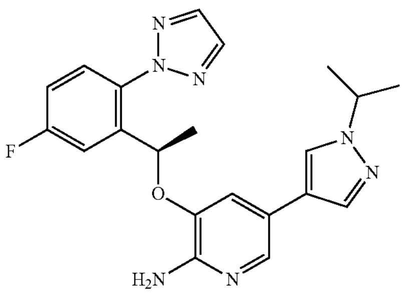 | 3-{(1R)-1-[5-fluoro-2-(2H-1,2,3-triazol-2-yl)phenyl]ethoxy}-5-[1-(propan-2-yl)-1H-pyrazol-4-yl]pyridin-2-amine | 400 MHz, DMSO-d₆: 8.29 (s, 2 H) 7.86 (s, 1 H) 7.71 (d, J = 1.77 Hz, 1 H) 7.60-7.69 (m, 2 H) 7.54 (s, 1 H) 7.33 (td, J = 8.40, 2.91 Hz, 1 H) 6.70 (d, J = 1.52 Hz, 1 H) 5.82 (s, 2 H) 5.40 (q, J = 6.15 Hz, 1 H) 4.44 (dt, J = 13.33, 6.60 Hz, 1 H) 1.62 (d, J = 6.32 Hz, 3 H) 1.42 (d, 6 H) |
| 77 | | 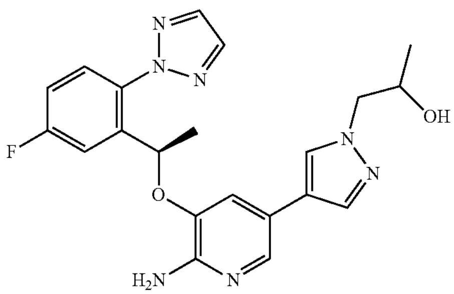 [SMILES: CC(O)Cn1cc(-c2cnc(N)c(O[C@H](C)c3cc(F)ccc3-n3nccn3)c2)cn1] | 1-[4-(6-amino-5-{(1R)-1-[5-fluoro-2-(2H-1,2,3-triazol-2-yl)phenyl]ethoxy}pyridin-3-yl)-1H-pyrazol-1-yl]propan-2-ol | 400 MHz, DMSO-d₆: 8.27 (s, 2 H) 7.77 (s, 1 H) 7.69 (d, J = 1.77 Hz, 1 H) 7.60-7.66 (m, 2 H) 7.53 (s, 1 H) 7.32 (td, J = 8.40, 2.91 Hz, 1 H) 6.70 (d, J = 1.77 Hz, 1 H) 5.82 (s, 2 H) 5.34-5.44 (m, 1 H) 4.87-4.94 (m, 1 H) 3.96 (s, 3 H) 1.59 (d, J = 6.06 Hz, 3 H) 0.99-1.05 (m, 3 H) |
| 78 | ABS | 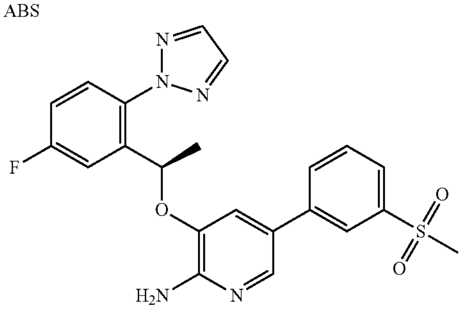 | 3-{(1R)-1-[5-fluoro-2-(2H-1,2,3-triazol-2-yl)phenyl]ethoxy}-5-[3-(methylsulfonyl)phenyl]pyridin-2-amine | 400 MHz, CDCl₃: 7.98-8.06 (m, 3 H) 7.89 (s, 1 H) 7.84 (d, J = 7.83 Hz, 1 H) 7.71 (d, J = 8.08 Hz, 1 H) 7.51-7.59 (m, 2 H) 7.31 (dd, J = 9.09, 2.78 Hz, 1 H) 7.18 (d, J = 1.52 Hz, 1 H) 7.06-7.15 (m, 1 H) 5.58 (q, J = 6.06 Hz, 1 H) 5.16 (br. s., 2 H) 3.09 (s, 3 H) 1.65 (d, 3 H) |
| 79 | | 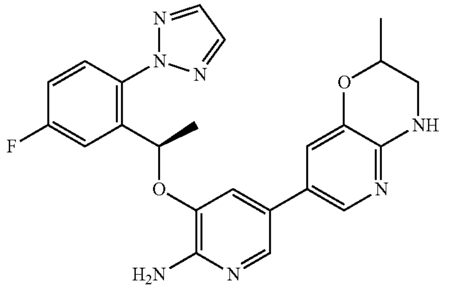 [SMILES: CC1CNc2ncc(-c3cnc(N)c(O[C@H](C)c4cc(F)ccc4-n4nccn4)c3)cc2O1] | 3-{(1R)-1-[5-fluoro-2-(2H-1,2,3-triazol-2-yl)phenyl]ethoxy}-5-(2-methyl-3,4-dihydro-2H-pyrido[3,2-b][1,4]oxazin-7-yl)pyridin-2-amine | 400 MHz, DMSO-d₆: 8.20 (s, 2 H) 7.61-7.69 (m, 3 H) 7.59 (d, J = 2.02 Hz, 1 H) 7.29-7.37 (m, 1 H) 6.97 (d, J = 2.02 Hz, 1 H) 6.71 (d, J = 1.52 Hz, 1 H) 6.67 (d, J = 3.28 Hz, 1 H) 5.91 (s, 2 H) 5.50-5.57 (m, 1 H) 4.10-4.18 (m, 1 H) 3.43 (dt, J = 12.32, 2.94 Hz, 1 H) 3.03-3.10 (m, 1 H) 1.59 (d, J = 6.32 Hz, 3 H) 1.31 (d, 3 H) |

| Ex No. | | Structure | NAME | $^1$H NMR, δ ppm |
|---|---|---|---|---|
| 80 | ABS | 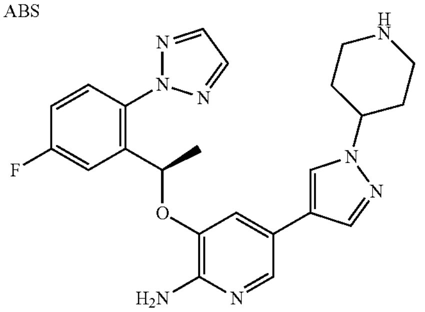 [SMILES: "ABS" ; C[C@@H](Oc1cc(-c2cnn(C3CCNCC3)c2)cnc1N)c1cc(F)ccc1-n1nccn1] | 3-{(1R)-1-[5-fluoro-2-(2H-1,2,3-triazol-2-yl)phenyl]ethoxy}-5-[1-(piperidin-4-yl)-1H-pyrazol-4-yl]pyridin-2-amine | 400 MHz, DMSO-d$_6$: 8.29 (s, 2 H), 7.85 (s, 1 H), 7.71 (d, J = 1.26 Hz, 1 H), 7.59-7.67 (m, 2 H), 7.55 (s, 1 H), 7.33 (td, J = 8.34, 2.53 Hz, 1 H), 6.69 (s, 1 H), 5.82 (s, 2 H), 5.39 (q, J = 6.06 Hz, 1 H), 4.02-4.28 (m, 1 H), 3.07 (d, J = 12.38 Hz, 2 H), 2.58-2.71 (m, 2 H), 1.97 (d, J = 11.37 Hz, 2 H), 1.70-1.84 (m, J = 12.00, 12.00, 11.62, 3.79 Hz, 2 H), 1.61 (d, J = 6.06 Hz, 3 H) |
| 81 | ABS | 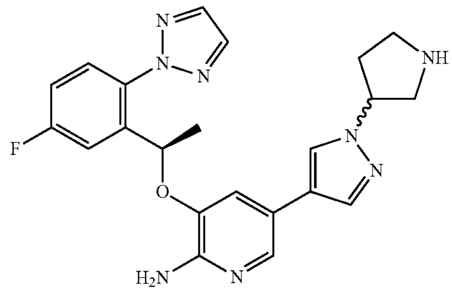 | 3-{(1R)-1-[5-fluoro-2-(2H-1,2,3-triazol-2-yl)phenyl]ethoxy}-5-[1-(pyrrolidin-3-yl)-1H-pyrazol-4-yl]pyridin-2-amine | 400 MHz, DMSO-d$_6$: 8.29 (s, 2 H), 7.93 (s, 1 H), 7.72 (d, J = 1.77 Hz, 1 H), 7.56-7.67 (m, 3 H), 7.33 (td, J = 8.34, 3.03 Hz, 1 H), 6.71 (d, J = 1.77 Hz, 1 H), 5.86 (s, 2 H), 5.40 (q, J = 5.89 Hz, 1 H), 4.82-5.03 (m, 1 H), 3.18-3.52 (m, 3 H, partially obscured by water), 3.01-3.16 (m, 1 H), 2.22-2.33 (m, 1 H), 2.06-2.19 (m, 1 H), 1.61 (d, J = 6.06 Hz, 3 H) |
| 82 | ABS | 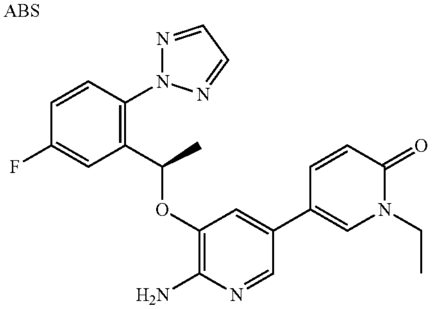 [SMILES: "ABS" ; CCn1cc(-c2cnc(N)c(O[C@H](C)c3cc(F)ccc3-n3nccn3)c2)ccc1=O] | 6'-amino-1-ethyl-5'-{(1R)-1-[5-fluoro-2-(2H-1,2,3-triazol-2-yl)phenyl]ethoxy}-3,3'-bipyridin-6(1H)-one | 400 MHz, DMSO-d$_6$: 8.25 (s, 2 H) 7.71 (d, J = 2.78 Hz, 1 H) 7.59-7.69 (m, 3 H) 7.49 (dd, J = 9.47, 2.65 Hz, 1 H) 7.30-7.36 (m, 1 H) 6.68 (d, J = 1.77 Hz, 1 H) 6.42 (d, J = 9.35 Hz, 1 H) 6.01 (s, 2 H) 5.41-5.49 (m, 1 H) 3.93 (qd, J = 6.78, 3.66 Hz, 2 H) 1.62 (d, J = 6.32 Hz, 3 H) 1.21-1.26 (m, 3 H) |
| 83 | ABS | 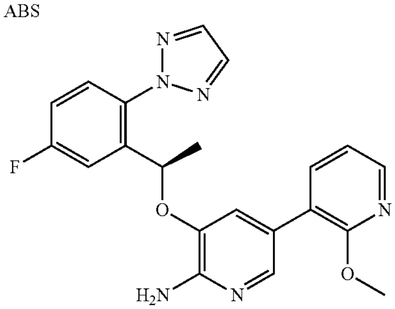 | 5-{(1R)-1-[5-fluoro-2-(2H-1,2,3-triazol-2-yl)phenyl]ethoxy}-2'-methoxy-3,3'-bipyridin-6-amine | 400 MHz, DMSO-d$_6$: 8.18 (s, 2 H) 8.05 (dd, J = 4.93, 1.64 Hz, 1 H) 7.59-7.70 (m, 3 H) 7.53 (dd, J = 7.33, 1.52 Hz, 1 H) 7.34 (td, J = 8.34, 3.03 Hz, 1 H) 7.00 (dd, J = 7.33, 5.05 Hz, 1 H) 6.81 (d, J = 1.26 Hz, 1 H) 6.08 (s, 2 H) 5.59 (q, J = 5.73 Hz, 1 H) 3.70 (s, 3 H) 1.59 (d, 3 H) |
| 84 | ABS | 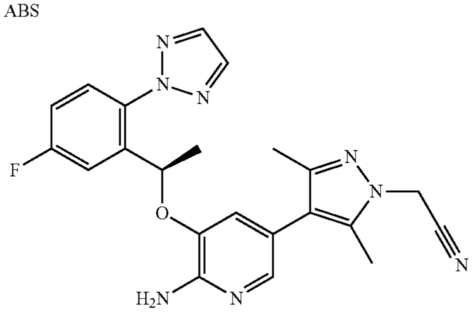 [SMILES: "ABS" ; Cc1nn(CC#N)c(C)c1-c1cnc(N)c(O[C@H](C)c2cc(F)ccc2-n2nccn2)c1] | [4-(6-amino-5-{(1R)-1-[5-fluoro-2-(2H-1,2,3-triazol-2-yl)phenyl]ethoxy}pyridin-3-yl)-3,5-dimethyl-1H-pyrazol-1-yl]acetonitrile | 400 MHz, CDCl$_3$: 7.87 (s, 2 H) 7.63 (dd, J = 8.84, 5.05 Hz, 1 H) 7.49 (d, J = 1.52 Hz, 1 H) 7.29-7.33 (m, 1 H) 7.08-7.14 (m, 1 H) 6.60 (d, J = 1.26 Hz, 1 H) 5.71-5.81 (m, 1 H) 4.93 (s, 2 H) 4.85 (br. s., 2 H) 2.13 (s, 3 H) 2.03 (s, 3 H) 1.62 (d, J = 6.32 Hz, 3 H) |

Example 85

4-(6-Amino-5-((R)-1-(5-fluoro-2-(2H-1,2,3-triazol-2-yl)phenyl)ethoxy)pyridin-3-yl)isoindolin-1-one

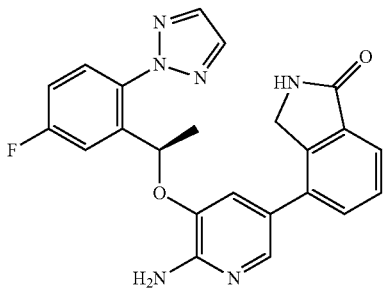 [SMILES: C[C@@H](Oc1cc(-c2cccc3c2CNC3=O)cnc1N)c1cc(F)ccc1-n1nccn1]

A mixture of preparation 45 (100 mg, 0.264 mmol), 4,4,5,5,4',4',5',5'-Octamethyl-[2,2']bi[[1,3,2]dioxaborolanyl] (114 mg, 1.7 eq), and potassium acetate (90.7 mg, 3.5 eq) in DMSO (1.0 mL) was deoxygenated with $N_2$ bubbler for 30 minutes before addition of the Pd(dppf)Cl$_2$ (9.5 mg, 0.05 eq). The mixture was then heated in 80° C. oil bath for 3 hr. LCMS indicated disappearance of starting bromide. To the crude boronate mixture was added 4-bromoisoindolin-1-one (84 mg, 1.5 eq), CsF (120 mg, 3.5 eq) and MeOH (2 mL). The mixture was thoroughly degassed and Pd(dppf)Cl$_2$ (9.5 mg, 0.05 eq) was added. The mixture was heated in the microwave at 120° C. for 1 hr. LCMS showed the desired product mass. Mixture was filtered and purified with a reverse phase preparative HPLC under acidic condition to give the title compound as an amorphous white solid (57.8 mg, 50.9%).

$^1$H NMR (600 MHz, DMSO-d$_6$) δ ppm 1.59 (d, J=6.14 Hz, 3H), 4.07-4.21 (m, 1H), 4.23-4.34 (m, 1H), 5.56 (q, J=6.06 Hz, 1H), 6.19 (s, 2H), 6.77 (s, 1H), 7.34 (td, J=8.26, 2.94 Hz, 1H), 7.41 (d, J=7.42 Hz, 1H), 7.51 (t, J=7.55 Hz, 1H), 7.57 (s, 1H), 7.63-7.67 (m, 1H), 7.70-7.72 (m, 1H), 7.72 (d, J=1.28 Hz, 2H), 8.20 (s, 1H), 8.64 (s, 1H).

Examples 86 to 109

Examples 86-109 were prepared by a similar method to that of example 85 using the appropriate 5-bromo-pyridin-2-amine or 5-bromo-pyrazin-2-amine and bromo, or chloro, or triflate aryl or heteroaryl stating materials.

| Ex No. | Structure | NAME | $^1$H NMR, δ ppm |
|---|---|---|---|
| 86 | ABS | 4-(6-amino-5-{(1R)-1-[5-fluoro-2-(2H-1,2,3-triazol-2-yl)phenyl]ethoxy}pyridin-3-yl)-1-methyl-1H-pyrazole-3-carbonitrile | 400 MHz, DMSO-d$_6$: 8.22 (s, 2 H) 7.98 (s, 1 H) 7.73 (d, J = 2.02 Hz, 1 H) 7.69 (dd, J = 9.73, 2.91 Hz, 1 H) 7.62 (dd, J = 8.84, 5.05 Hz, 1 H) 7.32 (td, J = 8.40, 2.91 Hz, 1 H) 6.81 (d, J = 1.52 Hz, 1 H) 6.20 (s, 2 H) 5.56 (q, J = 6.32 Hz, 1 H) 3.94 (s, 3 H) 1.57 (d, 3 H) |
| 87 | ABS | 3-{(1R)-1-[5-fluoro-2-(2H-1,2,3-triazol-2-yl)phenyl]ethoxy}-5-{3-[(methylsulfonyl)methyl]phenyl}pyridin-2-amine | 600 MHz, DMSO-d$_6$: 1.62 (d, J = 6.42 Hz, 3 H) 2.91 (s, 3 H) 4.47 (d, J = 5 67 Hz, 2 H) 5.57 (d, J = 6.04 Hz, 1 H) 6.14 (s, 2 H) 6.86 (d, J = 1.51 Hz, 1 H) 7.24-7.35 (m, 3 H) 7.40-7.48 (m, 2 H) 7.61-7.69 (m, 2 H) 7.80 (d, J = 1.89 Hz, 1 H) 8.25 (s, 2 H). |
| 88 | ABS | 5-{4-[(1R)-1-aminoethyl]phenyl}-3-{(1R)-1-[5-fluoro-2-(2H-1,2,3-triazol-2-yl)phenyl]ethoxy}-pyridin-2-amine | 600 MHz, DMSO-d$_6$: 1.51 (d, J = 6.80 Hz, 3 H) 1.68 (d, J = 6.04 Hz, 3 H) 4.44 (br. s., 1 H) 5.77 (d, J = 6.04 Hz, 1 H) 7.23 (br. s., 1 H) 7.31-7.41 (m, 1 H) 7.50-7.61 (m, 4 H) 7.65 (dd, J = 8.69, 4.91 Hz, 1 H) 7.68-7.72 (m, 1 H) 7.90 (s, 1 H) 8.25 (s, 2 H) 8.45 (br. s., 3 H) |

| Ex No. | Structure | NAME | $^1$H NMR, δ ppm |
|---|---|---|---|
| 89 | ABS | 5-(6-amino-5-{(1R)-1-[5-fluoro-2-(2H-1,2,3-triazol-2-yl)phenyl]ethoxy}pyridin-3-yl)-2,3-dihydro-1H-isoindol-1-one | 600 MHz, DMSO-$d_6$: 1.65 (d, J = 6.42 Hz, 3 H) 4.35-4.43 (m, 2 H) 5.57 (d, J = 6.42 Hz, 1 H) 6.21 (s, 2 H) 6.85 (d, J = 1.51 Hz, 1 H) 7.33 (d, J = 2.64 Hz, 1 H) 7.47 (d, J = 7.93 Hz, 1 H) 7.55 (s, 1 H) 7.58-7.67 (m, 2 H) 7.67-7.75 (m, 1 H) 7.87 (s, 1 H) 8.29 (s, 2 H) 8.51 (s, 1 H) |
| 90 | ABS | 5-(6-amino-5-{(1R)-1-[5-fluoro-2-(2H-1,2,3-triazol-2-yl)phenyl]ethoxy}pyridin-3-yl)-N,4-dimethyl-1,3-thiazole-2-carboxamide | 600 MHz, DMSO-$d_6$: 1.59 (d, J = 6.04 Hz, 3 H) 2.18 (s, 3 H) 2.76 (d, J = 4.53 Hz, 3 H) 5.58 (d, J = 6.42 Hz, 1 H) 6.37 (s, 2 H) 6.66 (s, 1 H) 7.35 (td, J = 8.31, 3.02 Hz, 1 H) 7.57-7.64 (m, 2 H) 7.62-7.70 (m, 1 H) 8.18 (s, 2 H) 8.64 (d, J = 4.53 Hz, 1 H). |
| 91 | ABS | 3-[4-(6-amino-5-{(1R)-1-[5-fluoro-2-(2H-1,2,3-triazol-2-yl)phenyl]ethoxy}pyridin-3-yl)-3,5-dimethyl-1H-pyrazol-1-yl]propane-1,2-diol | 600 MHz, DMSO-$d_6$: 8.17 (s, 2 H), 7.66 (ddd, J = 8.59, 5.19, 2.83 Hz, 1 H), 7.54 (dt, J = 9.73, 3.07 Hz, 1 H), 7.30-7.40 (m, 2 H), 6.42 (dd, J = 4.34, 1.70 Hz, 1 H), 5.85 (s, 2 H), 5.44-5.64 (m, 1 H), 3.99 (dd, J = 13.60, 3.78 Hz, 1 H), 3.71-3.86 (m, 2 H), 3.26-3.36 (m, 2 H), 1.98 (d, J = 9.44 Hz, 3 H), 1.85 (d, J = 1.51 Hz, 3 H), 1.56 (dd, J = 6.23, 2.08 Hz, 3 H) |
| 92 | ABS | 5-(6-amino-5-{(1R)-1-[5-fluoro-2-(2H-1,2,3-triazol-2-yl)phenyl]ethoxy}pyridin-3-yl)-N-methylpyrimidine-2-carboxamide | 600 MHz, DMSO-$d_6$: 1.59 (d, J = 6.42 Hz, 3 H) 2.78 (d, J = 4.91 Hz, 3 H) 5.49 (d, J = 6.04 Hz, 1 H) 6.39-6.43 (m, 2 H) 6.96 (d, J = 1.89 Hz, 1 H) 7.29 (td, J = 8.31, 3.02 Hz, 1 H) 7.58 (dd, J = 8.88, 5.10 Hz, 1 H) 7.65 (dd, J = 9.63, 2.83 Hz, 1 H) 8.00 (d, J = 1.89 Hz, 1 H) 8.20 (s, 2 H) 8.82 (q, J = 4.53 Hz, 1 H) 8.93 (s, 2 H). |
| 93 | ABS | (6'-amino-5'-{(1R)-1-[5-fluoro-2-(2H-1,2,3-triazol-2-yl)phenyl]ethoxy}-2-methoxy-3,3'-bipyridin-6-yl)methanol | 600 MHz, DMSO-$d_6$: 1.64 (d, J = 6.42 Hz, 3 H) 3.69 (s, 4 H) 4.49 (s, 2 H) 5.76 (d, J = 6.04 Hz, 1 H) 7.09-7.17 (m, 2 H) 7.39 (d, J = 3.02 Hz, 1 H) 7.59-7.67 (m, 2 H) 7.68-7.74 (m, 2 H) 7.84-7.96 (m, 2 H) 8.19 (s, 2 H) |

| Ex No. | Structure | NAME | ¹H NMR, δ ppm |
|---|---|---|---|
| 94 | 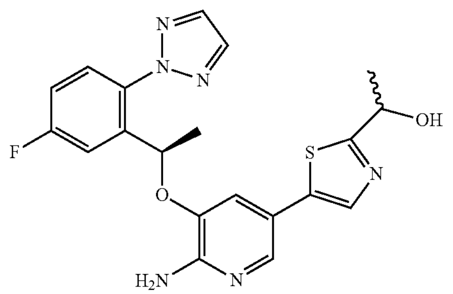 [SMILES: CC(O)c1ncc(-c2cnc(N)c(O[C@H](C)c3cc(F)ccc3-n3nccn3)c2)s1] | 1-[5-(6-amino-5-{(1R)-1-[5-fluoro-2-(2H-1,2,3-triazol-2-yl)phenyl]ethoxy}pyridin-3-yl)-1,3-thiazol-2-yl]ethanol | 400 MHz, CD₃CN: 8.04 (s, 2 H), 7.75 (d, J = 1.77 Hz, 1 H), 7.52-7.67 (m, 2 H), 7.42 (dd, J = 9.60, 2.78 Hz, 1 H), 7.20 (td, J = 8.34, 2.78 Hz, 1 H), 6.92 (d, J = 1.77 Hz, 1 H), 5.46-5.67 (m, 1 H), 5.26 (br. s., 2 H), 4.96 (q, J = 6.57 Hz, 1 H), 3.94 (br. s., 1 H), 1.64 (d, J = 6.32 Hz, 3 H), 1.50 (dd, J = 6.57, 1.01 Hz, 3 H) |
| 95 | Chiral | 5-{3,5-dimethyl-1-[(methylsulfonyl)methyl]-1H-pyrazol-4-yl}-3-{(1R)-1-[5-fluoro-2-(2H-1,2,3-triazol-2-yl)phenyl]ethoxy}pyridin-2-amine | 400 MHz, DMSO-d₆: 8.16 (s, 2 H), 7.65 (dd, J = 8.72, 5.18 Hz, 1 H), 7.58 (dd, J = 9.73, 2.91 Hz, 1 H), 7.26-7.42 (m, 2 H), 6.47 (d, J = 1.77 Hz, 1 H), 5.94 (s, 2 H), 5.42-5.68 (m, 3 H), 3.01 (s, 3 H), 2.07 (s, 3 H), 1.91 (s, 3 H), 1.56 (d, J = 6.32 Hz, 3 H) |
| 96 | 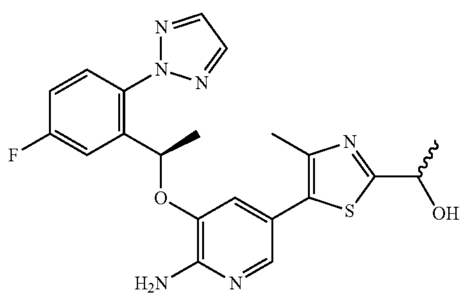 [SMILES: Cc1nc(C(C)O)sc1-c1cnc(N)c(O[C@H](C)c2cc(F)ccc2-n2nccn2)c1] | 1-[5-(6-amino-5-{(1R)-1-[5-fluoro-2-(2H-1,2,3-triazol-2-yl)phenyl]ethoxy}pyridin-3-yl)-4-methyl-1,3-thiazol-2-yl]ethanol | 400 MHz, DMSO-d₆: 8.20 (s, 2 H) 7.68 (dd, J = 8.84, 5.05 Hz, 1 H) 7.61 (dd, J = 9.73, 2.91 Hz, 1 H) 7.53 (d, J = 1.26 Hz, 1 H) 7.35 (td, J = 8.40, 2.40 Hz, 1 H) 6.62 (s, 1 H) 6.19 (s, 2 H) 6.00 (d, J = 4.55 Hz, 1 H) 5.55-5.66 (m, 1 H) 4.78-4.88 (m, 1 H) 2.07 (d, J = 2.78 Hz, 3 H) 1.59 (dd, J = 6.19, 1.39 Hz, 3 H) 1.42 (d, 3 H) |
| 97 | ABS | [5-(6-amino-5-{(1R)-1-[5-fluoro-2-(2H-1,2,3-triazol-2-yl)phenyl]ethoxy}pyridin-3-yl)-1-methyl-1H-imidazol-2-yl]methanol | 400 MHz, CD₃CN: 7.95 (s, 2 H), 7.58 (dd, J = 8.97, 5.18 Hz, 1 H), 7.54 (d, J = 1.77 Hz, 1 H), 7.39 (dd, J = 9.73, 2.91 Hz, 1 H), 7.18 (ddd, J=8.84, 7.96, 2.91 Hz, 1 H), 6.68 (s, 1 H), 6.64 (d, J = 1.77 Hz, 1 H), 5.59 (qd, J = 6.36, 0.88 Hz, 1 H), 5.20 (br. s., 2 H), 4.54 (s, 2 H), 3.35 (s, 3 H), 1.60 (d, J = 6.32 Hz, 3 H) |

| Ex No. | Structure | NAME | $^1$H NMR, δ ppm |
|---|---|---|---|
| 98 | 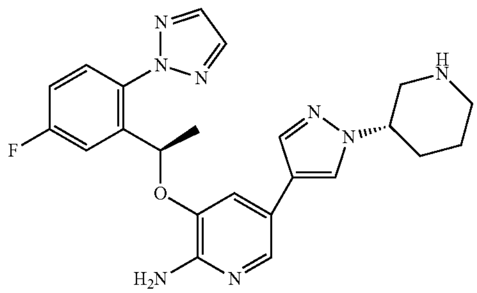 [SMILES: C[C@@H](Oc1cc(-c2cnn([C@H]3CCCNC3)c2)cnc1N)c1cc(F)ccc1-n1nccn1] | 3-{(1R)-1-[5-fluoro-2-(2H-1,2,3-triazol-2-yl)phenyl]ethoxy}-5-[1-(piperidin-3-yl)-1H-pyrazol-4-yl]pyridin-2-amine | 400 MHz, DMSO-d$_6$: 8.28 (s, 2 H), 7.88 (s, 1 H), 7.71 (d, J = 1.52 Hz, 1 H), 7.58-7.68 (m, 2 H), 7.54 (s, 1 H), 7.32 (td, J = 8.27, 2.91 Hz, 1 H), 6.70 (d, J = 0.76 Hz, 1 H), 5.82 (s, 2 H), 5.39 (q, J = 6.15 Hz, 1 H), 4.01-4.18 (m, 1 H), 3.17 (d, J = 12.63 Hz, 1 H, partially obscured by water), 2.89 (d, J = 12.38 Hz, 1 H), 2.68-2.78 (m, 1 H), 1.99-2.16 (m, 1 H), 1.79-1.90 (m, 1 H, partially obscured by Acetic Acid), 1.66-1.76 (m, 1 H), 1.61 (d, J = 6.32 Hz, 3 H), 1.44-1.58 (m, 1 H) |
| 99 | ABS | 5-(1,1-dioxido-2,3-dihydro-1-benzothiophen-5-yl)-3-{(1R)-1-[5-fluoro-2-(2H-1,2,3-triazol-2-yl)phenyl]ethoxy}pyridin-2-amine | 600 MHz, DMSO-d$_6$: 1.57-1.66 (m, 3 H) 2.50 (br. s., 2 H) 3.49-3.63 (m, 2 H) 5.54 (q, J = 5.80 Hz, 1 H) 6.33 (br. s., 2 H) 6.86 (s, 1 H) 7.24-7.38 (m, 1 H) 7.63-7.79 (m, 3 H) 7.89 (s, 1 H) 8.30 (s, 2 H). |
| 100 | Chiral | 5-{(1R)-1-[5-fluoro-2-(2H-1,2,3-triazol-2-yl)phenyl]ethoxy}-2'-methoxy-6'-[(methylamino)methyl]-3,3'-bipyridin-6-amine | 600 MHz, DMSO-d$_6$: 1.54-1.59 (m, 3 H) 2.57 (s, 3 H) 3.98-4.08 (m, 3 H) 4.13 (t, J = 6.02 Hz, 2 H) 5.53-5.63 (m, 1 H) 6.11 (s, 2 H) 6.79 (s, 1 H) 7.05 (d, J = 7.42 Hz, 1 H) 7.26-7.40 (m, 1 H) 7.56-7.63 (m, 2 H) 7.63-7.75 (m, 3 H) 8.18 (s, 2 H) |
| 101 | ABS | 3-{(1R)-1-[5-fluoro-2-(2H-1,2,3-triazol-2-yl)phenyl]ethoxy}-5-[2-methoxy-5-(methylsulfonyl)phenyl]pyridin-2-amine | 600 MHz, DMSO-d$_6$: 1.57 (d, J = 6.04 Hz, 3 H) 3.18 (s, 3 H) 3.68 (s, 3 H) 5.55 (d, J = 6.04 Hz, 1 H) 6.14 (br. s., 2 H) 6.84 (s, 1 H) 7.22 (d, J = 8.69 Hz, 1 H) 7.33 (t, J = 6.80 Hz, 1 H) 7.66 (br. s., 4 H) 7.78 (d, J = 7.93 Hz, 1 H) 8.16 (s, 2 H). |

| Ex No. | Structure | NAME | ¹H NMR, δ ppm |
|---|---|---|---|
| 102 | 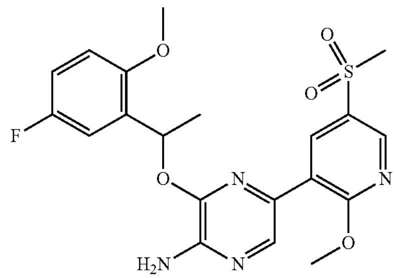 [SMILES: COc1ccc(F)cc1C(C)Oc1nc(-c2cc(S(C)(=O)=O)cnc2OC)cnc1N] | 3-[1-(5-fluoro-2-methoxyphenyl)ethoxy]-5-[2-methoxy-5-(methylsulfonyl)pyridin-3-yl]pyrazin-2-amine | 400 MHz, DMSO-d₆: 8.57 (d, J = 2.53 Hz, 1 H) 8.41 (d, J = 2.53 Hz, 1 H) 8.34 (s, 1 H) 7.33 (dd, J = 9.35, 2.78 Hz, 1 H) 7.01-7.05(m, 2 H) 6.90 (br. s., 2 H) 6.56 (d, J = 6.32 Hz, 1 H) 4.06 (s, 3 H) 3.86 (s, 3 H) 3.24 (s, 3 H) 1.56 (d, J = 6.57 Hz, 3 H) |
| 103 | ABS | 2-[5-(5-amino-6-{(1R)-1-[5-fluoro-2-(2H-1,2,3-triazol-2-yl)phenyl]ethoxy}pyrazin-2-yl)-4-methyl-1,3-thiazol-2-yl]propan-2-ol | 400 MHz, DMSO-d₆: 1.48 (s, 6 H) 1.61 (d, J = 6.32 Hz, 3 H) 2.26 (s, 3 H) 5.83 (br. s., 1 H) 6.54 (q, 1 H) 6.70 (br. s., 2 H) 7.34 (dt, 1 H) 7.66 (s, 1 H) 7.71 (dd, J = 8.97, 5.18 Hz, 1 H) 7.93 (dd, J = 9.98, 2.65 Hz, 1 H) 8.16 (s, 2 H) |
| 104 | ABS | 2-[5-(6-amino-5-{(1R)-1-[5-fluoro-2-(2H-1,2,3-triazol-2-yl)phenyl]ethoxy}pyridin-3-yl)-4-methyl-1,3-thiazol-2-yl]propan-2-ol | 400 MHz, DMSO-d₆: 1.47 (s, 6 H) 1.58 (d, J = 6.32 Hz, 3 H) 2.06 (s, 3 H) 5.56-5.66 (m, 1 H) 5.84 (s, 1 H) 6.17 (br. s., 2 H) 6.63 (s, 1 H) 7.31-7.39 (m, 1 H) 7.52 (d, J = 1.77 Hz, 1 H) 7.61 (dd, J = 9.60, 2.78 Hz, 1 H) 7.67 (dd, J = 8.72, 5.18 Hz, 1 H) 8.19 (s, 2 H) |
| 105 | ABS | [4-(6-amino-5-{(1R)-1-[5-fluoro-2-(2H-1,2,3-triazol-2-yl)phenyl]ethoxy}pyridin-3-yl)-1,3-thiazol-2-yl]methanol | 400 MHz, DMSO-d₆: 1.61 (d, J = 6.06 Hz, 3 H) 4.73 (s, 2 H) 5.56 (q, 1 H) 6.11 (s, 2 H) 7.04 (d, J = 1.52 Hz, 1 H) 7.33 (dt, 1 H) 7.45 (s, 1 H) 7.61-7.72 (m, 2 H) 8.06 (d, J = 1.52 Hz, 1 H) 8.27 (s, 2 H) |
| 106 | ABS | [5-(6-amino-5-{(1R)-1-[5-fluoro-2-(2H-1,2,3-triazol-2-yl)phenyl]ethoxy}pyridin-3-yl)-1,3-thiazol-2-yl]methanol | 400 MHz, DMSO-d₆: 1.60 (d, J = 6.32 Hz, 3 H) 4.66 (d, J = 5.81 Hz, 2 H) 5.52 (q, 1 H) 6.00 (t, J = 5.81 Hz, 1 H) 6.24 (s, 2 H) 6.80(d, J = 1.52 Hz, 1 H) 7.34 (dt, J = 8.46, 2.78 Hz, 1 H) 7.61-7.68 (m, 3 H) 7.72 (d, J = 1.52 Hz, 1 H) 8.25 (s, 2 H) |

| Ex No. | Structure | NAME | $^1$H NMR, δ ppm |
|---|---|---|---|
| 107 | ABS | [5-(6-amino-5-{(1R)-1-[5-fluoro-2-(2H-1,2,3-triazol-2-yl)phenyl]ethoxy}pyridin-3-yl)-4-methyl-1,3-thiazol-2-yl]methanol | 400 MHz, DMSO-$d_6$: 1.59 (d, J = 6.06 Hz, 3 H) 2.06 (s, 3 H) 4.62 (d, J = 5.31 Hz, 2 H) 5.59 (br. s., 1 H) 5.94 (t, J = 5.68 Hz, 1 H) 6.20 (br. s., 2 H) 6.62 (s, 1 H) 7.27-7.41 (m, 1 H) 7.53 (s) 1 H] 7.57 1-7.64 (m, 1 H) 7.67 (dd, J = 8.72, 4.93 Hz, 1 H) 8.19 (s, 2 H) |
| 108 | ABS | [5-(6-amino-5-{(1R)-1-[5-fluoro-2-(2H-1,2,3-triazol-2-yl)phenyl]ethoxy}pyridin-3-yl)-4-ethyl-1,3-thiazol-2-yl]methanol | 400 MHz, DMSO-$d_6$: 0.98 (t, J = 7.45 Hz, 3 H) 1.56 (d, J = 6.06 Hz, 3 H) 2.28-2.39 (m, 2 H) 4.63 (d, J = 5.56 Hz, 2 H) 5.63 (q, 1H) 5.94 (t, 1 H) 6.20 (s, 2 H) 6.60 (d, J = 1.52 Hz, 1 H) 7.36 (dt, 1 H) 7.50 (d, J = 1.77 Hz, 1 H) 7.58 (dd, J = 9.73, 2.91 Hz, 1 H) 7.69 (dd, J = 8.97, 5.18 Hz, 1 H) 8.18 (s, 2 H) |
| 109 | ABS | 3-{(1R)-1-[5-fluoro-2-(2H-1,2,3-triazol-2-yl)phenyl]ethoxy}-5-{2-[(methylsulfonyl)methyl]-1,3-thiazol-5-yl}pyridin-2-amine | 600 MHz, DMSO-$d_6$: 1.60 (d, J = 6.42 Hz, 3 H) 3.07 (s, 3 H) 4.97 (s, 2 H) 5.43-5.52 (m, 1 H) 6.34 (s, 2 H) 6.82 (s, 1 H) 7.29-7.36 (m, 1 H) 7.59-7.69 (m, 2 H) 7.77 (s, 1 H) 7.84 (s, 1 H) 8.26 (s, 2 H) |

Example 110

6-(6-amino-5-{(1R)-1-[5-fluoro-2-(2H-1,2,3-triazol-2-yl)phenyl]ethoxy}pyridin-3-yl)-2,3-dihydro-1-benzothiophene-3-ol 1,1-dioxide

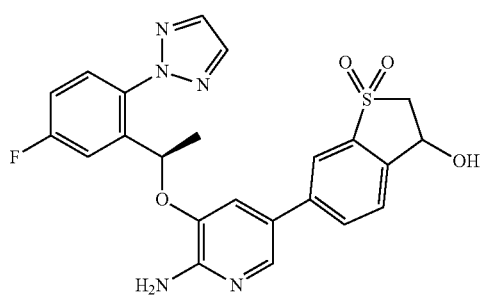 [SMILES: C[C@@H](Oc1cc(-c2ccc3c(c2)S(=O)(=O)CC3O)cnc1N)c1cc(F)ccc1-n1nccn1]

To a mixture (R)-3-(1-(5-fluoro-2-(2H-1,2,3-triazol-2-yl)phenyl)ethoxy)-5-(4,4,5,5-tetramethyl-1,3,2-dioxaborolan-2-yl)pyridin-2-amine of preparation 109 (100 mg, 0.235 mmol), 6-bromo-2,3-dihydrobenzo[b]thiophen-3-ol-1,1 dioxide (92.6 mg, 1.5 eq), and CsF (126 mg, 3.5 eq) was added MeOH (2 mL). The mixture was thoroughly degassed and Pd(dppf)Cl$_2$ (9.8 mg, 0.05 eq) was added. The mixture was heated in the microwave at 120° C. for 1 hr. LCMS showed the desired product mass. Mixture was filtered and purified with reverse phase preparative HPLC to give the title compound (66.08 mg, 58.4%).

Examples 111 to 120

Examples 111-120 were prepared by a similar method to that of example 110 using preparation 109, and bromo or chloro or tosylate-aryl or heteroaryl stating materials.

| Ex No. | Structure | NAME | $^1$H NMR, δ ppm |
|---|---|---|---|
| 111 | ABS | 2-[4-(6-amino-5-{(1R)-1-[5-fluoro-2-(2H-1,2,3-triazol-2-yl)phenyl]ethoxy}pyridin-3-yl)-2-(methylsulfonyl)phenyl]propan-2-ol | 600 MHz, DMSO-$d_6$: 1.57 (br. s., 3 H) 1.64 (br. s., 6 H) 3.41 (br. s., 3 H) 5.40 (br. s., 1 H) 5.55 (d, J = 5.29 Hz, 1 H) 6.24 (br. s., 2 H) 7.00 (br. s., 1 H) 7.32 (br. s., 1 H) 7.56-7.67 (m, 4 H) 7.83 (br. s., 1 H) 8.11 (br. s., 1 H) 8.26 (s, 2 H). |
| 112 | ABS | 5-[3-(dimethylphosphoryl)phenyl]-3-{(1R)-1-[5-fluoro-2-(2H-1,2,3-triazol-2-yl)phenyl]ethoxy}pyridin-2-amine | 400 MHz, CDCl$_3$: 1.63 (d, J = 6.06 Hz, 3 H) 1.75 (dd, J = 12.88, 7.83 Hz, 6 H) 5.18 (br. s., 2 H) 5.67 (d, J = 6.32 Hz, 1 H) 7.03-7.19 (m, 2 H) 7.31 (d, J = 8.59 Hz, 1 H) 7.51 (d, J = 7.33 Hz, 1 H) 7.54-7.69 (m, 3 H) 7.72 (d, J = 12.63 Hz, 1 H) 7.82-7.92 (m, 1 H) 7.95-8.04 (m, 2 H) |
| 113 | ABS | 3-(6-amino-5-{(1R)-1-[5-fluoro-2-(2H-1,2,3-triazol-2-yl)phenyl]ethoxy}pyridin-3-yl)benzenesulfonamide | 600 MHz, DMSO-$d_6$: 1.56 (d, J = 6.42 Hz, 3 H) 5.48-5.56 (m, 1 H) 6.20 (br. s., 2 H) 6.93 (s, 1 H) 7.24-7.32 (m, 1 H) 7.51-7.58 (m, 3 H) 7.64-7.69 (m, 2 H) 7.80 (s, 1 H) 7.86 (br. s., 1 H) 8.15-8.24 (m, 2 H) |
| 114 | ABS | 5-[3-(dimethylphosphoryl)-5-methylphenyl]-3-{(1R)-1-[5-fluoro-2-(2H-1,2,3-triazol-2-yl)phenyl]ethoxy}pyridin-2-amine | 600 MHz, DMSO-$d_6$: 1.56 (d, J = 6.42 Hz, 3 H) 5.48-5.56 (m, 1 H) 6.20 (br. s., 2 H) 6.93 (s, 1 H) 7.24-7.32 (m, 1 H) 7.51-7.58 (m, 3 H) 7.64-7.69 (m, 2 H) 7.80 (s, 1 H) 7.86 (br. s., 1 H) 8.15-8.24 (m, 2 H) |
| 115 | 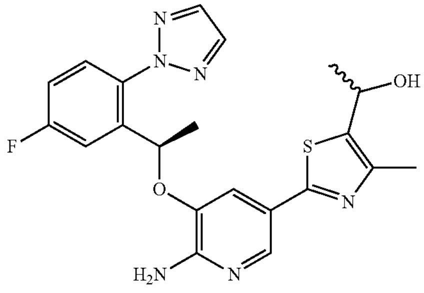 | 1-[2-(6-amino-5-{(1R)-1-[5-fluoro-2-(2H-1,2,3-triazol-2-yl)phenyl]ethoxy}pyridin-3-yl)-4-methyl-1,3-thiazol-5-yl]ethanol | 400 MHz, DMSO-$d_6$: 8.23 (d, J = 1.26 Hz, 2 H) 7.97 (dd, J = 3.03, 1.77 Hz, 1 H) 7.65-7.74 (m, 2 H) 7.34 (td, J = 8.34, 2.53 Hz, 1 H) 7.00 (d, J = 6.57 Hz, 1 H) 6.44 (s, 2 H) 5.70-5.79 (m, 1 H) 5.52 (br. s., 1 H) 4.97 (q, J = 6.23 Hz, 1 H) 2.26 (s, 3 H) 1.57-1.63 (m, 3 H) 1.35 (d, 3 H) |

| Ex No. | Structure | NAME | ¹H NMR, δ ppm |
|---|---|---|---|
| 116 | Chiral | 4-(6-amino-5-{(1R)-1-[5-fluoro-2-(2H-1,2,3-triazol-2-yl)phenyl]ethoxy}pyridin-3-yl)-1H-pyrazole-3-carbonitrile | 400 MHz, CDCl₃: 7.94 (s, 3 H) 7.74 (s, 1 H) 7.59 (dd, J = 8.84, 5.05 Hz, 1 H) 7.30 (dd, J = 9.09, 2.78 Hz, 1 H) 7.08-7.14 (m, 1 H) 7.01 (d, J = 1.26 Hz, 1 H) 5.69 (q, J = 6.23 Hz, 1 H) 5.15 (br. s., 2 H) 1.64 (d, 3 H) |
| 117 | ABS | 5-{(1R)-1-[5-fluoro-2-(2H-1,2,3-triazol-2-yl)phenyl]ethoxy}-6'-methyl-3,3'-bipyridin-6-amine | 400 MHz, DMSO-d₆: 8.47 (d, J = 2.27 Hz, 1 H) 8.24 (s, 2 H) 7.81 (d, J = 1.52 Hz, 1 H) 7.56-7.72 (m, 3 H) 7.33 (td, J = 8.40, 2.91 Hz, 1 H) 7.24 (d, J = 8.08 Hz, 1 H) 6.84 (d, J = 1.77 Hz, 1 H) 6.13 (s, 2 H) 5.54 (q, J = 5.98 Hz, 1 H) 2.45 (s, 3 H) 1.61 (d, 3 H) |
| 118 | ABS | 4-(6-amino-5-{(1R)-1-[5-fluoro-2-(2H-1,2,3-triazol-2-yl)phenyl]ethoxy}pyridin-3-yl)-3-methoxybenzamide | 400 MHz, DMSO-d₆: 8.19 (s, 2 H) 7.96 (br. s., 1 H) 7.58-7.74 (m, 3 H) 7.43-7.49 (m, 2 H) 7.35 (td, J = 8.34, 2.78 Hz, 2 H) 7.16 (d, J = 7.83 Hz, 1 H) 6.78 (d, J = 1.52 Hz, 1 H) 6.05 (s, 2 H) 5.60 (d, J = 6.32 Hz, 1 H) 3.63 (s, 3 H) 1.59 (d, 3 H) |
| 119 | ABS | [4-(6-amino-5-{(1R)-1-[5-fluoro-2-(2H-1,2,3-triazol-2-yl)phenyl]ethoxy}pyridin-3-yl)-2-(methylsulfonyl)phenyl]methanol | 400 MHz, DMSO-d₆: 8.25 (s, 2 H) 7.87 (d, J = 10.86 Hz, 2 H) 7.74-7.80 (m, 1 H) 7.57-7.74 (m, 3 H) 7.32 (td, J = 8.15, 2.40 Hz, 1 H) 7.01 (s, 1 H) 6.23 (s, 2 H) 5.54 (d, J = 6.06 Hz, 1 H) 5.46 (t, J = 5.05 Hz, 1 H) 4.90 (d, J = 4.80 Hz, 2 H) 3.27 (s, 3 H) 1.59 (d, 3 H) |

| Ex No. | Structure | NAME | $^1$H NMR, δ ppm |
|---|---|---|---|
| 120 | Chiral | 5-(6-amino-5-{(1R)-1-[5-fluoro-2-(2H-1,2,3-triazol-2-yl)phenyl]ethoxy}pyridin-3-yl)-2-methyl-1,3-oxazole-4-carbonitrile | 400 MHz, DMSO-$d_6$: 8.23 (s, 3 H) 8.04 (s, 1 H) 7.72 (dd, J = 9.73, 2.65 Hz, 1 H) 7.66 (dd, J = 8.84, 5.05 Hz, 1 H) 7.34 (td, J = 8.34, 2.78 Hz, 1 H) 6.92 (s, 2 H) 6.86 (s, 2 H) 5.70 (q, J = 6.15 Hz, 1 H) 1.61 (d, 4 H). |

Example 121

6'-amino-5'-{(1R)-1-[5-fluoro-2-(2H-1,2,3-triazol-2-yl)phenyl]ethoxy}-3,3'-bipyridin-6-ol

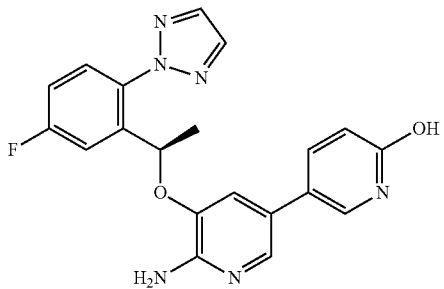 [SMILES: C[C@@H](Oc1cc(-c2ccc(O)nc2)cnc1N)c1cc(F)ccc1-n1nccn1]

A mixture of the 5-(4,4,5,5-tetramethyl-1,3,2-dioxaborolan-2-yl)pyridin-2-ol (470 mg, 2.13 mmol), (R)-5-bromo-3-(1-(5-fluoro-2-(2H-1,2,3-triazol-2-yl)phenyl)ethoxy)pyridin-2-amine of preparation 45 (510 mg, 1.35 mmol) and CsF (724 mg, 4.72 mmol) were taken up in MeOH (13 mL). The mixture was thoroughly degassed before Pd(dppf)Cl$_2$ (55 mg, 0.067 mmol) was added and the mixture was heated in the microwave at 120° C. for 2 hr. LCMS showed the presence of starting materials. Additional portions of Pd(dppf)Cl$_2$ (27 mg) and boronate (100 mg) were added. The mixture was degassed again and heated in the microwave at 120° C. for another 1 hr. LCMS indicated the complete consumption of bromide starting material. The mixture was filtered and the filtrate was concentrated. The residue was taken up in MeOH and purified by a reverse phase prep-HPLC to give the title compound (115 mg) as a fluffy white solid after lyophilization.

$^1$H NMR (400 MHz, DMSO-$d_6$) δ ppm 11.74 (br. s., 1H), 8.27 (s, 2H), 7.69 (dd, J=9.85, 3.03 Hz, 1H), 7.65 (d, J=2.02 Hz, 1H), 7.60 (dd, J=8.84, 5.05 Hz, 1H), 7.54 (dd, J=9.60, 2.78 Hz, 1H), 7.21-7.42 (m, 2H), 6.66 (d, J=2.02 Hz, 1H), 6.37 (d, J=9.60 Hz, 1H), 5.97 (s, 2H), 5.29-5.55 (m, 1H), 1.60 (d, J=6.32 Hz, 3H).

Example 122

5-{(1R)-1-[5-fluoro-2-(2H-1,2,3-triazol-2-yl)phenyl]ethoxy}-6'-(piperidin-4-yloxy)-3,3'-bipyridin-6-amine

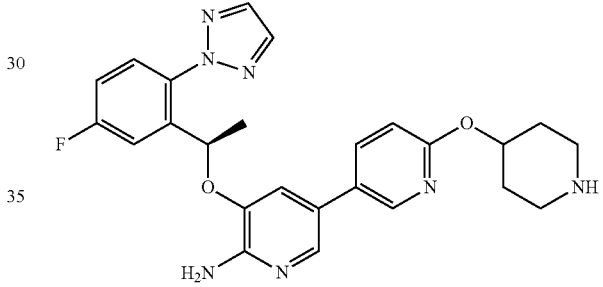

A mixture of example 121 (125 mg, 0.308 mmol), tert-butyl 4-(methylsulfonyloxy)piperidine-1-carboxylate (129 mg, 0.462 mmol) and cesium carbonate (301 mg, 0.924 mmol) was heated at 90° C. for 24 hr. LCMS indicated ~90% completion of the reaction. Two products were observed. The mixture was dropped into brine and the resulting precipitate was collected by filtration and rinsed with water. The partially dried solids were taken up in EtOAc, dried over magnesium sulfate and concentrated. The residue was purified with a Biotage silica gel cartridge eluting with 50-100% EtOAc/Heptane to give tert-butyl 4-[(6'-amino-5'-{(1R)-1-[5-fluoro-2-(2H-1,2,3-triazol-2-yl)phenyl]ethoxy}-3,3'-bipyridin-6-yl)oxy]piperidine-1-carboxylate (117 mg).

$^1$H NMR (400 MHz, CDCl$_3$) δ ppm 8.15 (d, J=2.27 Hz, 1H), 7.91 (s, 2H), 7.80 (d, J=1.77 Hz, 1H), 7.55-7.67 (m, 2H), 7.32 (dd, J=9.22, 2.91 Hz, 1H), 7.11 (ddd, J=8.84, 7.45, 2.91 Hz, 1H), 6.95 (d, J=1.77 Hz, 1H), 6.72 (d, J=8.34 Hz, 1H), 5.74 (q, J=6.57 Hz, 1H), 5.22 (tt, J=7.83, 3.66 Hz, 1H), 4.79 (s, 2H), 3.70-3.86 (m, 2H), 3.24-3.38 (m, 2H), 1.92-2.03 (m, 2H), 1.67-1.81 (m, 2H), 1.61 (d, J=6.32 Hz, 3H), 1.48 (s, 9H).

The other minor product was proved to be N-linked regioisomer 4-[6'-amino-5'-{(1R)-1-[5-fluoro-2-(2H-1,2,3-triazol-2-yl)phenyl]ethoxy}-6-oxo-3,3'-bipyridin-1(6H)-yl]piperidine-1-carboxylate (21 mg).

$^1$H NMR (400 MHz, CDCl$_3$) δ ppm 7.92 (s, 2H), 7.68 (d, J=1.77 Hz, 1H), 7.63 (dd, J=8.84, 4.80 Hz, 1H), 7.45 (dd, J=9.35, 2.53 Hz, 1H), 7.08-7.22 (m, 2H), 6.76 (d, J=1.77 Hz, 1H), 6.61 (d, J=9.60 Hz, 1H), 5.48 (q, J=6.74 Hz, 1H), 5.08 (tt, J=11.91 Hz, 3.63 Hz, 1H), 4.82 (s, 2H), 4.31 (br. S., 2H), 1.61-1.99 (m, 7H), 1.47 (s, 9H).

To a solution of the tert-butyl 4-[(6'-amino-5'-{(1R)-1-[5-fluoro-2-(2H-1,2,3-triazol-2-yl)phenyl]ethoxy}-3,3'-bipyridin-6-yl)oxy]piperidine-1-carboxylate (115 mg, 0.2 mmol) in MeOH (1 mL) was added HCl (4N in dioxane, 1 mL). The mixture was stirred at room temperature for 1 hr. The mixture was concentrated and the residue purified by a reversed phase prep-HPLC. The desired fractions were lyophillized to give the title compound (61 mg) as an off-white solid.

¹H NMR (400 MHz, DMSO-d₆) δ ppm 8.24 (s, 2H), 8.15 (d, J=2.02 Hz, 1H), 7.74 (d, J=2.02 Hz, 1H), 7.59-7.72 (m, 3H), 7.33 (td, J=8.40, 2.91 Hz, 1H), 6.80 (d, J=8.59 Hz, 1H), 6.75 (d, J=1.52 Hz, 1H), 6.05 (s, 2H), 5.53 (q, J=5.81 Hz, 1H), 4.87-5.11 (m, 1H), 2.96 (dt, J=12.69, 4.01 Hz, 2H), 2.54-2.64 (m, 2H), 1.91-1.99 (m, 2H), 1.61 (d, J=6.32 Hz, 3H), 1.39-1.55 (m, 2H).

Example 123

3-{(1R)-1-[5-fluoro-2-(2H-1,2,3-triazol-2-yl)phenyl]ethoxy}-5-(5-methyl-1H-pyrazol-4-yl)pyridin-2-amine

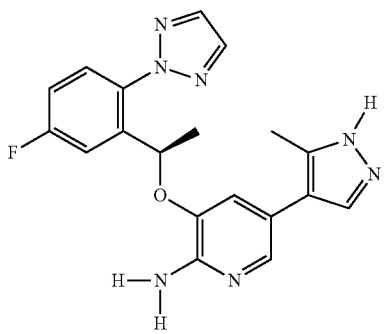 [SMILES: Cc1[nH]ncc1-c1cnc(N)c(O[C@H](C)c2cc(F)ccc2-n2nccn2)c1]

Example 123 was prepared with the same procedure as example 47 using the chiral 5-bromo-2-aminopyridine of preparation 45.

Example 124

3-{(1R)-1-[5-fluoro-2-(2H-1,2,3-triazol-2-yl)phenyl]ethoxy}-5-[3-methyl-1-(piperidin-4-yl)-1H-pyrazol-4-yl]pyridin-2-amine

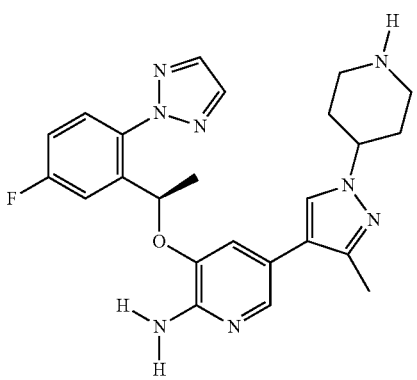 [SMILES: Cc1nn(C2CCNCC2)cc1-c1cnc(N)c(O[C@H](C)c2cc(F)ccc2-n2nccn2)c1]

A mixture of 3-((R)-1-(5-fluoro-2-(2H-1,2,3-triazol-2-yl)phenyl)ethoxy)-5-(3-methyl-1H-pyrazol-4-yl)pyridin-2-amine (example 123) (135 mg, 0.36 mmol), tert-butyl 4-(methylsulfonyloxy)piperidine-1-carboxylate (149 mg, 0.53 mmol) and cesium carbonate (348 mg, 1.07 mmol) in DMF (3 mL) was heated at 80° C. After 18 hr, additional mesylate (150 mg) was added and the mixture was heated at 80° C. for 6 hr. After which, another portion of mesylate (150 mg) and Cs₂CO₃ (350 mg) were added and the mixture was heated at 80° C. for 18 hr. After which, more mesylate (150 mg) was added and the mixture was heated at 80° C. for 3 days. LCMS showed >90% completion of the reaction. The reaction mixture was poured into brine (30 mL), and extracted with EtOAc (3×40 mL). The organics were washed with water and brine, dried over magnesium sulfate and concentrated. The residue was purified by a Biotage silica cartridge (25M) eluting with 50-100% EtOAc/heptane. Two products were obtained. One was confirmed as tert-butyl 4-[4-(6-amino-5-{(1R)-1-[5-fluoro-2-(2H-1,2,3-triazol-2-yl)phenyl]ethoxy}pyridin-3-yl)-3-methyl-1H-pyrazol-1-yl]piperidine-1-carboxylate (86 mg).

¹H NMR (400 MHz, DMSO-d₆) δ ppm 8.21 (s, 2H), 7.62-7.75 (m, 2H), 7.59 (dd, J=9.73, 2.91 Hz, 1H), 7.52 (d, J=1.77 Hz, 1H), 7.34 (td, J=8.53, 2.91 Hz, 1H), 6.58 (d, J=1.77 Hz, 1H), 5.84 (s, 2H), 5.47-5.60 (m, 1H), 4.21 (tt, J=11.43, 4.23 Hz, 1H), 3.91-4.09 (m, 2H), 2.89 (br. s., 2H), 1.93-2.02 (m, 5H), 1.65-1.79 (m, 2H), 1.59 (d, J=6.32 Hz, 3H), 1.41 (s, 9H). The other product is 4-[4-(6-amino-5-{(1R)-1-[5-fluoro-2-(2H-1,2,3-triazol-2-yl)phenyl]ethoxy}pyridin-3-yl)-5-methyl-1H-pyrazol-1-yl]piperidine-1-carboxylate (38 mg). ¹H NMR (400 MHz, DMSO-d₆) δ ppm 8.21 (s, 2H), 7.66 (dd, J=8.97, 5.18 Hz, 1H), 7.58 (dd, J=9.73, 2.91 Hz, 1H), 7.48 (d, J=1.77 Hz, 1H), 7.22-7.39 (m, 2H), 6.56 (d, J=1.52 Hz, 1H), 5.84 (s, 2H), 5.48-5.64 (m, 1H), 4.32 (quin, J=7.77 Hz, 1H), 3.95-4.12 (m, 2H), 2.90 (br. s., 2H), 2.10 (s, 3H), 1.74-1.86 (m, 4H), 1.57 (d, J=6.32 Hz, 3H), 1.41 (s, 9H)

To a solution of tert-butyl 4-[4-(6-amino-5-{(1R)-1-[5-fluoro-2-(2H-1,2,3-triazol-2-yl)phenyl]ethoxy}pyridin-3-yl)-3-methyl-1H-pyrazol-1-yl]piperidine-1-carboxylate (86 mg) in MeOH (1 mL) was added HCl (4N in dioxane, 0.73 mL). The mixture was stirred at RT for 1 hr. The mixture was concentrated and the residue purified by reverse phase prep-HPLC. The desired fractions were lyophillized to give the title compound (46 mg)

¹H NMR (400 MHz, DMSO-d₆) δ ppm 8.23 (s, 2H), 7.67 (dd, J=8.84, 5.31 Hz, 1H), 7.56-7.63 (m, 2H), 7.53 (d, J=1.77 Hz, 1H), 7.34 (td, J=8.34, 3.03 Hz, 1H), 6.58 (d, J=1.77 Hz, 1H), 5.84 (s, 2H), 5.53 (q, J=6.40 Hz, 1H), 4.04 (tt, J=11.72, 3.95 Hz, 1H), 3.03 (d, J=12.63 Hz, 2H), 2.57 (td, J=12.44, 2.15 Hz, 2H), 2.00 (s, 3H), 1.88-1.96 (m, 2H, partially obscured by Acetic acid), 1.65-1.81 (m, 2H), 1.60 (d, J=6.32 Hz, 3H).

Example 125

3-{(1R)-1-[5-fluoro-2-(2H-1,2,3-triazol-2-yl)phenyl]ethoxy}-5-[5-methyl-1-(piperidin-4-yl)-1H-pyrazol-4-yl]pyridin-2-amine Chiral

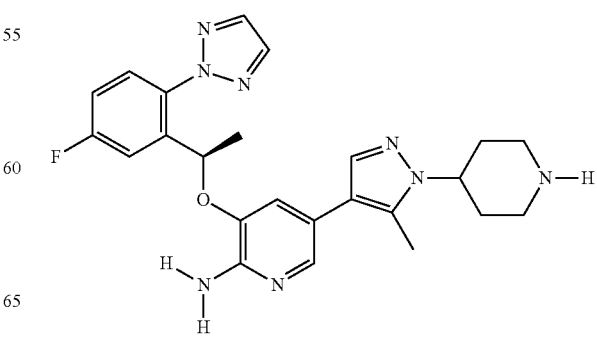

4-[4-(6-amino-5-{(1R)-1-[5-fluoro-2-(2H-1,2,3-triazol-2-yl)phenyl]ethoxy}pyridin-3-yl)-5-methyl-1H-pyrazol-1-yl]piperidine-1-carboxylate (38 mg) from the preparation of example 124 was converted to the title compound (18 mg) using the same procedure as example 124.

¹H NMR (400 MHz, DMSO-d₆) δ ppm 8.21 (s, 2H), 7.66 (dd, J=8.72, 5.18 Hz, 1H), 7.59 (dd, J=9.73, 2.91 Hz, 1H), 7.48 (d, J=1.52 Hz, 1H), 7.16-7.42 (m, 2H), 6.57 (d, J=1.77 Hz, 1H), 5.84 (s, 2H), 5.48-5.64 (m, 1H), 3.91-4.37 (m, 1H), 3.02 (d, J=12.38 Hz, 2H), 2.54-2.66 (m, 2H), 2.09 (s, 3H), 1.78-1.89 (m, 2H, partially obscured by Acetic acid), 1.65-1.76 (m, 2H), 1.57 (d, J=6.32 Hz, 3H).

Example 126

5-(3,5-Dimethyl-1H-pyrazol-4-yl)-3-{(1R)-1-[5-fluoro-2-(2H-1,2,3-triazol-2-yl)phenyl]ethoxy}pyridin-2-amine

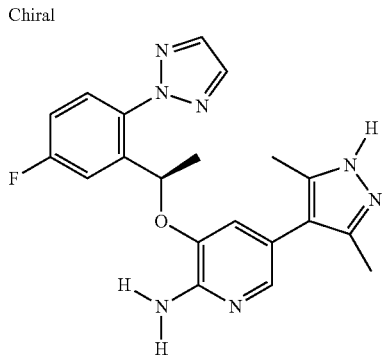 [SMILES: Cc1n[nH]c(C)c1-c1cnc(N)c(O[C@H](C)c2cc(F)ccc2-n2nccn2)c1]

Example 126 was prepared with the same procedure as example 47 using the chiral 5-bromo-2-aminopyridine of preparation 49.

Example 127

5-{1-[(3S)-1,1-dioxidotetrahydrothiophen-3-yl]-3,5-dimethyl-1H-pyrazol-4-yl}-3-{(1R)-1-[5-fluoro-2-(2H-1,2,3-triazol-2-yl)phenyl]ethoxy}pyridin-2-amine

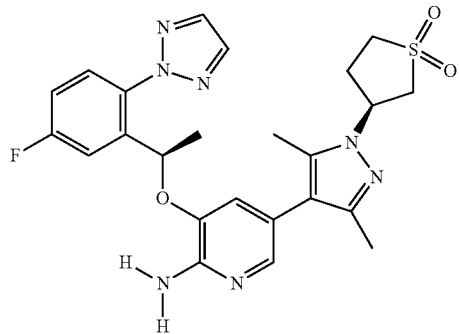 [SMILES: Cc1nn([C@H]2CCS(=O)(=O)C2)c(C)c1-c1cnc(N)c(O[C@H](C)c2cc(F)ccc2-n2nccn2)c1]

The alkylation procedure of example 124 was used for the preparation of example 127.

¹H NMR (400 MHz, DMSO-d₆) δ ppm 8.19 (d, 2H), 7.67 (dd, J=8.84, 5.05 Hz, 1H), 7.56 (dd, J=9.73, 2.91 Hz, 1H), 7.27-7.40 (m, 2H), 6.43 (d, J=1.52 Hz, 1H), 5.89 (s, 2H), 5.56 (q, J=5.73 Hz, 1H), 5.07-5.22 (m, 1H), 3.60-3.71 (m, 1H), 3.41-3.50 (m, 1H), 3.32-3.37 (m, 1H, partially obscured by water), 3.17-3.27 (m, 1H), 2.03 (d, J=2.53 Hz, 3H), 1.89 (d, J=0.76 Hz, 3H), 1.56 (d, J=6.32 Hz, 3H).

Example 128

1-{4-[4-(6-amino-5-{(1R)-1-[5-fluoro-2-(2H-1,2,3-triazol-2-yl)phenyl]ethoxy}pyridin-3-yl)-1H-pyrazol-1-yl]piperidin-1-yl}-2-(dimethylamino)ethanone

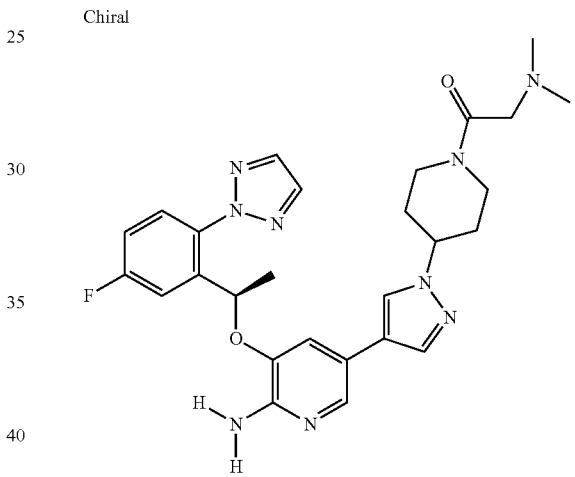

To a solution of 2-(dimethylamino)acetic acid (54 mg, 0.55 mmol) and HATU (105 mg, 0.27 mmol) in DMSO (1 mL) was added triethylamine (0.063 ml, 0.46 mmol). After stirring for ~15 min, the mixture was added to a flask containing 3-{(1R)-1-[5-fluoro-2-(2H-1,2,3-triazol-2-yl)phenyl]ethoxy}-5-[1-(piperidin-4-yl)-1H-pyrazol-4-yl]pyridin-2-amine (example 80) (43 mg, 0.09 mmol. The mixture was stirred at room temperature for 18 hr. Additional portion of 2-(dimethylamino)acetic acid (28 mg), HATU (105 mg) and TEA (63 μL) were added and the mixture was stirred at RT for 2 hr. LCMS indicated the reaction complete. The mixture was diluted with MeOH and purified by reverse phase prep-HPLC. The desired fractions were lyophilized to give the title compound as an acetic acid salt (17 mg).

¹H NMR (400 MHz, DMSO-d₆) δ ppm 8.28 (s, 2H), 7.88 (s, 1H), 7.71 (d, J=1.52 Hz, 1H), 7.59-7.67 (m, 2H), 7.56 (s, 1H), 7.33 (td, J=8.40, 2.91 Hz, 1H), 6.70 (d, J=1.52 Hz, 1H), 5.83 (s, 2H), 5.39 (q, J=6.06 Hz, 1H), 4.29-4.50 (m, 2H), 4.04-4.17 (m, 1H), 3.09-3.27 (m, 3H, partially obscured by water), 2.77 (t, J=10.99 Hz, 1H), 2.24 (s, 6H), 1.99-2.12 (m, 2H), 1.67-1.89 (m, 2H, partially obscured by Acetic acid), 1.61 (d, J=6.32 Hz, 3H).

Example 129

2',3'-difluoro-5-{(1R)-1-[5-fluoro-2-(2H-1,2,3-triazol-2-yl)phenyl]ethoxy}-3,4'-bipyridin-6-amine

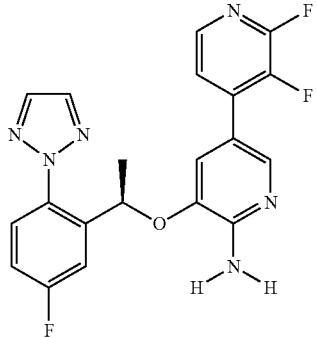

5-Bromo-3-[(R)-1-(5-fluoro-2-[1,2,3]triazol-2-yl-phenyl)-ethoxy]-pyridin-2-ylamine (example 45) (200 mg, 0.529 mmol, 1.0 eq) and 2,3-difluoropyridin-4-ylboronic acid (168 mg, 1.06 mmol, 2.0 eq) were dissolved in MeOH (5 mL), followed by the addition of freshly prepared aqueous solution of CsF (563 mg, 3.5 mmol, 7 eq) in water (3.34 mL) and Pd-132 (64 mg, 0.09 mmol, 0.17 eq), then degassed for three times. The mixture was heated up to 80° C. for overnight. LCMS showed >80% conversion to desired product, and ~10% of des-bromation of example 45. The reaction mixture was filtered. The filtrate was concentrated and purified via a Biotage silica gel cartridge to provide the title compound (174 mg) as a white solid.

¹H NMR (400 MHz, DMSO-d₆) δ ppm 8.21-8.23 (m, 2H) 8.00 (d, J=5.05 Hz, 1H) 7.91 (t, J=1.77 Hz, 1H) 7.70 (dd, J=9.73, 2.91 Hz, 1H) 7.64 (dd, J=8.84, 5.05 Hz, 1H) 7.33-7.37 (m, 2H) 6.87 (s, 1H) 6.57 (s, 2H) 5.59 (q, 1H) 1.62 (d, J=6.32 Hz, 3H).

Example 130

1-(6-amino-3'-fluoro-5-{(1R)-1-[5-fluoro-2-(2H-1,2,3-triazol-2-yl)phenyl]ethoxy}-3,4'-bipyridin-2'-yl)azetidin-3-ol

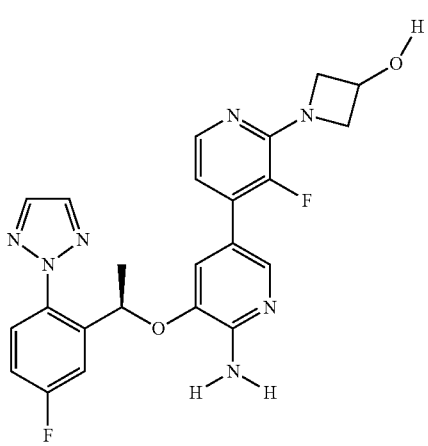 [SMILES: C[C@@H](Oc1cc(-c2ccnc(N3CC(O)C3)c2F)cnc1N)c1cc(F)ccc1-n1nccn1]

2',3'-Difluoro-5-[(R)-1-(5-fluoro-2-[1,2,3]triazol-2-yl-phenyl)-ethoxy-[3,4']bipyridinyl-6-ylamine (example 129) (35 mg, 0.085 mmol, 1.0 eq) and potassium carbonate (115 mg, 0.833 mmol, 9.8 eq) and 3-hydroxyazetidine hydrochloride (91.3 mg, 0.833 mmol, 9.8 eq) in anhydrous DMSO (2 mL) were microwaved for 10 min. at 150° C. The mixture was filtered, concentrated, and purified with a reverse phase pre-HPLC under acidic condition to give the title compound (11.8 mg, 30% yield) as a amorphous solid after lyophilization.

¹H NMR (400 MHz, DMSO-d₆) δ ppm 8.21 (s, 2H) 7.83 (d, J=5.05 Hz, 1H) 7.75-7.78 (m, 1H) 7.66-7.68 (m, 1H) 7.63-7.66 (m, 1H) 7.31-7.37 (m, 1H) 6.78 (br. s., 1H) 6.59 (t, J=5.18 Hz, 1H) 6.35 (s, 2H) 5.54-5.64 (m, 2H) 4.51-4.62 (m, 1H) 4.20-4.27 (m, 2H) 3.75-3.82 (m, 2H) 1.62 (d, J=6.32 Hz, 3H).

Examples 131 and 132

Examples 131 and 132 were prepared with the same procedure as example 130.

| Ex No. | Structure | NAME | ¹H NMR, δ ppm |
|---|---|---|---|
| 131 | ABS | 3'-fluoro-5-{(1R)-1-[5-fluoro-2-(2H-1,2,3-triazol-2-yl)phenyl]ethoxy}-2'-(morpholin-4-yl)-3,4'-bipyridin-6-amine | 400 MHz, DMSO-d₆: 8.19 (s, 2 H) 7.95 (d, J = 5.05 Hz, 1 H) 7.76 (s, 1 H) 7.62-7.68 (m, 2 H) 7.29-7.37 (m, 1 H) 6.81 (t, J = 5.18 Hz, 1 H) 6.76 (s, 1 H) 6.34 (s, 2 H) 5.57 (q, 1 H) 3.73 (t, J = 4.67 Hz, 4 H) 3.32-3.37 (m, 4 H) 1.64 (d, J = 6.32 Hz, 3 H) |

| Ex No. | Structure | NAME | $^1$H NMR, δ ppm |
|---|---|---|---|
| 132 | ABS 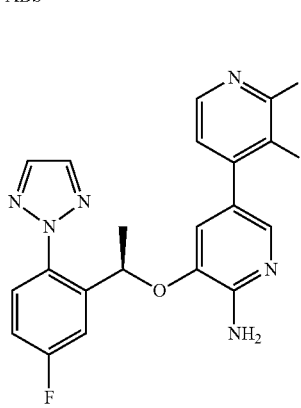 | 3'-fluoro-5-{(1R)-1-[5-fluoro-2-(2H-1,2,3-triazol-2-yl)phenyl]ethoxy}-2,-(4-methylpiperazin-1-yl)-3,4'-bipyridin-6-amine | 600 MHz, DMSO-d$_6$: 8.15-8.20 (m, 2 H) 7.92 (d, J = 4.91 Hz, 1 H) 7.75 (s, 1 H) 7.63 (d, J = 5.66 Hz, 2 H) 7.33 (t, J = 8.31 Hz, 1H) 6.74-6.80 (m, 2 H) 6.35 (br. s., 2 H) 5.56 (d, J = 5.29 Hz, 1 H) 3.32 (br. s., 4 H) 2.44 (br. s., 4 H) 2.21 (s, 3 H) 1.63 (d, J = 6.42 Hz, 3 H) |

Example 133

3-[1-(5-fluoro-2-methoxyphenyl)ethoxy]-5-[5-(methylsulfonyl)-1,2,4-thiadiazol-3-yl]pyridin-2-amine

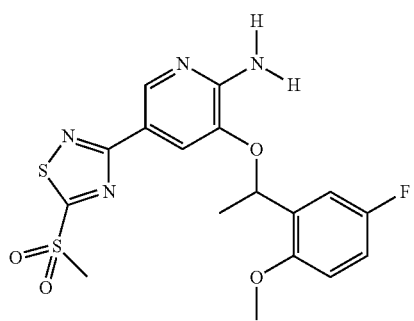 [SMILES: COc1ccc(F)cc1C(C)Oc1cc(-c2nsc(S(C)(=O)=O)n2)cnc1N]

A mixture of preparation 115 (44 mg, 0.18 mmol), preparation 118 (70 mg, 0.18 mmol) and Pd(PPh$_3$)$_4$ (20 mg, 0.016 mmol) in dry toluene (3 mL) was stirred at 120° C. under microwave condition for 2.5 hours. TLC (petroleum ether: EtOAc=3:1) indicated the reaction was completed. The mixture was concentrated in vacuo to give the residue, which was purified by a Biotage silica gel cartridge (petroleum ether: EtOAc 3:2 Rf, 0.34) to give the title compound (17 mg, 10.7%) as a yellow solid.

$^1$H NMR (400 MHz, DMSO-d$_6$): δ ppm 8.41 (s, 1H), 7.50 (s, 1H), 7.30-7.28 (d, 1H), 7.09-7.07 (d, 1H), 6.71 (s, 1H), 5.83-5.81 (m, 1H), 3.95 (s, 3H), 3.63 (s, 3H), 1.61-1.60 (d, 3H).

MS: m/z 425.1 [MH]+.

Examples 134 and 135

Examples 134 and 135 were prepared using the same method as example 133.

| Ex No. | Structure | NAME | $^1$H NMR, δ ppm |
|---|---|---|---|
| 134 | 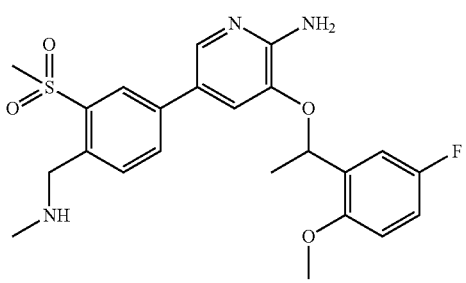 [SMILES: CNCc1ccc(-c2cnc(N)c(OC(C)c3cc(F)ccc3OC)c2)cc1S(C)(=O)=O] | 3-[1-(5-fluoro-2-methoxyphenyl)ethoxy]-5-{4-[(methylamino)methyl]-3-(methylsulfonyl)phenyl}pyridin-2-amine | 400 MHz, DMSO-d$_6$: 7.97-7.87 (m, 3H), 7.75-7.73 (d, 1H), 7.39-7.36 (d, 1H), 7.16-7.11 (m, 3H), 6.26 (s, 2H), 5.95-5.90 (m, 1H), 4.18 (s, 2H), 3.96 (s, 3H), 3.44 (s, 3H), 2.46 (s, 3H), 1.66-1.64(d, 3H). |

| Ex No. | Structure | NAME | ¹H NMR, δ ppm |
|---|---|---|---|
| 135 | 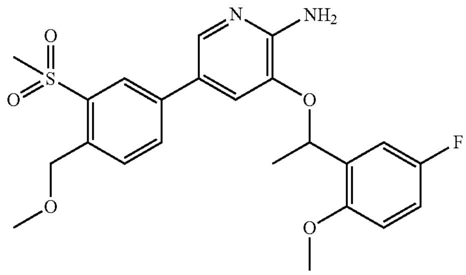 [SMILES: COCc1ccc(-c2cnc(N)c(OC(C)c3cc(F)ccc3OC)c2)cc1S(C)(=O)=O] | 3-[1-(5-fluoro-2-methoxyphenyl)ethoxy]-5-[4-(methoxymethyl)-3-(methylsulfonyl)phenyl]pyridin-2-amine | 400 MHz, DMSO-d: 7.91-7.90 (d, 1 H), 7.89-7.88 (d, 2H), 7.69 (d, 1H), 7.30 (d, 1H), 7.12-7.05 (m, 3H), 6.19 (s, 2H), 5.85 (m, 1H), 4.81 (s, 2H), 3.91 (s, 3H), 3.40-3.28 (m, 6H), 1.60-1.58 (d, 3H). |

Example 136

[4-{6-amino-5-[1-(5-fluoro-2-methoxyphenyl)ethoxy]pyridin-3-yl}-2-(methylsulfonyl)phenyl]methanol

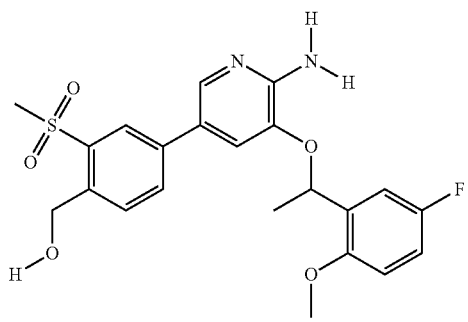 [SMILES: COc1ccc(F)cc1C(C)Oc1cc(-c2ccc(CO)c(S(C)(=O)=O)c2)cnc1N]

To a stirred solution of preparation 112 (90 mg, 0.37 mmol), preparation 117 (220 mg, 0.37 mmol) and K₂CO₃ (204 mg, 1.48 mmol) in dioxane (8 mL) and H₂O (2 mL) was added Pd(PPh₃)₄ (10 mg, 0.009 mmol) at room temperature under N₂ atmosphere. After the addition, the reaction mixture was refluxed overnight. TLC (petroleum ether:EtOAc 1:1) showed the reaction was complete. The reaction was cooled to room temperature and then poured into brine (10 mL) and extracted with EtOAc (10 mL×2). The combined organic layers were washed with brine (10 mL×2), dried over Na₂SO₄ and concentrated in vacuo to give the residue, which was purified by prep-HPLC to give Boc-protected title compound (90 mg, 40%) as a white solid, which was dissolved in EtOAc (5 mL). To the solution was added HCl (g) (6N) in EtOAc (2 mL). The mixture was stirred at room temperature overnight. LC-MS showed the reaction was complete. The mixture was basified to pH=8 with NaHCO₃, extracted with EtOAc (10 mL×2). The combined organic layers were washed with brine (10 mL×2), dried over sodium sulfate and concentrated in vacuo to give the residue which was purified by prep-HPLC to give the title compound (17 mg, 28%) as a yellow solid.

¹H NMR (400 MHz, DMSO-d₆): δ ppm 8.40 (brs, 1H), 7.85-7.83 (d, 2H), 7.78-7.74 (m, 1H), 7.30-7.27 (dd, 1H), 7.07-7.03 (m, 3H), 6.12 (s, 2H), 5.84-5.83 (m, 1H), 4.89 (s, 2H), 3.87 (s, 3H), 3.32-3.27 (s, 3H), 1.58-1.57 (d, 3H). MS: m/z 446.50 [MH]+.

Examples 137 and 138

Examples 137 and 138 were prepared using the same method as example 136.

| Ex No. | Structure | NAME | ¹H NMR, δ ppm |
|---|---|---|---|
| 137 | 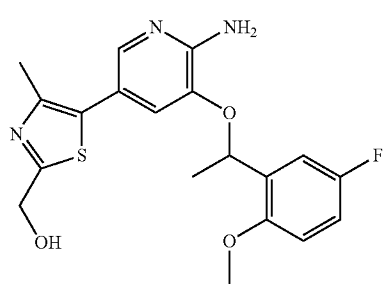 [SMILES: COc1ccc(F)cc1C(C)Oc1cc(-c2sc(CO)nc2C)cnc1N] | (5-{6-amino-5-[1-(5-fluoro-2-methoxyphenyl)ethoxy]pyridin-3-yl}-4-methyl-1,3-thiazol-2-yl)methanol | 400 MHz, DMSO-d₆: 7.52-7.53 (s, 1H), 7.19-7.22 (m, 1H), 7.04-7.07 (m, 2H) 6.71-6.72 (s, 1H), 6.11 (m, 2H), 5.93-5.96 (m, 1H), 5.69-5.71 (q, 1H), 4.60-4.62 (m, 2H), 3.85-3.84 (s, 3H), 2.12 (s, 3H), 1.49 (m, 3H). |

| Ex No. | Structure | NAME | ¹H NMR, δ ppm |
|---|---|---|---|
| 138 | 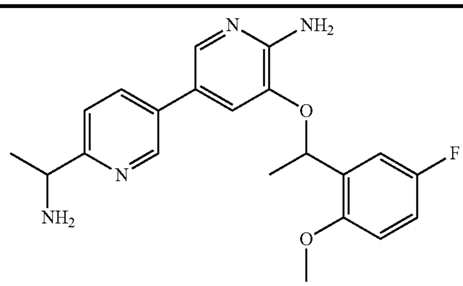 | 6'-(1-aminoethyl)-5-[1-(5-fluoro-2-methoxyphenyl)ethoxy]-3,3'-bipyridin-6-amine | 400 MHz, DMSO-$d_6$: 8.60 (d, 1H), 7.85 (m, 2H), 7.49 (m, 1H), 7.30 (d, 1H), 7.12-7.05 (m, 3H), 6.13 (s, 2H), 5.85 (m, 1H), 4.25-4.16 (m, 1H), 3.85 (s, 4H), 1.55 (m, 3H), 1.46-1.44 (d, 3H). |

Examples 139-141

Examples 139-141 were prepared using the same method as example 124.

| Ex No. | Structure | NAME | 1H NMR, δ ppm |
|---|---|---|---|
| 139 | | 3-[4-(6-amino-5-{(1R)-1-[5-fluoro-2-(2H-1,2,3-triazol-2-yl)phenyl]ethoxy}pyridin-3-yl)-3-methyl-1H-pyrazol-1-yl]pyrrolidin-2-one | 400 MHz, DMSO-d6: 8.24 (s, 2 H), 8.09 (s, 1 H), 7.64-7.70 (m, 2 H), 7.61 (dd, J = 9.73, 2.65 Hz, 1 H), 7.53 (d, J = 1.77 Hz, 1 H), 7.34 (td, J = 8.46, 3.03 Hz, 1 H), 6.60 (d, J = 1.52 Hz, 1 H), 5.87 (s, 2 H), 5.51-5.60 (m, 1 H), 4.91 (t, 1 H), 3.23-3.41 (m, 2 H, partially obscured by water), 2.28-2.57 (m, 2 H, partially obscured by DMSO), 2.00 (s, 3 H), 1.59 (d, J = 6.32 Hz, 3 H) |
| 140 ABS | | 4-(6-amino-5-{(1R)-1-[5-fluoro-2-(2H-1,2,3-triazol-2-yl)phenyl]ethoxy}pyridin-3-yl)-1-[(3-exo)-8-azabicyclo[3.2.1]oct-3-yl]-1H-pyrazole-3-carbonitrile | 400 MHz, DMSO-d6: 8.22 (s, 2 H), 8.07 (s, 1 H), 7.75 (d, J = 1.77 Hz, 1 H), 7.69 (dd, J = 9.60, 3.03 Hz, 1 H), 7.62 (dd, J = 8.97, 5.18 Hz, 1 H), 7.32 (td, J = 8.40, 2.91 Hz, 1 H), 6.81 (d, J = 1.77 Hz, 1 H), 6.19 (s, 2 H), 5.56 (q, J = 6.32 Hz, 1 H), 4.49-4.70 (m, 1 H), 3.54 (br. s., 2 H), 1.91-1.98 (m, 4 H), 1.65-1.79 (m, 4 H), 1.59 (d, J = 6.32 Hz, 3 H) |
| 141 ABS | | 4-(6-amino-5-{(1R)-1-[5-fluoro-2-(2H-1,2,3-triazol-2-yl)phenyl]ethoxy}pyridin-3-yl)-1-[(3-exo)-8-azabicyclo[3.2.1]oct-3-yl]-1H-pyrazole-5-carbonitrile | 400 MHz, DMSO-d6: 8.21 (s, 2 H), 7.83 (d, J = 2.02 Hz, 1 H), 7.78 (s, 1 H), 7.54-7.72 (m, 2 H), 7.32 (td, J = 8.46, 3.03 Hz, 1 H), 6.85 (d, J = 2.02 Hz, 1 H), 6.27 (s, 2 H), 5.56 (q, J = 6.65 Hz, 1 H), 4.52-4.74 (m, 1 H), 3.52 (br. s., 2 H), 1.80-2.07 (m, 4 H), 1.63-1.79 (m, 4 H), 1.57 (d, J = 6.32 Hz, 3 H) |

Examples 142-145

Examples 142-145 were prepared using the same method as example 110.

| Ex No. | Structure | NAME | ¹H NMR, δ ppm |
|---|---|---|---|
| 142 | ABS | 5-(6-amino-5-{(1R)-1-[5-fluoro-2-(2H-1,2,3-triazol-2-yl)phenyl]ethoxy}pyridin-3-yl)-2-methoxy-N-methylbenzenesulfonamide | 600 MHz, DMSO-17 mm: 1.57 (d, J = 6.04 Hz, 3 H) 2.39 (d, J = 4.91 Hz, 3 H) 3.90 (s, 3 H) 3.53 (q, J = 6.17 Hz, 1 H) 6.11 (s, 2 H) 6.94 (s, 1 H) 7.02 (q, J = 4.78 Hz, 1 H) 7.25 (d, J = 8.69 Hz, 1 H) 7.32 (td, J = 8.31, 3.02 Hz, 1 H) 7.56-7.62 (m, 2 H) 7.67 (dd, J = 9.44, 2.64 Hz, 1 H) 7.73 (d, J = 1.51 Hz, 1 H) 7.71 (d, J = 2.27 Hz, 1 H) 8.24 (s, 2 H) |
| 143 | ABS | 3-(6-amino-5-{(1R)-1-[5-fluoro-2-(2H-1,2,3-triazol-2-yl)phenyl]ethoxy}pyridin-3-yl)-4-methoxy-N-methylbenzenesulfonamide | 600 MHz, DMSO-17 mm: 1.55 (d, J = 6.42 Hz, 3 H) 2.36 (d, J = 4.53 Hz, 3 H) 3.66 (s, 3 H) 5.57 (q, J = 6.04 Hz, 1 H) 6.11 (s, 2 H) 6.84 (s, 1 H) 7.18 (d, J = 8.69 Hz, 1 H) 7.25 (d, J = 4.91 Hz, 1 H) 7.34 (td, J = 8.31, 3.02 Hz, 1 H) 7.50 (d, J = 1.89 Hz, 1 H) 7.55-7.68 (m, 4 H) 8.15 (s, 2 H) |
| 144 | ABS | 5-(6-amino-5-{(1R)-1-[5-fluoro-2-(2H-1,2,3-triazol-2-yl)phenyl]ethoxy}pyridin-3-yl)-2-methoxybenzenesulfonamide | 600 MHz, DMSO-17 mm: 1.58 (d, J = 6.42 Hz, 3 H) 3.91 (s, 3 H) 5.54 (q, J = 6.29 Hz, 1 H) 6.10 (s, 2 H) 6.90 (s, 1 H) 7.10 (s, 2 H) 7.24 (d, J = 8.69 Hz, 1 H) 7.32 (td, J = 8.31, 3.02 Hz, 1 H) 7.54 (dd, J = 8.69, 2.27 Hz, 1 H) 7.59 (dd, J = 8.88, 5.10 Hz, 1 H) 7.68-7.73 (m, 2 H) 7.75 (d, J = 2.27 Hz, 1 H) 8.25 (s, 2 H) |
| 145 | ABS | (R)-5-(4-ethyl-2-((methylsulfonyl)methyl)thiazol-5-yl)-3-(1-(5-fluoro-2-(2H-1,2,3-triazol-2-yl)phenyl)ethoxy)pyridin-2-amine | ¹H-NMR (400 MHz, CDCl₃): δ 1.11 (t, J = 7.45 Hz, 3H), 2.47-2.63 (m, 2H), 3.01 (s, 3H), 4.54 (s, 2H), 4.92 (br. s., 2H), 5.82 (q, 1H), 6.80 (d, J = 1.52 Hz, 1H), 7.09-7.17 (m, 1H), 7.29 (dd, J = 9.22, 2.91 Hz, 1H), 7.61-7.67 (m, 1H), 7.68 (d, J = 1.52 Hz, 1H), 7.90 (s, 2H). |

The ability of the compounds of the formula to act as potent ALK inhibitors, inhibitors of EML4-ALK and to cross the blood brain barrier as well as their selectivity over other kinases such as Cmet or TrkA may be determined using the assay disclosed below.

ALK Enzymatic Activity Assay 1

ALK enzymatic activity assays were performed using the purified ALK enzyme (purchased from Invitrogen, Cat# PV4185), fluorescently labelled peptide substrate, EAIYAAPFAKKK (American Peptide Cat# AP332319), ATP (Roche Cat#11140965) at final concentrations of 10 nM, 1.5 µM and 25 µM respectively. The ALK ATP Km was determined to be 25 µM, using above mentioned peptide. Kinase reactions were carried out in a final buffer concentration of 100 mM HEPES, 5 mM $MgCl_2$, 1 mM DTT, 1.5 µM $Na_3VO_4$, and 0.01% Brij-35. Compounds were added at a final concentration of 1% DMSO in half-log dilutions, starting at 20 µM final concentration. The reactions were initiated by the addition of 10 µL of peptide/ATP mix to 10 µL enzyme and 2 µL of compound in 384-well plate. The reactions were incubated at room temperature for 2 hrs before being stopped by the addition of 50 µL of buffer containing 100 mM HEPES, 0.018% Brij, 0.16% Coating Reagent 3 (Caliper LS), 23.3 mM EDTA, and 7.35% DMSO. Microfluidic separation assays were performed on the Caliper LabChip3000 System (Caliper Life Sciences, Hopkinton, Mass.). On the 12-sipper chip, substrate and phosphorylated product were separated with an upstream voltage of −2650 V, a downstream voltage of −500 V, and a screen pressure of −1.5 psi. The relative peak heights of substrate and product were measured and ratios were calculated using HTS Well Analyzer Software version 5.2.43 from the manufacturer.

ALK Enzyme Assays 2 and 3

Wild-type ALK (ALK enzyme assay 2) and L1196M mutant ALK (ALK enzyme assay 3) enzyme inhibition was measured using a microfluidic mobility shift assay. The reactions were conducted in 50 µL volumes in 96-well plates, and contained preactivated human recombinant wild-type (1.3 nM) or L1196M (0.5 nM) ALK kinase domain (amino acids 1093-1411), 1.5 µM phosphoacceptor peptide, 5'FAM-KKSRGDYMTMQIG-CONH2 (CPC Scientific, Sunnyvale, Calif.), test compound (11-dose 3-fold serial dilutions, 2% DMSO final) or DMSO only, 1 mM DTT, 0.002% Tween-20 and 5 mM $MgCl_2$ in 25 mM Hepes, pH 7.1, and were initiated by addition of ATP (60 µM final concentration, ~Km level) following a 20-min preincubation. The reactions were incubated for 1 h at room temperature, stopped by the addition of 0.1 M EDTA, pH 8, and the extent of reactions (~15-20% conversion with no inhibitor) was determined after electrophoretic separation of the fluorescently labeled peptide substrate and phosphorylated product on an LabChip EZ Reader II (Caliper Life Sciences, Hopkinton, Mass.). The inhibitors were shown to be ATP-competitive from kinetic and crystallographic studies. The Ki values were calculated by fitting the % conversion to the equation for competitive inhibition using non-linear regression method (GraphPad Prism, GraphPad Software, San Diego, Calif.) and experimentally measured ATP $K_m$=58 µM for wild-type and 55 µM for L1196M enzyme. ALK enzymes were produced in-house (baculoviral expression) and preactivated by auto-phosphorylation of 16 µM non-activated enzyme in the presence of 2 mM ATP, 10 mM $MgCl_2$ and 4 mM DTT in 20 mM Hepes, pH 7.5, at room temperature for ~1 h, and the full phosphorylation (~4 phosphates per protein molecule) of ALK kinase domain was verified by Q-TOF mass-spectrometry.

TRKA Enzymatic Activity Assay

TRKA assays were performed using purified GST tagged TRKA enzyme (Invitrogen Lot#20061221), fluorescently labeled peptide substrate, FITC-C6-EDPIYEFLPAKKK (American Peptide Cat#333779) and ATP (Roche Cat#11140965) at final concentrations of 10 nM, 1.5 µM and 20 µM respectively. TRKA ATP Km was determined to be 20 uM, using above mentioned peptide. Kinase reactions were carried out at final buffer concentrations of 100 mM HEPES, 10 mM $MnCl_2$, 1 mM DTT, 1.5 µM $Na_3VO_4$, and 0.01% Brij-35. Compounds were added at a final concentration of 2% DMSO in half-log dilutions, starting at 20 µM final concentration. The reactions were initiated by the addition of 10 µL of peptide/ATP mix to 10 uL enzyme and 5 µL of compound in 384-well plate. The reactions were incubated at room temperature for 1.5 hrs before being stopped by the addition of 50 µL of buffer containing 100 mM HEPES, 0.018% Brij, 0.16% Coating Reagent 3 (Caliper LS), 23.3 mM EDTA, and 7.35% DMSO. Microfluidic separation assays were performed on the Caliper LabChip3000 System (Caliper Life Sciences, Hopkinton, Mass.) using the 12-sipper chip. Substrate and phosphorylated product were separated with an upstream voltage of −500 V, a downstream voltage of −2500 V, and a screen pressure of −1.7 psi. The relative peak heights of substrate and product were measured and ratios were calculated using HTS Well Analyzer Software version 5.2.43 from the manufacturer.

cMet Enzymatic Activity Assay cMet assays were performed using purified cMet enzyme (RTC Lot#032006), fluorescently labeled substrate, FITC-C6-EAIYAAPFAKKK (American Peptide Cat#335894) and ATP (Roche Cat#11140965) at final concentrations of 7.5 nM, 1.5 µM and 17 µM respectively. cMet ATP Km was determined to be 17 µM, using above mentioned peptide. Kinase reactions were carried out at final buffer concentrations of 100 mM HEPES, 10 mM $MgCl_2$, 1 mM DTT, 1.5 µM $Na_3VO_4$, and 0.01% Brij-35. Compounds were added at a final concentration of 2% DMSO in half-log dilutions, starting at 20 µM final concentration. The reactions were initiated by addition of 10 µL of peptide/ATP mix to 10 µL enzyme and 5 µL of compound in 384-well plate. The reactions were incubated at room temperature for 1.5 hrs before being stopped by the addition of 50 µL of buffer containing 100 mM HEPES, 0.018% Brij, 0.16% Coating Reagent 3 (Caliper LS), 23.3 mM EDTA, and 7.35% DMSO. Microfluidic separation assays were performed on the Caliper LabChip3000 System (Caliper Life Sciences, Hopkinton, Mass.) using the 12-sipper chip. Substrate and phosphorylated product were separated with an upstream voltage of −2650 V, a downstream voltage of −500V, and a screen pressure of −1.5 psi. The relative peak heights of substrate and product were measured and ratios were calculated using HTS Well Analyzer Software version 5.2.43 from the manufacturer.

Karpas-299 Cell Based Assay

ALK functional cell based assays were performed using Karpas-299 cells, a human T-cell line (purchased from DSMZ, Germany). Cells were cultured in RPMI 1640 media (GIBCO #22400-121) containing 10% heat inactivated FBS and maintained at 37° C. in 5% $CO_2$. Cells were seeded in Falcon tissue culture treated 96 well plates (BD cat#353072) at 15,000 cells per well overnight. Compounds were added at a final concentration of 1% DMSO in half-log dilutions, starting at 30 µM final concentration for 1 hour at 37° C. in 5% $CO_2$. Cell plates were then centrifuged at 1000 RPMs for five minutes. Serum was removed and 100 µl of lysis buffer (Cell Signaling cat #7018) was added to the plate which was then left on ice for 5 minutes. The plates were then spun at 3000

RPMs for 15 min at 4° C. Subsequently, ALK phosphorylation was measured using the PathScan® Phospho-ALK (Tyr1604) Sandwich ELISA Kit purchased from Cell Signaling Technology (catalogue #7324). Cell lysates were incubated in antibody coated plates overnight at 4° C. Plates were then washed 4 times with 200 μl wash buffer (provided by manufacturer) and incubated with ALK detection antibody for 1 hour at 37° C. Plates were washed again 4 times with 200 μl wash buffer and then 100 μl of anti-mouse IgG HRP-Linked antibody was added for 1 hour at 37° C. After washing 4 more times with 200 μl wash buffer, 100 μl of TMB peroxidase substrate was added for 5 min at 37° C. The reaction was stopped with the addition of 100 μl of Stop buffer. Absorbance was measured at 450 nm using the Spectromax M5 reader. $IC_{50}$ values were calculated using concentration response curves generated by in house software.

Cellular Phospho-ALK (Tyr1604) ELISA Assay for EML4-ALK:

Cell Lines:

NIH-3T3 EML4-ALK wt v1 and NIH-3T3 EML4-ALK v1 L1196M cells are human stable cell lines established at Pfizer—La Jolla, Calif. The cells were maintained at 37° C. in a 5% $CO_2$ incubator in DMEM (Invitrogen, Carlsbad, Calif.) medium supplemented with 1% L-glutamine, 1% penicillin and streptomycin, 1 ug/ml puromycin and 10% new born calf serum (NCS) in T-75 flasks.

Assay:

Cells were washed with PBS and re-suspended in DMEM medium supplemented with 0.5% NCS and 1% pen/strep and seeded into 96-well plates at density of 20,000 cells/well/100 μl and incubated in the incubator at 37° C. and 5% $CO_2$. After 20 hours of incubation, 100 μl of assay media (DMEM) in presence of designated PF-compounds concentrations or controls (DMSO) were added into plates and incubated for 1 hour in the incubator. Media was then removed and lysis buffer, containing phosphatase inhibitors and phenylmethanesulfonyl fluoride (PMSF), was added to wells and shaken at 4° C. for 30 minutes to generate protein lysates. Subsequently, a PathScan phospho-ALK (Tyr1604) chemiluminescent sandwich ELISA kit (Cell Signal Technology Inc., cat #7020) was used to assess the phosphorylation of ALK as follows:

A phospho-ALK (Tyr1604) rabbit antibody was coated onto the 96-well microplates. 50 μl of cell lysates were added to the antibody coated plate and incubated at room temperature for 2 hours. Following extensive washing with 0.1% Tween 20 in PBS to remove unbound materials, ALK mouse mAb was added to detect captured phospho-ALK (Tyr1604) and phospho-ALK fusion proteins. Anti-mouse IgG, HRP-linked antibody was then used to recognize the bound detection antibody. Finally, the chemiluminescent reagent was added and incubated for 10 minutes for signal development. The assay plates were read in the Envision plate reader in the luminescent mode. $IC_{50}$ values were calculated by a concentration-response curve fitting using a four-parameter analytic method.

IC50 data obtained with the ALK enzymatic activity assay 1 and the cMet enzymatic activity assay disclosed above are shown in the below table.

| Example Number | ALK IC50 Enzymatic assay 1 | cMet-IC50 Enzymatic assay |
|---|---|---|
| 1 | 61.4 nM | >18800 nM |
| 2 | 135 nM | >20000 nM |
| 3 | 113 nM | >20000 nM |
| 4 | 51.7 nM | 7610 nM |
| 5 | 48.0 nM | 13000 nM |
| 6 | 33.6 nM | 6740 nM |
| 7 | 44.9 nM | 10200 nM |
| 8 | 98.2 nM | 17400 nM |
| 9 | 49.9 nM | 7140 nM |
| 10 | 86.0 nM | >20000 nM |
| 11 | 52.2 nM | >20000 nM |
| 12 | 70.6 nM | 8420 nM |
| 13 | 132 nM | >20000 nM |
| 14 | 74.8 nM | 8290 nM |
| 15 | 177 nM | >20000 nM |
| 16 | 38.1 nM | 11200 nM |
| 17 | 133 nM | 13200 nM |
| 18 | 92.6 nM | >20000 nM |
| 19 | 78.7 nM | >19700 nM |
| 20 | 38.0 nM | 10100 nM |
| 21 | 24.6 nM | 14400 nM |
| 22 | 38.0 nM | 3680 nM |
| 23 | 271 nM | >19100 nM |
| 24 | 43.2 nM | 10500 nM |
| 25 | 38.2 nM | 13200 nM |
| 26 | 24.1 nM | 4300 nM |
| 27 | 47.3 nM | >15400 nM |
| 28 | 63.5 nM | 13000 nM |
| 29 | 30.0 nM | 7480 nM |
| 30 | 29.3 nM | 6110 nM |
| 31 | 69.7 nM | 13000 nM |
| 32 | 105 nM | >20000 nM |
| 33 | 89.2 nM | >20000 nM |
| 34 | 71.1 nM | >17800 nM |
| 35 | 29.4 nM | 5610 nM |
| 36 | 120 nM | >15800 nM |
| 37 | 70.3 nM | 8090 nM |
| 38 | 90.9 nM | 4050 nM |
| 39 | 107 nM | 4500 nM |
| 40 | 23.8 nM | 1350 nM |
| 41 | 15.7 nM | 5590 nM |
| 42 | 58.1 nM | >15900 nM |
| 43 | 34.9 nM | 5090 nM |
| 44 | 57.0 nM | 6480 nM |
| 45 | 75.6 nM | 4160 nM |
| 46 | 44.9 nM | 6850 nM |
| 47 | 70.5 nM | 2850 nM |
| 48 | NA | NA |
| 49 | 114 nM | 13100 nM |
| 50 | 50.2 nM | 5070 nM |
| 51 | 45.2 nM | 7870 nM |
| 52 | 73.3 nM | 10400 nM |
| 53 | 27.0 nM | 4440 nM |
| 54 | 47.2 nM | >18200 nM |
| 55 | 87.6 nM | >20000 nM |
| 56 | 47.5 nM | >20000 nM |
| 57 | 58.7 nM | >20000 nM |
| 58 | 86.5 nM | >20000 nM |
| 59 | 126 nM | >20000 nM |
| 60 | 67.3 nM | >20000 nM |
| 61 | NA | NA |
| 62 | 50.5 nM | 2810 nM |

NA: not available

Ki and IC50 data obtained with the ALK enzymatic assays 2 and 3 and cellular phospho-ALK (Tyr1604) ELISA assay for WT EML4-ALK and L1196M EML4-ALK, disclosed above, are shown in the below table. In the table below, compounds that have no data indicate that those compounds were not tested against the assays listed in the table.

| Ex | ALK enzyme assay 2 (Ki) | ALK enzyme assay 3 (Ki) | ELISA assay for WT EML4-ALK (IC$_{50}$) | ELISA assay for L1196M EML4-ALK (IC$_{50}$) |
|---|---|---|---|---|
| 1 | 2.90 nM | 18.0 nM | 144 nM | 950 nM |
| 2 | 220 nM | 1700 nM | >1000 nM | >1000 nM |
| 3 | 6.00 nM | 76.0 nM | 481 nM | >1000 nM |
| 4 | 1.93 nM | 21.7 nM | 72.4 nM | 991 nM |
| 5 | | | | |
| 6 | 0.620 nM | 2.75 nM | | |
| 7 | 0.536 nM | 3.16 nM | 33.0 nM | 177 nM |
| 8 | | | | |
| 9 | 0.550 nM | 7.80 nM | 83.2 nM | 504 nM |
| 10 | | | 361 nM | 2830 nM |
| 11 | 6.30 nM | 64.0 nM | 245 nM | 2570 nM |
| 12 | 2.10 nM | 21.0 nM | 194 nM | >1000 nM |
| 13 | 5.50 nM | 56.0 nM | 591 nM | >1000 nM |
| 14 | | | | |
| 15 | 16.0 nM | 210 nM | 904 nM | >1000 nM |
| 16 | 1.30 nM | 15.0 nM | 123 nM | 918 nM |
| 17 | 11.0 nM | 110 nM | 672 nM | >1000 nM |
| 18 | 8.10 nM | 66.0 nM | 421 nM | 3390 nM |
| 19 | 1.05 nM | 7.05 nM | 53.5 nM | 369 nM |
| 20 | 3.58 nM | 27.7 nM | 23.8 nM | 3170 nM |
| 21 | 8.96 nM | 69.8 nM | 249 nM | 2650 nM |
| 22 | | | 47.5 nM | 496 nM |
| 23 | 45.0 nM | 360 nM | 1080 nM | >10000 nM |
| 24 | 4.50 nM | 52.3 nM | 165 nM | 3190 nM |
| 25 | | | | |
| 26 | <0.313 nM | 1.88 nM | 4.54 nM | 119 nM |
| 27 | 3.10 nM | 27.0 nM | 138 nM | 1200 nM |
| 28 | | | | |
| 29 | | | 151 nM | 914 nM |
| 30 | 1.00 nM | 10.0 nM | 102 nM | 610 nM |
| 31 | 3.10 nM | 30.0 nM | 247 nM | >1000 nM |
| 32 | 36.0 nM | 200 nM | 883 nM | 7220 nM |
| 33 | 4.80 nM | 33.0 nM | 380 nM | 3120 nM |
| 34 | 3.80 nM | 37.5 nM | 302 nM | >1000 nM |
| 35 | | | | |
| 36 | 22.0 nM | 160 nM | 862 nM | 7520 nM |
| 37 | 1.55 nM | 12.7 nM | 147 nM | 1120 nM |
| 38 | 3.24 nM | 16.3 nM | 233 nM | >1000 nM |
| 39 | 0.380 nM | 3.50 nM | 22.3 nM | 382 nM |
| 40 | 1.99 nM | 11.3 nM | 83.3 nM | 805 nM |
| 41 | 0.922 nM | 13.5 nM | 58.6 nM | 605 nM |
| 42 | 2.05 nM | 18.3 nM | 263 nM | >1000 nM |
| 43 | <0.249 nM | 3.72 nM | | |
| 44 | 6.90 nM | 50.0 nM | 411 nM | 3080 nM |
| 45 | 1.57 nM | 17.7 nM | 106 nM | 605 nM |
| 46 | 0.210 nM | 3.90 nM | 155 nM | >1000 nM |
| 47 | <0.200 nM | 2.10 nM | 45.7 nM | 336 nM |
| 48 | 1.56 nM | 13.9 nM | | |
| 49 | | | | |
| 50 | 0.739 nM | 4.61 nM | 58.4 nM | 382 nM |
| 51 | 61.0 nM | 640 nM | 1450 nM | >10000 nM |
| 52 | 1.10 nM | 7.50 nM | 14.5 nM | 418 nM |
| 53 | 0.401 nM | 3.07 nM | 23.3 nM | 164 nM |
| 54 | 1.30 nM | 16.0 nM | 194 nM | 452 nM |
| 55 | 43.0 nM | 200 nM | 1760 nM | 9280 nM |
| 56 | 6.40 nM | 64.0 nM | 361 nM | 2260 nM |
| 57 | 5.40 nM | 61.0 nM | 245 nM | 548 nM |
| 58 | 1.30 nM | 18.0 nM | 159 nM | 899 nM |
| 59 | 13.0 nM | 100 nM | 631 nM | >1000 nM |
| 60 | 6.40 nM | 59.0 nM | 555 nM | >1000 nM |
| 61 | | | | |
| 62 | 4.52 nM | 61.9 nM | 191 nM | 799 nM |
| 63 | 67.0 nM | 470 nM | 2350 nM | >10000 nM |
| 64 | 2.40 nM | 14.0 nM | 123 nM | 322 nM |
| 65 | 5.10 nM | 32.0 nM | 193 nM | 1140 nM |
| 66 | <0.200 nM | 0.670 nM | 16.4 nM | 59.3 nM |
| 67 | 0.560 nM | 4.30 nM | 40.9 nM | 149 nM |
| 68 | <0.200 nM | 0.218 nM | 4.50 nM | 83.1 nM |
| 69 | 1.10 nM | 6.20 nM | 52.6 nM | 315 nM |
| 70 | <0.200 nM | 0.490 nM | 5.48 nM | 17.6 nM |
| 71 | <0.200 nM | 1.00 nM | 30.3 nM | 107 nM |
| 72 | 0.240 nM | 1.70 nM | 10.4 nM | 50.5 nM |
| 73 | <0.200 nM | 0.362 nM | 6.73 nM | 36.9 nM |
| 74 | <0.200 nM | 0.340 nM | 6.77 nM | 48.4 nM |
| 75 | 0.341 nM | 3.82 nM | 24.6 nM | 232 nM |
| 76 | 0.216 nM | 3.78 nM | 25.5 nM | 137 nM |
| 77 | 0.200 nM | 3.50 nM | 15.3 nM | 78.0 nM |
| 78 | <0.200 nM | 1.16 nM | 5.48 nM | 52.7 nM |
| 79 | <0.200 nM | 1.40 nM | 15.5 nM | 119 nM |
| 80 | <0.200 nM | 0.443 nM | 6.58 nM | 51.7 nM |
| 81 | <0.200 nM | 1.45 nM | 9.90 nM | 90.6 nM |
| 82 | <0.200 nM | 3.20 nM | 75.3 nM | 540 nM |
| 83 | <0.200 nM | 1.30 nM | 10.2 nM | 106 nM |
| 84 | <0.200 nM | 1.50 nM | 13.2 nM | 115 nM |
| 85 | 0.370 nM | 2.50 nM | 6.81 nM | 76.2 nM |
| 86 | <0.275 nM | 2.82 nM | 18.1 nM | 105 nM |
| 87 | <0.200 nM | 0.730 nM | 4.14 nM | 40.5 nM |
| 88 | <0.200 nM | 0.330 nM | 2.61 nM | 18.1 nM |
| 89 | 0.220 nM | 2.50 nM | 43.6 nM | 180 nM |
| 90 | 1.20 nM | 12.0 nM | 58.9 nM | 413 nM |
| 91 | <0.200 nM | 1.01 nM | 0.793 nM | 12.2 nM |
| 92 | 7.20 nM | 59.0 nM | 729 nM | 3140 nM |
| 93 | 0.430 nM | 4.80 nM | 12.7 nM | 120 nM |
| 94 | <0.490 nM | 2.67 nM | 22.1 nM | 99.7 nM |
| 95 | 0.200 nM | 2.16 nM | 13.8 nM | 107 nM |
| 96 | <0.200 nM | 0.744 nM | 17.1 nM | 109 nM |
| 97 | 0.327 nM | 5.40 nM | 41.3 nM | 471 nM |
| 98 | <0.200 nM | 0.806 nM | 10.8 nM | 44.5 nM |
| 99 | 1.10 nM | 7.00 nM | 13.2 nM | 113 nM |
| 100 | <0.200 nM | 1.60 nM | 12.2 nM | 115 nM |
| 101 | <0.200 nM | 1.20 nM | 3.21 nM | 48.3 nM |
| 102 | 1.21 nM | 8.84 nM | 89.3 nM | 582 nM |
| 103 | <0.200 nM | 1.30 nM | 15.0 nM | 93.3 nM |
| 104 | <0.200 nM | 0.441 nM | 3.35 nM | 27.2 nM |
| 105 | 4.10 nM | 28.6 nM | 166 nM | 794 nM |
| 106 | 0.680 nM | 4.69 nM | 21.5 nM | 108 nM |
| 107 | <0.200 nM | 1.88 nM | 9.92 nM | 61.5 nM |
| 108 | <0.200 nM | 0.720 nM | 9.38 nM | 41.8 nM |
| 109 | 0.580 nM | 4.50 nM | 9.15 nM | 34.8 nM |
| 110 | 0.470 nM | 5.80 nM | 34.4 nM | 237 nM |
| 111 | <0.200 nM | <0.100 nM | 0.622 nM | 3.80 nM |
| 112 | 0.203 nM | 2.85 nM | 38.1 nM | 206 nM |
| 113 | 0.260 nM | 2.10 nM | 10.1 nM | 122 nM |
| 114 | 1.30 nM | 8.30 nM | 89.6 nM | 736 nM |
| 115 | 4.37 nM | 10.7 nM | 289 nM | 945 nM |
| 116 | <0.200 nM | 1.16 nM | 4.17 nM | 41.9 nM |
| 117 | 0.770 nM | 8.50 nM | 10.3 nM | 137 nM |
| 118 | 0.260 nM | 3.10 nM | 9.29 nM | 77.0 nM |
| 119 | <0.200 nM | 0.202 nM | 4.39 nM | 22.3 nM |
| 120 | 2.14 nM | 11.5 nM | 161 nM | 636 nM |
| 121 | 1.04 nM | 12.0 nM | 71.3 nM | 770 nM |
| 122 | <0.200 nM | 0.270 nM | 1.15 nM | 5.92 nM |
| 123 | 0.140 nM | 1.40 nM | 8.92 nM | 72.2 nM |
| 124 | <0.200 nM | 0.180 nM | 2.04 nM | 19.3 nM |
| 125 | <0.200 nM | 0.340 nM | 3.70 nM | 31.3 nM |
| 126 | <0.193 nM | 1.96 nM | 12.1 nM | 79.6 nM |
| 127 | <0.200 nM | 0.150 nM | 2.54 nM | 44.6 nM |
| 128 | <0.200 nM | 1.11 nM | 9.80 nM | 43.8 nM |
| 129 | 5.50 nM | 34.0 nM | 223 nM | 1350 nM |
| 130 | 0.260 nM | 2.90 nM | 2.25 nM | 30.0 nM |
| 131 | 0.638 nM | 3.71 nM | 17.6 nM | 103 nM |
| 132 | <0.200 nM | 0.330 nM | 5.67 nM | 44.6 nM |
| 133 | 1.28 nM | 13.0 nM | 687 nM | 1700 nM |
| 134 | 0.120 nM | 1.00 nM | 9.10 nM | 110 nM |
| 135 | 200 nM | 0.565 nM | 4.15 nM | 93.1 nM |
| 136 | 0.260 nM | 1.05 nM | 8.60 nM | 127 nM |
| 137 | 0.398 nM | 1.51 nM | 2.59 nM | 45.8 nM |
| 138 | 0.320 nM | 1.26 nM | 8.33 nM | 128 nM |
| 139 | <0.20 nM | 0.21 nM | 2.82 nM | 23.6 nM |
| 140 | <0.20 nM | 0.10 nM | 15.9 nM | 45.6 nM |
| 141 | <0.20 nM | 0.10 nM | 3.50 nM | 17.5 nM |
| 142 | <0.20 nM | 0.47 nM | 3.75 nM | 19.7 nM |
| 143 | <0.20 nM | 0.81 nM | 8.98 nM | 70.9 nM |
| 144 | <0.20 nM | 0.12 nM | 2.45 nM | 15.2 nM |
| 145 | <0.20 nM | 0.16 nM | 10.5 nM | 63.4 nM |

We claim:
1. A compound of formula (1),

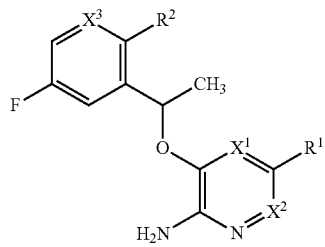

or a pharmaceutically acceptable salt thereof, wherein
$R^1$ is a thiazolyl, oxazolyl, imidazolyl, triazolyl or 1,2,4-thiadiazolyl wherein said thiazolyl, oxazolyl, imidazolyl, triazolyl and 1,2,4-thiadiazolyl are optionally substituted with one, two or three $R^3$ groups;
$X^1$ is CH and $X^2$ is CH;
$X^3$ is N or CH;
$R^2$ is a triazolyl;
each $R^3$ is independently selected from halogen, $C_1$-$C_6$ alkyl, $C_2$-$C_4$ alkenyl, —$(CH_2)_n$CN, —$(CH_2)_n$S(O)$_2$CH$_3$, —S(O)$_2$NR$^4$R$^5$, —PO(CH$_3$)$_2$, —(CR$^4$R$^5$)$_n$NR$^4$R$^5$, —(CR$^4$R$^5$)$_n$OR$^4$, —OCH$_2$(CR$^4$R$^5$)$_n$OR$^4$, —(CR$^4$R$^5$)$_n$CO(CR$^4$R$^5$)$_m$NR$^4$R$^5$, —(CR$^4$R$^5$)$_n$CR$^4$(OR$^5$)(CR$^4$R$^5$)OR$^5$, oxo, —O(4-6-membered heterocyclyl containing 1, 2 or 3 heteroatoms independently selected from O, N and S(O)$_p$), and 4-6-membered heterocyclyl containing 1, 2 or 3 heteroatoms independently selected from O, N and S(O)$_p$; wherein said $C_1$-$C_6$ alkyl is optionally substituted with one or two hydroxy groups, and wherein each said 4-6-membered heterocyclyl is optionally substituted with one or more halogen, hydroxy, oxo, —(CR$^4$R$^5$)$_n$CO(CR$^4$R$^5$)$_m$NR$^4$R$^5$ or $C_1$-$C_6$ alkyl, or substituents on two ring atoms of said 4-6-membered heterocyclyl may optionally combine to form a 5- or 6-membered bridged ring that is either carbocyclic or heterocyclic containing one, two or three ring heteroatoms selected from N, O and S(O)$_p$;
each $R^4$ or $R^5$ is independently H or $C_1$-$C_6$ alkyl;
each m is independently 0, 1, 2 or 3;
each n is independently 0, 1, 2 or 3; and
each p is independently 0, 1 or 2.

2. The compound of claim 1, or a pharmaceutically acceptable salt thereof, wherein
$R^1$ is thiazolyl optionally substituted with one, two or three $R^3$ groups independently selected from $C_1$-$C_4$ alkyl; wherein each said $C_1$-$C_4$ alkyl is optionally substituted with one or two hydroxy; and
$X^3$ is CH.

3. The compound of claim 1, wherein $R^1$ is selected from the group consisting of:

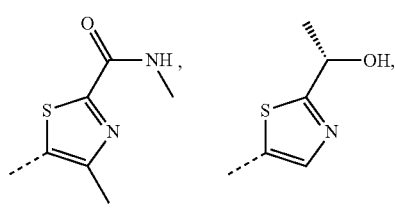

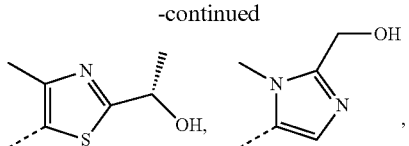

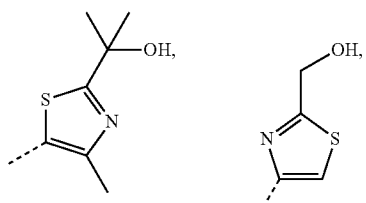

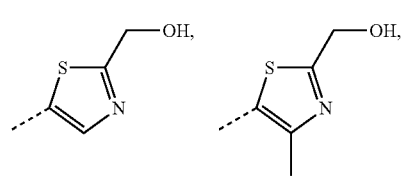

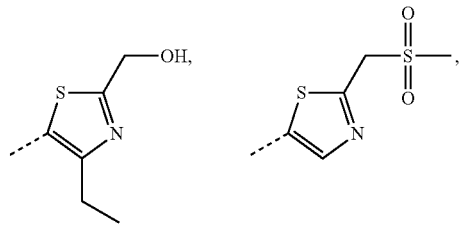

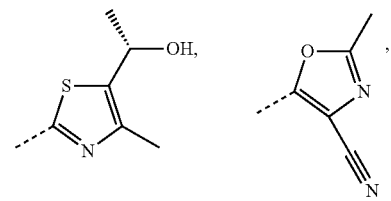

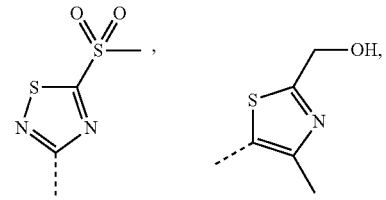

or a pharmaceutically acceptable salt thereof.

4. A compound selected from the group consisting of:
2-[5-(6-amino-5-{(1R)-1-[5-fluoro-2-(2H-1,2,3-triazol-2-yl)phenyl]ethoxy}pyridin-3-yl)-4-methyl-1,3-thiazol-2-yl]propan-2-ol; and
3-{(1R)-1-[5-fluoro-2-(2H-1,2,3-triazol-2-yl)phenyl]ethoxy}-5-{2-[(methylsulfonyl)methyl]-1,3-thiazol-5-yl}pyridin-2-amine;
or a pharmaceutically acceptable salt thereof.

5. A pharmaceutical composition comprising a compound of claim 1, or a pharmaceutically acceptable salt thereof, and a pharmaceutically acceptable excipient.

* * * * *